(12) United States Patent
Saulnier et al.

(10) Patent No.: US 9,169,295 B2
(45) Date of Patent: Oct. 27, 2015

(54) MACROCYCLES AND MACROCYCLE STABILIZED PEPTIDES

(75) Inventors: Mark G. Saulnier, Higganum, CT (US); Dolatrai M. Vyas, Madison, CT (US); David R. Langley, Meriden, CT (US); David B. Frennesson, Naugatuck, CT (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 13/879,513

(22) PCT Filed: Oct. 13, 2011

(86) PCT No.: PCT/US2011/056124
§ 371 (c)(1),
(2), (4) Date: Apr. 15, 2013

(87) PCT Pub. No.: WO2012/051405
PCT Pub. Date: Apr. 19, 2012

(65) Prior Publication Data
US 2013/0281657 A1  Oct. 24, 2013

Related U.S. Application Data

(60) Provisional application No. 61/392,818, filed on Oct. 13, 2010.

(51) Int. Cl.
*C07K 7/64* (2006.01)
*C07K 5/12* (2006.01)
(Continued)

(52) U.S. Cl.
CPC ............... *C07K 7/64* (2013.01); *C07D 277/42* (2013.01); *C07D 417/04* (2013.01); *C07K 1/1136* (2013.01); *C07K 5/123* (2013.01); *C07K 5/126* (2013.01)

(58) Field of Classification Search
CPC ..... A61K 38/00; A61K 49/106; A61K 38/12; A61K 47/48069; A61K 49/0054; A61K 49/0056; A61K 31/4439; A61K 47/48238; A61K 31/675; A61K 49/14; A61K 31/135; A61K 31/33; A61K 31/4184; A61K 31/4709; A61K 49/12; A61K 47/48061; C07D 487/22; C07D 498/22; C07D 491/08; C07D 291/08; C07D 277/42; C07D 487/04; C07D 487/18; C07D 498/04; C07D 213/71; C07D 235/20; C07D 257/02; C07D 401/12; C07D 417/10; C07D 417/12; C07D 498/08; C07D 209/20; C07D 233/64; C07D 285/00; C07D 409/12; C07D 498/18; C07D 513/08; C07K 7/56; C07K 1/047; C07K 1/1072; C07K 1/1075; C07K 5/0215; C07K 9/006
See application file for complete search history.

(56) References Cited

U.S. PATENT DOCUMENTS 7,981,998 B2   7/2011 Nash
2003/0096743 A1*  5/2003 Senter et al. .................... 514/12
2003/0198597 A1  10/2003 Meade et al.

FOREIGN PATENT DOCUMENTS

WO   WO 2004/077062   9/2004
(Continued)

OTHER PUBLICATIONS

John Whitfield. Back to Nature. Horizon symposia Charting Chemical Space. Apr. 2004:1-5.*
(Continued)

*Primary Examiner* — Karlheinz R Skowronek
*Assistant Examiner* — Jia-Hai Lee
(74) *Attorney, Agent, or Firm* — Hong Liu

(57) ABSTRACT

The invention provides methods of preparing macrocycles including macrocycle stabilized peptides (MSPs). Macrocycles and MSPs are prepared according to nucleophilic capture of an iminoquinomethide type intermediate generated from a suitably substituted 2-amino-thiazol-5-yl carbinol. The preferred nucleophile may be selected from an electron rich aromatic moiety in the case of macrocycles and, in the case of MSPs, at least one amino acid comprises an electron rich aromatic moiety. In addition, the concept can be extended to other related 5-membered heterocyclic systems in place of the thiazole, such as imidazole or oxazole. The conditions for the generation of the corresponding iminoquinomethide type intermediates may be similar or different than the conditions used for the 2-amino-thiazol-5-yl carbinol.

5 Claims, 5 Drawing Sheets

(51) Int. Cl.
*C07D 277/42* (2006.01)
*C07D 417/04* (2006.01)
*C07K 1/113* (2006.01)

(56) References Cited

FOREIGN PATENT DOCUMENTS

| WO | WO 2008/104000 | 8/2008 | |
|---|---|---|---|
| WO | WO 2008/104994 A2 * | 9/2008 | ........... C07D 213/40 |
| WO | WO 2009/099677 | 8/2009 | |
| WO | WO 2009/126292 | 10/2009 | |
| WO | WO 2009/149214 | 12/2009 | |
| WO | WO 2010/011313 | 1/2010 | |
| WO | WO 2010/033617 | 3/2010 | |
| WO | WO 2010/034026 | 3/2010 | |
| WO | WO 2010/034028 | 3/2010 | |
| WO | WO 2010/034031 | 3/2010 | |
| WO | WO 2010/034034 | 3/2010 | |

OTHER PUBLICATIONS

Xu et al. Combinatorial Library Approach for the Identification of Synthetic Receptors Targeting Vancomycin-Resistant Bacteria. J. Am. Chem. Soc. 1999; 121: 4898-4899.*
Macor et al. Direct displacement of -OH by nucleophiles in Hydroxymethylimidazoles. Tetrahedron Letters (2000) 41: 2777-2779.*
Poss et al. Quinone Methide p -Hydroxybenzylation of 1,3-Diketones. J. Org. Chem. 1988; 53:891-893.*
Gutheil et al. N-to-C solid-phase peptide and peptide trifluoromethylketone synthesis using amino acid tert-butyl esters. Chem Pharm Bull (Tokyo). May 2002;50(5):688-91.*
Turner 2007. Click Chemistry as a Macrocyclization Tool in the Solid-Phase Synthesis of Small Cyclic Peptides. Org. Lett., 2007, 9 (24), pp. 5011-5014.*
Driggers et al. The exploration of macrocycles for drug discovery-an underexploited structural class. Nat Rev Drug Discov. Jul. 2008;7(7):608-24.*
Katritzky et al. Short Course on Heterocyclic Chemistry. Handbook of Heterocyclic Chemistry 2nd Edition, 2000, Pergamon/Elsevier.*
Saulnier et al. Nucleophilic capture of the imino-quinone methide type intermediates generated from 2-aminothiazol-5-yl carbinols. Org Lett. Nov. 19, 2009;11(22):5154-7.*
Bernal, F. et al., "Reactivation of the p53 Tumor Suppressor Pathway by a Stapled p53 Peptide", J. Am. Chem. Soc., vol. 129, No. 9, pp. 2456-2457 (2007).
Chapman, R.N. et al., "Optimized Synthesis of Hydrogen-Bond Surrogate Helices: Surprising Effects of Microwave Heating on the Activity of Grubbs Catalysts", Organic Letters, vol. 8, No. 25, pp. 5825-5828 (2006).

Dieltens, N. et al., "Synthesis of $N$ (3),$N'$(3)-Polymethylene-bis-hydantoins and their Macrocyclic Derivatives", J. Org. Chem., vol. 71, No. 10, pp. 3863-3868 (2006).
Hili, R. et al., "Macrocyclization of Linear Peptides Enabled by Amphoteric Molecules", J. Am. Chem. Soc., vol. 132, No. 9, pp. 2889-2891 (2010).
Hughes, R.A. et al., "From Amino Acids to Heteroaromatics—Thiopeptide Antibiotics, Nature's Heterocyclic Peptides", Angew. Chem. Int. Ed., vol. 46, pp. 7930-7954 (2007).
Kawamoto, S.A., "Targeting the BCL9/B9L Binding Interaction with β-catenin as a Potential Anticancer Strategy", Dissertation, University of Michigan,. pp. 1-133 (2010).
Lewis, J.R., "Muscarine, imidazole, oxazole, thiazole and peptide alkaloids, and other miscellaneous alkaloids", Natural Product Reports, pp. 417-437 (1998).
Meyer, F.-M. et al., "Functionalization of Aromatic Amino Acids via Direct C—H Activation: Generation of Versatile Building Blocks for Accessing Novel Peptide Space", Organic Letters, doi: 10.1021/ol1015674 (received Jul. 7, 2010).
Nefzi, A. et al., "N-terminus 4-chloromethyl thiazole peptide as a macrocyclization tool in the synthesis of cyclic peptides: application to the synthesis of conformationally constrained RGD-containing integrin ligands", Tetrahedron Letters, vol. 52, pp. 817-819 (2011).
Nefzi, A. et al., "Two-Step Hantzsch Based Macrocyclization Approach for the Synthesis of Thiazole-Containing Cyclopeptides", J. Org. Chem., doi: 10.1021/jo1016822.(received Aug. 27, 2010).
Nicola, T. et al., "First Scale-Up to Production Scale of a Ring Closing Metathesis Reaction Forming a 15-Membered Macrocycle as a Precursor of an Active Pharmaceutical Ingredient", Organic Process Research & Development, vol. 9, No. 4, pp. 513-515 (2005).
Parks, D.J. et al., "*Alpha*-Helix Mimetics: Progress Toward Effective Modulation of Protein-Protein Complexes", Frontiers in Drug Design & Discovery, vol. 3, pp. 5-44 (2007).
Saulnier, M.G. et al., "Nucleophilic Capture of the Imino-Quinone Methide Type Intermediates Generated from 2-Aminothiazol-5-yl Carbinols", Organic Letters, vol. 11, No. 22, pp. 5154-5157 (2009).
Tron, G.C. et al., "Click Chemistry Reactions in Medicinal Chemistry: Applications of the 1,3-dipolar Cycloaddition Between Azides and Alkynes", Medicinal Research Reviews, vol. 28, No. 2, pp. 278-308 (2008).
Wessjohann, L.A. et al., "Strategies for Total and Diversity-Oriented Synthesis of Natural Product(-Like) Macrocycles", Top. Curr. Chem., vol. 243, pp. 137-184 (2005).
White, C.J. et al., "Contemporary strategies for peptide macrocyclization", Nature Chemistry, vol. 3, pp. 509-524 (2011).
Zhao, L. et al., "Inhibiting protein-protein interactions using designed molecules", Current Opinion in Structural Biology, vol. 15, pp. 31-34 (2005).

* cited by examiner

Formula 1 → N-terminal macrocyclization → Formula 2

X = OH, $NH_2$, $NHR_1$, $NR_1R_2$, $(a.a.)_z$ y-amino acid "Thia-Ty" peptide
macrocycles of ring size 3y + n + m + 12

$R_3$ = H, $CH_3$, lower alkyl      $R_4$ = H, $CH_3$, alkyl, hetroalkyl, halogen $R_5$ = H, $CH_3$, alkyl, hetroalkyl When n not equal to zero, $R_2$ = OH, $NH_2$, $NHR_1$, $NR_1R_2$ Formula 3 → C-terminal macrocyclization → Formula 4

W = H, CH$_3$, lower alkyl, CH$_3$CO, R$_a$CO, R$_a$OCO, R$_a$R$_b$NCO, (a.a.)$_x$ y-amino acid "Thia-Ty" peptide
macrocycles of ring size 3y + m + n + 12

R$_3$ = H, CH$_3$, lower alkyl      R$_4$ = H, CH$_3$, alkyl, hetroalkyl, halogen R$_5$ = H, CH$_3$, alkyl, hetroalkyl Y = H, CH$_3$, alkyl, hetroalkyl Formula 5

Formula 6
γ-amino acid "Thia-Ty" peptide
macrocycles of ring size 3y + m + n + 12

Formula 7

Formula 8
γ-amino acid "Thia-Ty" peptide
macrocycles of ring size 3y + m + n + 12

$R_3$ = H, $CH_3$, lower alkyl $R_5$ = H, $CH_3$, alkyl, hetroalkyl $R_4$ = H, $CH_3$, alkyl, hetroalkyl, halogen n = 0, 1, 2, 3, 4, 5 m = 0, 1, 2, 3, 4, 5

X = OH, $NH_2$, $NHR_1$, $NR_1R_2$, $(a.a.)_z$

W = H, $CH_3$, lower alkyl, $CH_3CO$, $R_aCO$, $R_aOCO$, $R_aR_bNCO$, $(a.a.)_x$ MSP of Example 91

Linear peptide of Example 93

SEQUENCE LISTING

<160> NUMBER OF SEQ ID NOS: 22

<210> SEQ ID NO 1
<211> LENGTH: 4
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: Amino acid is derivatized with a BOC moiety

<400> SEQUENCE: 1

Tyr Ala Ala Ala
1

<210> SEQ ID NO 2
<211> LENGTH: 4
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: Amino acid is derivatized with a BOC moiety

<400> SEQUENCE: 2

Tyr Ala Ala Ala
1

<210> SEQ ID NO 3
<211> LENGTH: 4
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: M = a tyrosine residue which has been
      macrocyclized to the thiazole, T, as opposed to Tyr which stands
      for a typical tyrosine residue itself

<400> SEQUENCE: 3

Tyr Ala Ala Ala
1

<210> SEQ ID NO 4
<211> LENGTH: 4
<212> TYPE: PRT
<213> ORGANISM: Artificial Sequence
<220> FEATURE:
<223> OTHER INFORMATION: Synthetic Peptide

```
<400> SEQUENCE: 4

Tyr Ala Ala Ala
1

<210> SEQ ID NO 5
<211> LENGTH: 7
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: Amino acid is derivatized with a FMOC moiety

<400> SEQUENCE: 5

Ala Ala Ala Tyr Ala Ala Gly
1               5

<210> SEQ ID NO 6
<211> LENGTH: 11
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: Amino acid is derivatized with a FMOC moiety

<400> SEQUENCE: 6

Ala Ala Ala Tyr Ala Ala Gly Tyr Ala Ala Ala
1               5                   10

<210> SEQ ID NO 7
<211> LENGTH: 11
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: Amino acid is derivatized with a thia-glycine
      moiety

<400> SEQUENCE: 7

Ala Ala Ala Tyr Ala Ala Gly Tyr Ala Ala Ala
1               5                   10

<210> SEQ ID NO 8
<211> LENGTH: 6
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: Amino acid is derivatized with a FMOC moiety

<400> SEQUENCE: 8

Tyr Ala Ala Gly Gly Phe
1               5

<210> SEQ ID NO 9
<211> LENGTH: 4
<212> TYPE: PRT
```

```
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: Amino acid is derivatized with a thia-glycine
      moiety

<400> SEQUENCE: 9

Gly Ala Ala Tyr
1

<210> SEQ ID NO 10
<211> LENGTH: 5
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: Amino acid is derivatized with a thia-glycine
      moiety

<400> SEQUENCE: 10

Gly Phe Ala Ala Tyr
1               5

<210> SEQ ID NO 11
<211> LENGTH: 4
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: Amino acid is derivatized with a thia-glycine
      moiety

<400> SEQUENCE: 11

Val Ala Ala Tyr
1

<210> SEQ ID NO 12
<211> LENGTH: 6
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: Amino acid is derivatized with a thia-glycine
      moiety

<400> SEQUENCE: 12

Val Ala Ala Ala Ala Tyr
1               5

<210> SEQ ID NO 13
<211> LENGTH: 5
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: Amino acid is derivatized with a thia-glycine
```

```
         moiety

<400> SEQUENCE: 13

Val Ala Ala Gly Tyr
1               5

<210> SEQ ID NO 14
<211> LENGTH: 4
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: Amino acid is derivatized  with a anisomycin
      moiety
<220> FEATURE:
<221> NAME/KEY: MISC_FEATURE
<222> LOCATION: (4)..(4)
<223> OTHER INFORMATION: Amino acid is derivatized with a thia-glycine
      moiety

<400> SEQUENCE: 14

Gly Gly Ala Gly
1

<210> SEQ ID NO 15
<211> LENGTH: 8
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: Amino acid is derivatized with a FMOC moiety

<400> SEQUENCE: 15

Tyr Gly Tyr Thr Thr Tyr Gly Tyr
1               5

<210> SEQ ID NO 16
<211> LENGTH: 4
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: Amino acid is derivatized with a FMOC moiety

<400> SEQUENCE: 16

Tyr Ala Ala Gly
1

<210> SEQ ID NO 17
<211> LENGTH: 7
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: Amino acid is derivatized with a FMOC moiety

<400> SEQUENCE: 17

Ala Ala Ala Tyr Ala Ala Gly
```

```
1               5
```

<210> SEQ ID NO 18
<211> LENGTH: 4
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (1)..(1)
<223> OTHER INFORMATION: Amino acid is derivatized with a FMOC moiety

<400> SEQUENCE: 18

```
Tyr Ala Ala Gly
1
```

<210> SEQ ID NO 19
<211> LENGTH: 7
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (1)..(1)
<223> OTHER INFORMATION: Amino acid is derivatized with a BOC moiety
<220> FEATURE:
<221> NAME/KEY: MISC_FEATURE
<222> LOCATION: (3)..(3)
<223> OTHER INFORMATION: carboxylic acid capping reagent
<220> FEATURE:
<221> NAME/KEY: MISC_FEATURE
<222> LOCATION: (4)..(4)
<223> OTHER INFORMATION: Amino acid is derivatized with a Fmoc moiety

<400> SEQUENCE: 19

```
Ala Ala Ala Tyr Ala Ala Gly
1               5
```

<210> SEQ ID NO 20
<211> LENGTH: 4
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (1)..(1)
<223> OTHER INFORMATION: Amino acid is derivatized with a Fmoc moiety

<400> SEQUENCE: 20

```
Tyr Ala Ala Gly
1
```

<210> SEQ ID NO 21
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Amino acid is derivatized with a Fmoc moiety
<220> FEATURE:
<221> NAME/KEY: MISC_FEATURE
<222> LOCATION: (5)..(5)
<223> OTHER INFORMATION: 2,3-diaminopropionic acid (DAP)

<400> SEQUENCE: 21

```
Tyr Ala Ala Gly Xaa Phe
1               5

<210> SEQ ID NO 22
<211> LENGTH: 7
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (3)..(3)
<223> OTHER INFORMATION: 1,3-diaminopropane derivative

<400> SEQUENCE: 22

Gly Tyr Xaa Tyr Gly Gly Tyr
1               5
```

MACROCYCLES AND MACROCYCLE STABILIZED PEPTIDES

CROSS-REFERENCE TO RELATED APPLICATION

This application is entitled to priority to U.S. Provisional Patent Application No. 61/392,818, filed on Oct. 13, 2010, which is incorporated herein in its entirety.

FIELD OF THE INVENTION

The invention relates to methods for preparing organic macrocycles, macrocycle stabilized peptides (MSPs), MSPs containing natural product templates, and MSPs containing common natural, rare natural, and/or unnatural amino acids. The invention also relates to methods for making peptides that are composed of linear, branched, and/or cyclic molecules and linking two or more linear, macrocyclic, and/or peptides containing linear and macrocyclic segments together to make non-natural protein mimics.

BACKGROUND OF THE INVENTION

Natural (e.g., Cyclosporine, Vancomycin, Rapamycin) and synthetic (e.g., IXEMPRA®) macrocycles (*Nature Reviews*, 7:608-624 (2008)) incorporating either peptidic or non-peptidic constituents have found successful utility as therapeutics in treating many human ailments ranging from cancer, infectious diseases, neuroscience, cardiovascular and immunological disorders. In spite of the success, many life threatening diseases remain untreatable. Accordingly, it would be desirable to develop novel synthetic methods for macrocyclization that facilitate access to novel macrocycles embedded with peptidic or non-peptidic scaffolds, with improved metabolic/pharmacokinetic and cell permeability properties, and with potential for activity towards novel biological disease targets of the future (*Molecular Diversity*, 9:171-186 (2005)). In this vein over the years synthetic methodologies towards constructing macrocycles have evolved beyond the classical lactam and lactone forming reactions to an armamentarium of methodologies that include, to mention a few, ring closing metathesis (RCM) reaction (*Angew. Chem. Int. Ed.*, 37:3281-3284 (1998)), "click" chemistry (*Drug Discovery Today*, 8:1128 (2003)), SnAr reactions (*J. Am. Chem. Soc.*, 71:8954-8956 (2006)), and cycloaddition reactions (*J. Am. Chem. Soc.*, 127:3473-3485 (2005); *Chem. Soc. Rev.*, 36:1674-1689 (2007)).

One of the challenges in specifically designing and synthesizing therapeutically useful macrocycles that inhibit protein-protein interactions central to many novel disease targets is the requirement of high-molecular weight molecules. Added accompanying prerequisite for such molecules is stereochemical and structural diversity in architecture such that they can adopt bioactive conformations to interact with protein target(s) and or a protein complex spanning large interacting surface areas (such as p53-MDM2, $BCl_2$, notch complex) and are also cell permeable, preferably endowed with oral bioavailability (*Angew. Chem. Int. Ed.*, 49:1-5 (2010)), and stable under physiological conditions. To address this from a future drug discovery perspective, the macrocycles field in parallel has shifted to the development of technology platforms of macrocycle stabilized peptides that encompass stabilized α-helix macrocycle stabilized peptides. In this regard, a few important technology platforms have emerged in recent years with several publications and patents disclosing biologically active molecules that target specific protein-protein interactions (e.g., transcription factor notch complex; *Nature*, 462(12):182-188 (2009)). It is noteworthy some these emerging technology platforms utilize macrocyclic forming reactions such as RCM reaction and the cycloaddition reaction mentioned above.

For example, WO 2004/077062 discloses a process for linking and cyclizing peptides containing cysteine groups. A peptide containing at least two cysteine moieties is alkylated with a scaffold-containing thiophile until two cysteine moieties are captured on to the scaffold to yield a macrocyclic or macrocycle stabilized peptide. This technique mimics the most common form of cyclization (i.e., disulfide bond) found among naturally occurring peptides and proteins, but does not provide a convenient means of preparing other types of cyclic structures due to its highly specific reactivity towards thiols only.

More recent publications such as WO 2010/034026, WO 2010/083347, and WO 2010/011313 disclose methods of producing macrocycle stabilized peptides by functionalizing two distant amino acid moieties on a protein or a peptide with olefinic residues that undergo ring closing metathesis (RCM) reactions to form a hydrocarbon staple. In particular, WO 2010/011313 discloses methods of ligating a macrocycle stabilized peptide to another peptide or a larger protein.

WO 2010/033617 discloses a method of preparing a macrocycle stabilized peptide by reacting (photochemical) an alkene moiety on a functionalized amino acid with a tetrazole moiety on another amino acid to form a pyrazoline cross-linking moiety via a (3+2) cycloaddition reaction.

To date, the widely used RCM based platform has been successful in making biologically active stabilized α-helix staple peptides with cell permeability and resistant to protease degradation. However, each platform's technology has limitations and synthetic challenges due to the reagents, reaction conditions, and potential compatibility issue with the composition of the peptidic substrate. For example, with the ring closing metathesis (RCM) platform there are potential issues and pitfalls involved with cost of reagents, length of synthetic sequences, toxicity of reagent (e.g., ruthenium catalyst), non-compatibility with methionine/cysteine, and scale-up and purification (*Organic Process Research & Development*, 513-515 (2005)). In addition, the potential lack of stereoselectivity of the product EZ double bond geometry during the construction of larger macrocycles can result in a product mixture of double bond regioisomers (*J. Org. Chem.*, 3863-3868 (2006)).

Consequently there exists a need for novel technologies towards building macrocycles and macrocycle stabilized peptides that potentially could offer versatility, simplicity, efficiency, cost advantages, and synthetic compatibility with peptides. Such a technology could be useful in preparing larger quantities of high molecular weight proteins (>60 amino acids) that contain stabilized α-helix macrocycle stabilized or stitched peptide segments. Thus a novel platform would offer excellent opportunities to construct biologically useful molecules (either agonists, antagonists, or with a new function) for novel therapeutic use in broad disease areas.

SUMMARY OF THE INVENTION

The present invention is based on applicants' surprising finding that 2-aminothiazol-5-yl carbinol, an iminoquinone methide type precursor, can readily react with an electron rich moiety such as the side chain of an amino acid, e.g., tyrosine and tryptophan, to form a covalent bond while the unprotected α-amino group and the acid moiety of the amino acid do not interfere with the observed chemoselectivity.

Accordingly, the present invention is related to methods of making macrocycle stabilized peptides (MSPs), macrocyclic peptides, and macrocycles.

In one aspect, the present invention relates to methods for preparing macrocycle stabilized peptides, comprising the steps of:

a) providing a linear peptide comprising at least two amino acids, wherein at least one said amino acid comprises an electron rich aromatic moiety and at least one said amino acid is a functionalized amino acid comprising an electrophilic moiety derived from an iminoquinone methide type precursor; and b) reacting the electron rich aromatic moiety with the electrophilic moiety in the presence of an activating reagent to form a macrocycle stabilized peptide comprising at least one covalent linkage between the two moieties.

The present invention also provides processes and intermediates for making the macrocycle stabilized peptides.

For ease of reference, these and further aspects of the present invention are now discussed under appropriate section headings. However, the teachings under each section are not necessarily limited to each particular section.

DETAILED DESCRIPTION OF THE INVENTION

Figure 1:
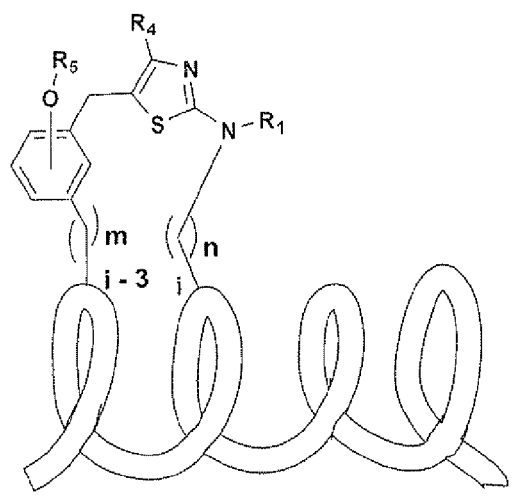
FIG. 1 is a graphic depiction of macrocycle stabilized α-helical peptides. The electrophile, i.e., the thiazole containing moiety, is in the "i" position and the nucleophile is in the "i+" or "i−" position. The "i−" positions are used when the nucleophile is to the N-terminal side of the electrophile while the "i+" positions denote that the nucleophile is to the C-terminal side of the electrophile. This is done to be consistent with the standard peptide/protein numbering system.
Figure 1:
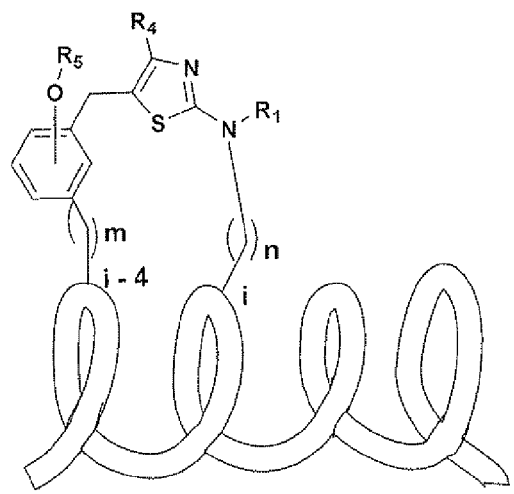
Figure 1:
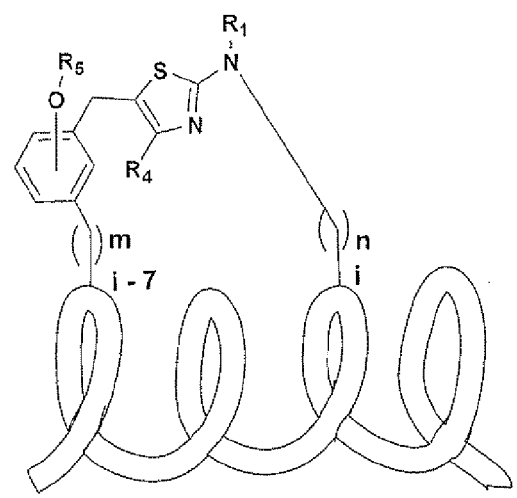
Figure 1:
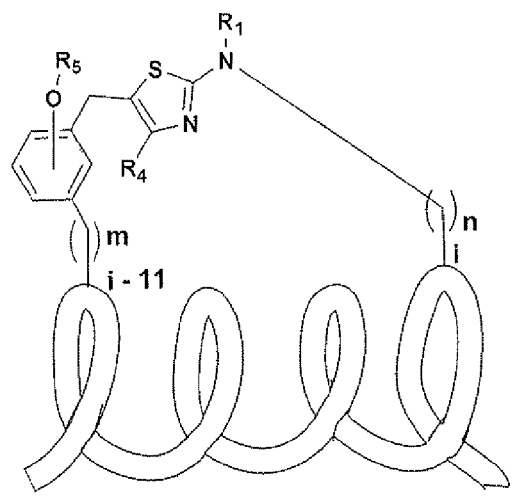

All publications and patent applications cited throughout this patent are incorporated by reference to the same extent as if each individual publication or patent/patent application is specifically and individually indicated to be incorporated by reference in their entirety.

Modifications and variations of this invention will be apparent to those skilled in the art. The specific embodiments described herein are offered by way of example only, and the invention is not to be construed as limited thereby.

Definitions

The following are definitions of terms used in this specification and appended claims. The initial definition provided for a group or term herein applies to that group or term throughout the specification and claims, individually or as part of another group, unless otherwise indicated.

In accordance with a convention used in the art,

is used in structural formulas herein to depict the bond that is the point of attachment of the moiety or substituent to the core or backbone structure.

A dash "-" that is not between two letters or symbols is used to indicate a point of attachment for a substituent. For example, —CONH$_2$ is attached through the carbon atom.

The term "amino acid" or "amino acid residue" typically refers to a natural amino acid having its art recognized definition such as an amino acid selected from the group consisting of alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, and valine. As used herein, amino acids are represented by the full name thereof, by the three letter code corresponding thereto, or by the one-letter code corresponding thereto, as indicated in the following table:

| Full Name | Three-Letter Code | One-Letter Code |
|---|---|---|
| Aspartic Acid | Asp | D |
| Glutamic Acid | Glu | E |
| Lysine | Lys | K |
| Arginine | Arg | R |
| Histidine | His | H |
| Tyrosine | Tyr | Y |
| Cysteine | Cys | C |
| Asparagine | Asn | N |
| Glutamine | Gln | Q |
| Serine | Ser | S |
| Threonine | Thr | T |
| Glycine | Gly | G |
| Alanine | Ala | A |
| Valine | Val | V |
| Leucine | Leu | L |
| Isoleucine | Ile | I |
| Methionine | Met | M |
| Proline | Pro | P |
| Phenylalanine | Phe | F |
| Tryptophan | Trp | W |

Amino acids can be subdivided into various sub-groups. Thus, amino acids can be grouped as having a nonpolar side chain (e.g., Gly, Cys, Ile, Leu, Met, Phe, Pro, Val); a negatively charged side chain (e.g., Asp, Glu); a positively charged side chain (e.g., Arg, His, Lys); an uncharged polar side chain (e.g., Asn, Cys, Gln, His, Met, Phe, Ser, Thr, Trp, and Tyr) or an electron rich side chain (e.g., Trp and Tyr) Amino acids can also be grouped as small amino acids (Gly, Ala), hydrophilic amino acids (Ser, His, Thr, Lys, Arg), hydrophobic amino acids (Val, Leu, Ile, Met, Pro), aromatic amino acids (Phe, Tyr, Trp), amides (Asn, Gln), and basic amino acids (Lys, Arg).

A "unnatural amino acid" or "non-naturally occurring amino acid" refers to a residue, other than those naturally occurring amino acid residues listed above, which is able to covalently bind adjacent amino acid residues(s) in a peptide chain. Examples of unnatural amino acid residues include norleucine, ornithine, norvaline, homoserine, homocysteine, and other amino acid residue analogues such as those described in Ellman et al., *Meth. Enzymol.*, 202:301 336 (1991). "Unnatural amino acid" also includes "amino acid analog," which refers to an amino acid in which one or more individual atoms have been replaced, either with a different atom, isotope, or with a different functional group. Modified, synthetic, or rare amino acids may also be used as desired. Thus, modified and unusual amino acids listed in 37 C.F.R. §1.822(p)(2) are included within this definition and expressly incorporated herein by reference.

An "amino acid modification" refers to an amino acid modified by a chemical reaction or a change in the amino acid sequence of a predetermined amino acid sequence. Exemplary modifications include an amino acid substitution, insertion and/or deletion.

An "amino acid modification at" a specified position, refers to the substitution or deletion of the specified residue, or the insertion of at least one amino acid residue adjacent the specified residue. By insertion "adjacent" a specified residue is meant insertion within one to two residues thereof. The insertion may be N-terminal or C-terminal to the specified residue.

An "amino acid replacement" refers to the substitution of at least one existing amino acid residue in a peptide with another different "replacement" molecule, which can be a natural amino acid (i.e., encoded by the genetic code), an unnatural amino acid, or a non-amino acid molecule such as a natural product template.

The term "peptide" is used broadly herein to include oligomers and polymers of amino acids or amino acid analogs that are linked by a peptide bond or an analog of a peptide bond. As such, the term "peptide" includes molecules commonly referred to as peptides, which generally contain about two to about fifty amino acids, as polypeptides, which generally contain about twenty to fifty amino acids or more, and as proteins, which can include peptides or polypeptides that. Thus, a peptide contains two or more amino acids, which can be L-amino acids or D-amino acids, chemically modified amino acids, which can be naturally occurring or non-naturally occurring amino acids, or amino acid analogs. Peptides comprising unnatural amino acids, chemically modified amino acids and amino acid analogs are also referred to as "peptide derivatives" or "peptidomimetics". The term "peptide derivatives" or "peptidomimetics" according to the invention not only includes peptides, which are modified, e.g., on the N- or C-terminus but also peptides altered by substitutions and/or modifications of one or more of the amino acid residues by chemical moieties other than natural protein-building amino acid residues, such as unnatural amino acids, or peptides with an altered backbone. Altered backbone meaning at least one peptide bond (amide bond) has been replaced by an analog of a peptide bond, e.g., a thioamide bond. Conventional notation is used herein to portray peptide sequences: the left-hand end of a peptide sequence is the amino-terminus; the right-hand end of a peptide sequence is the carboxyl-terminus.

The term "variant" with respect to a reference polypeptide refers to a polypeptide that possesses at least one amino acid mutation or modification (i.e., alteration) as compared to a native polypeptide. Variants generated by "amino acid modifications" can be produced, for example, by substituting, deleting, inserting and/or chemically modifying at least one amino acid in the native amino acid sequence.

A "recombinant polypeptide" is one which is produced upon expression of a recombinant polynucleotide.

The term "functionalized peptide" refers to a peptide, as defined herein, which has been modified site-specifically to contain a reactive group. Functionalized peptides also are intended to include peptide fragments which have been modified by the addition of one or more unnatural amino acids at the N- and C-terminus or the insertion of one or more unnatural amino acids within the peptide. The additional or inserted amino acid may serve as the reactive group or, alternatively, may itself be further modified to form a reactive group.

A "cyclic peptide" or "macrocycle stabilized peptide (MSP)" or "macrocyclic peptide" and the like in accordance with the present invention is a peptide intramolecularly forming a molecular ring structure within its primary amino acid sequence by at least one intramolecular linkage having covalent character. The forming of this molecular ring structure is, in context of this invention, also termed "cyclization" or "macrocyclization". Generally, "cyclization" or "macrocyclization" in accordance with this invention may occur by at least one linkage which is a covalent binding between an electron rich aromatic moiety and an electrophilic moiety derived from an iminoquinone methide type precursor. The macrocycle stabilized peptide as used herein may be comprised of a thiazole ring and incorporates at least two amino acids of the peptide. The size of the macrocyclic ring is determined by the number of peptide amino acids (y) in the ring and the number of linking groups in the moieties connecting the thiazole group to the peptide. In various embodiments, the macrocycle stabilized peptide has 1, 2, or 3 such connections. The term "macrocycle stabilized peptide" also refers to macrocycles comprising two or more peptides formed by intermolecular ligations. Cyclization may encompass any intramolecular bond between any two amino acids along a peptide chain, and include, but are not limited to intramolecular bonds between i and i+2 positions; i and i+3 positions; i and i+4 positions; i and i+5 positions; i and i+6 positions; at i and i+7 positions; i and i+8 positions; i and i+9 positions; i and i+10 positions; and i and i+4 positions; wherein "i" refers to the numerical position of an amino acid, and wherein "4" refers to a numeral greater than or equal to about 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or about 50 up to about 100 amino acids.

The term "iminoquinone methide type intermediate" as used herein does not substantially differ from the common meaning of this term in the art. It refers to a molecule having both an imino group (=N—) and a quinone methide type aromatic group, which can be schematically represented by the structure

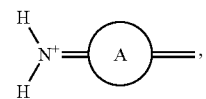

wherein Ring A is a 5- or 6-membered aryl or heteroaryl ring system having 1 to 3 heteroatoms selected from N, O, and S.

The term "natural product template" refers to a natural product or a natural product-like compound having a partial structure (e.g., a substructure) based on the full structure of a natural product. Exemplary natural products include steroids, penicillins, prostaglandins, venoms, toxins, morphine, paclitaxel (TAXOL®), morphine, cocaine, digitalis, quinine, tubocurarine, nicotine, muscarine, artemisinin, cephalosporins, tetracyclines, aminoglycosides, rifamycins, chloramphenicol, asperlicin, lovastatin, ciclosporin, curacin A, eleutherobin, discodermolide, bryostatins, dolostatins, cephalostatins, antibiotic peptides, anisomycin, and epibatidine.

The term "electron-rich" ("nucleophilic") and its counterpart "electron-deficient" ("electrophilic") are used in such a way that an aromatic ring system is modified by substituents and/or replacement of carbon atoms which are part of the ring system with heteroatoms such that they have a reduced (electron-deficient) or increased (electron-rich) electron density in the ring system compared to the unsubstituted and/or unreplaced systems, for example benzene.

An "aldehyde-protecting group" is a substituent attached to an aldehyde group that blocks or protects the carbonyl group of the aldehyde functionality in the compound. Suitable carbonyl protecting groups of the aldehyde functionality include, but are not limited to (a) cyclic acetals and ketals, (b) cyclic mono or di-thio acetals or ketals or other derivatives such as imines, hydrazones, cyanohydrin, oximes or semicarbazones, for example, dialkyl or diaryl acetals or 1,3 dithiane, (c) cyclic imines such as substituted methylene derivatives or N,N'-dimethylimidazolidine. For a general description of protecting groups and their use, see, Greene, T. W., *Protective Groups in Organic Synthesis*, John Wiley & Sons, N.Y. (1991) and Greene, T. W. et al., *Protective Groups in Organic Synthesis,* 3rd Edition, John Wiley & Sons (1999).

The term "amino protecting group" or "N-protected" as used herein refers to those groups intended to protect an amino group against undesirable reactions during synthetic procedures and which can later be removed to reveal the amine. Commonly used amino protecting groups are disclosed in Greene, T. W. et al., *Protective Groups in Organic Synthesis,* 3rd Edition, John Wiley & Sons (1999). Amino protecting groups include acyl groups such as formyl, acetyl, propionyl, pivaloyl, t-butylacetyl, 2-chloroacetyl, 2-bromoacetyl, trifluoroacetyl, trichloroacetyl, o-nitrophenoxyacetyl, α-chlorobutyryl, benzoyl, 4-chlorobenzoyl, 4-bromobenzoyl, 4-nitrobenzoyl, and the like; sulfonyl groups such as benzenesulfonyl, p-toluenesulfonyl and the like; alkoxy- or aryloxy-carbonyl groups (which form urethanes with the protected amine) such as benzyloxycarbonyl (Cbz), p-chlorobenzyloxycarbonyl, p-methoxybenzyloxycarbonyl, p-nitrobenzyloxycarbonyl, 2-nitrobenzyloxycarbonyl, p-bromobenzyloxycarbonyl, 3,4-dimethoxybenzyloxycarbonyl, 3,5-dimethoxybenzyloxycarbonyl, 2,4-dimethoxybenzyloxycarbonyl, 4-methoxybenzyloxycarbonyl, 2-nitro-4,5-dimethoxybenzyloxycarbonyl, 3,4,5-trimethoxybenzyloxycarbonyl, 1-(p-biphenylyl)-1-methylethoxycarbonyl, α-,α-dimethyl-3,5-dimethoxybenzyloxycarbonyl, benzhydryloxycarbonyl, t-butyloxycarbonyl (Boc), diisopropylmethoxycarbonyl, isopropyloxycarbonyl, ethoxycarbonyl, methoxycarbonyl, allyloxycarbonyl (Alloc), 2,2,2-trichloroethoxycarbonyl, 2-trimethylsilylethyloxycarbonyl (Teoc), phenoxycarbonyl, 4-nitrophenoxycarbonyl, fluorenyl-9-methoxycarbonyl (Fmoc), cyclopentyloxycarbonyl, adamantyloxycarbonyl, cyclohexyloxycarbonyl, phenylthiocarbonyl and the like; aralkyl groups such as benzyl, triphenylmethyl, benzyloxymethyl and the like; and silyl groups such as trimethylsilyl and the like. Amine protecting groups also include cyclic amino protecting groups such as phthaloyl and dithiosuccinimidyl, which incorporate the amino nitrogen into a heterocycle. Typically, amino protecting groups include formyl, acetyl, benzoyl, pivaloyl, t-butylacetyl, phenylsulfonyl, Alloc, Teoc, benzyl, Fmoc, Boc and Cbz. It is well within the skill of the ordinary artisan to select and use the appropriate amino protecting group for the synthetic task at hand.

The term "alcohol protecting group" as used herein refers to substituents of the alcohol group commonly employed to block or protect the alcohol functionality while reacting other functional groups on the compound. Examples of such alcohol-protecting groups include the 2-tetrahydropyranyl group, 2-ethoxyethyl group, the trityl group, the trichloroacetyl group, urethane-type blocking groups such as benzyloxycarbonyl, and the trialkylsilyl group, examples of such being trimethylsilyl, tert-butyldimethylsilyl, phenyldimethylsilyl, triiospropylsilyl and thexyldimethylsilyl. The choice of alcohol-protecting group employed is not critical so long as the derivatized alcohol group is stable to the condition of subsequent reaction(s) on other positions of the compound of the formulae and can be removed at the desired point without disrupting the remainder of the molecule. Further examples of groups referred to by the above terms are described by Barton, J. W., *Protective Groups in Organic Chemistry*, McOmie, J. G. W., ed., Plenum Press, New York, N.Y. (1973), and Greene, T. W., *Protective Groups in Organic Synthesis*, John Wiley & Sons, New York, N.Y. (1981). The related term "protected hydroxyl" or "protected alcohol" defines a hydroxyl group substituted with a hydroxyl-protecting group as discussed above.

The term "carboxylic acid protecting group" refers to any chemical compound that may be used to prevent a carboxylic acid on a molecule from undergoing a chemical reaction while chemical change occurs elsewhere in the molecule. Numerous carboxylic acid protecting groups are known to those skilled in the art and examples can be found in Greene supra. Examples of carboxylic acid protecting groups include, but are not limited to, amides, hydrazides, and esters such as, methyl esters, substituted methyl, phenacyl, tetrahydropyranyl, tetrahydrofuranyl, cyanomethyl, triisopropylsilylmethyl, desyl, ethyl 2-substituted ethyl, phenyl, 2,6 dialkyl phenyl, benzyl, substituted benzyl, silyl, and stannyl, or the like.

As used herein, substituent names which end in the suffix "-ene" refer to a biradical derived from the removal of two hydrogen atoms from the substituent. Thus, for example, acyl is acylene; alkyl is alkylene; alkenyl is alkenylene; alkynyl is alkynylene; heteroalkyl is heteroalkylene, heteroalkenyl is heteroalkenylene, heteroalkynyl is heteroalkynylene, aryl is arylene, and heteroaryl is heteroarylene.

As used herein, the term "alkyl" or "alkylene" is intended to include both branched and straight-chain saturated aliphatic hydrocarbon groups having the specified number of carbon atoms. For example, "$C_{1-10}$ alkyl" (or alkylene), is intended to include $C_1$, $C_2$, $C_3$, $C_4$, $C_5$, $C_6$, $C_7$, $C_8$, $C_9$, and $C_{10}$ alkyl groups. Additionally, for example, "$C_1$-$C_6$ alkyl" denotes alkyl having 1 to 6 carbon atoms. Alkyl groups can be unsubstituted or substituted so that one or more of its hydrogens are replaced by another chemical group. Example alkyl groups include, but are not limited to, methyl (Me), ethyl (Et), propyl (e.g., n-propyl and isopropyl), butyl (e.g., n-butyl, isobutyl, -butyl), pentyl (e.g., n-pentyl, isopentyl, neopentyl), and the like.

The term "heteroalkyl", as used herein, refers to an alkyl group having from 1 to 3 heteroatoms such as N, O and S. Additional heteroatoms can also be useful, including, but not limited to, B, Al, Si and P. The heteroatoms can also be oxidized, such as, but not limited to, —S(O)— and —S(O)$_2$—. For example, heteroalkyl can include ethers, thioethers and alkyl-amines.

"Haloalkyl" is intended to include both branched and straight-chain saturated aliphatic hydrocarbon groups having the specified number of carbon atoms, substituted with 1 or more halogen. Examples of haloalkyl include, but are not limited to, fluoromethyl, difluoromethyl, trifluoromethyl, trichloromethyl, pentafluoroethyl, pentachloroethyl, 2,2,2-trifluoroethyl, heptafluoropropyl, and heptachloropropyl. Examples of haloalkyl also include "fluoroalkyl" which is intended to include both branched and straight-chain saturated aliphatic hydrocarbon groups having the specified number of carbon atoms, substituted with 1 or more fluorine atoms.

The term "halogen" or "halo" refers to fluorine (F), chlorine (Cl), bromine (Br) and iodine.

"Haloalkoxy" or "haloalkyloxy" represents a haloalkyl group as defined above with the indicated number of carbon atoms attached through an oxygen bridge. For example, "$C_{1-6}$ haloalkoxy", is intended to include $C_1$, $C_2$, $C_3$, $C_4$, $C_5$, and $C_6$ haloalkoxy groups. Examples of haloalkoxy include, but are not limited to, trifluoromethoxy, 2,2,2-trifluoroethoxy, pentafluorothoxy, and the like. Similarly, "haloalkylthio" or "thiohaloalkoxy" represents a haloalkyl group as defined above with the indicated number of carbon atoms attached through a sulphur bridge; for example trifluoromethyl-S—, pentafluoroethyl-S—, and the like.

As used herein, "carbocycle," "carbocyclic residue," or "carbocyclyl" is intended to mean any stable 3-, 4-, 5-, 6-, or 7-membered monocyclic or bicyclic or 7-, 8-, 9-, 10-, 11-, 12-, or 13-membered bicyclic or tricyclic ring, any of which may be saturated, partially unsaturated, unsaturated or aromatic. Examples of such carbocycles include, but are not limited to, cyclopropyl, cyclobutyl, cyclobutenyl, cyclopentyl, cyclopentenyl, cyclohexyl, cycloheptenyl, cycloheptyl, cycloheptenyl, adamantyl, cyclooctyl, cyclooctenyl, cyclooctadienyl, [3.3.0]bicyclooctane, [4.3.0]bicyclononane, [4.4.0]bicyclodecane, [2.2.2]bicyclooctane, fluorenyl, phenyl, naphthyl, indanyl, adamantyl, anthracenyl, and tetrahydronaphthyl (tetralin). As shown above, bridged rings are also included in the definition of carbocycle (e.g., [2.2.2]bicyclooctane). A bridged ring occurs when one or more carbon atoms link two non-adjacent carbon atoms. Preferred bridges are one or two carbon atoms. It is noted that a bridge always converts a monocyclic ring into a tricyclic ring. When a ring is bridged, the substituents recited for the ring may also be present on the bridge. Preferred carbocycles, unless otherwise specified, are cyclopropyl, cyclobutyl, cyclopentyl, cyclohexyl, phenyl, and indanyl. When the term "carbocycle," "carbocyclic residue," or "carbocyclyl" is used, it is intended to include "aryl".

The term "aryl" refers to monocyclic, bicyclic, tricyclic aromatic hydrocarbon groups having 6 to 15 carbon atoms in the ring portion, such as phenyl, naphthyl, biphenyl and diphenyl groups, each of which may be substituted. Aryl groups which are bicyclic or tricyclic must include at least one fully aromatic ring but the other fused ring or rings may be aromatic or non-aromatic. When an aryl is substituted with a further heterocyclic ring, said ring may be attached to the aryl through a carbon atom or a heteroatom and said ring in turn is optionally substituted with one to two substituents as valence allows.

The term "arylene," as used herein refers to an aryl biradical derived from an aryl group, as defined herein, by removal of two hydrogen atoms. Arylene groups may be substituted or unsubstituted. Arylene group substituents include, but are not limited to, any of the substituents described herein, that result in the formation of a stable moiety (e.g., aliphatic, alkyl, alkenyl, alkynyl, heteroaliphatic, heterocyclic, aryl, heteroaryl, acyl, oxo, imino, thiooxo, cyano, isocyano, amino, azido, nitro, hydroxyl, thiol, halo, aliphaticamino, heteroaliphaticamino, alkylamino, heteroalkylamino, arylamino, heteroarylamino, alkylaryl, arylalkyl, aliphaticoxy, heteroaliphaticoxy, alkyloxy, heteroalkyloxy, aryloxy, heteroaryloxy, aliphaticthioxy, heteroaliphaticthioxy, allylthioxy, heteroalkylthioxy, arylthioxy, heteroarylthioxy, acyloxy, and the like, each of which may or may not be further substituted). Additionally, arylene groups may be incorporated as a linker group into an alkylene, alkenylene, alkynylene, heteroalkylene, heteroalkenylene, or heteroalkynylene group, as defined herein.

The terms "aryloxy", "arylamino", "arylalkylamino", "arylthio", "arylalkanoylamino", "arylsulfonyl", "arylalkoxy", "arylsulfinyl", "arylheteroaryl", "arylalkylthio", "arylcarbonyl", "arylalkenyl", or "arylalkylsulfonyl" refer to an aryl or substituted aryl bonded to an oxygen; an amino; an alkylamino; a thio; an alkanoylamino; a sulfonyl; an alkoxy; a sulfinyl; a heteroaryl or substituted heteroaryl; an alkylthio; a carbonyl; an alkenyl; or an alkylsulfonyl, respectively.

The term "alkenyl" refers to straight or branched chain hydrocarbon groups of 2 to 20 carbon atoms, preferably 2 to 15 carbon atoms, and most preferably 2 to 8 carbon atoms, having one to four double bonds.

The term "alkenylene", as used herein, refers to a biradical derived from an alkenyl group, as defined herein, by removal of two hydrogen atoms. Alkenylene groups may be cyclic or acyclic, branched or unbranched, substituted or unsubstituted. Alkenylene group substituents include, but are not limited to, any of the substituents described herein, that result in the formation of a stable moiety (e.g., aliphatic, alkyl, alkenyl, allynyl, heteroaliphatic, heterocyclic, aryl, heteroaryl, acyl, oxo, imino, thiooxo, cyano, isocyano, amino, azido, nitro, hydroxyl, thiol, halo, aliphaticamino, heteroaliphaticamino, alkylamino, heteroalkylamino, arylamino, heteroarylamino, alkylaryl, arylalkyl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, acyloxy, and the like, each of which may or may not be further substituted).

The term "alkynyl" refers to straight or branched chain hydrocarbon groups of 2 to 20 carbon atoms, preferably 2 to 15 carbon atoms, and most preferably 2 to 8 carbon atoms, having one to four triple bonds.

The term "cycloalkyl" refers to an optionally substituted, saturated cyclic hydrocarbon ring systems, preferably containing 1 to 3 rings and 3 to 7 carbons per ring. Exemplary groups include cyclopropyl, cyclobutyl, cyclopentyl, cyclohexyl, cycloheptyl, cyclooctyl, cyclodecyl, cyclododecyl, and adamantyl. Exemplary substituents include one or more alkyl groups as described above, or one or more groups described above as alkyl substituents.

As used herein, the term "heterocycle," "heterocyclyl," "heterocyclic ring" or "heterocyclic group" is intended to mean a stable 4-, 5-, 6-, or 7-membered monocyclic or, 7-, 8-, 9-, 10-, 11-, 12-, 13-, or 14-membered bicyclic heterocyclic ring which is saturated, partially unsaturated or fully unsaturated or aromatic, and which consists of carbon atoms and 1, 2, 3 or 4 heteroatoms independently selected from N, O, and S; and including any bicyclic group in which any of the above-defined heterocyclic rings is fused to a benzene ring. The nitrogen and sulfur heteroatoms may optionally be oxidized (i.e., N→O and $S(O)_p$). The nitrogen atom may be substituted or unsubstituted (i.e., N or NR wherein R is H or another substituent, if defined). The heterocyclic ring may be attached to its pendant group at any heteroatom or carbon atom that results in a stable structure. The heterocyclic rings described herein may be substituted on carbon or on a nitrogen atom if the resulting compound is stable. A nitrogen in the heterocycle may optionally be quaternized. It is preferred that when the total number of S and O atoms in the heterocycle exceeds 1, then these heteroatoms are not adjacent to one another. It is preferred that the total number of S and O atoms in the heterocycle is not more than 1. When the term "heterocycle," "heterocyclyl," "heterocyclic ring" or "heterocyclic group" is used, it is intended to include heteroaryl.

Examples of heterocycles include, but are not limited to, acridinyl, azocinyl, benzimidazolyl, benzofuranyl, benzothiofuranyl, benzoxazolyl, benzoxazolinyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isothiazolopyridinyl, isoxazolyl, isoxazolopyridinyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxindolyl, pyrimidinyl, phenanthridinyl, phenanthrolinyl, phenazinyl, phenothiazinyl, phenoxathinyi, phenoxazinyl, phthalazinyl, piperazinyl, piperidinyi, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyrimidinyl, pyrrolidinyl, pyrrolinyl, 2-pyrrolidonyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, and xanthenyl. Also included are fused ring and spiro compounds containing, for example, the above heterocycles.

Preferred 5- to 10-membered heterocycles include, but are not limited to, pyridinyl, furanyl, thienyl, pyrrolyl, pyrazolyl, pyrazinyl, piperazinyl, piperidinyl, imidazolyl, imidazolidinyl, indolyl, tetrazolyl, isoxazolyl, morpholinyl, oxazolyl, oxadiazolyl, oxazolidinyl, tetrahydrofuranyl, thiadiazinyl, thiadiazolyl, thiazolyl, triazinyl, triazolyl, benzimidazolyl, 1H-indazolyl, benzofuranyl, benzothiofuranyl, benztetrazolyl, benzotriazolyl, benzisoxazolyl, benzoxazolyl, oxindolyl, benzoxazolinyl, benzthiazolyl, benzisothiazolyl, isatinoyl, isoquinolinyl, octahydroisoquinolinyl, tetrahydroisoquinolinny, tetrahydroquinolinyl, isoxazolopyridinyl, quinazolinyl, quinolinyl, isothiazolopyridinyl, thiazolopyridinyl, oxazolopyridinyl, imidazolopyridinyl, and pyrazolopyridinyl.

Preferred 5- to 6-membered heterocycles include, but are not limited to, pyridinyl, furanyl, thienyl, pyrrolyl, pyrazolyl, pyrazinyl, piperazinyl, piperidinyl, imidazolyl, imidazolidinyl, indolyl, tetrazolyl, isoxazolyl, morpholinyl, oxazolyl, oxadiazolyl, oxazolidinyl, tetrahydrofuranyl, thiadiazinyl, thiadiazolyl, thiazolyl, triazinyl, and triazolyl. Also included are fused ring and spiro compounds containing, for example, the above heterocycles.

Bridged rings are also included in the definition of heterocycle. A bridged ring occurs when one or more atoms (i.e., C, O, N, or S) link two non-adjacent carbon or nitrogen atoms. Preferred bridges include, but are not limited to, one carbon atom, two carbon atoms, one nitrogen atom, two nitrogen atoms, and a carbon-nitrogen group. It is noted that a bridge always converts a monocyclic ring into a tricyclic ring. When a ring is bridged, the substituents recited for the ring may also be present on the bridge.

The term "heteroaryl" refers to substituted and unsubstituted aromatic 5- or 6-membered monocyclic groups, 9- or 10-membered bicyclic groups, and 11- to 14-membered tricyclic groups which have at least one heteroatom (O, S or N) in at least one of the rings, said heteroatom-containing ring preferably having 1, 2, or 3 heteroatoms selected from O, S, and N. Each ring of the heteroaryl group containing a heteroatom can contain one or two oxygen or sulfur atoms and/or from one to four nitrogen atoms provided that the total number of heteroatoms in each ring is four or less and each ring has at least one carbon atom. Heteroaryl groups can be substituted or unsubstituted. The nitrogen atom may be substituted or unsubstituted (i.e., N or NR wherein R is H or another substituent, if defined). The nitrogen and sulfur heteroatoms may optionally be oxidized (i.e., N→O and $S(O)_p$) and the nitrogen atoms may optionally be quaternized.

The term "heteroarylene," as used herein, refers to a biradical derived from an heteroaryl group, as defined herein, by removal of two hydrogen atoms. Heteroarylene groups may be substituted or unsubstituted. Additionally, heteroarylene groups may be incorporated as a linker group into an alkylene, alkenylene, alkynylene, heteroalkylene, heteroalkenylene, or heteroalkynylene group, as defined herein. Heteroarylene group substituents include, but are not limited to, any of the substituents described herein, that result in the formation of a stable moiety (e.g., aliphatic, alkyl, alkenyl, alkynyl, heteroaliphatic, heterocyclic, aryl, heteroaryl, acyl, oxo, imino, thiooxo, cyano, isocyano, amino, azido, nitro, hydroxyl, thiol, halo, aliphaticamino, heteroaliphaticamino, alkylamino, heteroalkylamino, arylamino, heteroarylamino, alkylaryl, arylalkyl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, acyloxy, and the like, each of which may or may not be further substituted).

Heteroaryl groups which are bicyclic or tricyclic must include at least one fully aromatic ring but the other fused ring or rings may be aromatic or non-aromatic, The heteroaryl group may be attached at any available nitrogen or carbon atom of any ring. The heteroaryl ring system may contain zero, one, two or three substituents, Exemplary monocyclic heteroaryl groups include pyrrolyl, pyrazolyl, pyrazolinyl, imidazolyl, oxazolyl, isoxazolyl, thiazolyl, thiadiazolyl, isothiazolyl, furanyl, thienyl, oxadiazolyl, pyridyl, pyrazinyl, pyrimidinyl, pyridazinyl, triazinyl and the like.

Exemplary bicyclic heteroaryl groups include indolyl, benzothiazolyl, benzodioxolyl, benzoxazolyl, benzothienyl, quinolinyl, dihydroisoquinolinyl, tetrahydroquinolinyl, isoquinolinyl, benzimidazolyl, benzopyranyl, benzoxazinyl, indolizinyl, benzofuranyl, chromonyl, coumarinyl, benzopyranyl, cinnolinyl, quinoxalinyl, indazolyl, pyrrolopyridyl, furopyridyl, dihydroisoindolyl, and the like.

Exemplary tricyclic heteroaryl groups include carbazolyl, benzidolyl, phenanthrollinyl, acridinyl, phenanthridinyl, xanthenyl and the like.

The term "heteroatoms" shall include oxygen, sulfur and nitrogen.

As referred to herein, the term "substituted" means that one or more hydrogen atoms is replaced with a non-hydrogen group, provided that normal valencies are maintained and that the substitution results in a stable compound. When a substituent is keto (i.e., =O), then 2 hydrogens on the atom are replaced. Keto substituents are not present on aromatic moieties. When a ring system (e.g., carbocyclic or heterocyclic) is said to be substituted with a carbonyl group or a double bond, it is intended that the carbonyl group or double bond be part (i.e., within) of the ring. Ring double bonds, as used herein, are double bonds that are formed between two adjacent ring atoms (e.g., C=C, C=N, or N=N).

When any variable occurs more than one time in any constituent or formula for a compound, its definition at each occurrence is independent of its definition at every other

Synthesis

The present invention provides methods for synthesis of macrocycle stabilized peptides. As schematically presented below, the methods of the present invention involve the reaction of an aromatic electron rich moiety (the "nucleophile"), such as the side chain of tyrosine or tryptophan with an electrophilic center derived from an iminoquinone methide type precursor (the "electrophile")

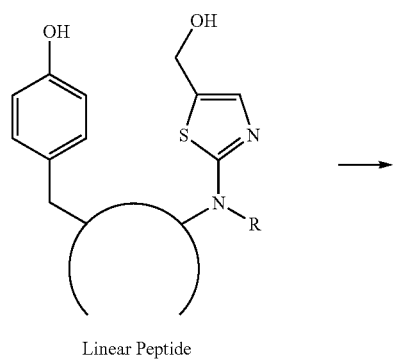

Linear Peptide

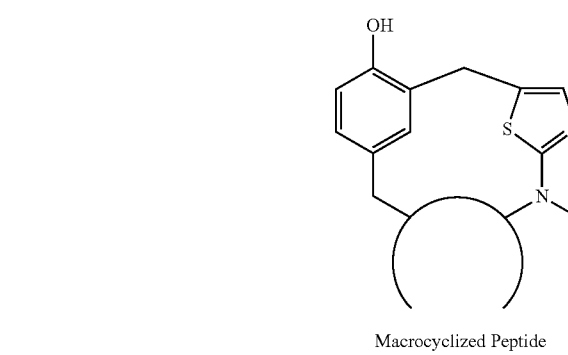

Macrocyclized Peptide

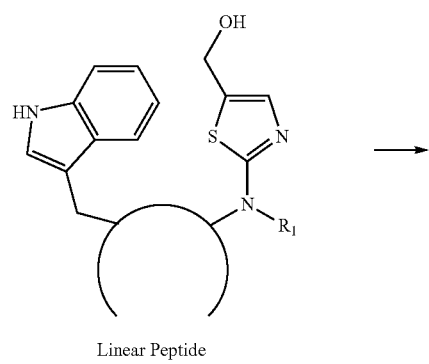

Linear Peptide

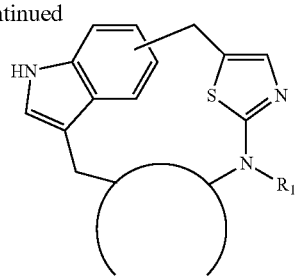

Macrocyclized Peptide

The reaction described above has wide applications. The methods of the present invention can be applied to any nucleophilic chemical reaction in which an electrophilic iminoquinone methide type intermediate is generated and captured by an electron rich aromatic ring such as those present in the side chains of tyrosine, homotyrosine, tryptophan, or in natural product templates. Therefore, the chemistry described in the present invention has general utility for accomplishing the macrocyclization reaction not only for macrocycle stabilized peptides shown above but also peptide macrocycles, organic macrocycles, and MSPs containing natural product templates comprising electron rich aromatic moieties.

In one embodiment, the present invention provides a method for preparing a macrocycle stabilized peptide (MSP), comprising the steps of:

a) providing a linear peptide comprising at least two amino acids, wherein at least one said amino acid comprises an aromatic moiety and at least one said amino acid is a functionalized amino acid comprising an iminoquinone methide type precursor;

b) reacting the electron rich aromatic moiety with the iminoquinone methide type precursor in the presence of an activating reagent to form a MSP comprising at least one covalent linkage.

The linear peptide may include both natural and unnatural amino acids. The term "amino acid" as defined above refers to a molecule which contains both an amino group and a carboxyl group bound to a carbon which is designated the α-carbon. Suitable amino acids include, but are not limited to, both the L and the D-isomers of the natural amino acids selected from any one of the twenty amino acids commonly found in peptides in nature.

The term "amino acid" also refers to non-naturally occurring amino acids, or "unnatural amino acid" or "synthetic amino acid," which can be prepared by organic synthesis or other routes. Non-limiting examples of unnatural amino acids include homo-amino acid, α,α-di-substituted amino acid, norleucine, ornithine, norvaline, homoserine, homocysteine, and other amino acid residue analogues such as those described in Ellman et al., *Meth. Enzymol.*, 202:301 336 (1991). Unless the context specifically indicates otherwise, the term amino acid as used herein, is intended to include amino acid analogs, which refers to a molecule which can be substituted for an amino acid in the formation of a macrocycle stabilized peptide.

It will also be appreciated by those skilled in the art that one or several of the amino acids forming the macrocycle stabilized peptide of the present invention may be modified. In accordance therewith any amino acid as used herein may also represent its modified form. For example, an alanine residue as used herein may comprise a modified alanine residue. Such modifications may, among others, be a methylation or acylation or the like. Thus modified amino acid and more particularly the peptide containing said modified amino acid is still functionally active as defined herein.

It will also be appreciated by those skilled in the art that amino acid modification in the present invention involves functionalization of amino acid for preparation of reaction with an electron rich moiety. Thus, a functionalized amino acid of the present invention comprises an electrophilic moiety. The functionalized amino acid may be obtained by converting an amino acid or amino acid analog into an iminoquinone methide type of precursor such as a 2-aminothiazole, yielding a "thia-amino acid ($^T$a.a.)" such as "thiaglycine ($^T$G)" or a "thia-amino acid" analog.

Accordingly, the present invention also provides functionalized amino acids as macrocyclizing reagents and methods of making these reagents.

A peptide having functionalized amino acids incorporated therein is considered a functionalized peptide. Accordingly, a functionalized peptide may be prepared by first obtaining a functionalized amino acid and then incorporating the functionalized amino acid into the peptide. As will be apparent to one of ordinary skill in the art that the aforementioned functionalized amino acids may be readily incorporated into a linear peptide to form the functionalized peptide. In general, such a linear peptide can be any peptide.

A functionalized peptide may also be obtained by directly functionalizing the amino acids in the peptide. For example, a 2-aminothiazole derivative may directly react with an amino acid residue such as lysine or cysteine in the peptide to yield a functionalized amino acid comprising an electrophilic moiety.

The linear peptide can include any combination of amino acids in addition to the functionalized amino acids. In one embodiment, a functionalized peptide can have from 2 to 42 amino acids (including at least one functionalized amino acid), including every integer from 2 to 42. For example, the functionalized peptide can have 7 or 12 amino acids.

in one embodiment, at least one amino acid is functionalized to form an electrophilic moiety comprising a substituted 5-membered heteroaromatic ring.

In another embodiment, the substituents on 5-membered heteroaromatic ring are selected from $C_{1-6}$alkyl, heteroalkyl, halogen, an aldehyde or an aldehyde with a protecting group, and —$CH_2OP$, wherein P can be 1H or an alcohol protecting group.

In still another embodiment, the 5-membered heteroaromatic ring is selected from pyrrole, pyrazole, oxazole, imidazole, triazoles, furan, thiophene, and thiazole.

In a preferred embodiment, the 5-membered heteroaromatic moiety is thiazole substituted with —$CH_2OP$, wherein P can be H or an alcohol protecting group.

In another preferred embodiment, the linear peptide comprises at least one functionalized amino acid comprising an electrophilic moiety and at least one amino acid comprising an electron rich moiety.

In still another embodiment, the electron rich aromatic moiety is part of the side chain of a natural amino acid. In still another embodiment, the electron rich aromatic moiety is part of the side chain of an unnatural amino acid.

In still another embodiment, the electron rich amino acid is either tyrosine or tryptophan. In a preferred embodiment, the electron rich amino acid is tyrosine. A preferred example of the invention relates to a variety of linear peptides with at least one tyrosine or tryptophan residue that reacts with a variety of thiazole containing electrophilic moieties.

One skilled in the art would recognize that one or more amino acids of the functionalized peptide may be replaced by other one or more naturally occurring or synthetic amino acids or amino acid analogs. In this context, it is preferred that these amino acid exchanges are conservative amino acid exchanges, i.e., that the replacement amino acid belongs to the same category of amino acids as the amino acid to be replaced. For example, an acidic amino acid may be replaced by another acidic amino acid, a basic amino acid may be replaced by another basic amino acid, an aliphatic amino acid may be replaced by another aliphatic amino acid, and/or a polar amino acid may be replaced by another polar amino acid.

Accordingly, one amino acid with an electron rich moiety in the side chain of a functionalized peptide may be replaced by an amino acid with an electron rich moiety in the side chain. For example, a tyrosine residue may be replaced with a tryptophan residue, both of which contain an electron rich side chain.

Such replacement need not be limited to natural amino acids comprising electron rich side chains. It may also apply to amino acid analogs comprising electron rich (nucleophilic) aromatic ring or ring system. The nucleophilic aromatic ring or ring system would mimic the reactivity of tyrosine or tryptophan but be attached to the amino acid backbone via a shorter or longer alkyl or heteroalkyl chain. In addition, the nucleophilicity of the aromatic ring or ring system could be elevated over that of tyrosine or tryptophan by the addition of multiple electron donating substituents such as hydroxyl, alkyloxy, and the like on the aromatic ring or ring system. The enhanced nucleophilicity of the reactive center would afford greater selectivity for reacting with the reactive center over a tyrosine or tryptophan that may also be contained within the peptide. If the nucleophilic aromatic ring or ring system contained an amine it could be readily prepared by the formation of an amide bond between the side chain carboxylic acid of aspartic acid, glutamic acid, and/or C-terminus. If the nucleophilic aromatic ring or ring system contained a carboxylic acid it could be readily prepared by the formation of an amide between sidechain amine of DAP, DAB, Ornithine, Lysine, and/or N-terminus.

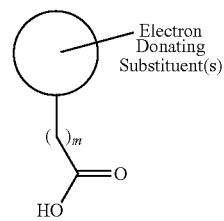

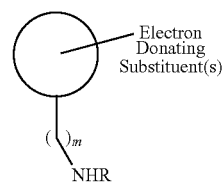

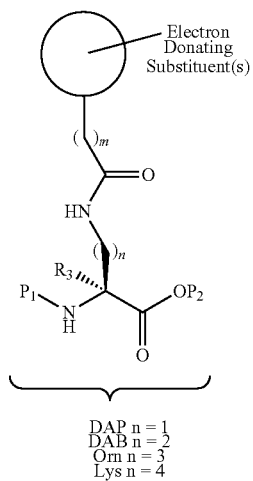

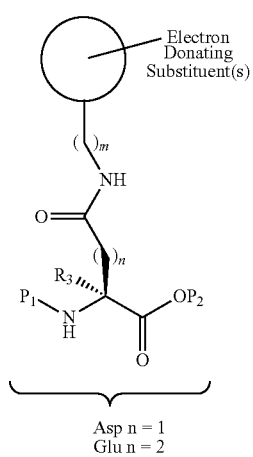

m = 0, 1, 2, 3, 4, 5

These reagents include, but are not limited to, those combinations of reagents made by standard amide bond formation, using many coupling reagents common in the art and discussed herein above, with asparic acid, glutamic acid, DAP, DAB, Ornithine, Lysine. Exemplary aromatic ring or ring systems that can be used in the amide bond formation are:

N-terminal reagents

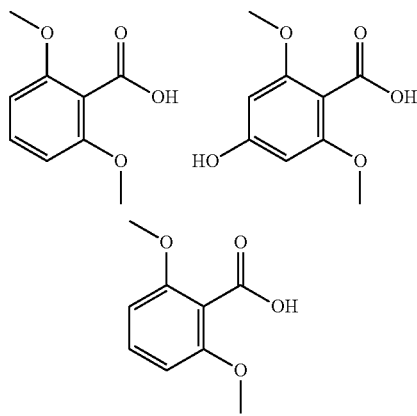

C-terminal reagents

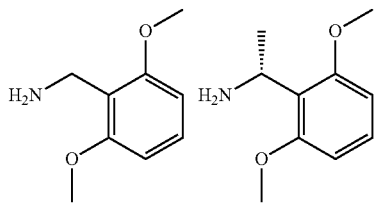

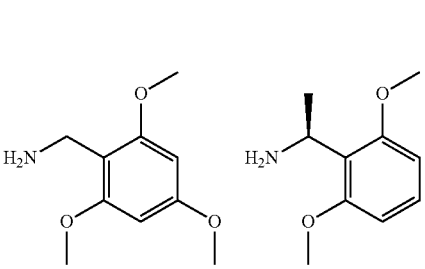

Thus, the present invention further provides extended nucleophilic aromatic ring or ring system reagents. In another embodiment, this invention provides the composition of novel N-terminal and C-terminal capping groups, as well as, novel amino acids that contain a reactive center or partner for the thiazole.

Exemplary amino acid analogs derived from such reagents have Formulae 32 and 33.

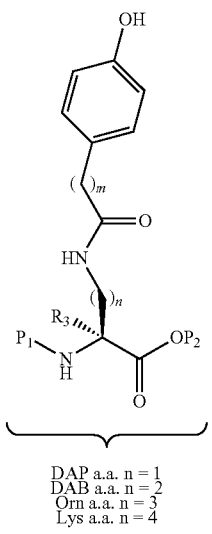

Formula 32

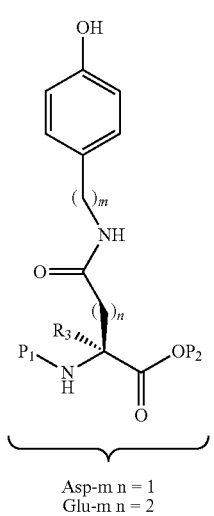

Formula 33

Asp-m n = 1
Glu-m n = 2 m = 0, 1, 2, 3, 4, 5

In Formulae 32 and 33, the number of methylene carbons in the side chain is defined by integer n. Note also that the methylene carbon positions defined by integer n, may be, all together or separately, differentially substituted with substituents, particularly lower $C_{1-7}$alkyl carbon substituents, such as methyl and gem-dimethyl, or such n methylene substituents may be taken together to form a ring, preferentially 3- to 7-membered. Within this embodiment are also included other amino acid analogs that would be obviously included within the spirit of these aforementioned reagents.

It will also be acknowledged by the ones skilled in the art that one or several of the amino acids in the functionalized peptides may be further replaced with a natural product template containing an electron rich aromatic moiety. Such a natural product template may replace an electron rich amino acid such as tyrosine and participate in the intramolecular cross-linking of a peptide in which its electron rich aromatic moiety reacts with an iminoquinone methide type precursor to form a covalent linkage. It will be appreciated by those skilled in the art that introduction of natural product templates into peptides increases diversity of the macrocyclic molecules to be generated from the methods provided herein.

Thus, in one embodiment, this invention provides methods for the synthesis of MSPs containing natural product templates, wherein the natural product template contains an electron rich aromatic ring such as phenyl and substituted phenyl (for example substituted with alkoxy and hydroxyl groups) which is capable of reacting with the iminoquinone methide type precursor generated from the activation (with suitable acid) of 2-aminothiazole-5-carbinols, which have been incorporated into the peptide portion itself, using the various reagents (see Scheme 5 and related discussions).

Exemplary natural products include, without being limited to, steroids, penicillins, prostaglandins, venoms, toxins, morphine, paclitaxel (TAXOL®), morphine, cocaine, digitalis, quinine, tubocurarine, nicotine, muscarine, artemisinin, cephalosporins, tetracyclines, aminoglycosides, rifamycins, chloramphenicol, aspericlin, lovastatin, ciclosporin, curacin A, eleutherobin, discodermolide, bryostatins, dolostatins, cephalostatins, antibiotic peptides, anisomycins, and epibatidine. In a preferred embodiment, the natural product template is anisomycin.

The linear and functionalized peptide of the invention can be prepared by any technique known to those skilled in the art or by techniques hereafter developed. For example, the peptides can be prepared using the solid-phase synthetic technique (Merrifield, *J. Am. Chem. Soc.*, 15:2149-2154 (1963); Bodanszky, M. et al., *Peptide Synthesis*, 2nd Edition, John Wiley & Sons, (1976); Kent et al., in *Synthetic Peptides in Biology and Medicine*, pp. 295-358, Alitalo, K. et al. eds., Science Publishers (Amsterdam 1985). Solid-phase synthetic technique is a quick and easy approach to synthesizing peptides and small proteins. The C-terminal amino acid is, for instance, attached to a cross-linked polystyrene resin via an acid labile bond with a linker molecule. This resin is insoluble in the solvents used for synthesis, making it relatively simple and fast to wash away excess reagents and by-products.

The synthesis of peptides by solution methods may also be used, as described in *The Proteins*, Vol. II, 3rd Edition, pp. 105-237, Neurath, H., et al., eds., Academic Press, New York, N.Y. (1976). The synthesized peptides may be substantially purified by preparative high performance liquid chromatography or other comparable techniques available in the art. The composition of the synthetic peptides can be confirmed by any technique for amino acid composition analysis.

As is exemplified herein, MSPs ranging from as small as 3 amino acids in length to polypeptides of 27 residues have been successfully used in the method provided. The maximal length or size of a suitable peptide or peptidomimetic essentially depends on the length or size that can be achieved using peptide synthesis. In general, peptides of up to 30 amino acid residues can be synthesized without major problems.

The linear peptides can also be produced by recombinant engineering techniques. The techniques such as culturing recombinant host cells under conditions such that the linear peptide is expressed and recovered are well known in the art (e.g., Sambrook). By this kind of production of said linear peptides particular advantage can be taken of the herein disclosed and described nucleic acid molecules, vectors and/or host cells.

In one embodiment, the method of the present invention consists essentially of the steps provided above. In another embodiment, the method of the present invention consists of the steps provided above.

In still another embodiment, the present invention includes macrocycle stabilized peptides prepared according to the above-described method.

In synthesizing the linear peptides, the functionalized amino acids may be incorporated anywhere within the peptide by standard coupling reactions. For example, the functionalized amino acid may be incorporated at the N- or C-terminal end of the peptide. The functionalized amino acid may also be incorporated at the non-terminal position within the peptide. As used herein, the sequences of the peptides are indicated from the N-terminus to the C-terminus, whereby the N-terminus is at the left side and the C-terminus is at the right side of the respective depicted amino acid sequence.

In general, the N- and C-terminal end of a linear peptide provided herein may be any amino acid pair lying in direct proximity to each other. In other words, cyclization (ring closure) of the peptide may generally occur between any of said amino acid pairs. The skilled person is readily in the position to find out such particular amino acid pairs which are effective/suitable to act as N- and C-terminal ends of a herein disclosed linear peptide, i.e., which are effective/suitable to act as an amino acid pair being involved in the ring closure/cyclization.

In one embodiment, the functionalized amino acid is placed at the N-terminal end of a linear peptide and cyclization of the peptide may occur between this functionalized amino acid and another amino acid having an electron rich aromatic moiety within the peptide. For instance the cyclization may occur between Gly and Tyr, i.e., the N-terminal amino acid of this linear peptide would be functionalized Gly and the C-terminal amino acid would be Tyr.

Thus, one aspect of the present invention is to provide a method for the synthesis of N-terminal MSPs and therefore also a method for the synthesis of the corresponding N-terminal macrocycle stabilized peptides, and N-terminal macrocycle stabilized α-helical peptides (see Scheme 1 and related discussions).

The linear peptide suitable for N-terminal macrocyclization may be represented by Formula (I):

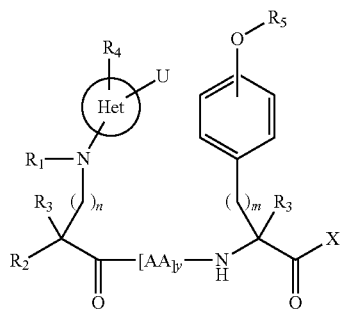

wherein
Het is a 5-membered heteroaromatic ring;
$R_1$ is selected from H, $C_{1-6}$alkyl, and an amino protecting group; preferably $R_1$ is Boc;
$R_2$ is the side chain of a natural or unnatural amino acid; or $R_1$ and $R_2$, $R_2$ and $R_3$, $R_1$ and $R_3$ are taken together with the atom(s) to which they are attached to form a ring;
$R_3$, at each occurrence, is independently selected from H and $C_{1-6}$alkyl;
$R_4$ is selected from H, $C_{1-6}$alkyl, heteroalkyl, and halogen;
$R_5$ is selected from H, $C_{1-6}$alkyl, and heteroalkyl;
U is selected from an aldehyde, a protected aldehyde, and —$CH_2OP$;
P is selected from H, $C_{1-6}$ alkyl, and an alcohol protecting group; preferably P is H or an alcohol protecting group such as trialkylsilyl;
X is selected from OB, $NR_aR_a$, and -$[AA]_z$;
B is selected from H, $C_{1-6}$alkyl, and a carboxylic acid protecting group;
AA is any natural or unnatural amino acid;
n and m are each an integer from 0-6, provided when n is not zero, $R_2$ is X except that X is not -$[AA]_z$;
y is an integer from 0 to 500; and
z is an integer from 0 to 500.

In one embodiment, the present invention provides a linear peptide having Formula (Ia):

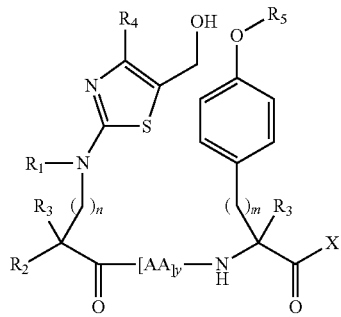

wherein all the variables in Formula (Ia) have the same meanings as those in Formula (I).

In another embodiment, in the linear peptide having Formula (Ia), n is 0. $R_2$ is a side chain of an amino acid selected from H, methyl, isopropyl, isobutyl, sec-butyl, hydroxymethyl, 1-hydroxyethyl, sulfhydryl methyl, 2(methylthio)ethyl, benzyl, 4-hydroxybenzyl, 3-indolylmethyl, carboxymethyl, 2-carboxyethyl, carbamidomethyl, 2-carbamidomethyl, 4-aminobutyl, 3-guanadinylpropyl and 4-imidzaolylmethyl; or $R_1$ and $R_2$ are taken together to form a pyrrolidine ring.

Exemplary N-terminal macrocycle stabilized peptides synthesized by the method according to the present invention are as follows:

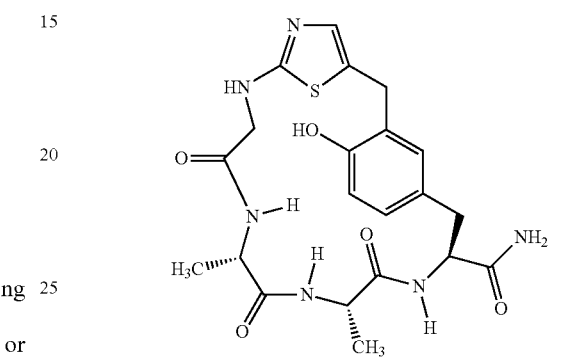

19-membered macrocycle

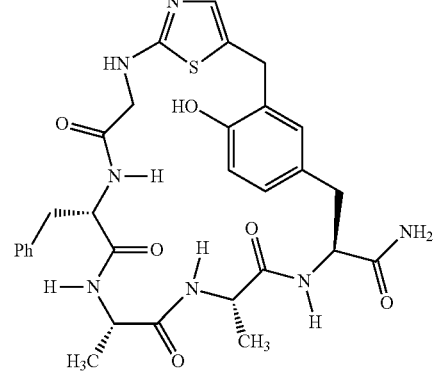

22-membered macrocycle

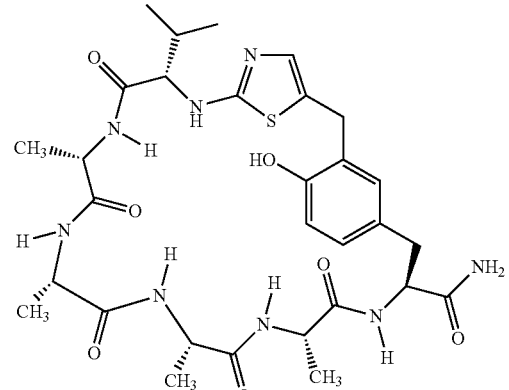

25-membered macrocycle

In one embodiment, the functionalized amino acid is placed at the C-terminal end of a linear peptide and cyclization of the peptide may occur between this functionalized amino acid and another amino acid having an electron rich aromatic moiety within the peptide. For instance the cyclization may occur between Tyr and Gly, i.e., the N-terminal amino acid of this linear peptide would be Tyr and the C-terminal amino acid would be a functionalized reagent.

Thus, the present invention also provides a method for the synthesis of C-terminal MSPs and therefore also a method for the synthesis of the corresponding C-terminal macrocycle stabilized peptides, and C-terminal macrocycle stabilized α-helical peptides (see Scheme 2 and related discussions).

The linear peptide suitable for C-terminal macrocyclization may be represented by Formula (II):

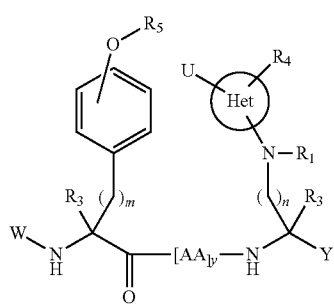

(II)

wherein
Het is a 5-membered heteroaromatic ring;
$R_1$ is selected from H, $C_{1-6}$alkyl, and an amino protecting group; preferably $R_1$ is Boc;
$R_3$, at each occurrence, is independently selected from H and $C_{1-6}$alkyl;
$R_4$ is selected from H, $C_{1-6}$alkyl, heteroalkyl, and halogen;
$R_5$ is selected from H, $C_{1-6}$alkyl, and heteroalkyl;
U is selected from an aldehyde, a protected aldehyde, and —$CH_2OP$;
P is selected from H or $C_{1-6}$alkyl and an alcohol protecting group; preferably P is H or an alcohol protecting group such as trialkylsilyl;
W is selected from H, $C_{1-6}$alkyl, $CH_3C(=O)—$, $R_eC(=O)—$, $R_aOC(=O)—$, $R_1R_bNC(O)—$, -[AA]$_x$ and an amino protecting group;
Y is selected from H, $C_{1-6}$alkyl, and heteroalkyl;
$R_a$ and $R_b$ are each independently H or $C_{1-6}$alkyl;
AA is any natural or unnatural amino acid;
n and m are each an integer from 0-6;
x is an integer from 0 to 500;
y is an integer from 0 to 500.

In one embodiment, the present invention provides a linear peptide having Formula (IIa):

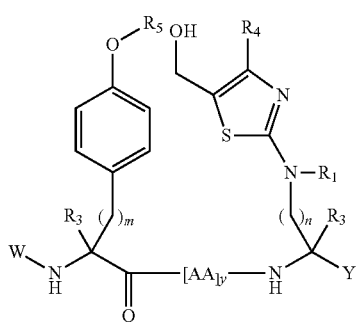

(IIa)

wherein all the variables in Formula (IIa) have the same meanings as those in Formula (II).

In another embodiment, the functionalized amino acid is placed in the non-terminal position of a linear peptide and cyclization of the peptide may occur between this functionalized amino acid and another non-terminal amino acid having an electron rich aromatic moiety within the peptide. In one embodiment, the functionalized amino acid is positioned to the left side of the non-terminal electron rich amino acid. In another embodiment, the functionalized amino acid is positioned to the right side of the non-terminal electron rich amino acid.

Thus, in one aspect of the present invention is to provide a method for the synthesis of internally cyclized peptides and therefore also a method for the synthesis of the corresponding internally macrocycle stabilized peptides or internally macrocycle stabilized α-helical peptides (see Schemes 3-4 and related discussions).

In one embodiment, the present invention provides a linear peptide having Formula (III) or (IV):

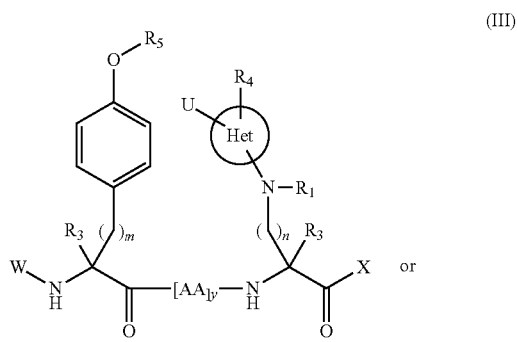

(III)

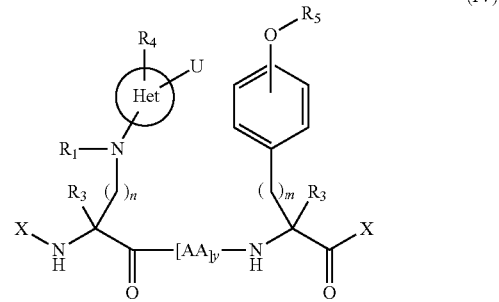

(IV)

wherein
Het is a 5-membered heteroaromatic ring;
$R_1$ is selected from H, $C_{1-6}$alkyl, and an amino protecting group; preferably $R_1$ is Boc;
$R_3$, at each occurrence, is independently selected from H and $C_{1-6}$alkyl;
$R_4$ is selected from H, $C_{1-6}$alkyl, heteroalkyl, and halogen;
$R_5$ is selected from H, $C_{1-6}$alkyl, and heteroalkyl.
U is selected from an aldehyde, a protected aldehyde, and —$CH_2OP$;
W is H, $C_{1-6}$alkyl, $CH_3C(=O)—$, $R_aC(=O)—$, $R_aOC(=O)—$, $R_aR_bNC(=O)—$, -[AA]$_x$, and an amino protecting group;
X is OB, $NR_aR_a$ and -[AA];
B is selected from H, $C_{1-6}$alkyl, and a carboxylic acid protecting group;
AA is any natural or unnatural amino acid;
n and m are each an integer from 0-6;
x is an integer from 0 to 500;
y is an integer from 0 to 500; and
z is an integer from 0 to 500.

In one embodiment, the present invention provides a linear peptide having Formula (IIIa) or (IVa):

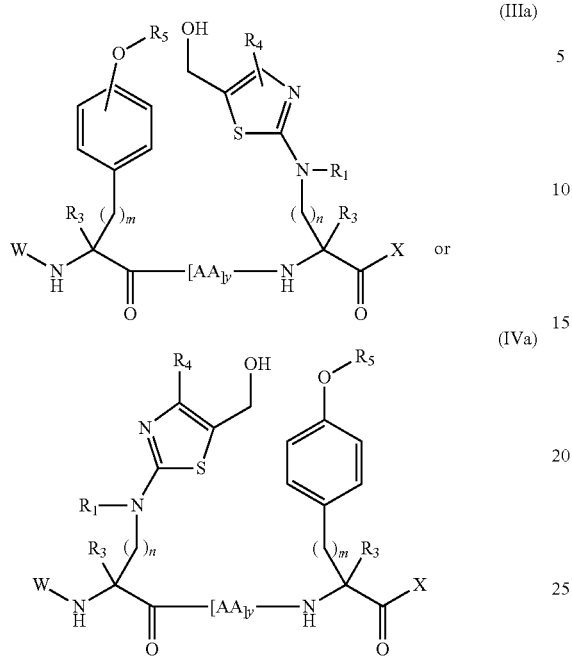

wherein all the variables in Formulae (IIIa) and (IVa) have the same meanings as those in Formulae (III) and (IV), respectively.

The linear peptides of Formula (I)-(IVa) may be viewed as intermediates in a procedure of producing the macrocycle stabilized peptides of this invention. Thus, the present invention not only relates to a macrocycle stabilized peptide obtainable or obtained by the above described method, but also to a corresponding linear peptide obtainable or obtained by the above described method as some kind of an intermediate product (particularly a product obtainable or obtained by step a) of the above described method). In general, the present invention encompasses any peptide containing a thiazole moiety.

The present invention further provides novel macrocyclization reagents useful in the synthesis of the macrocycle stabilized peptides provided herein, which include, but are not limited to, thia-amino acids and thia-amino acid analogs, Formula 9

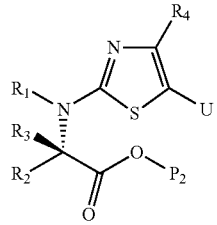

| $^T G$ $R_2 = H$ | $^T S$ $R_2 = CH_2OH$ |
|---|---|
| $^T A$ $R_2 = CH_3$ | $^T T$ $R_2 = CH(OH)CH_3$ |
| $^T V$ $R_2 = CH(CH_3)_2$ | $^T D$ $R_2 = CH_2CO_2H$ |
| $^T L$ $R_2 = CH_2CH(CH_3)_2$ | $^T E$ $R_2 = CH_2CH_2CO_2H$ |
| $^T I$ $R_2 = CH(CH_3)CH_2CH_3$ | $^T N$ $R_2 = CH_2CONH_2$ |
| $^T M$ $R_2 = CH_2CH_2SCH_3$ | $^T Q$ $R_2 = CH_2CH_2CONH_2$ |
| $^T F$ $R_2 = CH_2Ph$ | $^T K$ $R_2 = CH_2CH_2CH_2CH_2NH_2$ |
| $^T Y$ $R_2 = CH_2(p\text{-}OH\text{—}Ph)$ | $^T Orn$ $R_2 = CH_2CH_2CH_2NH_2$ |
| $^T H$ $R_2 = CH_2\text{imidazole}$ | $^T DAB$ $R_2 = CH_2CH_2NH_2$ |
| $^T W$ $R_2 = CH_2\text{indole}$ | $^T DAP$ $R_2 = CH_2NH_2$ |
| $^T C$ $R_2 = CH_2SH$ | $^T R$ $R_2 = CH_2CH_2CH_2NHC(NH_2)_2$ |

Formula 9A

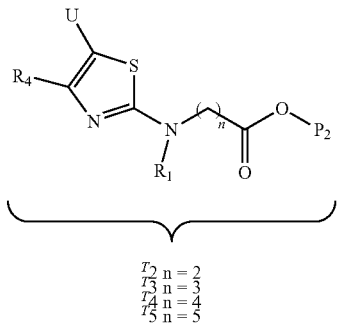

$^T2$ n = 2
$^T3$ n = 3
$^T4$ n = 4
$^T5$ n = 5

Formula 10

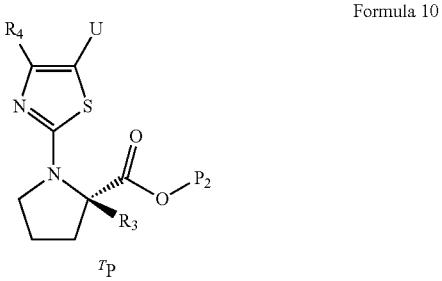

in which $R_1$ is selected from H, $C_{1-6}$alkyl, and an amino protecting group; preferably $R_1$ is Boc; $R_3$, at each occurrence, is independently selected from H and $C_{1-6}$alkyl; U is selected from an aldehyde, a protected aldehyde, and —CH$_2$OP; P is selected from H or $C_{1-6}$alkyl and an alcohol protecting group; preferably P is H or trialkylsilyl; $P_2$ is H or a carboxylic acid protecting group;

carboxylic acid capping reagents,

Formula 11

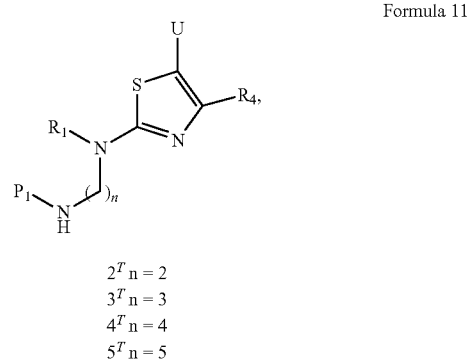

$2^T$ n = 2
$3^T$ n = 3
$4^T$ n = 4
$5^T$ n = 5 in which $R_1$ and $P_1$ are independently selected from H, and an amino protecting group; preferably $R_1$ and $P_1$ are independently Boc and/or Fmoc; U is selected from an aldehyde, a protected aldehyde, and —CH$_2$OP; P is selected from H and an alcohol protecting group. The number of methylene carbons in the side chain is defined by integer n. The methylene carbon positions defined by integer n, may be, all together or separately, differentially substituted with substituents, particularly lower ($C_1$-$C_7$) alkyl carbon substituents, such as methyl and gem-dimethyl, or such n methylene substituents may be taken together to form a ring, preferentially 3- to 7-membered;

$Lys^T$, $Orn^T$, $DAB^T$, and $DAP^T$ analogs,

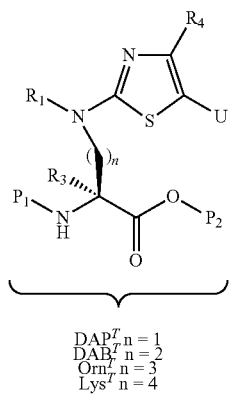

Formula 12

$DAP^T$ n = 1
$DAB^T$ n = 2
$Orn^T$ n = 3
$Lys^T$ n = 4 in which $R_1$ and $P_1$ are independently selected from H, and an amino protecting group; preferably $R_1$ and $P_1$ are independently Boc or Fmoc; $R_3$, at each occurrence, is independently selected from H and $C_{1-6}$alkyl; U is selected from an aldehyde, a protected aldehyde, and —$CH_2OP$; P is selected from H and an alcohol protecting group. The number of methylene carbons in the side chain is defined by integer n. The methylene carbon positions defined by integer n, may be, all together or separately, differentially substituted with substituents, particularly $C_1$-$C_7$ alkyl carbon substituents, such as methyl and gem-dimethyl, or such n methylene substituents may be taken together to form a ring, preferentially 3- to 7-membered; $P_2$ is H or a carboxylic acid protecting group;

extended Thia-amino acids (internal) reagents,

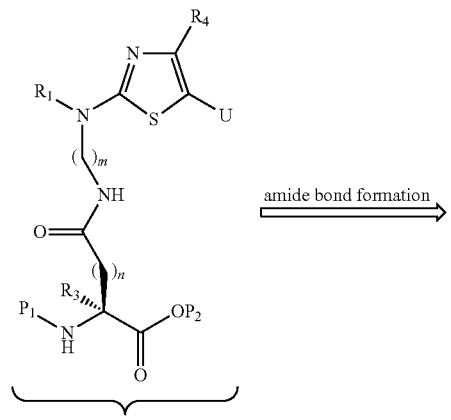

$Asp-m^T$ n = 1
$Glu-m^T$ n = 2

Formula 13

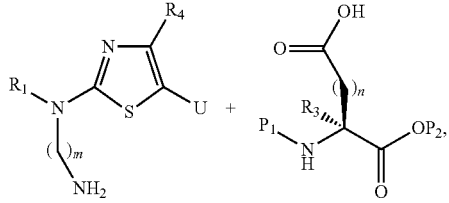

Formula 11      Formula 14 in which $R_1$ and $P_1$ are independently selected from H and an amino protecting group; preferably $R_1$ and $P_1$ are independently Boc or Fmoc; $R_3$, at each occurrence, is independently selected from H and $C_{1-6}$alkyl; U is selected from an aldehyde, a protected aldehyde, and —$CH_2OP$; P is selected from H or an alcohol protecting group; The number of methylene carbons in the side chain is defined by integer n, which is an integer from 0-4. m is an integer from 2-5; and $P_2$ is H or a carboxylic acid protecting group;

extended Thia-amino acids (internal) reagents,

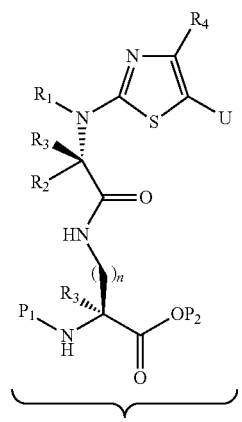

Formula 15

$DAP^T$a.a. n = 1
$DAB^T$a.a. n = 2
$Orn^T$a.a. n = 3
$Lys^T$a.a. n = 4

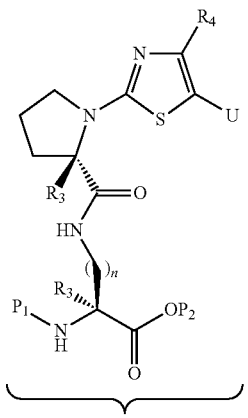

Formula 16

$DAP^TP$ n = 1
$DAB^TP$ n = 2
$Orn^TP$ n = 3
$Lys^TP$ n = 4

Formula 17

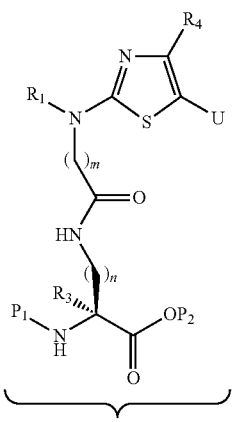

DAP$^T$P m = 1
DAP$^T$P m = 2
Orn$^T$P m = 3
Lys$^T$P m = 4 m = 1, 2, 3, 4, 5

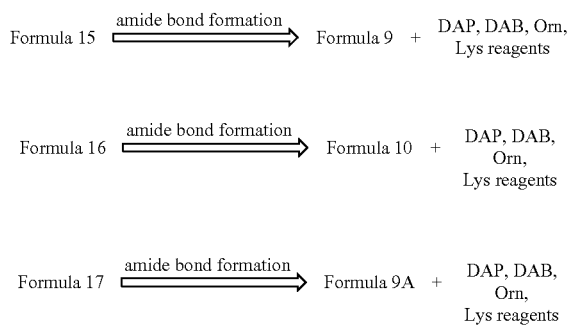

in which $R_1$, $R_2$, $R_3$, and $R_4$ are defined in Formulae 9 and 10; U, $P_1$, $P_2$, and n are as defined in Formulae 12-14; m is defined as in Formula 11.

The present invention further provides methods for cyclizing the linear peptides of Formulae (I)-(IVa) under suitable reaction conditions. Without intending to be bound by any particular theory, it is considered that upon acid activation, the electron rich moiety in the side chain of an amino acid in the peptide undergoes a nucleophilic capture reaction with the imino-quinone methide type precursor moiety, resulting in formation of a covalent bond between the two moieties. Non-limiting examples of the acids that can be used in the reaction include methanesulfonic acid or trifluoromethanesulfonic acid.

In one embodiment, cyclization of the above disclosed linear peptides is performed at room temperature which is in general between 20 to 25° C. In a method provided, the desired compound can be obtained in good yield. The reaction may be performed with any organic or inorganic solvent suitable for the reaction. Non-limiting examples of such solvents include, without limitation, nitromethane, nitroethane, 2-nitropropane, dichloromethane, dichloroethane, trichloroethane, and toluene.

The method of the present invention may proceed with an unprotected peptide wherein none of the amino acid side chains are protected or treated otherwise to prevent unwanted participation in the coupling reaction. Thus, a method is provided for making a macrocycle stabilized peptide, wherein the amino acid in the peptide is essentially unprotected. Importantly, a method provided herein using an unprotected peptide saves costly time, effort and money because it does not require multistep protection/deprotection steps.

However, the method of the present invention may also proceed with protected tyrosine(s) or tryptophan(s) to prevent the unwanted participation of additional tyrosine(s) or tryptophan(s) in the same linear peptide in the macrocyclization reaction. In one embodiment, a peptide is used that contains at least one protected tyrosine, such as the phosphate of tyrosine or the benzyl carbonate of tyrosine, to allow selective masking of a tyrosine phenol group as shown below. Selective masking of an aromatic group in the side chain of an amino acid according to the invention allows the making of the tyrosine phenol group available for reacting at a desired moment, such as following completion of formation of the first covalent linkage.

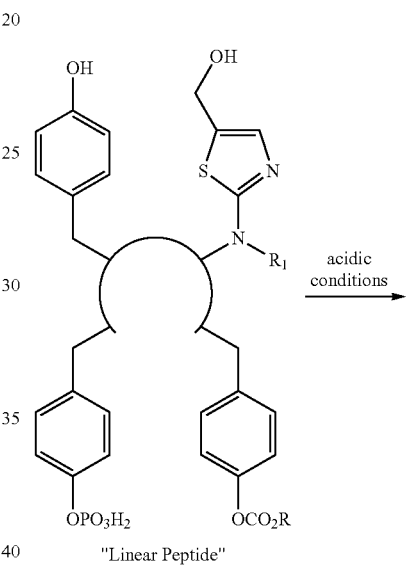

"Linear Peptide"

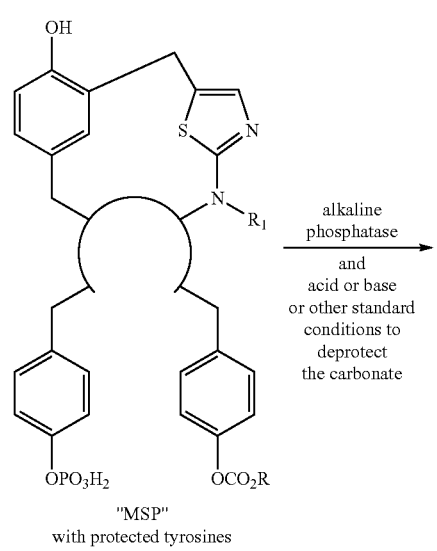

"MSP"
with protected tyrosines

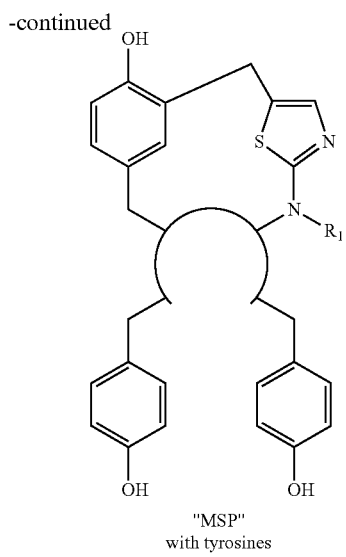

"MSP"
with tyrosines

The person skilled in the art is readily able to put the herein disclosed methods for producing cyclic or macrocycle stabilized peptides into practice, based on his common general knowledge. Also, the teachings of the invention in experimental part provide further enabling technical guidance.

α-Helical Peptides

The macrocycle stabilized peptides so produced according to the methods provided herein are capable of adopting peptide secondary structures such as α-helix, β-sheets, turns and loops. Secondary structures are essential conformational components for peptides and proteins because bioactive conformations are fixed to a high degree by such structural elements. Because of the biological importance of these secondary structures, the development of novel structures incorporating these secondary structures has been a subject of intense research (see, for example, Liskamp, R. M. J., *Recl. Trav. Chim. Pays-Bas,* 113:1 (1994); Giannis, T. K., *Angew. Chem. Int. Ed. Engl.,* 32:1244 (1993); Bailey, P. D., *Peptide Chemistry,* p. 182, Wiley, N.Y. (1990)). In particular, the formation of α-helices by peptides has been of interest because many biologically important protein interactions, such as p53/MDM2 and Bcl-X1/Bak, are mediated by one protein donating a helix into a cleft of its α-helix-accepting partner.

In one embodiment, the present invention provides α-helical peptides that incorporate the thiazole moiety as part of an exogenous macrocyclic structure, where a portion of the macrocyclic structure is formed by the peptide. Such a peptide may be an α-helical peptide where two loops of a peptide helix are linked together by an exogenous macrocyclic structure formed at least in part by a thiazole moiety. The α-helical peptides prepared according to the methods of the present invention can be determined by the far-UV circular dichrosim (CD) spectra.

It is well known in the art that certain amino acids are capable of promoting formation of α-helix structures and other desirable secondary structures, and thus these amino acids are particularly useful in the present invention, depending on the desired secondary structure to be generated. For example, in the N-terminal macrocycle stabilized peptides, appropriate selection of the number and type of amino acids within the MSP and at the C-terminal end, external to the cyclized portion of the macrocycle stabilized peptide, would be expected to control the α-helical content of the N-terminal macrocycle stabilized peptide thus synthesized. Moreover, the macrocycle stabilized peptide itself would be expected to enhance the α-helicity of a corresponding linear peptide if constructed appropriately. For example, if the macrocycle had i, i+3 (or i, i−3), i+4 (or i−4), i+7 (or i−7), or i+11 (or i−11) amino acids within the macrocycle itself, one would expect this configuration to enhance α-helicity.

Furthermore, it may be desirable to mimic an existing protein α-helical structure, or other secondary structure, have the linkages incorporated therein according to the method of the present invention. Thus, any peptide with a known primary amino acid sequence which contains a secondary structure believed to impart biological activity is a subject of the present invention.

Multiple Intramolecular Linkages

The present invention further provides methods for generating peptides with multiple intramolecular linkages. Based on the thiazole-tyrosine ("Thia-Ty") macrocyclization technology disclosed herein, not only the above mentioned one intramolecular covalent linkage may be formed but also further intramolecular linkages may occur, with the proviso that the functionality of the macrocycle stabilized peptides is maintained and that the macrocycle stabilized peptides can still easily be characterized biochemically, which, for example, means that no isomer mixtures are formed during cyclization of the corresponding amino acid sequence.

In one embodiment, the MSP of this invention has two intramolecular linkages, wherein one of linkages is an intramolecular linkage between an N-terminal amino acid and a non-terminal amino acid and the other one is an intramolecular linkage between a non-terminal amino acid and a C-terminal end amino acid of this peptide (see Scheme 2, bottom).

Alternatively, the double linkages may occur between two pairs of non-terminal amino acids (see Scheme 4, bottom).

Macrocyclization Reagents

The present invention further provides novel macrocyclization reagents with multiple reactive groups or centers to serve as tether or scaffold molecules to couple one or more peptides. The reactive groups or centers may be derived from iminoquinone methide type precursors (electrophilic moieties) or electron rich aromatic ring systems (nucleophilic moieties). A "macrocyclization reagent," or "macrocyclizing reagent", "coupling reagent," or "linking reagent," or "capping reagent," as used herein is a synthetic molecule comprising a core structure or skeleton and at least one reactive group. The reaction group may be an electrophilic moiety capable of reacting with a nucleophilic moiety or a nucleophilic moiety capable of reacting with an electrophilic moiety while the core structure or skeleton does not participate directly in the reaction.

In one embodiment, a macrocyclization reagent comprises at least one electrophilic moiety derived from an iminoquinone methide type precursor, which, in turn, comprises at least one 5-membered heteroaromatic moiety.

Since the electrophilic moiety of the macrocyclization reagent is derived from an iminoquinone methide type precursor, suitable macrocyclization reagents according to the invention also include reagents comprising aromatic ring systems other than thiazole. Accordingly, a method provided is also suitably practiced using macrocyclization reagents containing a 5-membered heterocyclic aromatic ring such as pyrrole, pyrazole, oxazole, furan, thiophene, and imidazole. It is thus obvious that suitable macrocyclization reagents for practicing a method according to the invention are numerous.

In a preferred embodiment, the 5-membered heteroaromatic moiety comprises a thiazole ring. Provided below are some exemplary macrocyclization reagents with multiple electrophilic reactive centers:

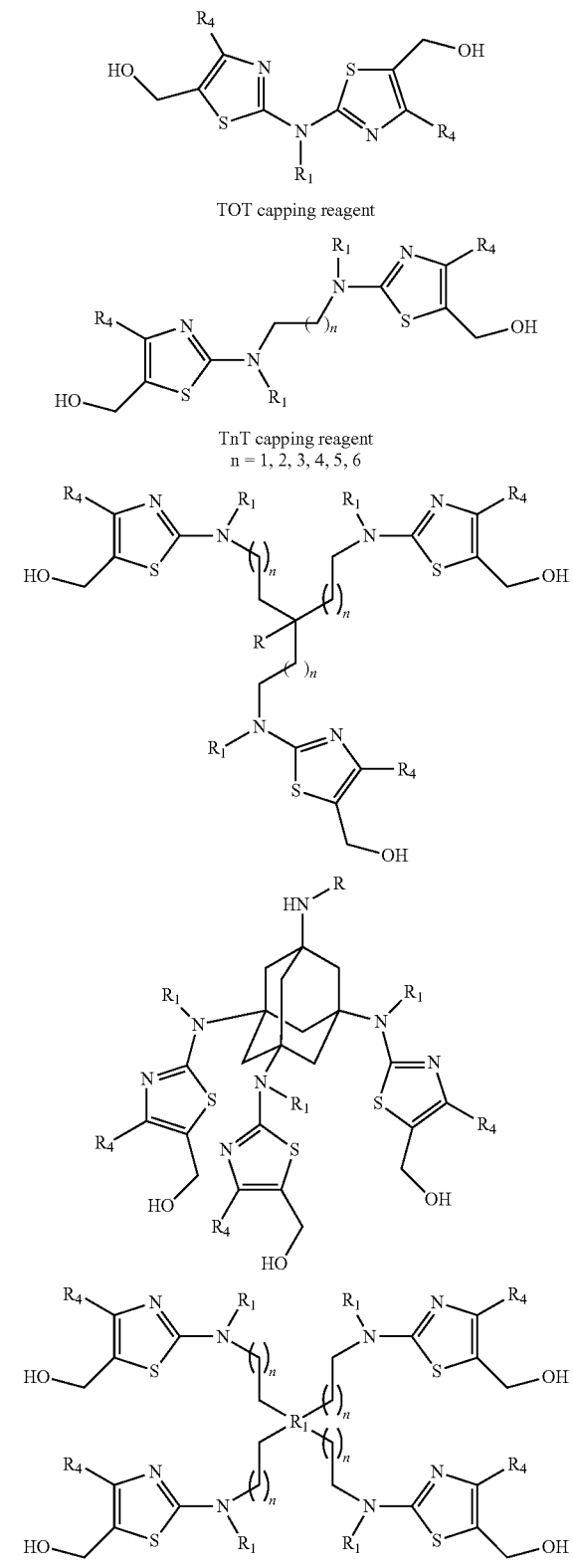

TOT capping reagent

TnT capping reagent
n = 1, 2, 3, 4, 5, 6

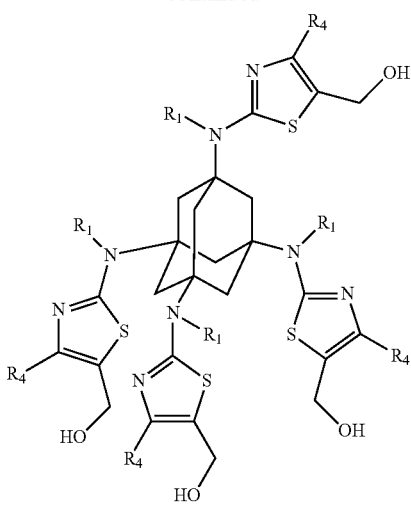

R = alkyl, heteroalkyl, etc

In another embodiment, a macrocyclization reagent comprises at least one nucleophilic moiety derived from an electron rich aromatic ring system. The nucleophilicity of such aromatic ring systems could be enhanced by multiple electron donating substituents such as hydroxyl, alkyloxy, and the like on the aromatic ring systems. The enhanced nucleophilicity of such macrocyclization reagents may afford greater rates of reactivity with other electrophilic moieties. Provided below are some exemplary macrocyclization reagents with multiple nucleophilic reactive centers:

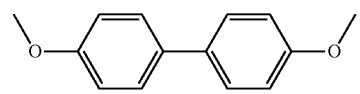

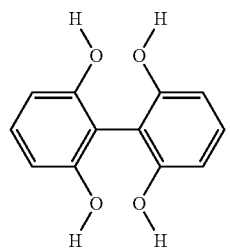

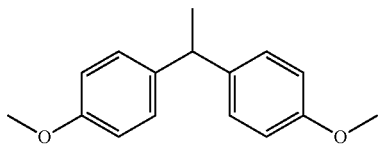

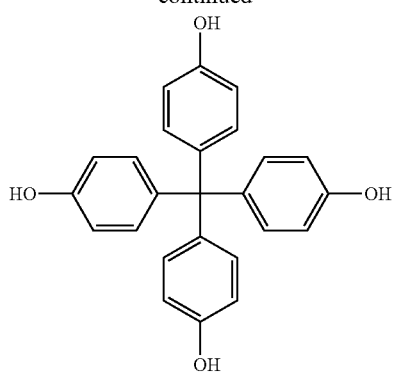

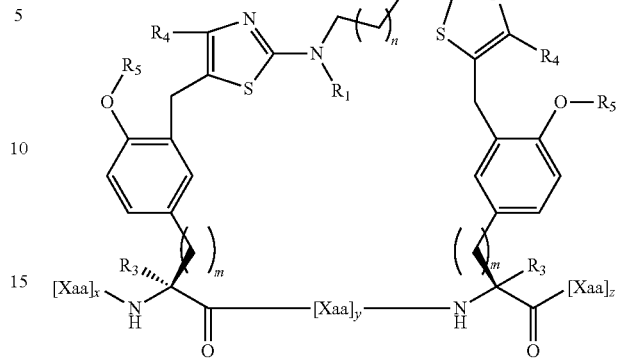

The macrocyclization reagents can be used to synthesize macrocycle stabilized peptides consisting of one or more looped molecular segments. In a preferred embodiment, the present invention provides a method for the synthesis of macrocycle stabilized peptides consisting of one or more looped peptide segments.

In one embodiment, the present invention provides a method for making at least one looped peptide structure utilizing the macrocyclization reagents. The method comprises providing a macrocyclization reagent with at least two electrophilic moieties derived from iminoquinone methide type precursors, contacting the macrocyclization reagent with at least one essentially linear peptide under conditions that allow the formation of at least two linkages between the macrocyclization reagent and at least one peptide in a reaction, to form the at least one looped or cyclic structure peptide structure. For example, a macrocyclization reagent comprising at least two thiazole reactive groups is reacted with a peptide having at least two tyrosines or tyrosine analogs in such a manner that at least two linkages are formed between the macrocyclization reagent and the peptide to form at least one looped structures, as shown below.

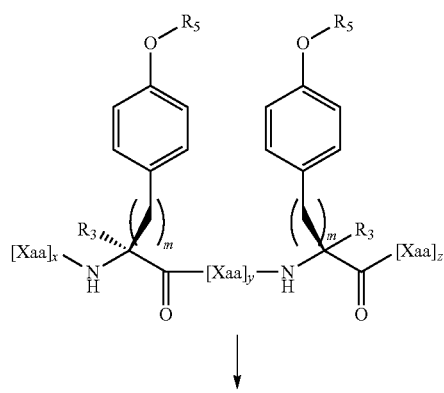

Peptides of various nature can be used in the method provided. For example, biomolecules as well as synthetic molecules can be used including molecules of mainly peptidic nature, such as peptides or peptidomimetics or molecules that are based on fatty acids. A peptidomimetic is a compound containing non-peptidic structural elements that is capable of mimicking or antagonizing the biological action(s) of a natural parent peptide. A peptidomimetic no longer has all the classical peptide characteristics.

Thus, the present invention provides a method for attaching synthetic non-natural peptides, or pseudopeptides to a macrocyclization reagent in a rapid and efficient manner. The present invention also provides a method to attach or constrain natural peptide sequences comprising a modification, for example, a peptide comprising a bioisosteric replacement, to a macrocyclization reagent. A bioisostere comprises a compound resulting from the exchange of an atom or of a group of atoms with another, broadly similar, atom or group of atoms. The objective of a bioisosteric replacement is to create a new compound with similar biological properties to the parent compound. The bioisosteric replacement may be physicochemically or topologically based.

The methods provided herein are not limited to the making of one looped peptide structures. Depending on the nature of the macrocyclization reagents, peptide constructs consisting of one or more looped peptide segments can also be made. In another embodiment, multiple looped structures are obtained using a method provided wherein a molecular macrocyclization reagent is contacted with multiple molecules, each molecule being capable of forming at least one linkage or connection with the macrocyclization reagent.

In one embodiment, the present invention provides macrocyclization reagents with more than two electrophilic moieties. Provided herein are tri-thiazole macrocyclization reagents comprising three thiazole-containing electrophilic moieties, and tetra-thiazole macrocyclization reagents comprising four thiazole-containing electrophilic moieties. Such macrocyclization reagents may react with a peptide that comprises two, three, or Four electron rich amino acids to form multiple linkages, resulting in macrocycle stabilized peptides consisting of one or more looped peptide segments, as shown below.

Recombinant peptides containing all natural amino acids can react with such tri-, tetra-, or higher order macrocyclization reagents via tyrosine and/or tryptophan to afford mixed macrocycles. This is a useful technique for making libraries of mixed well samples that can later be deconvoluted once a mixed well sample has been identified that contains peptides with desired properties. For synthetic peptides the synthesis can be controlled via the use of appropriate protecting groups, plug and play, the incorporation of one or more of highly reactive N-terminal, C-terminal, or non-natural amino acids containing a nucleophilic aromatic ring or nucleophilic ring system described above in this patent.
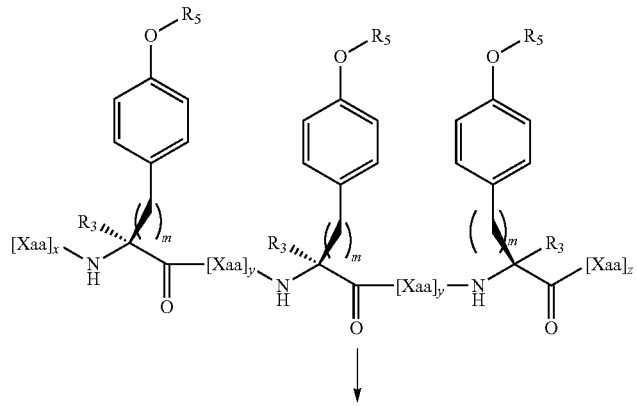
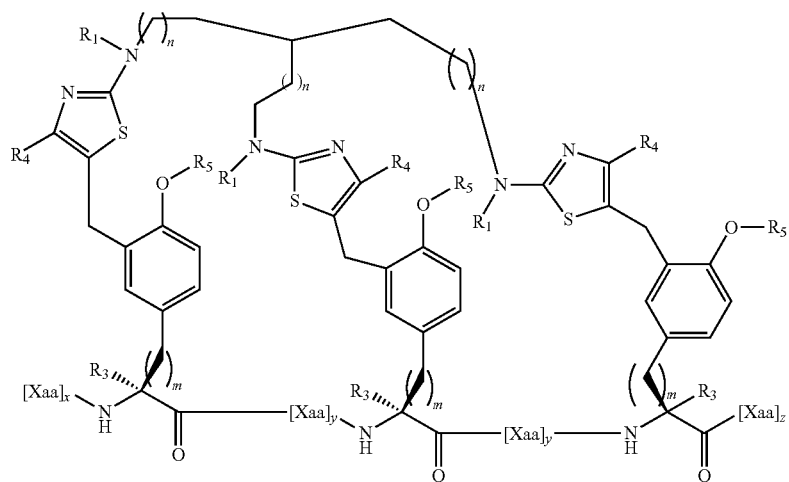
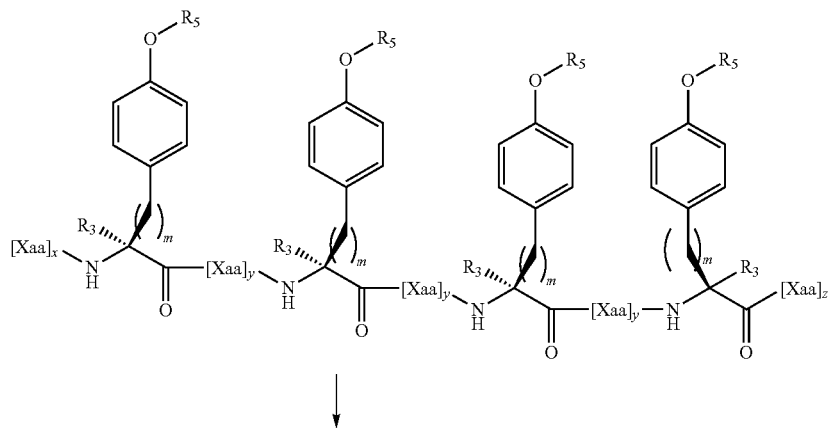

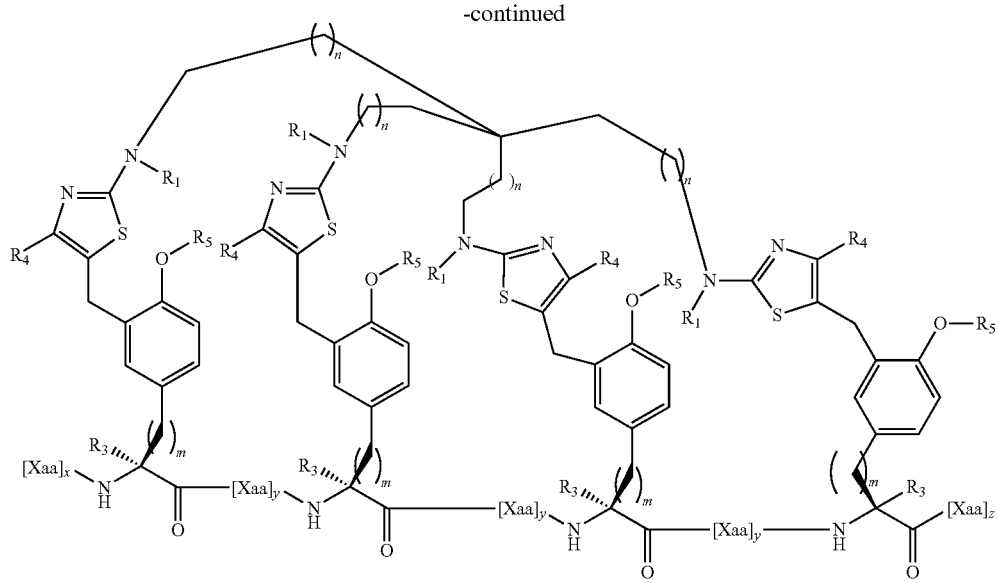

It is important to emphasize a method according to the invention not only provides a rapid and straightforward procedure for the synthesis of macrocycle stabilized peptides comprising one macrocyclization reagent molecule and multiple potential peptides, such as looped peptides, but also for the synthesis of even more complex synthetic platforms comprising multiple macrocyclization reagents and multiple attached molecules.

In general, intramolecular processes have a far more favorable entropy than the analogous intermolecular reactions because it is not necessary for two separate molecules to come together. However, the macrocyclization reagents of the present invention may also be used to link separate peptides together through an intermolecular process.

In one embodiment, the present invention provides a method of ligating two peptides one containing thiazole and the other containing tyrosine or tryptophan, as shown below.

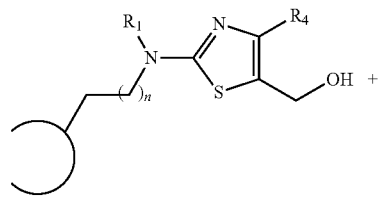

"Linear Peptide" containing activated thiazole

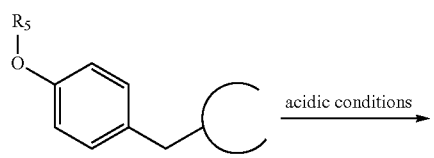

"Linear Peptide" containing tyrosine

→ acidic conditions

-continued

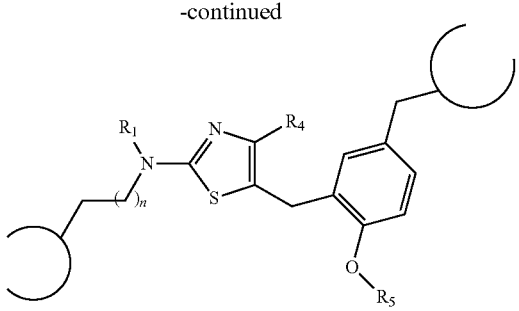

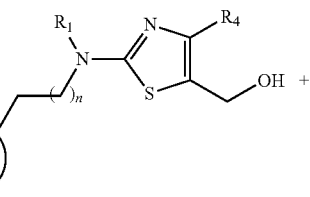

"Linear Peptide" containing activated thiazole

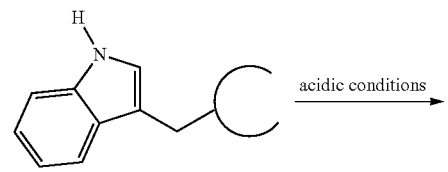

"Linear Peptide" containing tryptophan

→ acidic conditions

-continued

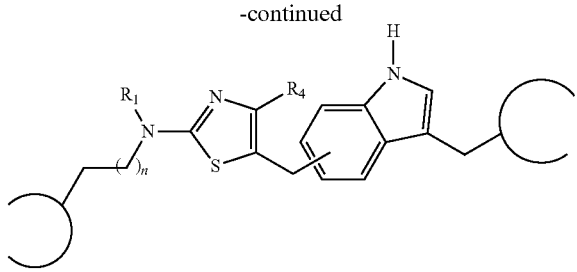

In another embodiment, this invention provides for the ligation of two or more peptides where one contains a single activated thiazole and the other peptide contains reactive centers. Using reagents described above the thiazole could be on the N-terminal (head), C-terminal (tail), or internal (central) portion of the peptide. Likewise the reactive center of the non-thiazole containing peptide could be on the N-terminal (head), C-terminal (tail), or internal (central) of the peptide. The typical reactive center would contain a nucleophilic aromatic ring or ring system, described above. The peptides could be linear, macrocyclic, or containing linear and macrocyclic segments. Two peptides when ligated would result in a head-to-head, head-to-tail, tail-to-tail, tail-to-head, head-to-central, tail-to-central, or central-to-central nano-protein depending on the type and combination of peptides going into the reaction.

For example, to demonstrate this embodiment, a thiazole containing tripeptide, Boc-NH$_2$-A-A-A-3$^T$ (made from Example 73), was ligated with the tripeptide Fmoc-NH$_2$—Y-A-A-G-CO2H (SEQ ID NO. 18) to give the tail-to-head Boc-NH$_2$-A-A-A-3$^T$-Fmoc-NH$_2$—Y$^m$-A-A-G-CO$_2$H (SEQ ID NO. 19) using TfOH in nitromethane at room temperature.

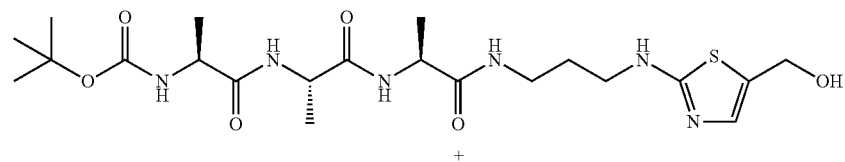

+

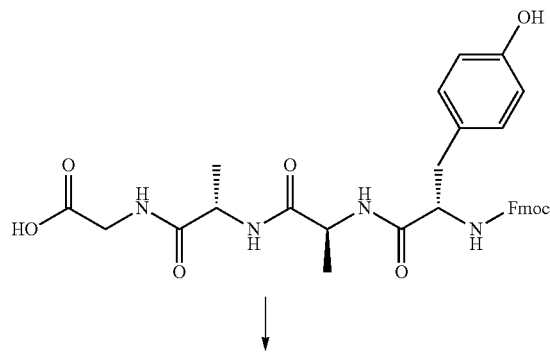

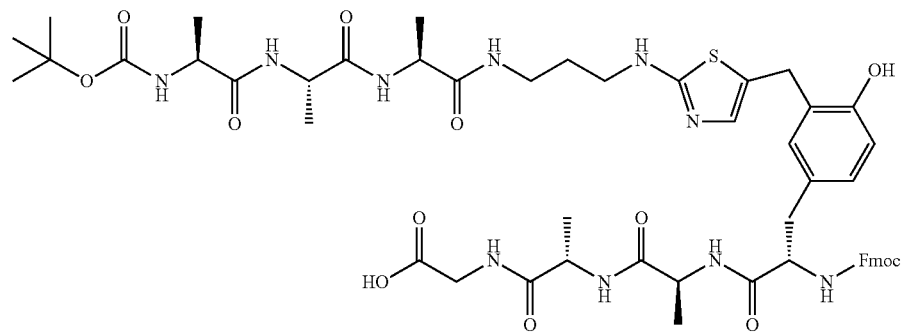

In still another embodiment, this invention provides for the ligation of two or more peptides that each contain a single activated thiazole together through a nucleophilic macrocyclization reagent with two or more reactive centers described above. The peptides (linear, macrocyclic, or containing linear and macrocyclic segments) could contain the activated thiazole on the N-terminal (head of the peptide), C-terminal (tail of the peptide), or within the peptide (central). Two peptides linked through a di-functional reagent would result in a head-to-head, head-to-tail, tail-to-tail, tail-to-head, head-to-central, tail-to-central, or central-to-central nano-protein depending on the type and combination of peptides going into the reaction.

For example, to demonstrate this embodiment, two thiazole containing tripeptides, Boc-NH$_2$-A-A-A-3$^T$ (made from Example 73), can be linked together using biphenyl-4,4'-diol reagent as the ligating reagent to give the tail-to-tail biphenyl-3,3'-di(Boc-NH$_2$-A-A-A-3$^T$)-4-4'diol using TfOH in nitromethane or nitroethane at room temperature.

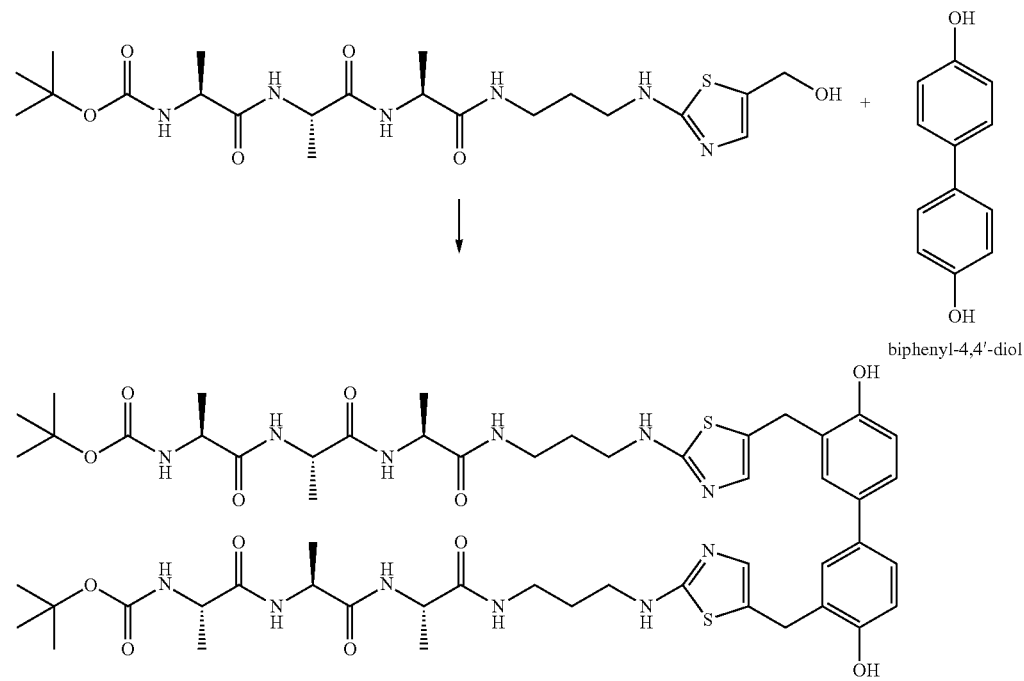

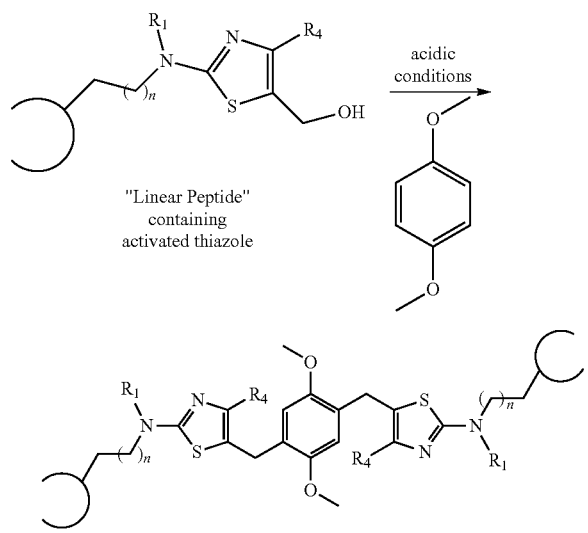

In still another embodiment, the present invention provides a method for linking two tyrosine containing peptides together though an electrophilic macrocyclization reagent. For example, two peptides each containing at least one tyrosine residue may be attached to an electrophilic macrocyclization reagent wherein each molecule is attached to the macrocyclization reagent via at least one linkage. In this way, the macrocyclization reagents are part of a structure which links at least two peptides together. Such a peptide may have two peptide domains which are connected by a linking structure comprising two thiazole moieties, as shown in Schemes 6-8.

Such attachment is particularly useful when, for example, synthesizing a peptidomimetic of a discontinuous epitope comprising multiple peptide segments. These peptides can be synthesized on cellulose membranes that can be incubated with a solution of the target protein or ligand. Bound targets are then detected directly on the cellulose membrane, for example, using standard ELISA reactions. Two or more linear peptide fragments identified to specifically bind to a binding partner of interest in a screening procedure can be readily immobilized on a macrocyclization reagent using the method provided.

The method provided above is not limited to a single coupling reaction. Multiple coupling reactions may be performed, each involving the attachment of at least one peptide to a macrocyclization reagent. One should realize that in this embodiment of the method provided, a macrocyclization reagent provided in a first coupling reaction can serve as a macrocyclization reagent in a second coupling reaction and so on, depending on the number of reactive moieties the macrocyclization reagent possesses. Likewise, multiple macrocyclization reagents may be used to link two or more peptides.

such as the (phenol) phosphate of tyrosine or the (phenol) benzyl carbonate of tyrosine, serves to slow or block reaction to these derivatives, vis-à-vis Tyr itself, thereby allowing selective coupling of a peptide to a multiplicity of different linking reagents, like two or three, in a structurally coordinated fashion.

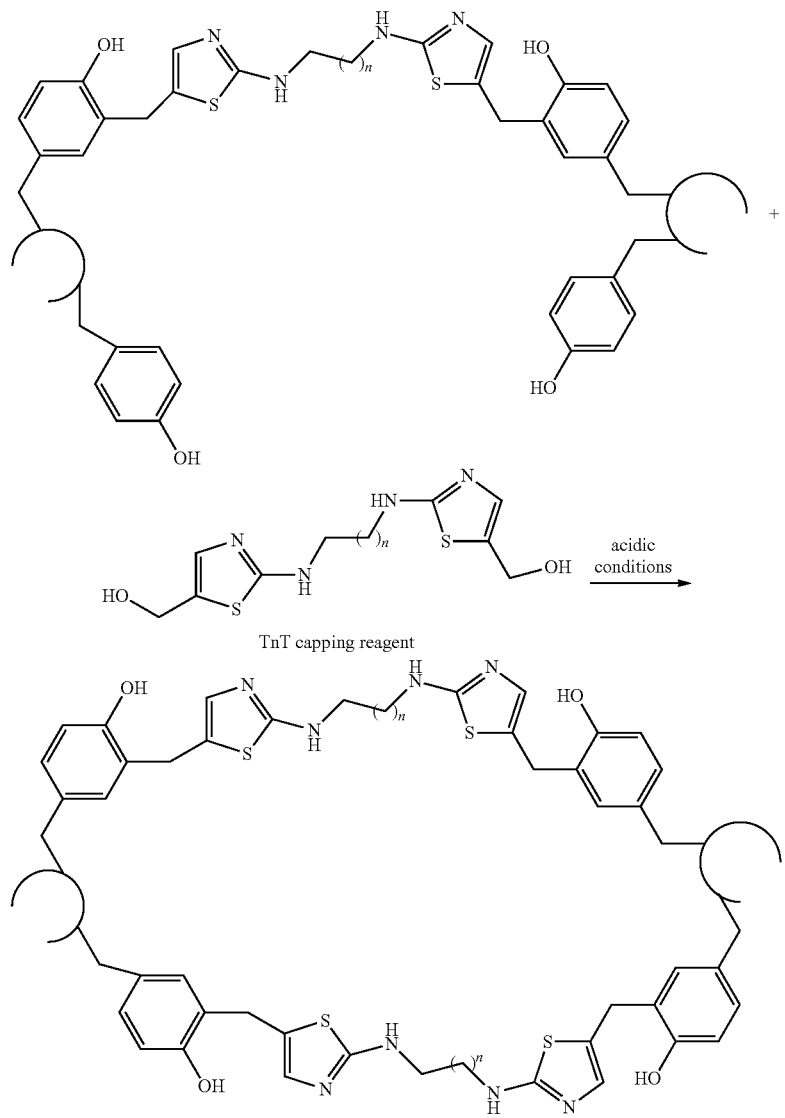

Macrocyclization reagents used can be different from each other, but they can also be identical. As is exemplified herein a method provided involving multiple coupling reactions can be advantageously used for the simple and straightforward synthesis of pharmaceutical peptide constructs.

In another embodiment, a two looped peptide segments may be formed by using one of the macrocyclization reagents comprising four reactive groups. For example, two linear peptides, peptide A and peptide B, are synthesized, each comprising two Tyr residues. Thereafter, the two peptides are coupled to the macrocyclization reagent comprising four thiazole reactive groups, resulting in the structural fixation of two looped peptide segments on a macrocyclization reagent.

When synthesizing a macrocycle stabilized peptide, it is especially advantageous to be able to use peptides which allow intramolecular or intermolecular bond formation. Furthermore, the use of protected (phenol) tyrosine derivatives, Macrocycle stabilized peptides with one or multiple loops or multiple peptides linked by one or more macrocyclization reagents may be attached to activated surfaces in a structurally controlled fashion. In one embodiment, the invention provides a method for attaching a peptide via at least one linkage to a macrocyclization reagent, further comprising attaching the macrocyclization reagent via at least one bond to a surface, comprising contacting the molecule with a surface to allow the formation of at least one bond. A surface comprises any solid support surface, for example, a microarray surface but also a resin or carrier material used in chromatographic applications, ELISA-type assays.

In one embodiment, at least one bond comprises a bond between a macrocyclization reagent and a surface, more preferably between a reactive group of the macrocyclization reagent and the surface. For example, a method is provided wherein a macrocyclization reagent reacts via its reactive group with a surface. A surface comprises a chemically activated surface, for example, a surface provided with one or more nucleophilic functionalities. For example, a nucleophilic functionality of a surface comprises a thiol or amine group. It will be understood that, for a macrocyclization reagent to be capable of forming at least one linkage with at least one peptide and at least one linkage with a surface, it is preferred that the macrocyclization reagent comprises at least three reactive groups.

In one embodiment, a method is provided comprising at least the following steps: providing a macrocyclization reagent comprising at least three thiazole reactive groups, providing at least one peptide capable of reacting with at least two thiazole reactive groups, providing a surface capable of reacting with at least one thiazole reactive group, contacting the macrocyclization reagent with at least one peptide and the solid surface under conditions that allow the formation of at least two linkages between the macrocyclization reagent and at least peptide and at least one linkage between the macrocyclization reagent and the surface in a coupling reaction.

In certain embodiments, the invention provides a method for selecting a suitable drug candidate peptide compound, for example, a peptide compound capable of binding with a target molecule such as an antibody, a receptor, or other desired binding molecule, from among a library of compounds wherein binding of the target molecule with the candidate compound is, preferably first, determined on a solid support provided with the candidate compound or, preferably, on an array provided with the library of compounds and also is determined with the candidate compound not bound to a solid support, the method comprising selecting the candidate compound from among compounds composed of a macrocyclization reagent to which a potential peptide is linked, preferably via at least two linkages, the link allowing presentation of the potential binding site in a constrained fashion, allowing the interaction of the binding site with the target molecule in an essentially similar fashion, be it when the compound is present on a solid support or not, such as in solution, or at least free from the solid support such as in a bioassay.

MSP Library

The invention provides a method for producing a library of compounds for identification or detection of a binding site comprising providing the library with a plurality of macrocyclic and macrocycle stabilized peptides. Such peptides may be obtained by intramolecular cyclization of an electrophilic moiety derived from an iminoquinone methide type precursor and the electron rich side chain of an amino acid. They may also be obtained by or intermolecular interaction between one variant peptide and an invariant molecular macrocyclization reagent. The invention provides a method for producing a molecular library comprising plurality of conformationally constrained or looped peptides.

In one embodiment, at least one peptide is mainly of peptidic nature. Further, a method is provided for producing a library comprising at least one peptidomimetic compound. Also provided is a library obtainable by a method according to the invention.

In another embodiment, the invention provides a library comprising MSPs, wherein the peptide is positionally or spatially addressable, for example, in an array fashion, if desired aided by computer directed localization and/or recognition of a specific molecule or set of molecules within the dimensions (e.g., plane or surface) of the support of the library used. In an array, the peptides are, for example, addressable by their positions in a grid or matrix.

In another embodiment, the invention provides a support of polymeric material (a polymeric support) provided with a library of compounds in a density of at least 25 molecules per square centimeter or preferably at least 50, but more advantageously preferably at least 100, or more, such as 200 to 500 or even 1000 cyclic or looped molecules per square centimeter.

The invention thus provides a method for producing a molecular library for identification or detection of a binding site capable of interacting with a binding molecule, and thus for the identification of a candidate drug compound, the method comprising providing the library with a plurality of compounds, wherein at least part of the compounds, preferably a greater part, most preferably essentially all of the compounds, are composed of at least one macrocycle and macrocycle stabilized peptide. For example, a library is provided comprising a plurality of peptides, for instance unprotected peptides comprising a thiazole moiety. Also provided herein is a library of constrained potential peptides at least comprising a macrocyclization reagent according to the invention. For example, a library is provided comprising an array of cyclized peptide segments. Segments or stretches of amino acids can be derived from the sequence of a naturally occurring protein. They may, however, also be randomly synthesized, for example, using a combinatorial chemistry approach.

When providing such a library of compounds bound to a solid support according to the invention, there is no specific order or sequence by which a macrocyclization reagent, a variant peptide and a solid support need to be contacted with each other. For example, following a coupling reaction in solution to attach a potential peptide to a macrocyclization reagent to provide a candidate compound according to the invention, the compound, typically comprising a cyclic or constrained peptide, can be attached to a solid surface, for example, by spotting techniques. For instance, a peptide comprising a tyrosine or tryptophan residue is synthesized using standard Fmoc peptide chemistry and spotted onto a solid phase provided with a macrocyclization reagent molecule.

In another embodiment, variant peptides capable of reacting with a macrocyclization reagent as provided are first synthesized or spotted on a solid surface, followed by contacting the potential peptide with a macrocyclization reagent as provided to induce cyclization.

A macrocyclization reagent can be applied to every single spot, preferably in an automated fashion, each spot containing at least one molecule capable of reacting with the macrocyclization reagent. In a preferred embodiment, however, a macrocyclization reagent is contacted with at least one molecule, such as a peptide, wherein the molecule is synthesized at the solid phase. In theory, the molecule can be sequentially synthesized wherein in a repetitive fashion, one monomer (e.g., an amino acid or a nucleotide) to another, until a (in essence polymeric) molecule of the desired length has been obtained. Not only are naturally occurring monomers used, synthetic molecules, such as peptide nucleic acid (PNA) molecules, or non-naturally occurring amino acids, functionalized amino acids or even 1)-amino acids, are routinely used as monomers.

In one embodiment, a library of compounds is provided wherein each compound is composed of a macrocyclization reagent molecule and one or more variant peptides. In that case, contacting a molecule and a macrocyclization reagent can be performed by the simple immersion or "dipping" of a solid support, for instance, a library minicard or another type of biochip, in a solution containing a macrocyclization reagent. Of course, following cyclization of a first peptide on a macrocyclization reagent, it is possible to link a second peptide to the macrocyclization reagent, and even a third or fourth molecule. A candidate drug compound, be it in solution or on a solid support, also comprises more than one molecular macrocyclization reagent. For example, a peptide that mimics the binding properties of natural peptides or proteins may be made. The invention herewith provides a molecular library that is particularly well suited for detecting or screening for binding sites, in particular in relation to binding molecule-ligand interactions, such as, for example, protein-protein, protein-nucleic acid, and nucleic acid-nucleic acid interactions.

In yet another embodiment, a solid support is first provided with an macrocyclization reagent comprising at least two electrophilic moieties onto which at least one peptide is attached in one or more subsequent cyclization steps. A macrocyclization reagent can be applied as a uniform layer onto a solid surface or by using spotting or edging technology. A surface comprises a chemically activated surface capable of reacting, be it reversible or irreversible, with a macrocyclization reagent. Cyclization of at least one variant peptide is then achieved by applying the molecule onto the surface provided with a macrocyclization reagent, be it coated uniformly or applied in spots. Similar to what was mentioned before herein, here it is also possible to construct more complex candidate drug compounds comprising multiple constrained peptides using one or more molecular macrocyclization reagents according to the invention.

As said, it is in general very convenient and time-saving to use a dipping or immersion procedure for providing a library of compounds according to a method as provided. For example, dipping is advantageously used for applying a macrocyclization reagent onto a solid support (e.g., followed by spotting of variant peptides) or for contacting spotted variant peptides with a macrocyclization reagent molecule.

in addition, the invention provides a method to screen for a binding site capable of interacting with a target molecule, comprising screening a library according to the invention with at least one potential target molecule and detecting binding between a compound of the library and the target molecule. For example, those comprising constrained peptides, against one or more potential binding partners. Detection of binding is in general achieved with directly labeled probes comprising optically detectable (in general, fluorescent) nucleotides or antibodies.

In a preferred embodiment, enzyme-linked (ELISA-type) assays are used, because these are typically very sensitive. Screening of such a compound library with any given molecule is simple, fast and straightforward. Hits can be translated directly into the amino acid sequence or molecular make-up of the looped structure due to the positionally defined array. For example, an antibody can be shown to bind strongly to a cyclized peptide but does not bind to any significant extent on a polymeric surface functionalized with the corresponding linear peptides because only some of the looped peptide segments can bind strongly to the antibodies. These types of assays illustrate the importance of conformationally constrained peptides in mimicking molecular recognition.

A MSP library according to the invention will provide a straightforward and simple procedure for the synthesis, immobilization, screening and selection of a candidate drug compound composed of a variant peptide linked to a macrocyclization reagent molecule.

Also provided is a chip or minicard provided with variant peptides that can be used in a variety of bioanalytical procedures, for example, in one or more methods currently used in drug discovery, diagnostics and cell biology. These methods comprise, among others, assays, be it qualitative or quantitative, to monitor the activity of an enzyme, such as a kinase, a phosphatase or a protease. Protein kinases represent almost 2% of all expressed genes and regulate a variety of essential cellular events, including proliferation, differentiation, and metabolism. Kinases have emerged as one of the most promising targets for new drug discovery since compounds that regulate kinase activity have significant potential to treat many diseases, including cancer, diabetes, and asthma. Moreover, such kinase inhibitors have the potential for significant efficacy with minimal side effects. The invention thus provides a technology which allows researchers to identify high-specificity in vitro substrates of kinases and physiological substrates for kinase target validation. Traditional approaches, evaluating individual peptides against a kinase until a substrate is found, are time consuming and often result in substrates that lack the selectivity needed for drug discovery efforts. Approaches for identifying physiological substrates for new kinases are even more complicated and time consuming.

In one embodiment of the invention, a library of compounds composed of macrocycles, macrocycle stabilized peptides, variant peptides linked to a macrocyclization reagent is provided wherein at least one of the compounds comprises a potential substrate of an enzyme. For instance, a peptide chip comprising variant peptides linked to a macrocyclization reagent is provided, each compound representing a protein kinase consensus site motif, to characterize the specificity of a protein kinase. The determination of consensus phosphorylation site motifs by amino acid sequence alignment of known substrates has proven useful in this pursuit. These motifs can be helpful for predicting phosphorylation sites for specific protein kinases within a potential protein substrate. Researchers have used peptide chips with a library of short, linear amino-acid sequences describing the primary structure around the phosphoacceptor residue. Typically, such a linear peptide is highly flexible because it is attached to a solid support via one linkage. However, since the determinants of protein kinase specificity involve complex 3-dimensional interactions, these linear motifs are a significant oversimplification of the issue. They do not take into account possible secondary and tertiary structural elements or determinants from other polypeptide chains or from distant locations within the same chain. Furthermore, not all of the residues described in a particular specificity motif may carry the same weight in determining recognition and phosphorylation by the kinase. Thus, whereas a given linear peptide motif may be identified as an in vitro substrate for a given protein kinase, this does not necessarily reflect the in vivo situation. In contrast, the invention now provides a library of conformationally constrained peptides or peptide-like molecules which is of use for monitoring the activity of enzymes, such as protein kinases.

The invention further provides a method for constraining a variant potential peptide via intramolecular cyclization between a functionalized amino acid and an electron rich amino acid, or intermolecular reaction with an invariant molecular macrocyclization reagent to provide a candidate drug compound. The later method comprises providing a macrocyclization reagent comprising at least two electrophilic moieties, providing at least one peptide capable of reacting with the electrophilic moieties, contacting the macrocyclization reagent with at least one peptide, to form at least two linkages between the macrocyclization reagent and at least one molecule in a coupling reaction. Many published methods for constraining a molecule to a macrocyclization reagent either relate to solid-phase or solution phase cyclization. Synthesis on a solid support greatly simplifies the problem of product isolation from reaction mixtures. A solid phase methodology also facilitates the division of products into multiple aliquots for multiple simultaneous reactions. However, a lead compound identified through screening of a library of compounds while being constrained to a solid surface often does not display the same features once tested in solution. Typically, several rounds of lead compound optimization are required to transform a lead compound into a soluble candidate drug compound. Importantly, a method provided herein for constraining a peptide onto a macrocyclization reagent molecule can be performed both on a solid support as well as in solution. Herewith, the invention provides a method for providing a candidate drug compound wherein the compound is bound to a solid support and wherein the compound is not bound to a solid support. This versatility has many advantages. For instance, a large variety of compounds, such as peptides, can be synthesized on a solid phase. Immobilization of a compound on a support surface, preferably in a spatially addressable fashion, allows for rapid screening of the compounds.

After completion of the selection or the screening process, selected candidate drug compounds can subsequently be synthesized in solution, if desired at a larger scale, according to the same procedure. Thus, according to a method provided, it is possible to synthesize a compound in solution that has essentially the same binding properties as a compound attached, be it directly or via a linker, to a solid support, for example, to an array surface. Herewith, the invention allows synthesis of a large variety of candidate drug compounds in an array fashion, enabling rapid and convenient compound selection and to simply resynthesize the selected compounds in solution. Thus, in marked contrast to conventional approaches, the cumbersome transition from (solid phase) lead compound selection to the design of a soluble drug candidate is no longer required. A method provided is advantageously used to speed up the process of drug discovery and drug development as it elegantly integrates solid phase lead compound synthesis and solution phase candidate drug compound synthesis.

A method provided herein is particularly suitable to accelerate the discovery of peptide-based drugs. Existing procedures for the development of a protein mimic or peptidomimetic for use as a pharmaceutical compound typically involve multiple screening rounds of one or more peptide segments with certain binding properties. Short linear peptides are, however, not ideal for use as a drug because of their inherent flexibility and susceptibility to proteolytic degradation. Thus, once an active peptide segment has been identified, for example, using a peptide library, current peptide-based drug discovery strategies still require modification of such a peptide lead into either a peptidomimetic or other type of soluble small-molecule drug candidate that mimics the binding characteristics of the peptide lead. According to a method provided, lead peptide modification is no longer required because the lead peptide is already a peptidomimetic itself. In fact, since the invention provides the synthesis of a large number of peptidomimetics, only peptidomimetics which have a desired binding characteristic need to be selected.

In yet a further embodiment of the invention, a method is provided for constraining at least one potential peptide to a molecular macrocyclization reagent, further comprising immobilizing at least one molecule attached to the macrocyclization reagent via at least one bond onto a surface, comprising contacting the molecule attached to a macrocyclization reagent with a surface to allow the formation of at least one bond. Such an immobilized compound comprising at least one constrained molecule allows for selecting a candidate drug compound from among a library of compounds wherein binding of a target is determined with the candidate compound bound to a solid support. For instance, an array provided with a plurality of immobilized compounds, each compound being composed of a macrocyclization reagent molecule to which a variant potential binding site is linked. According to a method provided, a compound comprising a macrocyclization reagent and a binding molecule can be bound or immobilized to a solid surface in various ways. In one example, a compound is bound to a solid support via at least one bond between the macrocyclization reagent and the surface. For instance, a macrocyclization reagent comprising a thiazole reactive group reacts with a solid support surface capable of reacting with the reactive group. Preferably, the surface comprises an activated surface like a surface provided with at least one free nucleophile functionality, such as a thiol or an amine group. In another example, a compound composed of a macrocyclization reagent and at least one peptide is bound to a solid support via a linkage between the binding molecule and the solid support. As a specific example, standard solid phase peptide chemistry is performed to synthesize a set of peptides in an array-like fashion on a solid support.

In one embodiment, variant peptides are subsequently contacted with a macrocyclization reagent molecule, for example, by simply dipping the solid support into a solution of the macrocyclization reagent to yield an array provided with a library of cyclic peptides bound to a solid support. This array is of use for selecting a candidate drug compound capable of binding a target molecule, wherein binding of the target molecule is determined with the candidate compound bound to a solid support. In existing procedures related to drug development, many promising lead compounds identified while being attached to a solid support lose their attraction as a candidate drug when tested for the interaction with their target molecule in solution.

Methods of Preparation

Macrocycle stabilized peptides of the present invention may be prepared by methods such as those illustrated in the following Schemes. Solvents, temperatures, pressures, and other reaction conditions may readily be selected by one of ordinary skill in the art. Starting materials are commercially available or readily prepared by one of ordinary skill in the art. These Schemes are illustrative and are not meant to limit the possible techniques one skilled in the art may use to manufacture compounds disclosed herein. Different methods may be evident to those skilled in the art. Additionally, the various steps in the synthesis may be performed in an alternate sequence or order to give the desired peptide(s). All documents cited herein are incorporated by reference in their entirety.

Unless otherwise specified, the various substituents of the compounds are defined in the same manner as the formulae of the invention shown above.

MSPs may be prepared according to the following Schemes utilizing chemical transformations familiar to anyone of ordinary proficiency in the art of organic/medicinal chemistry.

Schemes

The Schemes provided below are for the purpose of illustration only and the invention should in no way be construed as being limited to these Schemes and specific Examples, but rather should be construed to encompass any and all variations which become evident as a result of the teaching provided herein.

Figure 2:
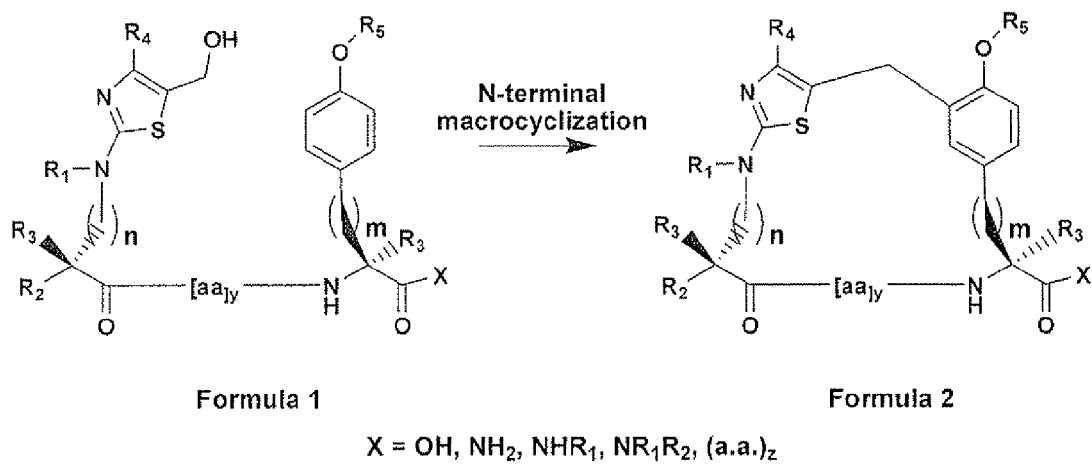
FIG. 2 illustrates the N-terminal macrocyclization reaction.
Figure 3:
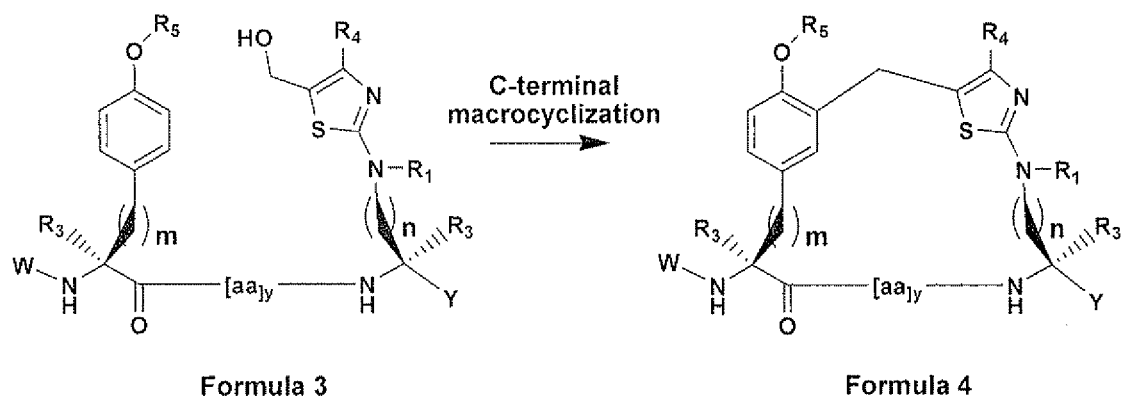
FIG. 3 illustrates the C-terminal macrocyclization reaction.
Figure 4:
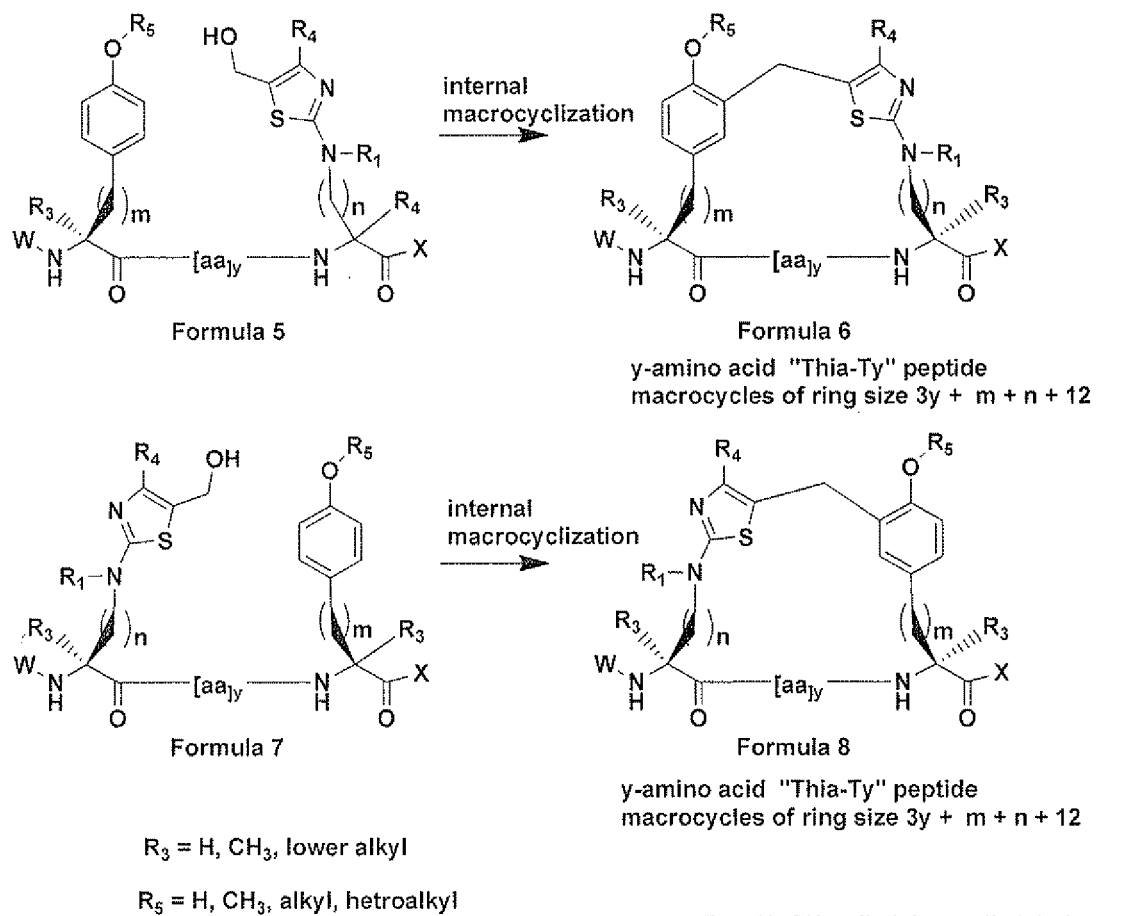
FIG. 4 illustrates the internal-terminal macrocyclization reaction.

The general schemes of preparing MSPs are represented in FIGS. 2-4. In these Figures, $R_1$ can be H or an alkyl group with 1 to 6 carbons, or $R_1$ is Boc. $R_2$ is generally representative of all the side chains of the natural amino acids. For example, if $R_2$ is methyl, it is derived from alanine or if $R_2$ is hydrogen, then it is derived from glycine, etc. For purposes of illustration, the structures in FIGS. 2-4 are represented using the natural (L) configurations of the amino acid side chains when $R_3$ is hydrogen, but the method can apply to the D-isomers as well. Moreover, $R_2$ could include other typical R groups beyond those within the scope of the natural amino acids. $R_3$ is preferably hydrogen, but could also be methyl or an alkyl group with 1 to 6 carbons. In FIGS. 2-4, $[AA]_x$, $[AA]_y$, and $[AA]_z$ can be any natural or synthetic amino acid combined together in a peptide bond in x, y, z combinations of the individual amino acids. The number of amino acids in the peptide chain (in addition to functionalized amino acids) is represented by x, y, and z, each of which can independently be integer values of 0, 1, 2, 3, 4, 5, etc. The R groups (including the alkyl groups of the previously cited R groups, which can be linear or branched) can be substituted with functional groups such as halogens, alcohols, amines, ethers, esters, amides, and the like.

Upon treatment of the linear peptide defined in Formula 1, 3, 5, and 7 with acid (such as methanesulfonic acid (MSA), trifluoromethanesulfonic acid (TfOH), or other organic or inorganic acids or acid containing media such as appropriate buffer solutions and the like), the macrocyclization occurs to give the peptide containing macrocycles or MSPs of Formula 2, 4, 6, and 8, respectively. MSPs of Formula 2 can be considered to represent N-terminal cyclized peptides when X is $[AA]_z$. MSPs of Formula 4 can be considered to represent C-terminal MSP's when W is $[AA]_x$. Also, MSPs of Formulae 6 and 8 can be considered to represent internally cyclized peptides when W is [AA] and X is $[AA]_z$.

(a) Preparation of N-terminal Cyclized MSPs

Preparation of N-terminal MSPs starts with preparation of thia-amino acid reagents. Representative thia-amino acids are shown in Formula 9, 9A, and Formula 10. For example, thia-glycine ($^TG$; $R_2$, $R_3$=H), is derived from glycine by (formally, or literally) using the α-amino group to fashion the 2-aminothiazole ring by, for example, first converting the α-amino group of the corresponding amino acid (or its ester derivative) to a thiourea and then by employing a common synthetic method known in the art for thiazole ring construction as the "Hantzsch reaction" for conversion of the thiourea into the 2-aminothiazole ring. Similarly provided are thia-alanine ($^TA$; $R_2$=CH$_3$, $R_3$=H), thia-valine ($^TV$; $R_2$=i-Pr, $R_3$=H), etc as shown in Formula 9, thia-proline ($^TP$) as shown in Formula 10, and $^T2$, $^T3$, $^T4$, and $^T5$ as shown in Formula 9A. Both Formulae 9, 9A, and 10 are further specified with C-5 thiazole substitution with group "U" defined specifically as aldehyde (CHO) and its derived alcohol (CH$_2$OH). Furthermore, the aldehyde form is considered "unactivated" and the alcohol form is considered "activated" for the macrocyclization chemistry described herein. Groups $R_1$-$R_4$ are also defined in the first aspects of this invention hereinabove. While the natural (L) amino acid stereochemistry is shown, the (D) is also claimed. The aldehyde (for U=CHO) can be protected, for example, as an acetal, with groups (such as ethylenedioxy) that are standard and well-known in the art for making acetals from aldehydes.

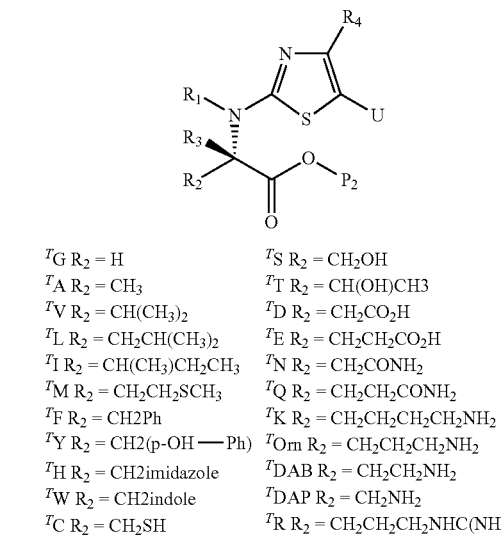

Formula 9

$^TG$ $R_2$ = H
$^TA$ $R_2$ = CH$_3$
$^TV$ $R_2$ = CH(CH$_3$)$_2$
$^TL$ $R_2$ = CH$_2$CH(CH$_3$)$_2$
$^TI$ $R_2$ = CH(CH$_3$)CH$_2$CH$_3$
$^TM$ $R_2$ = CH$_2$CH$_2$SCH$_3$
$^TF$ $R_2$ = CH2Ph
$^TY$ $R_2$ = CH2(p-OH—Ph)
$^TH$ $R_2$ = CH2imidazole
$^TW$ $R_2$ = CH2indole
$^TC$ $R_2$ = CH$_2$SH $^TS$ $R_2$ = CH$_2$OH
$^TT$ $R_2$ = CH(OH)CH3
$^TD$ $R_2$ = CH$_2$CO$_2$H
$^TE$ $R_2$ = CH$_2$CH$_2$CO$_2$H
$^TN$ $R_2$ = CH$_2$CONH$_2$
$^TQ$ $R_2$ = CH$_2$CH$_2$CONH$_2$
$^TK$ $R_2$ = CH$_2$CH$_2$CH$_2$CH$_2$NH$_2$
$^TOrn$ $R_2$ = CH$_2$CH$_2$CH$_2$NH$_2$
$^TDAB$ $R_2$ = CH$_2$CH$_2$NH$_2$
$^TDAP$ $R_2$ = CH$_2$NH$_2$
$^TR$ $R_2$ = CH$_2$CH$_2$CH$_2$NHC(NH$_2$)$_2$

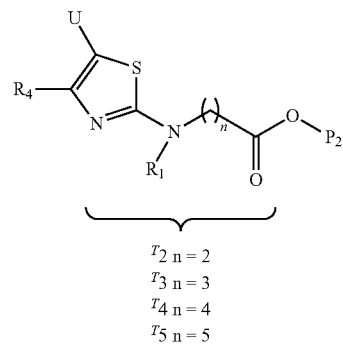

Formula 9A $^T2$ n = 2
$^T3$ n = 3
$^T4$ n = 4
$^T5$ n = 5

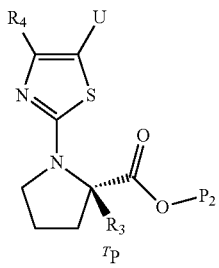

Formula 10

P2 = H or an acid protecting group
U = CHO and CH$_2$OH
R3 = H, CH$_3$, lower alkyl Syntheses for thia-glycine ($^TG$) and thia-proline ($^TP$) are shown below. Specific Examples 3 and 80 describe the protocols for the preparation of $^TG$ and $^TP$, respectively. As shown in these examples, common reagents for forming thioureas from amines, such as thiophosgene and 1,1'-thiocarbonyldipyridin-2(1H)-one are preferably employed, but other reagents well-known in the art for this type of conversion, such as thiocarbonyldiimidazole, can also be utilized. In the case of primary amines, thiophogene and related reagents are known to generate an isothiocyanate which is then converted to the corresponding thiourea derivative by treatment preferably with ammonia (for example see $^TG$ synthesis below). In the case of tertiary amines (as in proline), thiophogene and related reagents are known to generate a carbothioyl chloride or related intermediate which is then converted to the corresponding thiourea derivative by treatment preferably with ammonia (for example see $^TP$ synthesis below). These thiourea intermediates are then used to fashion the 2-aminothiazole ring system using a substrate such as commercially available 2-bromomalonaldehyde, using either neutral, acidic, or basic reaction conditions (such as triethylamine, diisopropylethylamine, sodium acetate/acetic acid, etc) in a variety of typical solvents (such as THF, dioxane, DMF, etc). This reaction, which constructs the thiazole ring system, is related to the old and well-known "Hantzsch reaction" in the art for the synthesis of thiazoles.

Synthesis of thia-glycine ($^TG$) and thia-proline ($^TP$)

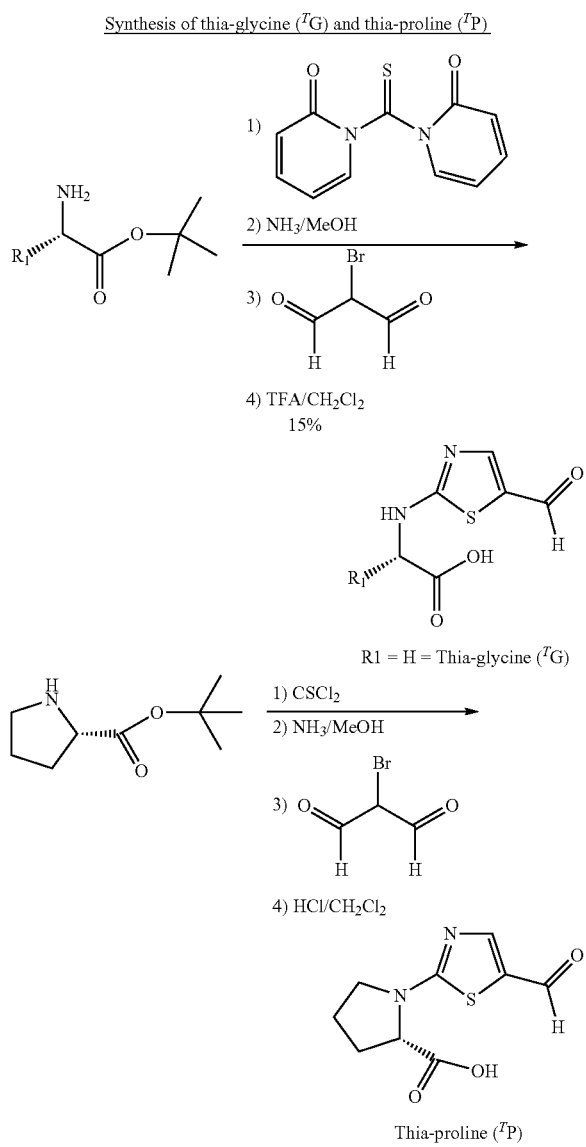

Syntheses of N-terminal macrocyclic peptides and corresponding N-terminal MSPs, and N-terminal macrocycle stabilized α-helical peptides are exemplified in Scheme 1. For example, using the novel thiazole containing amino acids ($^Ta.a.$) of Formula 9 and Formula 10 in a standard peptide coupling reaction with an amine-containing peptide substrate (such as $NH_2A$-$YCONH_2$ shown in Scheme 1 with $^TG$), the corresponding thiazole containing peptide intermediates are readily synthesized. There are many reagents and conditions used in the art for such a common peptide coupling reaction, many of which are employed to eliminate or reduce epimerization of the amino acid bearing α-carbon. There are numerous review articles of this subject. The reagent combination EDC/HOAt and weak base N-methylmorpholine are employed in Scheme 1 but in this case $^TG$ does not have a chiral carbon to epimerize (whereas the other $^Ta.a$'s would have such a chiral center). Therefore the choice of coupling reagent is by no means limited to EDC but can be selected from a numerous list of such reagents well-known to one skilled in the art.

In the example in Scheme 1, the "Thia-G-A-Y" tripeptide has an aldehyde group which is considered to be "unactivated" towards the subsequent macrocyclization. This same intermediate also bears an amide derivative ($CONH_2$) at the tyrosine carboxyl center for purposes of illustration, but this center could also have been chosen to be an appropriately protected acid, for example a tertiary-butyl ester. When this "Thia-G-A-Y" tripeptide (aldehyde; unactivated) is reduced to the corresponding primary alcohol, it is considered to be "activated" for the subsequent acid-induced macrocyclization reaction. The reduction of the aldehyde with sodium borohydride is shown in Scheme 1b using a solvent consisting of an ethanol water mixture, but this reaction is not limited to these conditions since other solvents and reducing reagents well-known in the art for the reduction of aldehydes could also be employed. When the "Thia-G-A-Y" tripeptide (alcohol; activated) intermediate is treated with acid, for example preferably trifluoromethanesulfonic acid (TfOH), in a suitable solvent, for example preferably nitromethane or nitroethane, macrocyclization to the $^TG$-A-Y—$CONH_2$ 16-membered macrocycle shown in Scheme 1 b readily occurs. Various other inorganic and organic acids, including aqueous acidic buffers, as well as other solvents, could be expected to also facilitate this macrocyclization. In addition, the amide derivative ($CONH_2$) at the tyrosine carboxyl center is shown for purposes of illustration, but this center could also have been chosen to be an appropriately protected acid, for example a tertiary-butyl ester. Under such acidic conditions as TfOH/nitromethane or nitroethane used in the macrocyclization, the tertiary-butyl ester would be readily converted to the carboxylic acid. Such a carboxylic acid could then be used in standard peptide coupling reactions to assemble one or many additional amino acids, (a.a.)$_z$, to form an N-terminal MSP (see Scheme 1 bottom).

Scheme 1
Synthesis of an N-terminal macrocyclic peptide,
Thia-Ty (G-A-Y) macrocycle; ($^TGAY$
16-membered macrocycle)

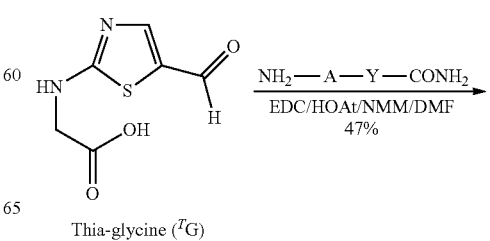

Thia-glycine ($^TG$)

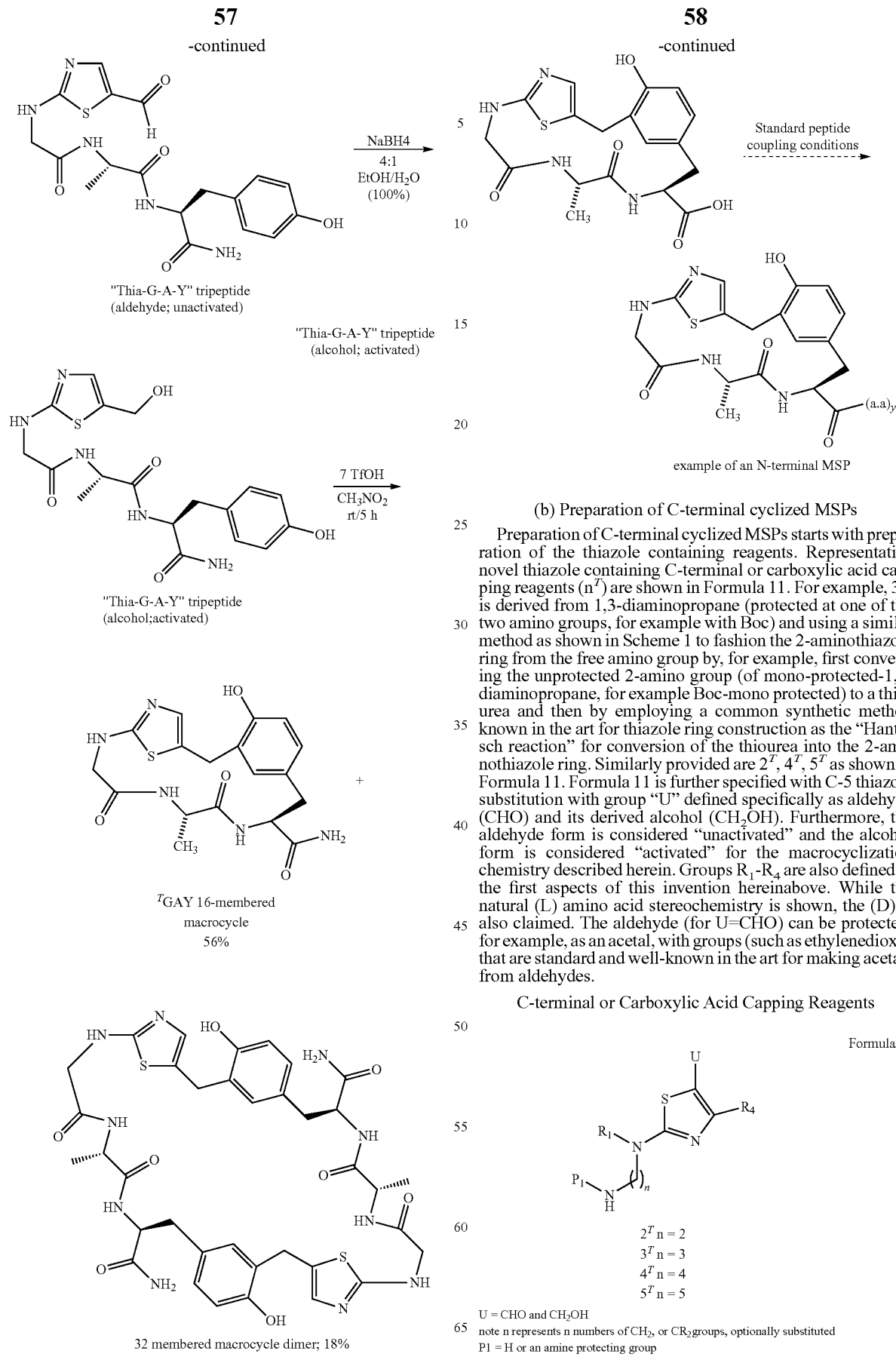

(b) Preparation of C-terminal cyclized MSPs

Preparation of C-terminal cyclized MSPs starts with preparation of the thiazole containing reagents. Representative novel thiazole containing C-terminal or carboxylic acid capping reagents ($n^T$) are shown in Formula 11. For example, $3^T$, is derived from 1,3-diaminopropane (protected at one of the two amino groups, for example with Boc) and using a similar method as shown in Scheme 1 to fashion the 2-aminothiazole ring from the free amino group by, for example, first converting the unprotected 2-amino group (of mono-protected-1,3-diaminopropane, for example Boc-mono protected) to a thiourea and then by employing a common synthetic method known in the art for thiazole ring construction as the "Hantzsch reaction" for conversion of the thiourea into the 2-aminothiazole ring. Similarly provided are $2^T$, $4^T$, $5^T$ as shown in Formula 11. Formula 11 is further specified with C-5 thiazole substitution with group "U" defined specifically as aldehyde (CHO) and its derived alcohol ($CH_2OH$). Furthermore, the aldehyde form is considered "unactivated" and the alcohol form is considered "activated" for the macrocyclization chemistry described herein. Groups $R_1$-$R_4$ are also defined in the first aspects of this invention hereinabove. While the natural (L) amino acid stereochemistry is shown, the (D) is also claimed. The aldehyde (for U=CHO) can be protected, for example, as an acetal, with groups (such as ethylenedioxy) that are standard and well-known in the art for making acetals from aldehydes.

A representative syntheses for $3^T$ is described in specific Examples 58, 59, 60, and 68 using the synthetic sequence shown below.

Synthesis of $3^T$

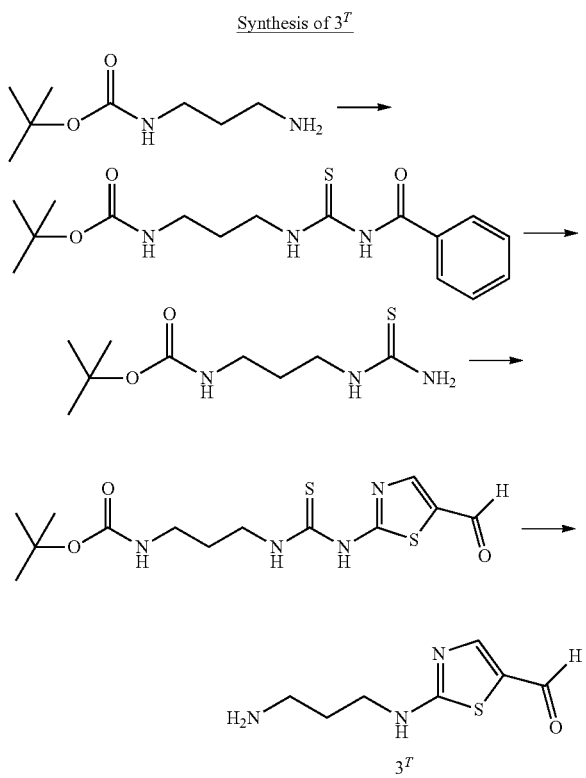

$3^T$

As shown above for $3^T$, benzoyl isothiocyanate followed by alkaline hydrolysis, is employed therein for forming the corresponding thiourea from the amine, but other reagents well-known in the art for this type of conversion such as thiophosgene, 1,1'-thiocarbonyldipyridin-2(1H)-one, and thiocarbonyldiimidazole can also be employed. In the case of primary amines, thiophogene and related reagents are known to generate an isothiocyanate which is then converted to the corresponding thiourea derivative by treatment preferably with ammonia (for example see $^TG$ synthesis above). In the case of tertiary amines ($R_1$ in Formula 11 is carbon), thiophogene and related reagents are known to generate a carbothioyl chloride or related intermediate which is then converted to the corresponding thiourea derivative by treatment preferably with ammonia. These thiourea intermediates are then used to fashion the 2-aminothiazole ring system using a substrate such as commercially available 2-bromomalonaldehyde, using either neutral, acidic, or basic reaction conditions (such as triethylamine, diisopropylethylamine, sodium acetate/acetic acid, etc) in a variety of typical solvents (such as THF, dioxane, DMF, etc). This reaction, which constructs the thiazole ring system, is related to the old and well-known (in the art) "Hantzsch reaction" for the synthesis of thiazoles. Deprotection of a standard protecting group for an amino group known in the art (such as acid induced N-Boc deprotection to $NH_2$, or NHR) then gives the C-Terminal or carboxylic acid capping reagents, $n^T$ (for example $3^T$ shown above).

Syntheses of C-terminal macrocyclic peptides and the corresponding C-terminal MSPs, and C-terminal macrocycle stabilized α-helical peptides are exemplified in Scheme 2.

For example, using the novel C-Terminal or carboxylic acid capping reagents (n) of Formula 11 in a standard peptide coupling reaction with an acid-containing peptide substrate (such as BocNHY-A-A-ACOOH (SEQ ID NO. 1) with $3^T$), the corresponding thiazole containing peptide intermediates are readily synthesized. There are many reagents and conditions used in the art for such a common peptide coupling reaction, many of which are employed to eliminate or reduce epimerization of the amino acid bearing α-carbon. There are numerous review articles of this subject. The reagent combination EDC/HOAt and weak base N-methylmorpholine are employed below in Scheme 2. The choice of coupling reagent is by no means limited to EDC but can be selected from a numerous list of such reagents well-known in the field. In the example in Scheme 2, the Boc-Tyr-Ala-Ala-Ala-$3^T$ (SEQ ID NO. 2) peptide substrate has an aldehyde group which is considered to be "unactivated" towards the subsequent macrocyclization. This same intermediate also bears an Boc-protected amine derivative (BocNH) at the tyrosine amine center for purposes of illustration. When this Boc-Tyr-Ala-Ala-Ala-$3^T$ (SEQ ID NO. 2) peptide (aldehyde; unactivated) is reduced to the corresponding primary alcohol, it is considered to be "activated" for the subsequent acid-induced macrocyclization reaction. The reduction of the aldehyde with sodium borohydride is shown in Scheme 2 using a solvent consisting of an ethanol water mixture, but this reaction is not limited to these conditions since other solvents and reducing reagents well-known in the art for the reduction of aldehydes could also be employed. When the Boc-Tyr-Ala-Ala-Ala-$3^T$ (SEQ ID NO. 2) peptide (alcohol; activated) intermediate is treated with acid, for example preferably trifluoromethanesulfonic acid (TfOH), in a suitable solvent, for example preferably nitromethane or nitroethane, macrocyclization to the $NH_2$-Tyr'''-Ala-Ala-Ala-$3^T$ (SEQ ID NO. 3) 24-membered macrocycle shown in Scheme 2 occurs with simultaneous deprotection of the Boc NH group to the free primary amine. Various other organic and inorganic acids, including methanesulfonic acid (MsOH) and aqueous acidic buffers, as well as other solvents, could be expected to also facilitate this macrocyclization. This free primary amine could then be used in standard peptide coupling reactions to assemble one or many additional amino acids, $(a.a.)_x$, to form a C-terminal MSP (see Scheme 2, bottom). The appropriate selection and number of amino acids within the macrocycle and at the N-terminal end, external to the macrocycle, would be expected to control the α-helical content of the C-terminal MSP thus synthesized. Moreover, the macrocycle itself would be expected to enhance the α-helicity of a corresponding linear peptide (not macrocyclized) if constructed appropriately. For example, if the macrocycle had i, i+3 (or i, i−3), i+4 (or i−4), i+7 (or i−7), or i+11 (or i−11) amino acids within the macrocycle itself, one would expect this configuration to enhance α-helicity. Note in the case in Scheme 2, the $NH_2$-Tyr-Ala-Ala-Ala-$3^T$ (SEQ ID NO. 4) 24-membered macrocycle would be i−4. However, other C-terminal macrocycles analogous to those N-terminal macrocycles shown on Page 29 could also have been made in analogous fashion. Many such C-terminal MSPs would be expected to be α-helical, as controlled by the selection of the number and type of amino acids internal and external to the macrocyclic portion as discussed above.

Scheme 2
Synthesis of a C-terminal macrocyclic peptide and its use for a C-terminal macrocycle stabilized α-helix with potential for double macrocyclization

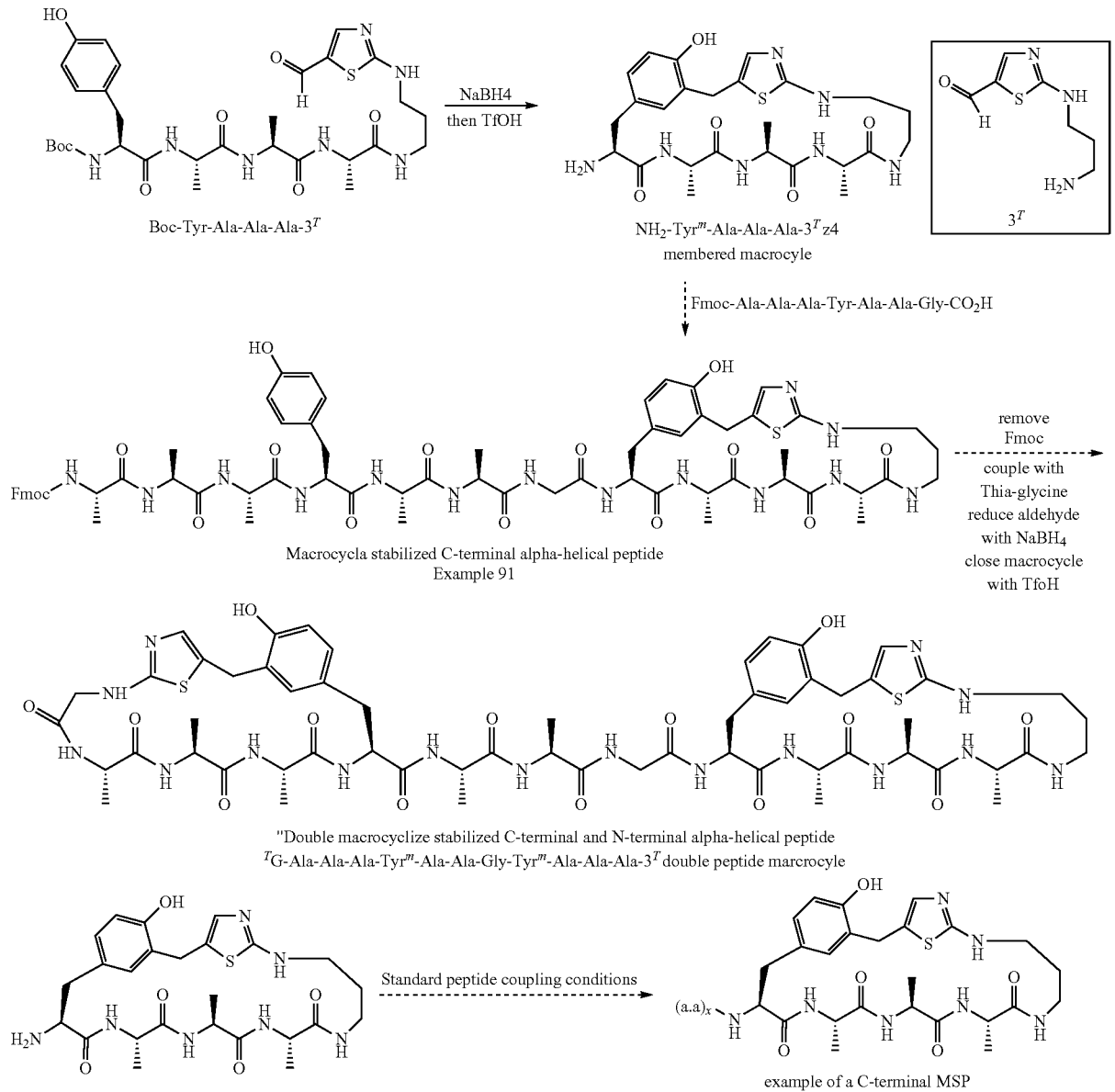

note Tyr$^m$ refers t a Tyr residue which has been macrocyclized to a thiazole, T In another embodiment, this invention provides a method for the synthesis of C-terminal and N-terminal double macrocycle stabilized peptides and therefore also a method for the synthesis C-terminal and N-terminal double macrocycle stabilized α-helical peptides as exemplified in Scheme 2. For example, the NH$_2$-Tyr$^m$-Ala-Ala-Ala-3$^T$ 24-membered macrocycle shown in Scheme 2 can be readily coupled using standard peptide coupling conditions known in the art and as discussed above, with, for example, an acid containing peptide substrate with the amine terminus protected using standard amino protecting groups (such as, for example, N-Boc or N-Fmoc). For example using Fmoc-Ala-Ala-Ala-Tyr-Ala-Ala-Gly-CO$_2$H (SEQ ID NO. 5), the FmocNH-Ala-Ala-Ala-Tyr-Ala-Ala-Gly-Tyr$^m$-Ala-Ala-Ala-3$^T$ (SEQ ID NO. 6) 24-membered macrocycle peptide substrate shown in Scheme 2 can be obtained. (Note that Tyr$^m$ represents a tyrosine residue which has been macrocyclized to the thiazole, T as opposed to Tyr which stands for a typical tyrosine residue itself). Following the sequential steps of Fmoc deprotection using standard conditions well known in the art for such deprotection, coupling with thia-glycine ($^T$G) using standard peptide coupling conditions as described above and known in the art, reduction of the thiazole aldehyde (with reducing agents such as sodium borohydride and those others discussed above and known in the art), and closing of the macrocycle with acid (preferably TfOH or MsOH) as discussed above will give the C-terminal and N-terminal double macrocycle stabilized peptides (for example $^T$G-Ala-Ala-Ala-Tyr$^m$-Ala-Ala-Gly-Tyr$^m$-Ala-Ala-Ala-3$^T$ (SEQ ID NO. 7) double peptide macrocycle shown in Scheme 2 above).

(c) Preparation of Internally Cyclized MSPs

The making of the internal MSPs starts with the preparation of the functionalized amino acids suitable for incorporating the amino acids internally in a peptide sequence. Thus, the present invention provides the composition of novel thiazole containing internal amino acid (a.a.$^T$) reagents shown in Formula 12 and a method for their synthesis. These reagents include, but are not limited to Lys$^T$, Orn$^T$, DAB$^T$, and DAP$^T$ analogs (Formula 12) as well as similar reagents derived by substitution of their corresponding methylene carbons (with groups such as methyl, gem-dimethyl, alkyl substitution, and the like).

For example, DAB$^T$, is derived from (S)-tert-butyl 4-amino-2-(tert-butoxycarbonylamino)butanoate and using a similar method as shown in the preparation of $^T$G and $^T$P to fashion the 2-aminothiazole ring from the free amino group by, for example, first converting the unprotected 4-amino group of (S)-tert-butyl 4-amino-2-(tert-butoxycarbonylamino)butanoate to a thiourea and then by employing a common synthetic method known in the art for thiazole ring construction as the "Hantzsch reaction" for conversion of the thiourea into the 2-aminothiazole ring. Similarly provided are DAP$^T$, Orn$^T$, and Lys$^T$ as shown in Formula 12. Formula 12 is further specified with C-5 thiazole substitution with group "U" defined specifically as aldehyde (CHO) and its derived alcohol (CH$_2$OH). Furthermore, the aldehyde form is considered "unactivated" and the alcohol form is considered "activated" for the macrocyclization chemistry described herein. Groups R$_1$, R$_3$, and R$_4$ are also defined in the first aspects of this invention hereinabove, with R$_3$ preferentially being H or CH$_3$. While the natural (L) amino acid stereochemistry is shown, the (D) is also claimed. The aldehyde (for U=CHO) can be protected, for example, as an acetal, with groups (such as ethylenedioxy) that are standard and well-known in the art for making acetals from aldehydes. The number of methylene carbons in the side chain is defined by integer n, where n=1 refers to DAP$^T$, n=2 for DAB$^T$, etc. as shown in Formula 12. Note also that the methylene carbon positions defined by integer n, may be, all together or separately, differentially substituted with substituents, particularly lower (C$_1$-C$_7$) alkyl carbon substituents, such as methyl and gem-dimethyl, or such n methylene substituents may be taken together to form a ring, preferentially 3- to 7-membered. Formula 12 bear groups differentially protected with groups P$_1$ and P$_2$ which represent all such common groups known in the art for protection of amino with P$_1$ (such as Boc, Fmoc and the like) and carboxyl with P$_2$, (such as 1-butylester, alkyl ester, allyl ester and the like). For the parent acids and amines, P$_2$ and P$_1$ are each hydrogen, respectively.

Formula 12

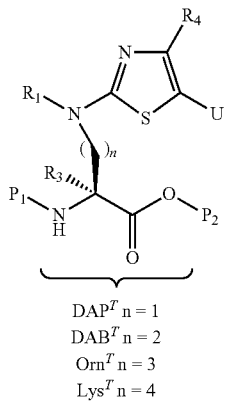

DAP$^T$ n = 1
DAB$^T$ n = 2
Orn$^T$ n = 3
Lys$^T$ n = 4

U = CHO and CH$_2$OH
R$_3$ = H, CH$_3$
Lys$^T$, Orn$^T$, DAB$^T$, and DAP$^T$ analogs
P2 = H (preferred) and acid protecting groups such as esters for example
P1 = H (preferred) and amine protecting groups, such as Boc for example In another, embodiment, this invention provides the composition of novel thiazole containing internal amino acid (a.a.$^T$) reagents of Formula 13 and a method for their synthesis. These reagents include, but are not limited to, those combinations of reagents made by standard amide bond formation, using many coupling reagents common in the art and discussed herein above, between those C-terminal capping reagents of Formula 11 with reagents of Formula 14 which are composed themselves of reagents containing two carboxyl moieties and one amine moiety, differentially protected with groups P$_1$ and P$_2$ which represent all such common groups known in the art for protection of amino with P (such as Boc, Fmoc and the like) and carboxyl with P$_2$, (such as t-butylester, alkyl ester, allyl ester and the like). Preferential reagents that are part of the set of reagents represented by Formula 14, include those derived from the common amino acids Asp (aspartic acid) and Glu (glutamic acid) wherein n=1 and 2, respectively, and R$_3$=H. Derivatives of Asp and Glu wherein R$_3$=CH$_3$ are also preferred. Such reagents of Formula 14 are already known in the art, some of which are commercially available (with different groups P$_1$ and P$_2$). It is the products of the amide bond forming reaction of reagents of Formula 11 with those of Formula 14 to give the reagents of Formula 13 which represent this particular embodiment of this invention. Such an amide bond formation between and amine and acid so invoked is common in the art and thus the formation of reagents of Formula 13 is so expected to be exemplified using such common reagents as EDC and the like within the peptide synthesis literature.

Extended Thia-amino acids (internal) reagents

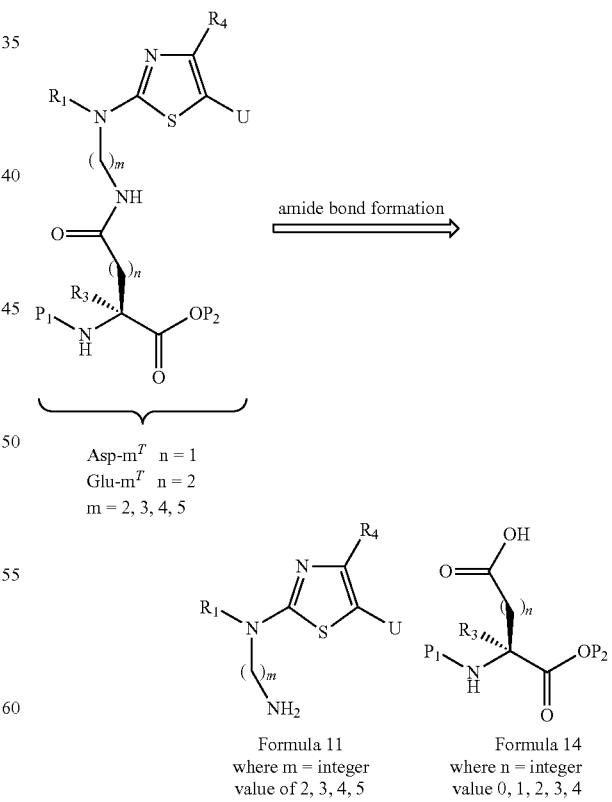

Asp-m$^T$ n = 1
Glu-m$^T$ n = 2
m = 2, 3, 4, 5

Formula 11
where m = integer value of 2, 3, 4, 5

Formula 14
where n = integer value 0, 1, 2, 3, 4

U = CHO and CH$_2$OH
Formula 13

In another, embodiment, this invention provides the composition of novel thiazole containing internal amino acid (a.a.$^T$) reagents of Formula 15, 16, 17 (see Scheme below) and a method for their synthesis. These reagents include, but are not limited to, those combinations of reagents made by standard amide bond formation (using those many coupling reagents common in the art and discussed herein above, for example EDC), between those compounds of Formula 9, 9A, and Formula 10 with common reagents derived from commercially available or easily made derivatives of Lysine (Lys), ornithine (Orn), 2,4-diaminobutyric acid (DAB), and 2,3-diaminopropionic acid (DAP) reagents, to give the products of Formula 15 and 16, respectively. Similarly, standard amide coupling of reagents of Formula 9A with the same commercially available or easily made derivatives of Lysine (Lys), ornithine (Orn), 2,4-diaminobutyric acid (DAB), and 2,3-diaminopropionic acid (DAP) reagents would give the products of Formula 17. Formulae 15, 16, and 17 bear groups differentially protected with groups $P_1$ and $P_2$ which represent all such common groups known in the art for protection of amino with $P_1$ (such as Boc, Fmoc and the like) and carboxyl with $P_2$, (such as t-butylester, alkyl ester, allyl ester and the like). Preferential reagents that are used to make, and therefore compose, part of the set of compounds represented by Formula 15, 16, 17, include those derived from the common amino acids Lysine (Lys), ornithine (Orn), 2,4-diaminobutyric acid (DAB), and 2,3-diaminopropionic acid (DAP), wherein n=4, 3, 2, and 1, respectively, and R3=H or $CH_3$. Such reagents are already known in the art, some of which are commercially available (with different groups $P_1$ and $P_2$). It is the products of the amide bond forming reaction of reagents of Formula 9 and Formula 10 with those Lysine (Lys), ornithine (Orn), 2,4-diaminobutyric acid (DAB), and 2,3-diaminopropionic acid (DAP) reagents to give the reagents of Formula 15, and 16, respectively, that represent this particular embodiment of this invention. Similarly, reagents of Formula 9A can be similarly made and coup led with these Lysine (Lys), ornithine (Orn), 2,4-diaminobutyric acid (DAB), and 2,3-diaminopropionic acid (DAP) reagents to give the compounds of Formula 17. Such an amide bond formation between an amine and a carboxylic acid so invoked is common in the art, and thus the formation of reagents of Formulae 15, 16, and 17 is so obviously expected to be successfully accomplished and exemplified using such common reagents as EDC and the like within the peptide synthesis literature.

Extended Thia-amino Acids (Internal) Reagents

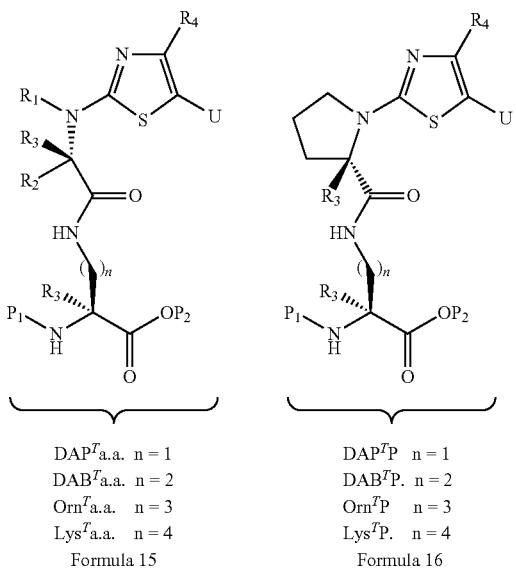

DAP$^T$a.a. n = 1
DAB$^T$a.a. n = 2
Orn$^T$a.a. n = 3
Lys$^T$a.a. n = 4
Formula 15

DAP$^T$P n = 1
DAB$^T$P. n = 2
Orn$^T$P n = 3
Lys$^T$P. n = 4
Formula 16

-continued

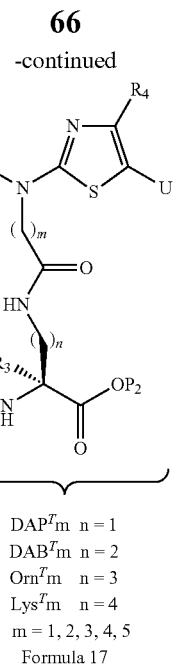

DAP$^T$m n = 1
DAB$^T$m n = 2
Orn$^T$m n = 3
Lys$^T$m n = 4
m = 1, 2, 3, 4, 5
Formula 17

U = CHO and $CH_2OH$
R1, R2, R3, R4 as defined in Formula 9 and 10
P1 and P2 and n are as defined in Formula 12, 13, 14
m ad defined as in Formula 11

Formula 15 $\xrightarrow{\text{amide bond formation}}$ Formula 9 + DAP, DAB, Orn, Lys reagents Formula 16 $\xrightarrow{\text{amide bond formation}}$ Formula 10 + DAP, DAB, Orn, Lys reagents Formula 17 $\xrightarrow{\text{amide bond formation}}$ Formula 9A + DAP, DAB, Orn, Lys reagents A representative syntheses for DAB$^T$ is described in specific Examples 48, 49, 50, and 51 using the synthetic sequence shown below.

Synthesis of DAB$^T$

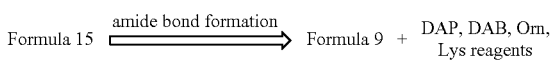

Ex 48

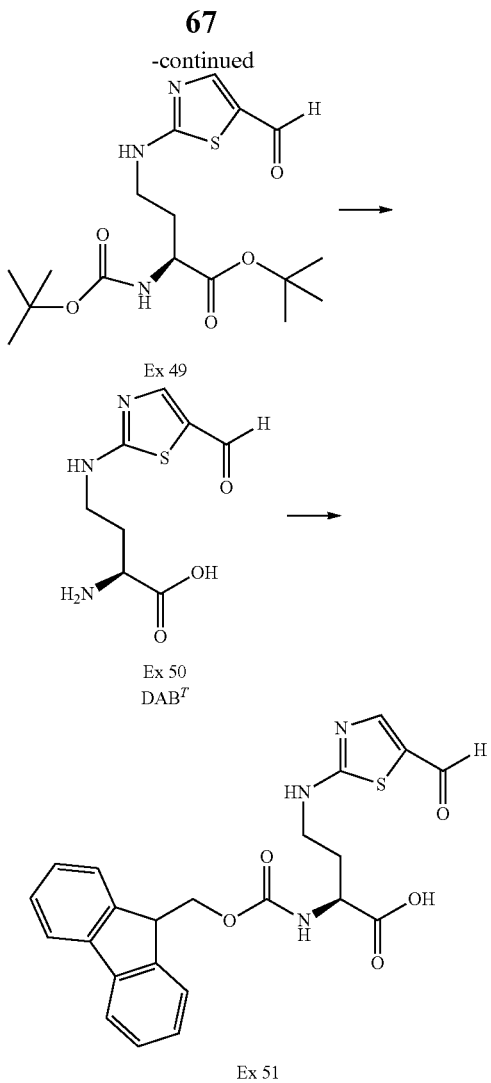

Ex 49

Ex 50
DAB$^T$

Ex 51

As shown above for DAB$^T$, thiophosgene followed by ammonia is employed therein for forming the corresponding thiourea from the amine, but other reagents well-known in the art for this type of conversion such as 1,1'-thiocarbonyldipyridin-2(1H)-one, and thiocarbonyldiimidazole can also be employed.

In the case of primary amines, thiophogene and related reagents are known to generate an isothiocyanate which is then converted to the corresponding thiourea derivative by treatment preferably with ammonia (for example see $^T$G synthesis above). In the case of tertiary amines ($R_1$ in Formulae 12-13 is carbon), thiophogene and related reagents are known to generate a carbothioyl chloride or related intermediate which is then converted to the corresponding thiourea derivative by treatment preferably with ammonia. These thiourea intermediates are then used to fashion the 2-aminothiazole ring system using a substrate such as commercially available 2-bromomalonaldehyde, using either neutral, acidic, or basic reaction conditions (such as triethylamine, diisopropylethylamine, sodium acetate/acetic acid, etc) in a variety of typical solvents (such as THF, dioxane, DMF, etc). This reaction, which constructs the thiazole ring system, is related to the old and well-known (in the art) "Hantzsch reaction" for the synthesis of thiazoles. Deprotection of a standard protecting group for an amino group and carboxyl group known in the art (such as acid induced N-Boc deprotection to $NH_2$ or NHR, and acid-induced O-t-butyl ester deprotection to $CO_2H$) then gives, for example, the thiazole amino acid of Example 50. Protection of the amine moiety of Example 50 with Fmoc under standard conditions known in the art gives, for example, Fmoc DAB$^T$ (shown above).

Syntheses of internal macrocyclic peptides and corresponding internal MSPs, and internal macrocycle stabilized α-helical peptides are exemplified in Schemes 3-4.

For example in Scheme 3, the Fmoc-Boc-DAP-Phe-CONH$_2$ dipeptide (made in one step from commercial reagents as shown in Example 84) is combined (following standard Fmoc removal with piperidine, see Example 85) with the Fmoc-Tyr-Ala-Ala-Gly-CO$_2$H tetrapeptide (SEQ ID. NO. 20), made using automated peptide synthesis) in a standard peptide coupling reaction using, for example, EDC to give the Fmoc-Tyr-Ala-Ala-Gly-DAP-Phe-CONH$_2$ (SEQ ID NO. 21) hexapeptide product of Example 86 (after Boc deprotection). Using EDC as the peptide coupling reagent, $^T$G is then reacted with the free amine of Example 86 to give the product of Example 87 shown in Scheme 3. There are many reagents and conditions used in the art for such a common peptide coupling reaction, many of which are employed to eliminate or reduce epimerization of the amino acid bearing α-carbon. There are numerous review articles of this subject. The reagent combination EDC/HOAt and weak base N-methylmorpholine are employed below in Scheme 3. The choice of coupling reagent is by no means limited to EDC but can be selected from a numerous list of such reagents well-known in the field. In the example in Scheme 3, the product of Example 87 has an aldehyde group which is considered to be "unactivated" towards the subsequent macrocyclization. When this peptide (aldehyde; unactivated) is reduced to the corresponding primary alcohol, it is considered to be "activated" for the subsequent acid-induced macrocyclization reaction. The reduction of the aldehyde with sodium borohydride is shown in Scheme 3 using a solvent consisting of an ethanol water mixture, but this reaction is not limited to these conditions since other solvents and reducing reagents well-known in the art for the reduction of aldehydes could also be employed. When this peptide (alcohol; activated) intermediate is treated with acid, for example preferably trifluoromethanesulfonic acid (TfOH) or methanesulfonic acid (MsOH) in a suitable solvent, for example preferably nitromethane or nitroethane, macrocyclization to the 26-membered internal peptide macrocycle shown in Scheme 3 is expected to occur, based on the examples of similarly sized macrocyclizations already discussed hereinabove. Various other inorganic and organic acids, including aqueous acidic buffers, as well as other solvents, could be expected to also facilitate this macrocyclization.

In addition, the internal peptide macrocycle depicted in Scheme 3 bears a primary amide derivative (CONH$_2$) at the tyrosine carboxyl center, but this center could also have been chosen to be an appropriately protected acid, for example a tertiary-butyl ester. Under such acidic conditions as TfOH/nitromethane or nitroethane used in the macrocyclization, the tertiary-butyl ester would be readily converted to the carboxylic acid. Such a carboxylic acid could then be used in standard peptide coupling reactions and methods (such as solid phase peptide synthesis) to assemble one or many additional amino acids, (a.a.)$_z$, to form N-protected-N-terminal MSPs of Formula 18, wherein the N-terminal amine is protected, for example with Fmoc (shown below), Boc, or other well known N-protecting groups in the art. Standard deprotection of said N-protecting group (for example Fmoc shown below) gives the free amino (NH$_2$) group and such an amine could then be used in standard peptide coupling reactions and methods (such as solid phase peptide synthesis) to assemble one or many additional amino acids, $(a.a.)_x$, to form many different internal MSPs of Formula 19.

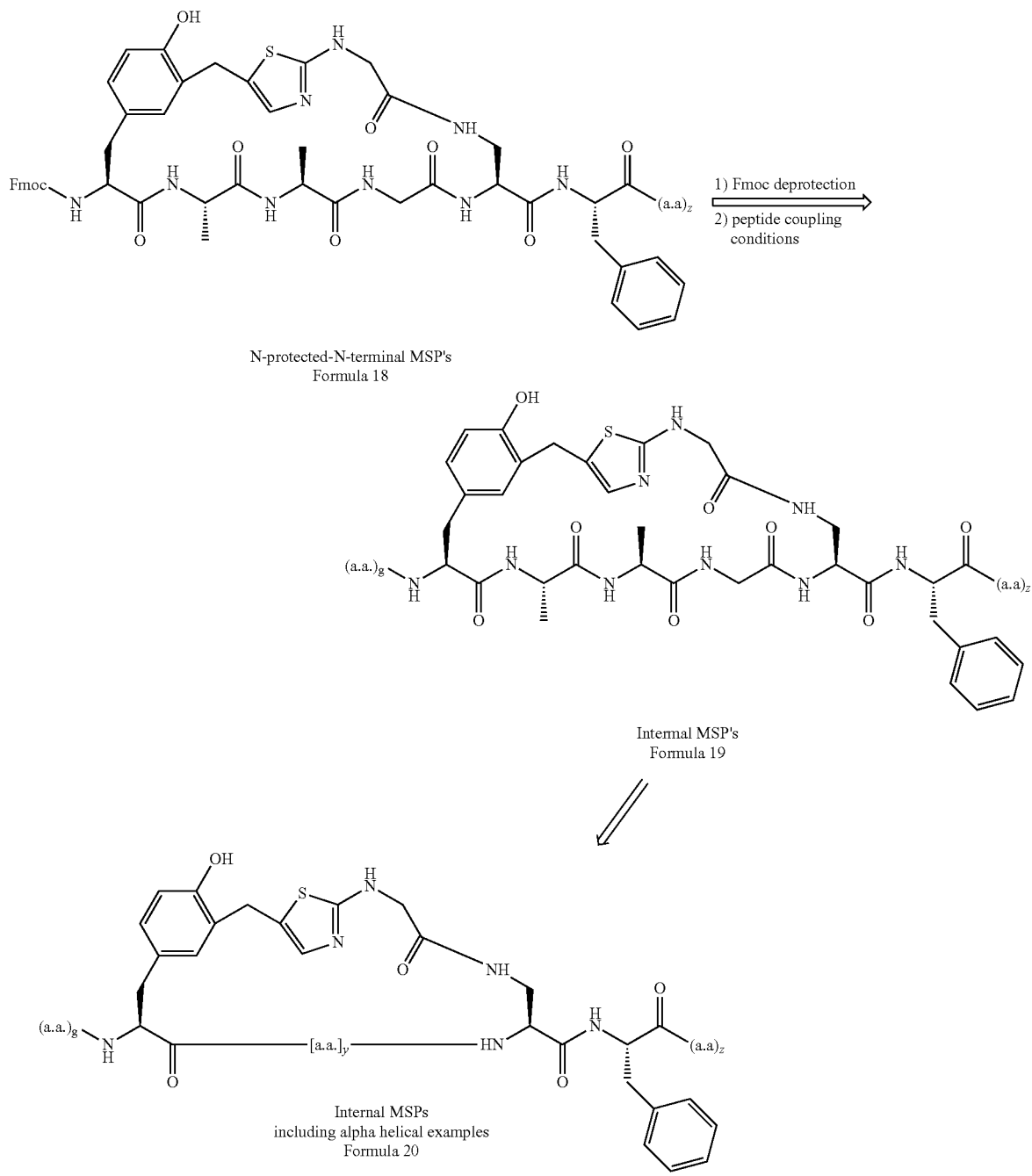

N-protected-N-terminal MSP's
Formula 18

Internal MSP's
Formula 19

Internal MSPs
including alpha helical examples
Formula 20

The appropriate selection and number of amino acids within the macrocycle itself $(a.a.)_y$ and at both the N-terminal end $(a.a.)_x$ and C-terminal end $(a.a.)_z$, external to the macrocycle, would be expected to control the α-helical content of the internal MSPs thus synthesized (represented by Formula 20). Moreover, the macrocycle itself would be expected to enhance the α-helicity of a corresponding linear peptide (not macrocyclized) if constructed appropriately. For example, preferable if the macrocycle had i, i+3 (or i, i–3), i+4 (or i–4), i+7 (or i–7), or i+11 (or i–11) amino acids within the macrocycle itself, one would expect this configuration to enhance α-helicity of these internal MSPs. Many such internally MSPs of Formula 20 would be expected to be α-helical, as controlled by the selection of the number and type of amino acids internal and external to the macrocyclic portion as discussed above. Moreover, the linking element which connects the thiazole ring to the peptide shown in Formula 20 is shown, for example, as the $DAP^7G$ represented in Formula 15 discussed hereinabove, but could also have been selected from those compositions described in Formulae 12, 13, 16, and 17.

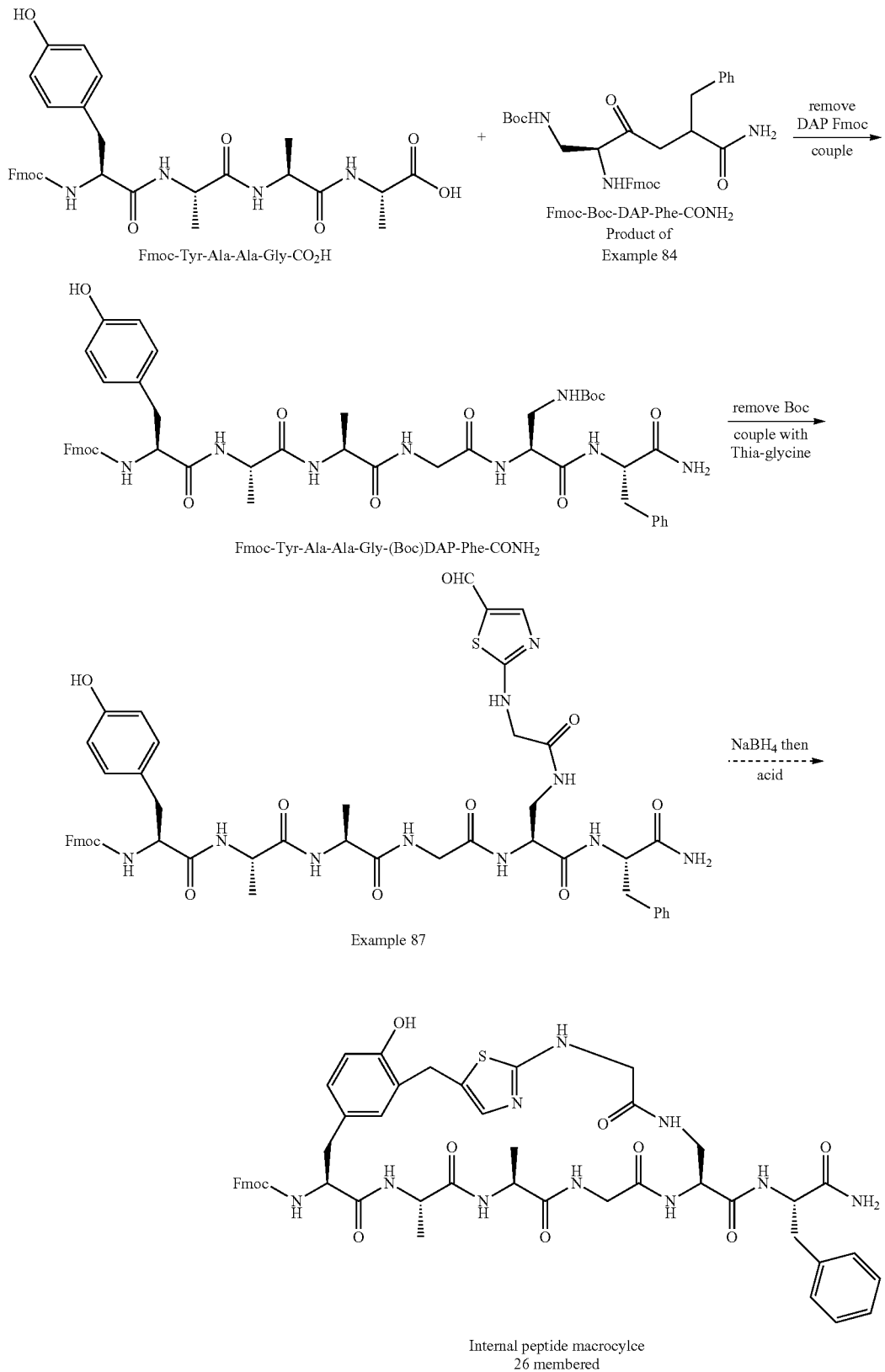

-continued

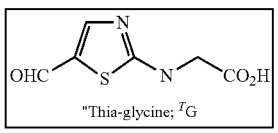
"Thia-glycine; $^TG$"

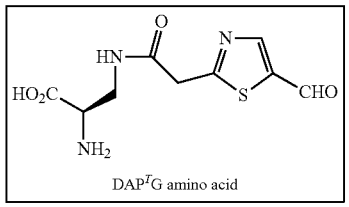
$DAP^TG$ amino acid

In another embodiment, this invention provides a method for the synthesis of terminal and internal double MSPs and therefore also a method for the synthesis of such double macrocycle stabilized α-helical peptides as exemplified in Scheme 4. For example, the Fmoc-Tyr$^m$-Ala-Ala-Gly-DAP$^T$G-Phe-CONH$_2$ (SEQ ID NO. 8) macrocycle shown in Scheme 4 could be readily transformed using standard peptide coupling conditions and protecting group deprotection known in the art and as discussed above, to give the internal and terminal double MSP of Formula 21 shown in Scheme 4.

(Note that Tyr represents a tyrosine residue which has been macrocyclized to the thiazole, T, as opposed to Tyr which stands for a typical tyrosine residue itself). Finally, and as discussed above for related examples, Formula 21 implicates Formula 22. Moreover, the linking element which connects the thiazole ring to the peptide shown in Formula 22 is shown, for example, as the DAP$^T$G represented in Formula 15 discussed hereinabove, but could also have been selected from those compositions described in Formulae 12, 13, 16, and 17.

Formula 22

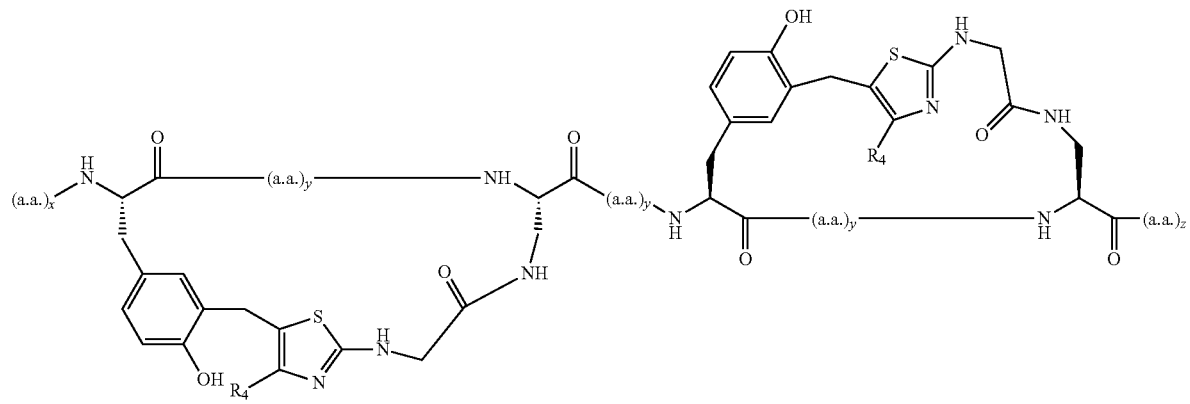

Terminally and Internally
double macrocyclized peptides
including alpha helical examples Scheme 4
"Plug and Play" internal macrocyclic amino acid derivative for making an α-helical peptide
with potential for double macrocycliztion

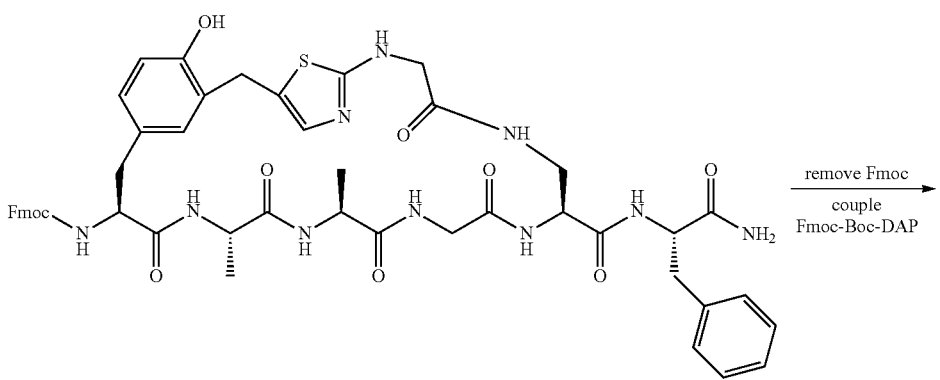

Fmoc-Tyr$^m$-Ala-Ala-Gly-DAP$^T$G-Phe-CONH$_2$ macrocycle

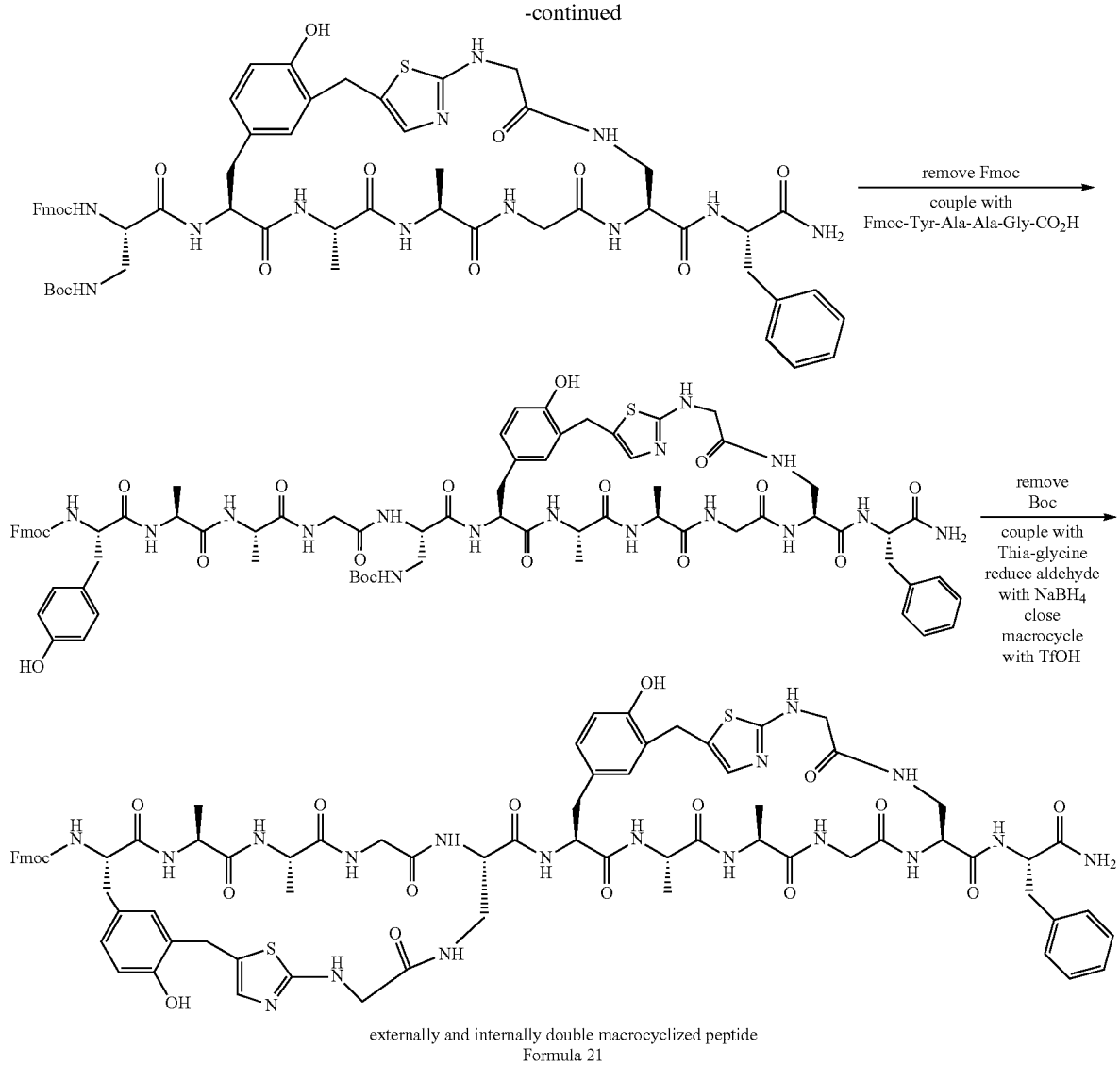

externally and internally double macrocyclized peptide
Formula 21

(d) Preparation of Macrocyclic Peptides Containing Natural Product Templates and Organic Macrocycles The following Schemes describe the method for the synthesis of macrocyclic peptides containing natural product templates, wherein the natural product template contains an electron rich aromatic ring (the "nucleophile", such as phenyl and substituted phenyl (for example substituted with alkoxy or hydroxyl groups) which is capable of reacting with the imino-quinone methide type intermediate (the "electrophile") generated from the activation (with suitable activation (with suitable acid) of 2-aminothiazole-5-carbinols, which have been incorporated into the peptide portion itself, using the various reagents, which are also considered embodiments of this invention, containing such thiazoles discussed hereinabove in the context of MSPs. For example, the natural product anisomycin contains a p-methoxyphenyl moiety as well as a secondary amine (Scheme 5). Starting with anisomycin, the synthetic sequence is executed as shown in Scheme 5 and delineated in Examples 39-46 in the experimental section. This sequence culminates in the successful formation (in good yield) of a 22-membered macrocyclic peptide wherein the anisomycin template encompasses a portion of such macrocycle. The steps applied to this sequence were of the generally the same type and applied the same reagents, or type of reagents, as already described hereinabove for the MSPs. By variation of the number and variety of amino acids within the peptide chain, some of the macrocycles containing the anisomycin template which could be synthesized with this technology are shown in Formula 23. While Formula 23 represents one type of macrocycle, one can imagine using the other thiazole reagents discussed herein above, and which are also embodiments of this invention, to synthesize a wide variety of similar macrocycles. Moreover, if one used another natural product (instead of anisomycin) which also contains a nucleophilic aromatic ring, the macrocyclic peptides represented generally by Formula 24 could be similarly synthesized. In fact it is obvious that one aspect of the utility of the natural product template is to simply provide bifunctional reactivity (i.e., NH group in anisomycin to attach to a carboxyl of another amino acid and aromatic ring needed to participate in the macrocyclization). Therefore, a bifunctional reagent (for example, 4-methoxyphenethylamine), could be used in place of the natural product template to give organic macrocycles of general Formula 25.
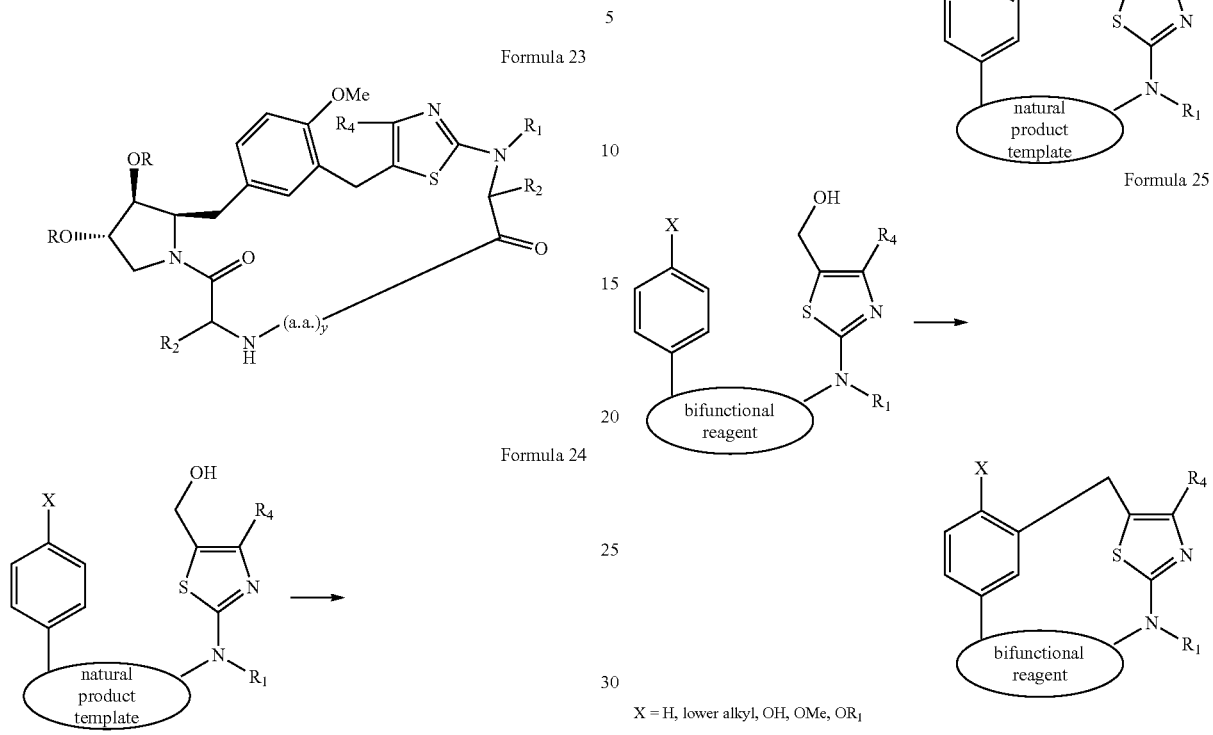
Formula 23
Formula 24
X = H, lower alkyl, OH, OMe, OR₁
Formula 25
Scheme 5
Synthesis of a natural product containing (anisomycin) peptide macrocycle
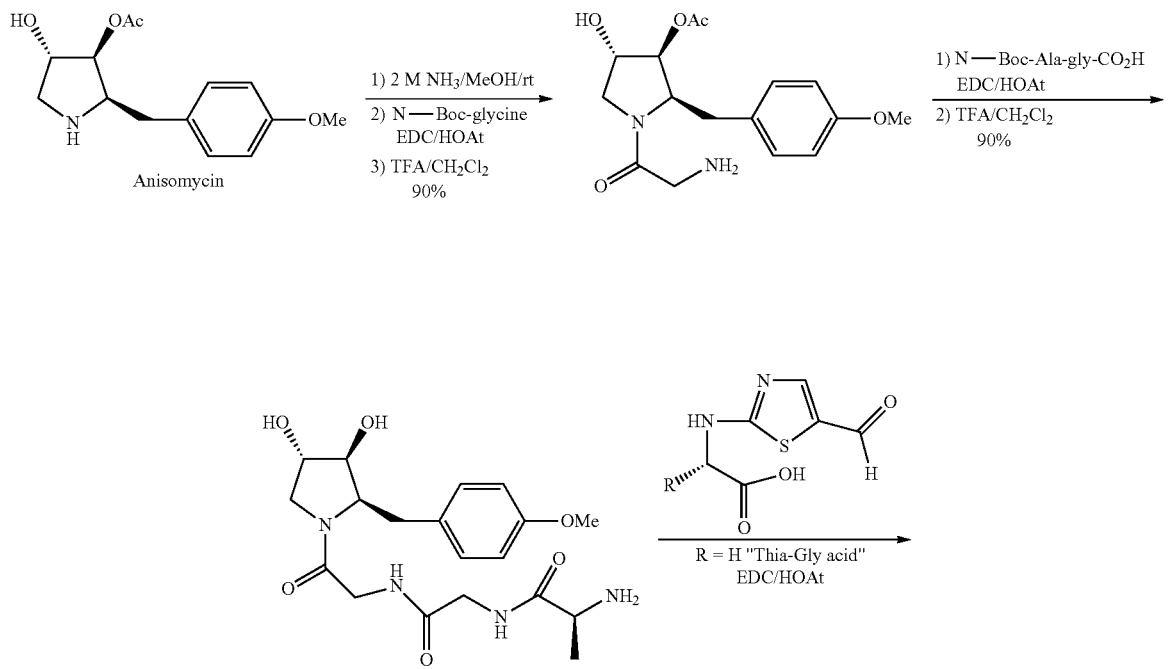

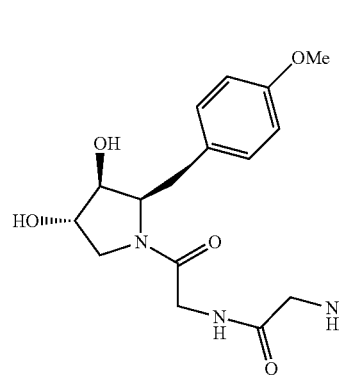
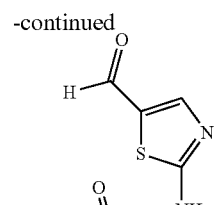
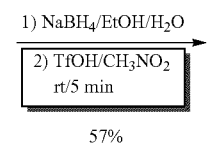

1) NaBH$_4$/EtOH/H$_2$O
2) TfOH/CH$_3$NO$_2$
rt/5 min

57%

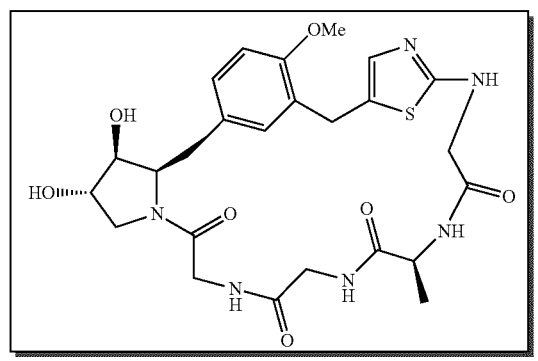

anisomycin dio; G-G-A-$^T$G
macrocylce
(22 membered)

(e) Linking Two Tyrosine Containing Peptides Together

In another embodiment, this invention provides the composition of novel thiazole containing bifunctional (TnT) reagents of Formulae 26-27 and a method for their synthesis. These reagents include, but are not limited to, T0T, T1T, T2T, T3T, T4T analogs as well as similar reagents derived by substitution of their corresponding methylene carbons (with groups such as methyl, gem-dimethyl, alkyl substitution, and the like). Within this embodiment is also included higher order reagents of Formulae 28-31, as well as related reagents (not shown) that would be obviously included within the spirit of these aforementioned reagents. For example, T3T, is derived from 1,3-diaminopropane and using a similar method as shown in $^T$G and $^T$P syntheses to fashion the 2-aminothiazole ring from the free amino groups by, for example, first converting each of these 2 amino groups to a thiourea and then by employing a common synthetic method known in the art for thiazole ring construction as the "Hantzsch reaction" for conversion of the thiourea into the 2-aminothiazole rings. Similarly provided are T2T and T4T as shown in Formula 27 as well as the higher order reagents shown in Formulae 28-31. Formulae 26-31 are further specified with C-5 thiazole substitution with group "U" defined specifically as aldehyde (CHO) and its derived alcohol (CH$_2$OH). Furthermore, the aldehyde form is considered "unactivated" and the alcohol form is considered "activated" for the macrocyclization chemistry described herein. Groups R$_1$, R$_3$ and R$_4$ are also defined in the first aspects of this invention hereinabove, with R$_3$ preferentially being H or CH$_3$, or Boc. While the natural (L) amino acid stereochemistry is shown, the (D) is also claimed. The aldehyde (for U=CHO) can be protected, for example, as an acetal, with groups (such as ethylenedioxy) that are standard and well-known in the art for making acetals from aldehydes. The alcohol group (for U=CH$_2$OH) can be similarly protected at the OH with all those common groups standard in the art for protecting alcohols. The number of methylene carbons in the side chain is defined by integer n (but n not equal to 0 in Formula 27), where n=1 refers to T2T, n=2 refers to T3T, etc. as shown in Formula 27. Note also that the methylene carbon positions defined by integer n, may be, all together or separately, differentially substituted with substituents, particularly lower (C$_1$-C$_7$) alkyl carbon substituents, such as methyl and gem-dimethyl, or such n methylene substituents may be taken together to form a ring, preferentially 3- to 7-membered.

(f) Linking Two or More Tyrosine Containing Peptides Together

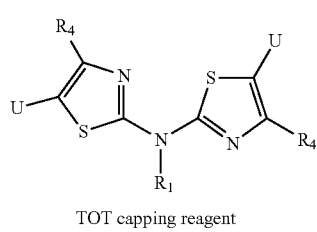

Formula 26

TOT capping reagent

Formula 27

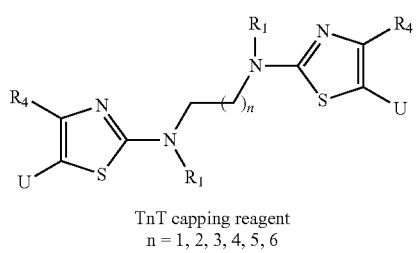

TnT capping reagent
n = 1, 2, 3, 4, 5, 6

Formula 28

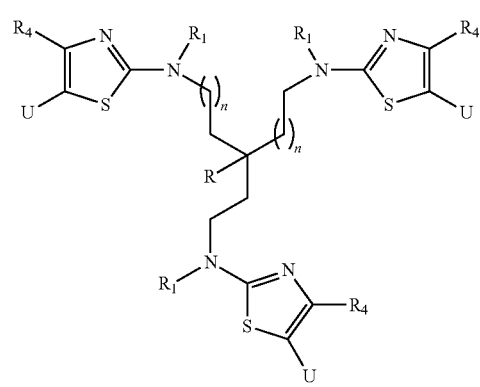

Formula 29

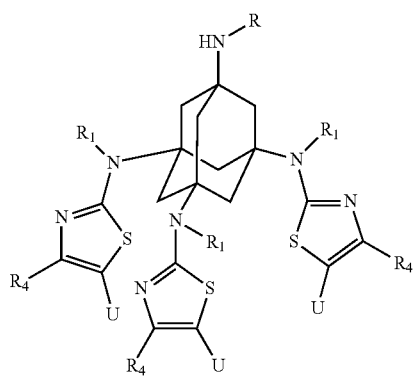

Formula 30

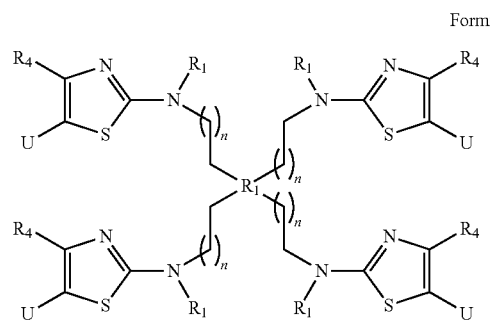

Formula 31

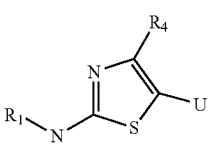

note n represents n numbers of CH$_2$, or CR$_2$ groups, optionally substituted
U = CHO and CH$_2$OH A representative synthesis of T3T is described in specific Examples 55, 56, and 57 using the synthetic sequence shown below.

Synthesis of 3T3

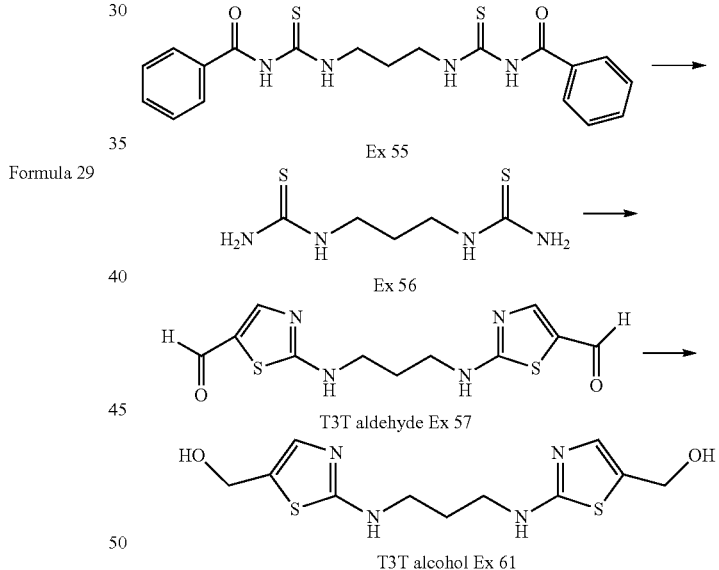

Ex 55

Ex 56

T3T aldehyde Ex 57

T3T alcohol Ex 61

As shown above for T3T, benzoyl isothiocyanate followed by alkaline hydrolysis, is employed therein for forming the corresponding symmetrical bis-thioureas from the 1,3-diaminopropane, but other reagents well-known in the art for this type of conversion such as thiophosgene, 1,1'-thiocarbonyldipyridin-2(1H)-one, and thiocarbonyldiimidazole can also be employed. In the case of primary amines, thiophogene and related reagents are known to generate an isothiocyanate which is then converted to the corresponding thiourea derivative by treatment preferably with ammonia (for example see $^T$G synthesis above in Scheme 6). In the case of tertiary amines (R$_1$ in Formulae 26-31 is carbon), thiophogene and related reagents are known to generate a carbothioyl chloride or related intermediate which is then converted to the corresponding thiourea derivative by treatment preferably with ammonia. These thiourea intermediates are then used to fashion both of the 2-aminothiazole ring systems using a substrate such as commercially available 2-bromomalonaldehyde, using either neutral, acidic, or basic reaction conditions (such as triethylamine, diisopropylethylamine, sodium acetate/acetic acid, etc) in a variety of typical solvents (such as THF, dioxane, DMF, etc). This reaction, which constructs the thiazole ring system, is related to the old and well-known (in the art) "Hantzsch reaction" for the synthesis of thiazoles gives the TnT reagents (for example T3T, as shown above).

In another embodiment, this technology can be used to link together two tyrosine peptides using the bifunctional thiazole reagent, TnT, as shown below in Scheme 6. Therein is shown the case where the same tyrosine containing peptide is linked together using a bifunctional TnT reagent (for example T3T) although two different peptides may be similarly linked.

Alternatively, tri or tetrafunctional thiazole reagents such as those shown in Formulae 28-31 may be used to link 3 or 4 peptides containing tyrosine together as well. For example, to demonstrate this embodiment, two tyrosine containing dipeptides, $NH_2$-G-Y—$CONH_2$, were linked together using the T3T reagent to give the G-Y-T3T-Y-G-Y-G (SEQ ID NO. 22) dimer in 66% isolated yield using TfOH in nitromethane at room temperature. This product was then further elaborated by standard amide peptide coupling using EDC and N-Fmoc-tyrosine as also shown in Scheme 7 to attach tyrosines on each of the two peptides. In principle, such an intermediate can be then reacted again with T3T or the like to form large macrocyclic, double-macrocyclization dimeric peptide macrocycles as shown in Scheme 8.

Scheme 6
Linking two or more tyrosine containing peptides with bi, tri, or tetra-functional thiazole reagents, TnT, etc.

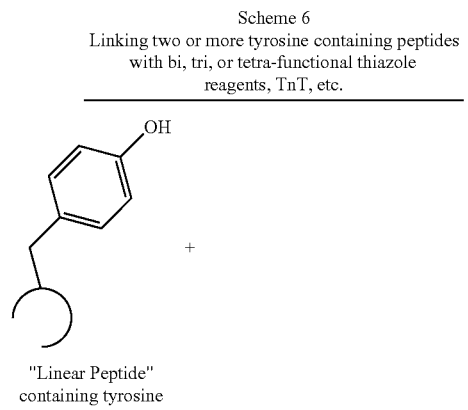

"Linear Peptide" containing tyrosine

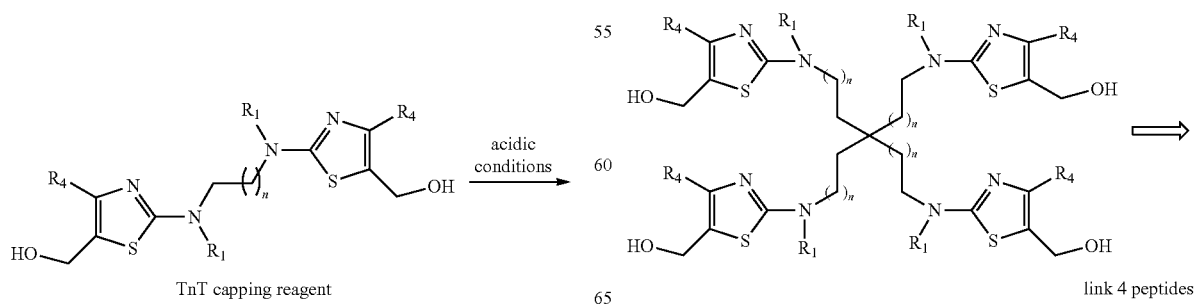

TnT capping reagent

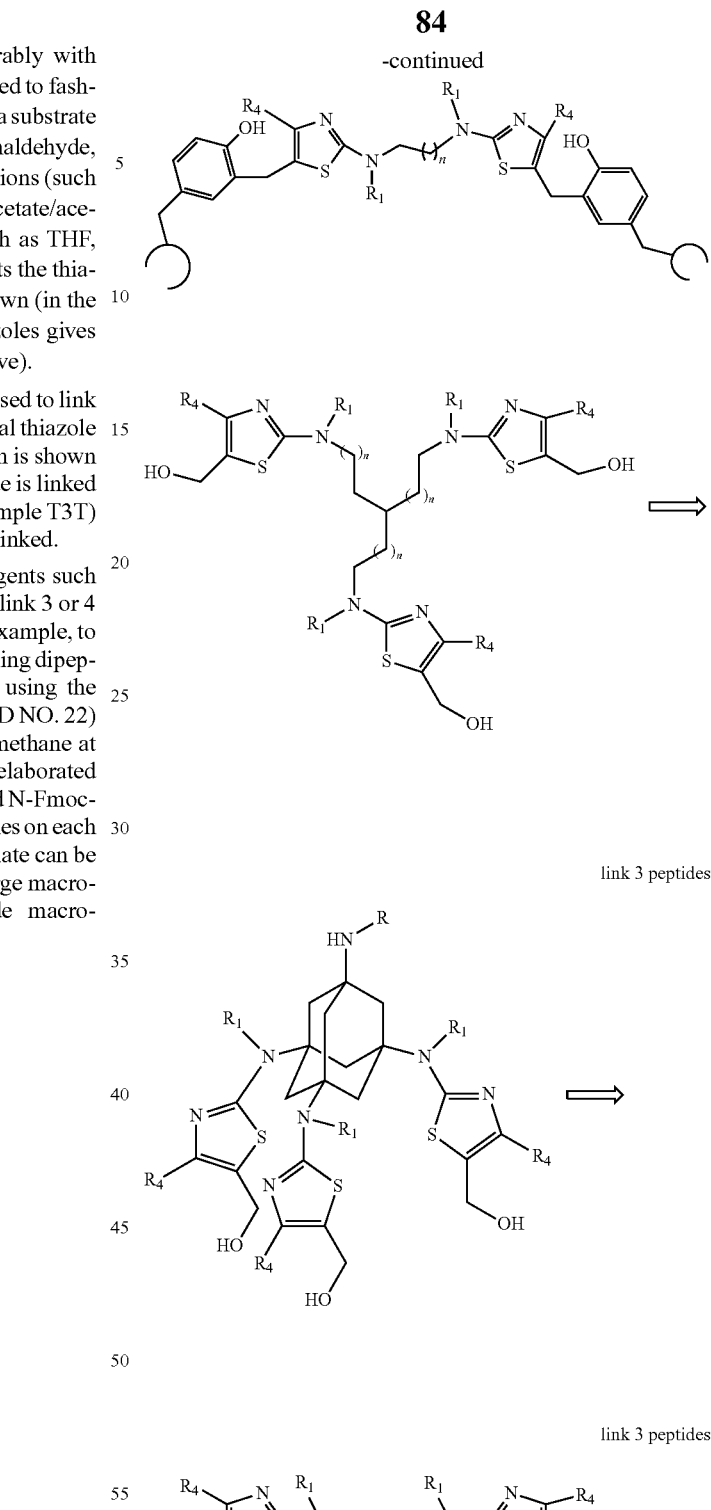

85
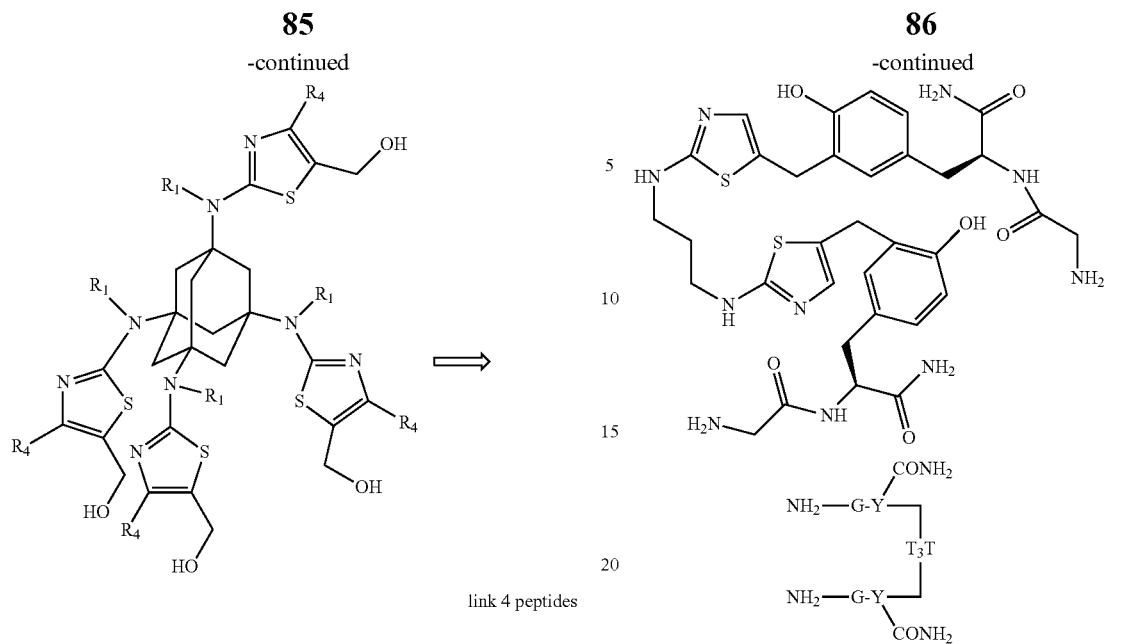
Scheme 7
Linking of two dipeptides, Gly-Tyr-amide, with T3T
86
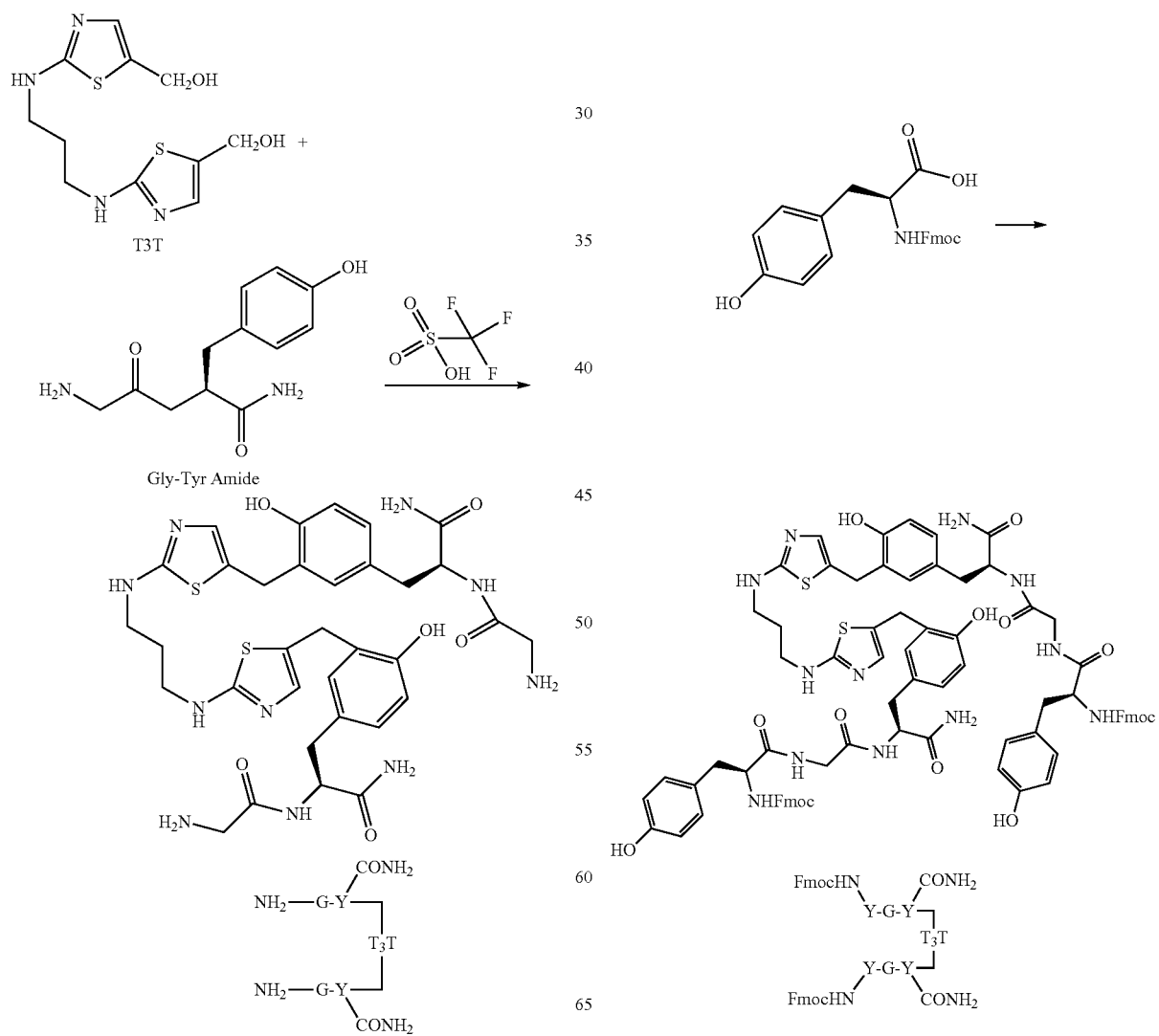
link 4 peptides Scheme 8

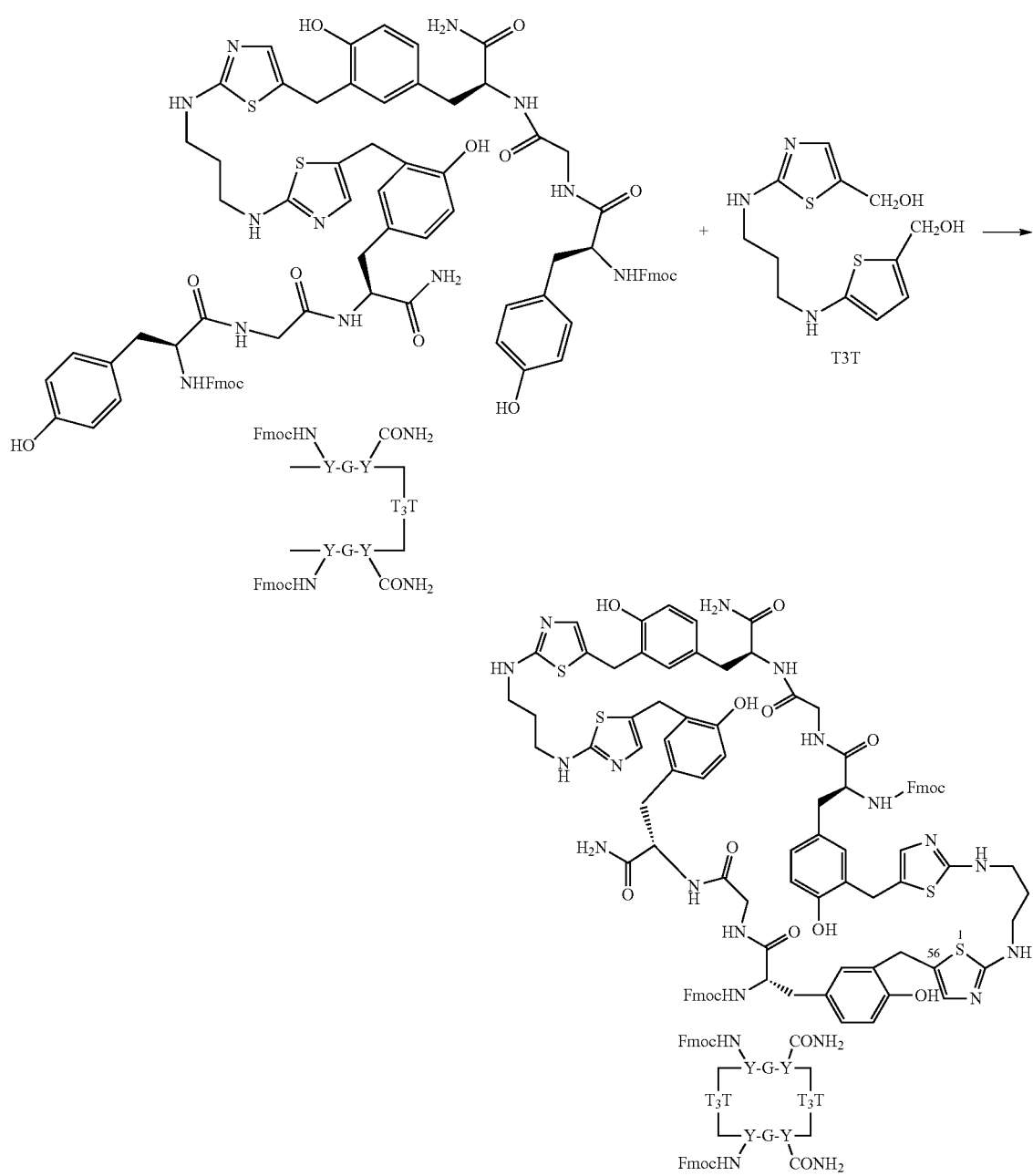

SPECIFIC EXAMPLES

The present invention is further defined in the following Examples. It should be understood that these Examples are given by way of illustration only. From the above discussion and this example, one skilled in the art can ascertain the essential characteristics of this invention, and without departing from the spirit and scope thereof, can make various changes and modifications to the invention to adapt the invention to various uses and conditions. As a result, the present invention is not limited by the illustrative Examples set forth herein below, but rather defined by the claims appended hereto.

All temperatures are in degrees Celsius (° C.) unless indicated otherwise herein.

All reactions were carried out with continuous magnetic stirring under an atmosphere of dry nitrogen. All evaporations and concentrations were carried out on a rotary evaporator under reduced pressure. Commercial reagents were used as received without additional purification. Solvents were commercial anhydrous grades and were used without further drying or purification unless otherwise stated. Nitromethane was purchased from Fluka Chemical Company and was used without further purification. Yields obtained with Fluka nitromethane were generally superior to those where nitromethane was purchased from an alternative supplier. Nitroethane was purchased from Aldrich Chemical Company and was passed through a column of silica gel prior to its use. Flash chromatography is performed using silica gel (EMerck Kieselgel 60, 0.040-0.060 mm).

Abbreviations

AcOH acetic acid
$Ac_2O$ acetic anhydride
$CH_2Cl_2$ dichloromethane
DMAP dimethylaminopyridine
DIEA diisopropylethylamine
DMF dimethylformamide
DMSO dimethylsulfoxide
EDC N-Ethyl-N'-(3-dimethylaminopropyl)carbodiimide hydrochloride
Et ethyl
$Et_2O$ diethyl ether
EtOAc ethyl acetate
EtOH ethanol
$Et_3N$ triethyl amine
$Et_3SiH$ triethylsilane
h hour
HCl hydrochloric acid
iPr isopropyl
iPrOH isopropanol
Me methyl
MeOH methanol
min minute
NBS N-bromosuccinimide
n-BuLi n-butyl lithium
NaOMe sodium methoxide
$PMe_3$ trimethyl phosphine
TBSCl tert-butyldimethylsilylchloride
TFA trifluoroacetic acid
$Tf_2O$ trifluoromethylsulfonic anhydride
THF tetrahydrofuran
VCD vibrational circular dichroism
L liter
mL milliliter
μL microliter
g gram(s)
mg milligram(s)
mol moles
mmol millimole(s)
RT or rt room temperature
ret. T HPLC retention time (minutes)
sat or sat'd saturated
aq. aqueous
TLC thin layer chromatography
TFA trifluoroacetic acid
HPLC high performance liquid chromatography
Prep HPLC preparative reverse phase HPLC
LC/MS liquid chromatography/mass spectrometry
MS mass spectrometry
NMR nuclear magnetic resonance
mp melting point
DMF N,N-dimethylformamide
DCM dichloromethane
HOBt N-hydroxybenzotriazole
HCTU 2-(6-Chloro-1-H-benzotriazol-1-yl)-1,1,3,3-tetramethyluronium hexafluorophosphate
DIEA Diisopropylethylamine
AcCN acetonitrile
TFA trifluoroacetic acid
RP-HPLC reverse phase high performance liquid chromatography LC/MS high performance liquid chromatography/mass spectrometry
MS or
Mass Spec mass spectrometry All final products were characterized by $^1H$ NMR, HPLC, electrospray ionization (ESI MS) or atmospheric pressure ionization (API MS) mass spectrometry. $^1H$ NMR spectra were obtained on either a 500 MHz JEOL or a 400 MHz Bruker instrument. $^{13}C$ NMR spectra were recorded at 100 or 125 MHz. Field strengths are expressed in units of (parts per million, ppm) relative to the solvent peaks, and peak multiplicities are designated as follows: s, singlet; d, doublet; dd, doublet of doublets; dm, doublet of multiplets; t, triplet; q, quartet; br s, broad singlet; m, multiplet.

LC/MS Conditions:

Condition A: PHENOMENEX® Luna 2.0×50 mm 3 μm column, 4 min gradient time, flow rate: 0.8 mL/min; Solvent A: 10% MeOH/90% water/0.1% TFA; Solvent B: 90% MeOH/0% water/0.1% TFA, wavelength at either 220 nM or 254 nM.

Preparative HPLC Conditions:

Condition A: Shimadzu preparative HPLC system using a gradient of Solvent A (10% MeOH/90% water/0.1% TFA) and Solvent B (90% MeOH/10% water/0.1% TFA), monitoring at a wavelength of 254 nM, with flow rate=36 mL/min (unless otherwise noted).

Condition B: Shimadzu preparative HPLC system using a gradient of Solvent A (10% ACN/90% water/0.1% TFA) and Solvent B (90% ACN/10% water/0. % TFA), monitoring at a wavelength of 254 nM, with flow rate=36 mL/min (unless otherwise noted).

Analytical HPLC Conditions:

Condition A: Waters X-Bridge C 18, 3.0×150 mm 3.5 μM (high pH), 10% B-100% B with flow rate mL/min and gradient time 30 min. Solvent A: 95% water/5% MeOH/10 mM ammonium bicarbonate; Solvent B: 95% MeOH/5% water/10 mM ammonium bicarbonate, wavelength 220/254 nM.

Condition B: Waters X-Bridge phenyl, 3.0×150 mm 3.5 μM (high pH), 10% B-100% B with flow rate 1 mL/min and gradient time 30 min. Solvent A: 95% water/5% MeOH/10 mM ammonium bicarbonate; Solvent B: 95% MeOH/5% water/10 mM ammonium bicarbonate, wavelength 220/254 nM.

Condition C: Waters Sunfire C18, 3.0×150 mm 3.5 μM (low pH), 10% B-100% B with flow rate 1 mL/min and gradient time 30 min. Solvent A: 5% ACN/95% water/0.1% TFA; Solvent B: 95% ACN/5% water/0.1% TFA, wavelength 220/254 nM.

Condition D: Waters X-Bridge phenyl, 3.0×150 mm 3.5 μM (low pH), 10% B-100% B with flow rate 1 mL/min and gradient time 30 min. Solvent A: 5% ACN/95% water/0.11% TFA; Solvent B: 95% ACN/5% water/0.1% TFA, wavelength 220/254 nM.

Example 1 tert-Butyl 2-thioureidoacetate

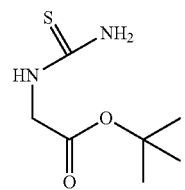

To a magnetically stirred suspension of tert-butyl 2-aminoacetate (11.2 g, 85 mmol) in CH$_2$Cl$_2$ (200 mL) under nitrogen is added 1,1'-thiocarbonyldipyridin-2(1H)-one (21 g, 90 mmol) and the resulting mixture is stirred at room temp. for 18 h. The solvent is removed in vacuo, the residue treated with 2M ammonia in methanol (600 mL, 1200 mmol) and stirred at room temperature for 45 min. The solvent is removed in vacuo and dried under high vacuum to give the title compound as a reddish oil that is used "as is" without further purification in the next step. LC/MS (Condition A): ret. T=2.19 min, (M+H)$^+$ 191—actually see (M−55) 134.95 (this is characteristic of BOC fragmentation pattern).

Example 2 tert-Butyl 2-(5-formylthiazol-2-ylamino)acetate

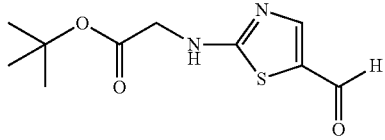 [SMILES: CC(C)(C)OC(=O)CNc1ncc(C=O)s1]

To the crude product from Example 1 in anhydrous THF (200 mL) is added N,N-diisopropylethylamine (25 mL, 143 mmol) followed by 2-bromomalonaldehyde (18.5 g, 123 mmol). The resulting mixture is allowed to stir at room temperature for 18 h, heated to 70° C. for 6 h, and then stirred at room temperature for an additional 18 h. The solvent is removed in vacuo and the residue is partitioned between EtOAc (400 mL) and water (350 mL). The water layer is back extracted with EtOAC (300 mL), the organic layers are combined, washed with brine (1×200 mL), dried over Na$_2$SO$_4$, filtered and the solvent removed in vacuo. The residue is purified by BIOTAGE® Silica gel chromatography on a 300 g Thompson Single Step silica cartridge using a linear gradient from 100% CH$_2$Cl$_2$ to 45% EtOAc/CH$_2$Cl$_2$ over 8 column volumes to give 3.5 g (17%, 2 steps) of the title compound as a tan solid. LC/MS (Condition A): ret. T=2.66 min, (M+Na) 265.09. $^1$H NMR (500 MHz, chloroform-d) δ ppm 9.73 (1 H, s), 7.86 (1 H, s), 4.05 (2 H, s), 1.49 (9 H, s).

Example 3

2-(5-Formylthiazol-2-ylamino)acetic acid

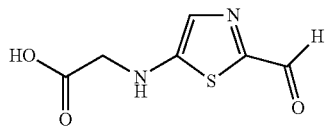 [SMILES: O=Cc1ncc(NCC(=O)O)s1]

To a magnetically stirred solution of material from Example 2 (2.19 g, 9.04 mmol) in CH$_2$Cl$_2$ (50 mL) is added TFA (25 mL, 324 mmol). The resulting solution is allowed to stir at room temperature for 8 h and then evaporated to dryness under a gentle stream of N$_2$ over 18 h. The resulting tan residue is dissolved in CH$_2$Cl$_2$, sonicated briefly and the solvent is removed in vacuo to give 3.05 g (96%) the title compound as a tan solid as a •1.3 TFA salt by weight. LC/MS (Condition A): ret. T=0.82 min, (M+H)$^+$ 187.00. $^1$H NMR (500 MHz, DMSO-d$_6$) δ ppm 9.67 (1 H, s), 9.11 (1 H, br. s.), 8.05 (1 H, s), 4.12 (2 H, d, J=5.19 Hz).

Example 4

(S)-N-((S)-1-Amino-3-(4-hydroxyphenyl)-1-oxopropan-2-yl)-2-(2-(5-formylthiazol-2-ylamino)acetamido)propanamide

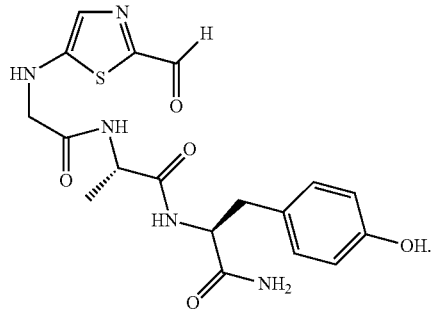 [SMILES: C[C@H](NC(=O)CNc1cnc(C=O)s1)C(=O)N[C@@H](Cc1ccc(O)cc1)C(N)=O]

To a mixture of material from Example 3 (32.2 mg, 0.107 mmol), (S)-2-amino-N-((S)-1-amino-3-(4-hydroxyphenyl)-1-oxopropan-2-yl)propanamide (42.7 mg, 0.170 mmol), EDC (31.7 mg, 0.165 mmol) and 1-hydroxy-7-azabenzotriazole (10.0 mg, 0.073 mmol) is added anhydrous DMF (1.0 mL). The reaction is flushed with N$_2$, treated with N-methylmorpholine (59 μl, 0.537 mmol), flushed with N$_2$ and allowed to stir at room temp for 18 h. The reaction is diluted with DMF and purified by preparative HPLC (Condition A) using a PHENOMENEX® Luna Axia 30×100 mm S10 column from 10% Solvent B to 80% Solvent B over 12 min, ret. T=5.2 min. The product fractions are evaporated to dryness in a speedvac for 18 h to give 26.7 mg (46.7%) of the title compound as a yellow solid as a TFA salt. LC/MS (Condition A): ret. T=1.65 min, (M+H)$^+$ 420.09.

Example 5

(S)-N-((S)-1-Amino-3-(4-hydroxyphenyl)-1-oxopropan-2-yl)-2-(2-(5-(hydroxymethyl)thiazol-2-ylamino)acetamido)propanamide

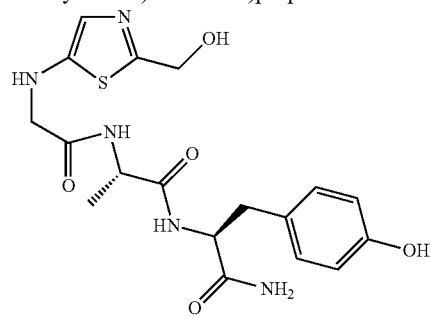

To a suspension of material from Example 4 (26.7 mg, 0.050 mmol) in a mixture of EtOH/Water (4:1) (3 mL) is added sodium borohydride (18.4 mg, 0.486 mmol) in 3 portions over ~5 min. The resulting pale white suspension is allowed to stir at room temp for 3 h. The reaction is diluted with EtOAC (75 mL) and saturated aqueous NH$_4$Cl (12 mL). The water layer is back extracted with EtOAc (6×20 mL), the organic layers were combined, extracted with water (2×10 mL), brine (1×10 mL), dried over Na$_2$SO$_4$, filtered and evaporated to dryness. The aqueous layers were combined, evaporated to dryness, and purified by preparative HPLC (Condition A) using a PHENOMENEX® Luna Axia 30×100 mm S10 column from 5% Solvent B to 45% Solvent B over 10 min, ret. T=4.12 min. The fractions containing the desired product were evaporated to dryness to give 7.3 mg (35%) of a 1:1 mixture of the title compound and its methyl ether as a colorless film as a TFA salt. LC/MS (Condition A): ret. T=0.8 min, (M+Na) 424.12 and ret. T=1.49 min, (M+Na) 444.12.

Example 6

"Thia-G-A-Y" Macrocycle

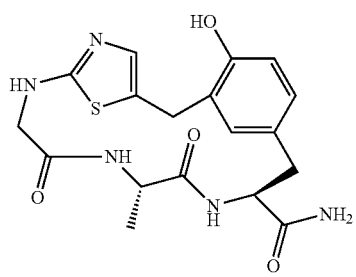 [SMILES: C[C@@H]1NC(=O)CNC2=NC=C(Cc3cc(ccc3O)C[C@@H](C(N)=O)NC1=O)S2]

To a solution of material from Example 5 (7.3 mg, 0.014 mmol) in nitromethane (2.0 mL) is added trifluoromethanesulfonic acid (12.0 µl, 0.136 mmol). The reaction is allowed to stir at room temp for 90 min, then placed in a −20° C. freezer for 18 h. The reaction is warmed to room temperature and allowed to stir for an additional 2.5 h. The solvent is evaporated and the residue purified by preparative HPLC (Condition A) using a PHENOMENEX® Luna Axia 30×100 mm S10 column from 0% Solvent B to 70% Solvent B over 12 min, ret. T=5.45 min. The fractions containing the desired product were evaporated to dryness to give 2.0 mg (56%) of the title compound as a white film as a TFA salt. LC/MS (Condition A): ret. T=1.1 min, (M+H)$^+$ 404.15. Analytical HPLC: (Condition A): >99%, ret. T=7.60 min, (Condition B): >99%, ret. T=8.12 min. $^1$H NMR (500 MHz, methanol-d$_4$) δ ppm 7.23 (1 H, s), 7.07 (1 H, dd, J=8.24, 2.14 Hz), 7.01 (1 H, d, J=1.83 Hz), 6.75 (1 H, d, J=8.24 Hz), 4.52 (1 H, d, J=7.02 Hz), 3.88-4.14 (4 H, m), 3.17 (1 H, dd, J=14.80, 3.20 Hz), 2.80 (1 H, dd, J=15.11, 11.75 Hz), 1.29 (3 H, d, J=6.71 Hz).

Example 7

(S)-N-((S)-1-Amino-3-(4-hydroxyphenyl)-1-oxopropan-2-yl)-2-((S)-2-(2-(5-formylthiazol-2-ylamino)acetamido)propanamido)propanamide

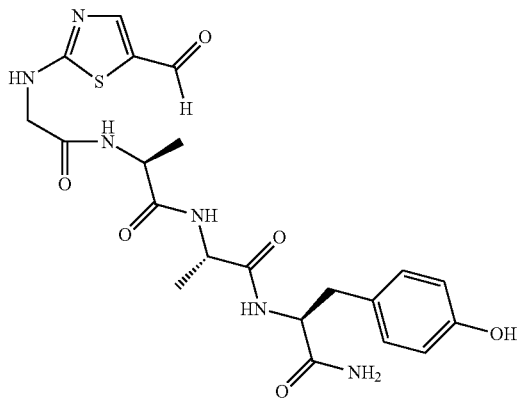 [SMILES: C[C@H](NC(=O)CNc1ncc(C=O)s1)C(=O)N[C@@H](C)C(=O)N[C@@H](Cc1ccc(O)cc1)C(N)=O]

To a mixture of material from Example 3 (62 mg, 0.207 mmol), 1-hydroxy-7-azabenzotriazole (7.2 mg, 0.126 mmol), and (S)-2-amino-N-((S)-1-((S)-1-amino-3-(4-hydroxyphenyl)-1-oxopropan-2-ylamino)-1-oxopropan-2-yl)propanamide (53.8 mg, 0.167 mmol) in anhydrous DMF (2.0 mL) is added sequentially N-methylmorpholine (125 µL, 1.137 mmol) and EDC (51.8 mg, 0.270 mmol). The resulting solution is stirred at room temperature for 6 h, diluted with MeOH (8 mL) and purified by preparative HPLC (Condition A) using a PHENOMENEX® Luna Axia 30×100 mm S10 column from 10% Solvent B to 80% Solvent B over 11 min, ret. T=4.19-5.20 min. The fractions containing the desired product were evaporated to dryness to give 42.4 mg (34%) of the title compound as a yellow solid as a TFA salt. LC/MS (Condition A): ret. T=1.81 min, (M+H)$^+$ 491.15.

Example 8

(S)-N-((S)-1-Amino-3-(4-hydroxyphenyl)-1-oxopropan-2-yl)-2-((S)-2-(2-(5-(hydroxymethyl)thiazol-2-ylamino)acetamido)propanamido)propanamide

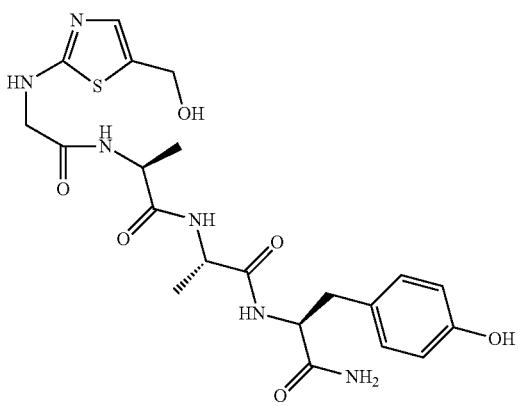 [SMILES: C[C@H](NC(=O)CNc1ncc(CO)s1)C(=O)N[C@@H](C)C(=O)N[C@@H](Cc1ccc(O)cc1)C(N)=O]

To a suspension of material from Example 7 (13.2 mg, 0.022 mmol) in EtOH/H$_2$O (4:1) (1.5 mL) is added solid sodium borohydride (7.8 mg, 0.206 mmol) in 2 equal portions over 1 b. After the addition is complete, the reaction is stirred at room temp for 1.5 h and evaporated to dryness to give the title compound (quantitative yield) as a white solid that is used crude in the next step. LC/MS (Condition A): ret. T=0.94-1.16 min, (M+Na) 515.

Example 9

"Thia-G-A-A-Y" (SEQ ID NO. 9) Macrocycle

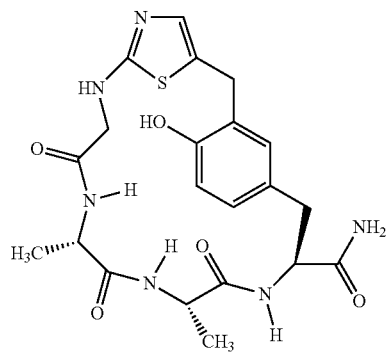 [SMILES: C[C@@H]1NC(=O)CNc2ncc(s2)Cc2cc(ccc2O)C[C@@H](C(N)=O)NC(=O)[C@H](C)NC1=O]

To a magnetically stirred suspension of material from Example 8 in nitromethane (1.5 mL) is added trifluoromethanesulfonic acid (90 μl, 1.013 mmol). The resulting colorless solution is stirred at rt for 4 h, the solvent evaporated off and the residue is purified by preparative HPLC (Condition A) using a PHENOMENEX® Luna Axia 30×100 mm S10 column from 5% Solvent B to 85% Solvent B over 12 min, ret. T=4.63 min. The fractions containing the desired product are evaporated to dryness to give 8.7 mg (70.2%) of the title compound as a white solid as a TFA salt. LC/MS (Condition A): ret. T=1.38 min, (M+H)$^+$ 475.2. Analytical HPLC: (Condition A): >94%, ret. T=8.84 min, (Condition B): >93%, ret. T=9.19 min, (Condition C): >98%, ret. T=2.3 min, (Condition D): >98%, ret. T=2.42 min. $^1$H NMR (500 MHz, methanol-d$_4$) δ ppm 7.19 (1 H, d, J=19.23 Hz), 6.91-7.05 (1 H, m), 6.61-6.75 (1 H, m), 4.80 (1 H, dd, J=1.90, 3.05 Hz), 4.32 (1 H, d, J=18.01 Hz), 4.15-4.26 (2 H, m), 4.08 (1 H, dd, J=7.02, 1.83 Hz), 3.99 (1 H, d, J=18.01 Hz), 3.73 (1 H, d, J=15.26 Hz), 3.16 (1 H, d, J=14.04 Hz), 2.61-2.75 (1 H, m), 1.30-1.40 (6 H, m).

Example 10

(S)-tert-Butyl 2-(2-(5-formylthiazol-2-ylamino)acetamido)-3-phenylpropanoate

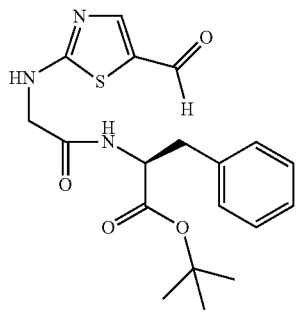 [SMILES: CC(C)(C)OC(=O)[C@H](Cc1ccccc1)NC(=O)CNc1ncc(C=O)s1]

Following the procedure as described in Example 7, except using material from Example 3 (39.7 mg, 0.096 mmol), (S)-tert-butyl 2-amino-3-phenylpropanoate, HCl (35.4 mg, 0.137 mmol), 1-hydroxy-7-azabenzotriazole (6.4 mg, 0.047 mmol), DMF (1.5 mL), N-methylmorpholine (75 μl, 0.682 mmol) and EDC (27.5 mg, 0.143 mmol), 27.3 mg (73%) of the title compound is isolated as an amber solid as a TFA salt. Purification is done by preparative HPLC (Condition A) using a PHENOMENEX® Luna Axia 30×100 mm S10 column from 20% Solvent B to 100% Solvent B over 11 min, ret. T=10.1 min. LC/MS (Condition A): ret. T=3.39 min, (M+H)$^+$ 390.10.

Example 11

(S)-2-(2-(5-Formylthiazol-2-ylamino)acetamido)-3-phenylpropanoic acid

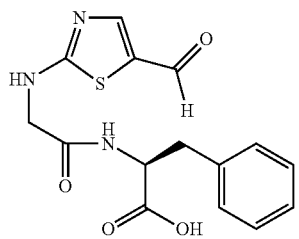 [SMILES: O=Cc1cnc(NCC(=O)N[C@@H](Cc2ccccc2)C(=O)O)s1]

To a solution of material from Example 10 (27 mg, 0.07 mmol) in CH$_2$Cl$_2$ (6 mL) is added trifluoroacetic acid (2.5 mL, 32.4 mmol). The resulting solution is stirred at room temperature for 1 h, then evaporated to dryness over 18 h to give the title compound as a TFA salt that is used crude, and in its entirety in the next step. LC/MS (Condition A): ret. T=2.45 min, (M+1-H)$^+$ 334.08.

Example 12

(S)-N-((S)-1-((S)-1-((S)-1-Amino-3-(4-hydroxyphenyl)-1-oxopropan-2-ylamino)-1-oxopropan-2-ylamino)-1-oxopropan-2-yl)-2-(2-(5-formylthiazol-2-ylamino)acetamido)-3-phenylpropanamide

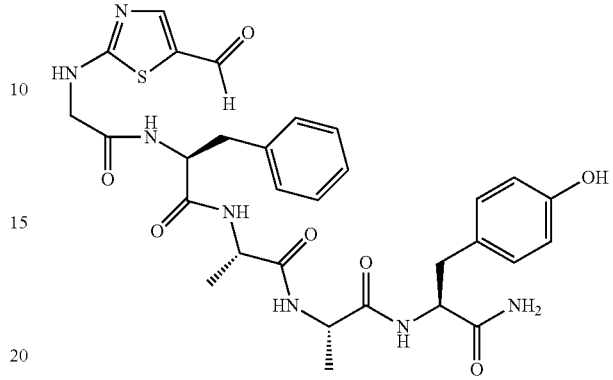

Following the procedure as described in Example 7, except using the material from Example 11 (31.3 mg, 0.07 mmol), (S)-2-amino-N-((S)-1-((S)-1-amino-3-(4-hydroxyphenyl)-1-oxopropan-2-ylamino)-1-oxopropan-2-yl)propanamide (24.5 mg, 0.076 mmol), 1-hydroxy-7-azabenzotriazole (7.3 mg, 0.054 mmol), DMF (1.5 mL), N-methylmorpholine (56 μl, 0.509 mmol) and EDC (22 ng, 0.115 mmol), 32.5 mg (69.2%, 2 steps) of the title compound is isolated as a pale yellow solid as a TFA salt. Purification is done by preparative HPLC (Condition A) using a PHENOMENEX® Luna Axia 30×100 mm S10 column from 15% Solvent B to 90% Solvent B over 11 min, ret. T=7.70 min. LC/MS (Condition A): ret. T=2.54 min, (M+H)$^+$ 638.34. $^1$H NMR (500 MHz, DMSO-d$_6$) δ ppm 9.65 (1 H, s), 8.90-9.04 (1 H, m), 8.28 (2 H, dd, J=7.63, 4.58 Hz), 7.90-8.10 (2 H, m), 7.70 (1 H, d, J=7.93 Hz), 7.31 (1 H, br. s.), 7.23 (4 H, d, J=4.27 Hz), 7.15-7.20 (1 H, m), 7.06 (1 H, br. s.), 6.99 (2 H, d, J=8.55 Hz), 6.63 (2 H, d, J=8.24 Hz), 4.51-4.64 (1 H, m), 4.24-4.38 (2 H, m), 4.14-4.23 (1 H, m), 3.03 (1 H, dd, J=13.58, 3.81 Hz), 2.89 (1 H, dd, J=14.04, 5.19 Hz), 2.69-2.81 (2 H, m), 1.11-1.25 (6 H, m).

Example 13

(S)-N-((S)-1-((S)-1-((S)-1-Amino-3-(4-hydroxyphenyl)-1-oxopropan-2-ylamino)-1-oxopropan-2-ylamino)-1-oxopropan-2-yl)-2-(2-(5-(hydroxymethyl)thiazol-2-ylamino)acetamido)-3-phenylpropanamide

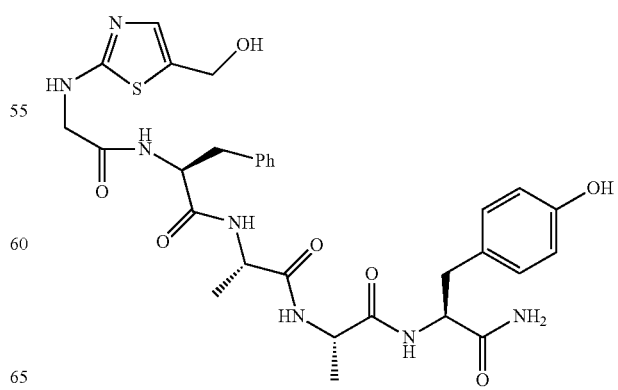

Following the procedure as described in Example 8, except using the material from Example 12 (15 mg, 0.024 mmol), EtOH/H$_2$O (4:1) (2.0 mL), THF (1 mL), sodium borohydride (5.5 mg, 0.145 mmol) and stirring at room temperature for 3 h, the title compound is obtained in quantitative yield that is used crude in the next step. LC/MS (Condition A): ret. T=2.13 min, (M+H)$^+$ 640.39.

Example 14

Thia-G-F-A-A-Y—CONH$_2$ (SEQ ID NO. 10) macrocycle

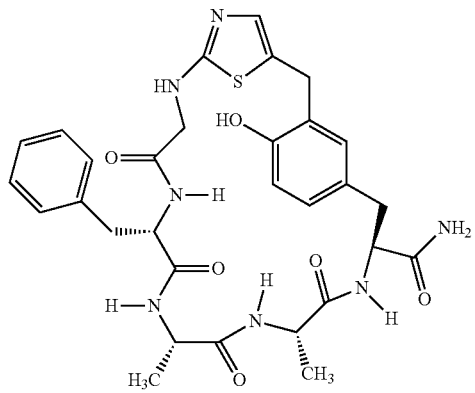 [SMILES: C[C@@H]1NC(=O)[C@H](C)NC(=O)[C@H](Cc2ccccc2)NC(=O)CNc2ncc(s2)Cc2cc(ccc2O)C[C@@H](C(N)=O)NC1=O]

Following the procedure as described in Example 9, except using the crude material from Example 13 (15 mg, 0.023 mmol), nitromethane (2.0 mL), trifluoromethanesulfonic acid (100 µl, 1.126 mmol) and stirring at room temperature for 45 min, 11.9 mg of the title compound (68.5%, 2 steps) is obtained as a white solid as a TFA salt. Purification is done by preparative HPLC (Condition A) using a PHENOMENEX® Luna Axia 30×100 mm S10 column from 15% Solvent B to 90% Solvent B over 11 min, ret. T=6.29 min. LC/MS (Condition A): ret. T=2.16 min, (M+H)$^+$ 622.33. Analytical HPLC: (Condition A): >99%, ret. T=14.83 min, (Condition B): >99%, ret, T=15.78 min, (Condition C): >98%, ret. T=4.57 min, (Condition D): >99%, ret. T=4.67 min. $^1$H NMR (500 MHz, methanol-d$_4$) δ ppm 7.21-7.36 (5 H, m), 6.96-7.13 (3 H, m), 6.75 (1 H, d, J=8.24 Hz), 4.58 (1 H, dd, J=9.31, 4.12 Hz), 4.36 (1 H, dd, J=8.85, 6.41 Hz), 3.95-4.23 (5 H, m), 3.80 (1 H, d, J=15.26 Hz), 3.08-3.23 (2 H, m), 2.99 (1 H, dd, J=13.58, 9.00 Hz), 2.89 (1 H, dd, J=14.34, 9.16 Hz), 1.23 (3 H, d, J=7.32 Hz), 1.12 (3 H, d, J=7.32 Hz).

Example 15

(S)-2-(2-(2-(5-Formylthiazol-2-ylamino)acetamido)acetamido)-3-(4-hydroxyphenyl)propanamide

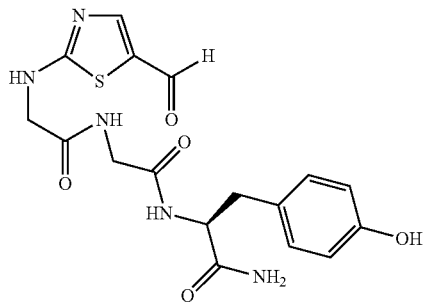 [SMILES: NC(=O)[C@H](Cc1ccc(O)cc1)NC(=O)CNC(=O)CNc1ncc(C=O)s1]

Following the procedure as described in Example 4, except using material from Example 3 (39.5 mg, 0.095 mmol), (S)-2-(2-aminoacetamido)-3-(4-hydroxyphenyl)propanamide, 1.00HCl (40.5 mg, 0.148 mmol), EDC (28.0 mg, 0.146 mmol), 1-hydroxy-7-azabenzotriazole (7.9 mg, 0.058 mmol), anhydrous DMF (1.2 mL), and N-methylmorpholine (65 µl, 0.591 mmol), 35 mg of the title compound (70.7%) is obtained as a yellow film as a TFA salt. Purification is done by preparative HPLC (Condition A) using a PHENOMENEX® Luna Axia 30×100 mm S10 column from 10% Solvent B to 85% Solvent B over 11 min, ret. T=4.73 min (broad peak). LC/MS (Condition A): ret. T=1.72 min, (M+H)$^+$ 406.08.

Example 16

(S)-2-(2-(2-(5-(Hydroxymethyl)thiazol-2-ylamino)acetamido)acetamido)-3-(4-hydroxyphenyl)propanamide

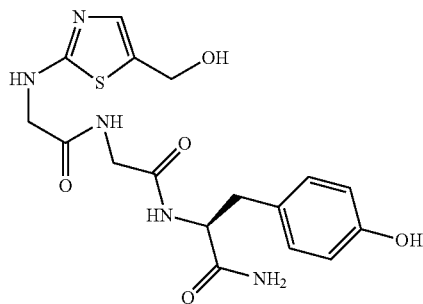 [SMILES: NC(=O)[C@H](Cc1ccc(O)cc1)NC(=O)CNC(=O)CNc1ncc(CO)s1]

Following the procedure as described in Example 8, except using the material from Example 15 (35 mg, 0.067 mmol), EtOH/H$_2$O (4:1) (2.0 mL), and sodium borohydride (21.7 mg, 0.574 mmol), the title compound is obtained in quantitative yield. LC/MS (Condition A): ret. T=0.73 min, (M+Na) 430.11.

Example 17

Macrocycle Thia-GGY and (S)-3-(4-hydroxyphenyl)-2-(2-(2-(5-methylthiazol-2-ylamino)acetamido)acetamido)propanamide

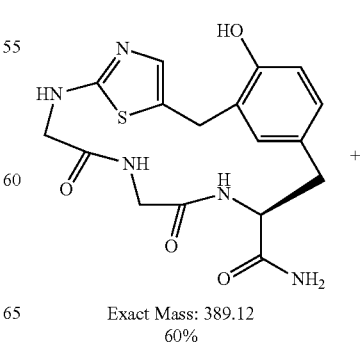

Exact Mass: 389.12
60%

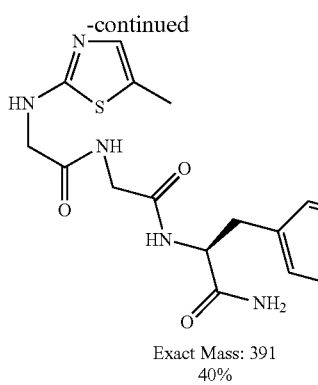

Exact Mass: 391
40%

To a suspension of the crude material from Example 16 in nitromethane (5.0 mL) is added trifluoromethanesulfonic acid (275 μL, 3.10 mmol) and the resulting solution is allowed to stir at room temperature for 68 min. The reaction is cooled to −20° C. for 10 min, then quenched with N-methylmorpholine (500 μlit, 4.55 mmol), and evaporated to dryness under a gentle stream of $N_2$. Purification is done by preparative HPLC (Condition A) using a PHENOMENEX® Luna Axia 30×100 mm S10 column from 5% Solvent B to 80% Solvent B over 14 min, ret. T=4.75 min. The fractions containing the desired product are evaporated to dryness. LC/MS (Condition A): ret. T=1.38 min, (M+H) 390.14 and 392.16. $^1$HNMR indicates that the desired macrocycle is present in a 60:40 ratio along with (S)-3-(4-hydroxyphenyl)-2-(2-(2-(5-methylthiazol-2-ylamino)acetamido)acetamido)propanamide. The desired macrocycle is not isolated from the mixture of compounds.

Example 18

(S)-tert-Butyl 3-methyl-2-thioureidobutanoate

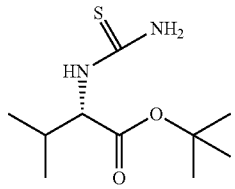

To a suspension of (S)-tert-butyl 2-amino-3-methylbutanoate, HCl (3.90 g, 18.60 mmol) and 1,1'-thiocarbonyldipyridin-2(11H)-one (6.14 g, 26.4 mmol) in $CH_2Cl_2$ (100 mL) is added N,N-diisopropylethylamine (3.25 mL, 18.60 mmol) and the reaction is stirred at room temp for 18 h. The solvent is removed in vacuo and the residue is treated with 2M $NH_3$/MeOH (300 mL, 600 mmol) for 1.5 h. The solvent is removed in vacuo to give 13 g of the title compound as an amber syrup that is used directly without further purification in the next step. LC/MS (Condition A): ret. T=3.16 min, (M+H)$^+$ 233.13.

Example 19

(S)-tert-Butyl 2-(5-formylthiazol-2-ylamino)-3-methylbutanoate

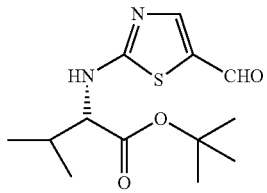

To the entire crude amount from Example 18 (4.32 g, 18.6 mmol) in anhydrous THF (100 mL) under $N_2$ is added N,N-diisopropylethylamine (8.5 mL, 48.7 mmol) and 2-bromomalonaldehyde (4.8 g, 31.8 mmol). The reaction is purged with $N_2$ and heated to 55° C. for 18 h. Additional 2-bromomalonaldehyde (2.8 g, 0.019 mmol) is added and the reaction is heated at 67° C. for an additional 3.25 h. The solvent is removed in vacuo and the residue is partitioned between EtOAc (400 mL) and water (300 mL). The aqueous later is extracted again with EtOAc (300 mL), the organic layers combined, extracted with water (1×150 mL), brine (1×150 mL), dried over $Na_2SO_4$, filtered and evaporated to dryness. The resulting residue is purified by BIOTAGE® Silica gel chromatography on a 160 g Thompson Single Step silica cartridge using a linear gradient from 100% Hexanes to 50% EtOAc/Hexanes over 11 column volumes to give 3.03 g (57.3%, 2 steps) of the title compound as a pale yellow solid. LC/MS (Condition A): ret. T=3.41 min, (M+H)$^+$ 285.16. $^1$H NMR (500 MHz, chloroform-d) δ ppm 9.72 (1 H, s), 7.85 (1 H, s), 4.07 (1 H, d, J=3.66 Hz), 2.31 (1 H, td, J=6.94, 4.73 Hz), 1.48 (9 H, s), 1.03 (6 H, dd, J=6.87, 4.73 Hz).

Example 20

(S)-2-(5-Formylthiazol-2-ylamino)-3-methylbutanoic acid

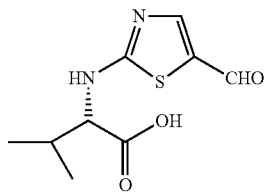

Following the procedure described in Example 3, except using the material from Example 19 (2.99 g, 10.51 mmol), $CH_2Cl_2$ (200 mL) and TFA (51 mL, 662 mmol), 4.8 g (quantitative yield) of the title compound is obtained as a tan syrup as a bis TFA salt. LC/MS (Condition A): ret. T=2.33 min, (M+H)$^+$ 229.04.

Example 21

N-((S)-1-((S)-1-((S)-1-Amino-3-(4-hydroxyphenyl)-1-oxopropan-2-ylamino)-1-oxopropan-2-ylamino)-1-oxopropan-2-yl)-2-(5-formylthiazol-2-ylamino)-3-methylbutanamide

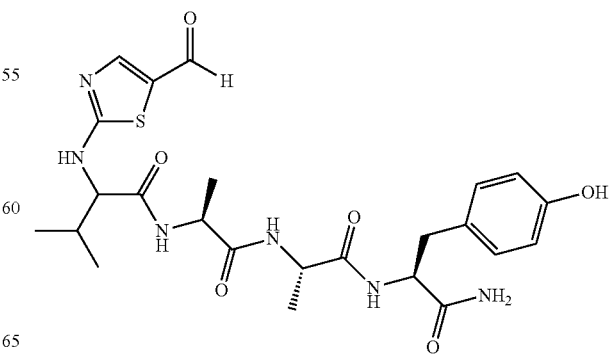

Following the procedure described in Example 4, except using the material from Example 20 (77 mg, 0.169 mmol), (S)-2-amino-N-((S)-1-((S)-1-amino-3-(4-hydroxyphenyl)-1-oxopropan-2-ylamino)-1-oxopropan-2-yl)propanamide (61.2 mg, 0.19 mmol), EDC (56.2 mg, 0.293 mmol), 1-hydroxy-7-azabenzotriazole (19.2 mg, 0.141 mmol), anhydrous DMF (2 mL) and N-methylmorpholine (104 μL, 0.946 mmol), 67 mg (54.5%) of the title compound is obtained as a yellow solid as a TFA salt. Purification is done by preparative HPLC (Condition A) using a PHENOMENEX® Luna Axia 30×100 mm S10 column from 15% Solvent B to 90% Solvent B over 1 min, ret. T=6.98 min.

LC/MS (Condition A): ret. T=2.33 min, (M+H)$^+$ 533.27.

Example 22

N-((S)-1-((S)-1-((S)-1-Amino-3-(4-hydroxyphenyl)-1-oxopropan-2-ylamino)-1-oxopropan-2-ylamino)-1-oxopropan-2-yl)-2-(5-(hydroxymethyl)thiazol-2-ylamino)-3-methylbutanamide

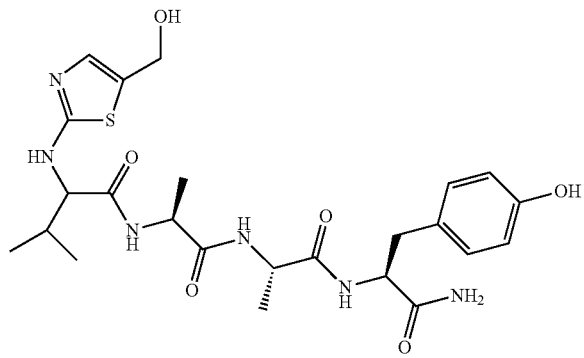 [SMILES: CC(C)C(Nc1ncc(CO)s1)C(=O)N[C@@H](C)C(=O)N[C@@H](C)C(=O)N[C@@H](Cc1ccc(O)cc1)C(N)=O]

To a solution of the material from Example 21 (21.5 mg, 0.033 mmol) in EtOH/H$_2$O (4:1) (2.5 mL) is added sodium borohydride (8.35 mg, 0.221 mmol) in 2 portions, separated by ~5 min and the resulting off white slurry is allowed to stir at room temp for 1.5 h. The reaction is quenched with MeOH (750 μlit) and evaporated to dryness under a gentle stream of N$_2$ to give the title compound that is used directly in the next step. LC/MS (Condition A): ret. T=1.74 min, (M+H)$^+$ 535.

Example 23

2 Macrocycles Isolated—Thia-V(l)AAY (SEQ ID NO. 11) and Thia-V(d)AAY—Epimiers

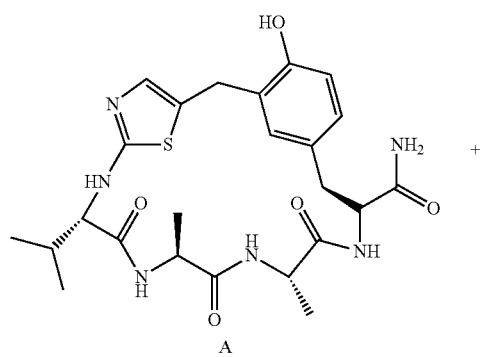

A

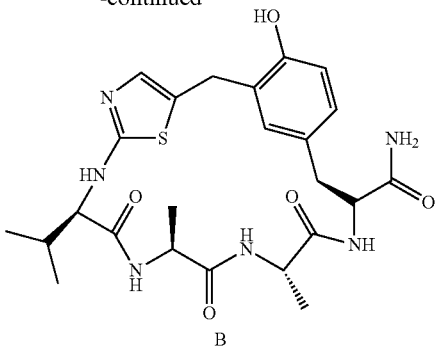

B

To suspension of the crude material from Example 22 (17.64 mg, 0.033 mmol) in nitromethane (3.0 mL) is added trifluoromethanesulfonic acid (140 μL, 1.577 mmol). The resulting colorless solution is stirred at room temp for 35 min, cooled to −20° C., quenched with N-methylmorpholine (200 μlit, 1.82 mmol) and evaporated to dryness. The resulting residue is purified by preparative HPLC (Condition A) using a PHENOMENEX® Luna Axia 30×100 mm S10 column from 15% Solvent B to 90% Solvent B over 12 min, ret. T=5.19 min. and 5.67 min. The fractions containing the desired products are evaporated to dryness to give 2.7 mg (11.03%) of Thia-V(l)AAY macrocycle (Compound A) as a white solid and 3.8 mg (16.43%) of Thia-V(d)AAY macrocycle (Compound B) as a white solid.

For Macrocycle A:

LC/MS (Condition A): ret. T=1.79 min, (M+H)$^+$ 517.29. Analytical HPLC: (Condition A): >86%, ret. T=14.19 min, (Condition B): >80%, ret. T=14.17 min, (Condition C): >88%, ret. T=3.20 min, (Condition D): >78%, ret. T=3.00 min. $^1$H NMR (500 MHz, methanol-d$_4$) δ ppm 6.95-7.19 (3 H, m), 6.72 (1 H, d, J=8.24 Hz), 4.58-4.74 (1 H, m), 4.24-4.42 (1 H, m), 3.87-4.09 (3 H, m), 3.76 (1 H, d, J=7.02 Hz), 3.13 (1 H, dd, J=14.19, 3.20 Hz), 2.72 (1 H, dd, J=14.19, 11.44 Hz), 2.19-2.41 (1 H, m), 1.33 (6 H, dd, J=19.07, 7.17 Hz), 1.08 (6 H, d, J=6.71 Hz).

For Macrocycle B:

LC/MS (Condition A): ret. T=2.06 min, (M+H)$^+$ 517.30. Analytical HPLC: (Condition A): >91%, ret. T=15.28 min, (Condition B): >92%, ret. T=15.00 min, (Condition C): >91%, ret. T=3.62 min, (Condition D): >93%, ret. T=3.39 min. $^1$H NMR (500 MHz, methanol-d$_4$) δ ppm 6.94-7.21 (3 H, m), 6.74 (1 H, d, J=7.93 Hz), 4.45-4.52 (1 H, m), 4.34-4.44 (1 H, m), 4.01-4.16 (2 H, m), 3.77-3.91 (2 H, m), 2.99 (1 H, dd, J=13.89, 3.20 Hz), 2.84 (1 H, dd, J=14.04, 9.16 Hz), 2.20-2.33 (1 H, m), 1.22-1.38 (6 H, m), 1.10 (6 H, dd, J=8.24, 7.02 Hz).

Example 24

(2S)-tert-Butyl 2-(2-(5-formylthiazol-2-ylamino)-3-methylbutanamido)-3-phenylpropanoate

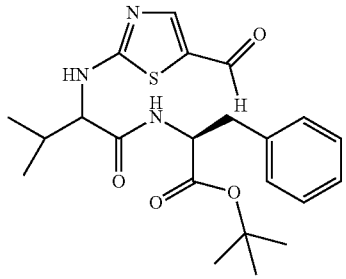 [SMILES: CC(C)C(Nc1ncc(C=O)s1)C(=O)N[C@@H](Cc1ccccc1)C(=O)OC(C)(C)C]

To a solution of material from Example 20 (1.4 g, 3.07 mmol), (S)-tert-butyl 2-amino-3-phenylpropanoate, HCl (1.05 g, 4.07 mmol), and 1-hydroxy-7-azabenzotriazole (235 mg, 1.727 mmol) in anhydrous CH$_2$Cl$_2$ (70 mL) is added N-methylmorpholine (2.2 mL, 20.01 mmol), followed by EDC (810 mg, 4.23 mmol). The resulting solution is stirred at room temp for 18 h, evaporated to dryness and the residue is purified by BIOTAGE® Silica gel chromatography on a 90 g Thompson Single Step silica cartridge using a linear gradient from 100% CH$_2$Cl$_2$ to 50% EtOAc/CH$_2$Cl$_2$ over 11 column volumes to give 1.19 g (90%) of the title compound as a white solid. LC/MS (Condition A): ret. T=3.73 min, (M+H)$^+$ 432.20.

Example 25

(2S)-2-(2-(5-Formylthiazol-2-ylamino)-3-methylbutanamido)-3-phenylpropanoic acid

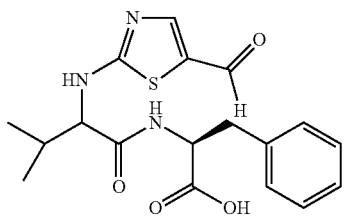 [SMILES: CC(C)C(Nc1ncc(C=O)s1)C(=O)N[C@@H](Cc1ccccc1)C(=O)O]

Following the procedure as described in Example 11, except using the material from Example 24 (1.15 g, 2.66 mmol), CH$_2$Cl$_2$ (50 mL), TFA (5 mL, 64.9 mmol) and stirring at room temp for 18 h, 1.38 g of the title compound (quantitative yield) is obtained as a white solid as a mono TFA salt. LC/MS (Condition A): ret. T=2.86 min, (M+H)$^{+\ 376.13}$, and ret. T=3.03 min, (M+H)$^+$ 376.13.

Example 26

(2S)-tert-Butyl 2-((2S)-2-(2-(5-formylthiazol-2-ylamino)-3-methylbutanamido)propanamido)propanoate

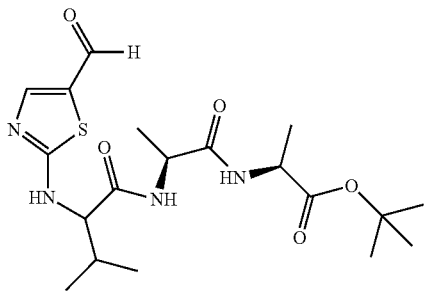 [SMILES: CC(C)C(Nc1ncc(C=O)s1)C(=O)N[C@@H](C)C(=O)N[C@@H](C)C(=O)OC(C)(C)C]

To a material from Example 20 (560 mg, 1.227 mmol), H-Ala-Ala-OtBu.HCl (300 mg, 1.187 mmol), EDC (341 mg, 1.780 mmol), and 1-hydroxy-7-azabenzotriazole (97 mg, 0.712 mmol) in CH$_2$Cl$_2$ (12 mL) is added N-methylmorpholine (0.783 mL, 7.12 mmol) and the resulting solution is allowed to stir at room temp for 18 h. The solvent is removed in vacuo and the residue is purified by BIOTAGE® Silica gel chromatography on a 25 g Thompson Single Step silica cartridge using a linear gradient from 100% CH$_2$Cl$_2$ to 100% EtOAc over 12 column volumes to give 213 mg (42.1%) of the title compound as an off-white solid. LC/MS (Condition A): ret. T=3.17 min, (M+H)$^+$ 427.22.

Example 27

(2S)-2-((2S)-2-(2-(5-Formylthiazol-2-ylamino)-3-methylbutanamido)propanamido)propanoic acid

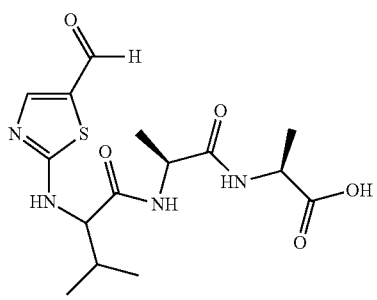 [SMILES: CC(C)C(Nc1ncc(C=O)s1)C(=O)N[C@@H](C)C(=O)N[C@@H](C)C(=O)O]

Following the procedure as described in Example 11, except using material from Example 26 (213 mg, 0.499 mmol), CH$_2$Cl$_2$ (75 mL) and TFA (25 mL, 324 mmol), 268.4 mg (quantitative yield) of the title compound is obtained as a white solid as a mono TFA salt. LC/MS (Condition A): ret. T=2.15 min, (M+H)$^+$ 371.14.

Example 28

N-((2S,5S,8S,11S,14S)-Amino-2-(4-hydroxybenzyl)-5,8,1-trimethyl-1,4,7,10,13-pentaoxo-3,6,9,12-tetraazapentadecan-14-yl)-2-(5-formylthiazol-2-ylamino)-3-methylbutanamide

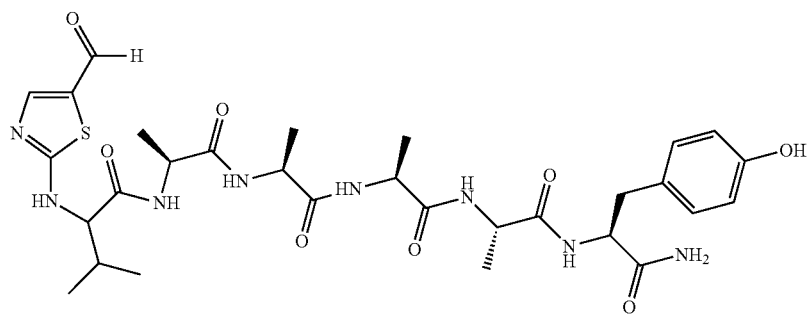 [SMILES: CC(C)C(Nc1ncc(C=O)s1)C(=O)N[C@@H](C)C(=O)N[C@@H](C)C(=O)N[C@@H](C)C(=O)N[C@@H](C)C(=O)N[C@@H](Cc1ccc(O)cc1)C(N)=O]

Following the procedure as described in Example 7, except using material from Example 27 (79.1 mg, 0.163 mmol), (S)-2-amino-N-((S)-1-((S)-1-amino-3-(4-hydroxyphenyl)-1-oxopropan-2-ylamino)-1-oxopropan-2-yl)propanamide (40.2 mg, 0.125 mmol), EDC (36.2 mg, 0.189 mmol), 1-hydroxy-7-azabenzotriazole (13.0 mg, 0.096 mmol), DMF (2.0 mL) and N-methylmorpholine (90 μL, 0.819 mmol), 35.8 mg (42.5%) of the title compound is isolated as a light tan solid as a mono TFA salt. Purification is done by preparative HPLC (Condition A) using a PHENOMENEX® Luna Axia 30×100 mm S10 column from 20% Solvent B to 95% Solvent B over 12 min, ret. T=6.69 min. LC/MS (Condition A): ret. T=2.44 min, (M+H)⁺ 675.36. $^1$H NMR (500 MHz, methanol-$d_4$) δ ppm 7.19-7.30 (1 H, m), 7.08 (2 H, d, J=7.63 Hz), 6.62-6.78 (2H, m), 5.42-5.59 (1 H, m), 4.48 (1 H, br. s.), 4.18-4.41 (3 H, m), 3.94-4.09 (1 H, m), 3.11 (1 H, dd, J=14.19, 4.73 Hz), 2.83-2.98 (1 H, m), 2.22-2.45 (1 H, m), 1.22-1.50 (12 H, m), 1.00-1.14 (6 H, m).

Example 29

N-((2S,5S,8S,11S,14S)-1-Amino-2-(4-hydroxybenzyl)-5,8,1,1-trimethyl-1,4,7,10,13-pentaoxo-3,6,9,12-tetraazapentadecan-14-yl)-2-(5-(hydroxymethyl)thiazol-2-ylamino)-3-methylbutanamide

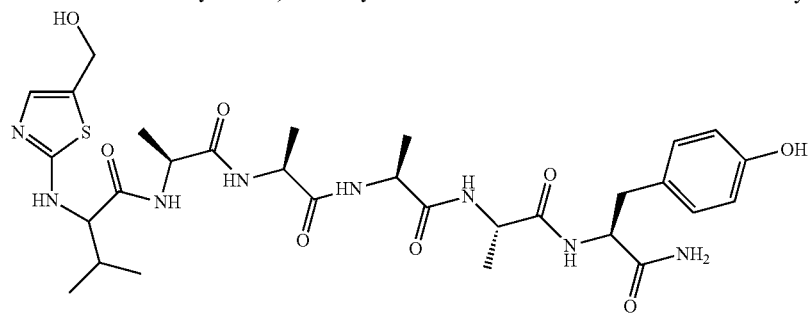

Following the procedure as described in Example 22, except using material from Example 28 (18.8 mg, 0.024 mmol), sodium borohydride (5.7 mg) and EtOH/H₂O (4:1) (2.0 mL), the title compound (quantitative yield) is obtained. LC/MS (Condition A): ret. T=1.93 min, (M+H)⁺ 677.40.

Example 30

2 Macrocycles—Thia-V(d)AAAAY and Thia-V(l)AAAAY (SEQ ID NO. 12)

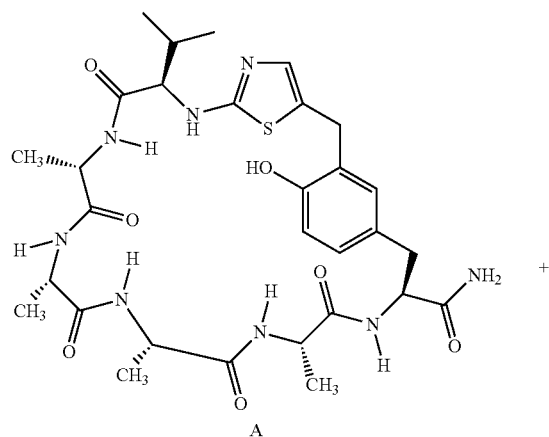

A

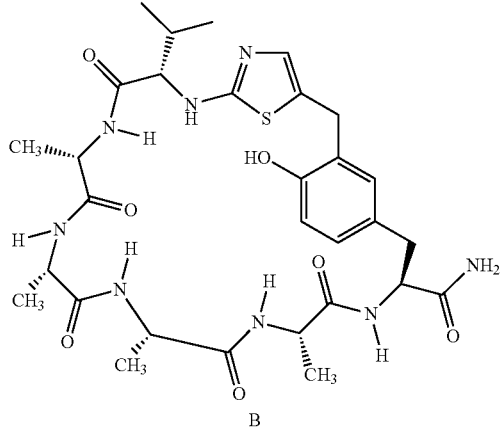

B

Following the procedure as described in Example 23, except using material from Example 29, nitromethane (4.0 mL), trifluoromethanesulfonic acid (110 μl, 1.239 mmol), N-methylmorpholine (180 μlit, 1.637 mmol), and stirring at room temp. for 40 min, 4.6 mg (22.3%) of Thia-V(d)AAAAY macrocycle (Compound A) and 6.8 mg (35.2%) of Thia-V(l) AAAAY macrocycle (Compound B) are obtained as a white solids. Purification is done by preparative HPLC (Condition A) using a PHENOMENEX® Luna Axia 30×100 mm S10 column from 15% Solvent B to 90% Solvent B over 12 min, ret, T=6.25 min. and 6.77 min, macrocycles A and B, respectively.

For Macrocycle A:
LC/MS (Condition A): ret. T=2.17 min, (M+H)⁺ 659.39. Analytical HPLC: (Condition A): >90%, ret. T=15.42 min, (Condition B): >91%, ret. T=15.43 min, (Condition C): >99%, ret. T=3.79 min, (Condition D): >99%, ret. T=3.62 min. $^1$H NMR (500 MHz, methanol-$d_4$) δ ppm 6.94-7.06 (3 H, m), 6.73 (1 H, d, J=8.24 Hz), 4.63 (1 H, br. s.), 4.36 (1 H, d, J=7.02 Hz), 4.21-4.29 (1 H, m), 3.88-4.14 (4 H, m), 3.79 (1H, d, J=7.32 Hz), 3.18 (1 H, br. s.), 2.97 (1 H, dd, J=14.95, 9.16 Hz), 2.17-2.30 (1 H, m), 1.27-1.41 (12 H, m), 1.06 (6 H, t, J=7.48 Hz).

For Macrocycle B:
LC/MS (Condition A): ret. T=2.25 min, (M+H)⁺ 659. Analytical HPLC: (Condition A): >96%, ret. T=14.75 min, (Condition B): >97%, ret. T=14.90 min, (Condition C): >90%, ret. T=4.17 min, (Condition D): >98%, ret. T=3.97 min. $^1$H NMR (500 MHz, methanol-$d_4$) δ ppm 6.94-7.11 (3 H, m), 6.78 (1 H, d, J=8.24 Hz), 4.62 (1 H, dd, J=11.90, 3.97 Hz), 4.37 (1 H, d, J=7.02 Hz), 4.14 (1 H, d, J=7.32 Hz), 3.98-4.05 (2 H, m), 3.93 (2 H, d, J=7.02 Hz), 3.83 (1 H, d, J=7.02 Hz), 3.74 (1 H, d, J=7.02 Hz), 2.95 (1 H, dd, J=14.95, 11.90 Hz), 2.26-2.36 (1 H, m), 1.41 (6 H, dd, J=9.61, 7.48 Hz), 1.31 (3 H, d, J=7.32 Hz), 1.04-1.14 (9 H, m).

Example 31

N-(2-((S)-1-Amino-3-(4-hydroxyphenyl)-1-oxopropan-2-ylamino)-2-oxoethyl)-2-(5-formylthiazol-2-ylamino)-3-methylbutanamide

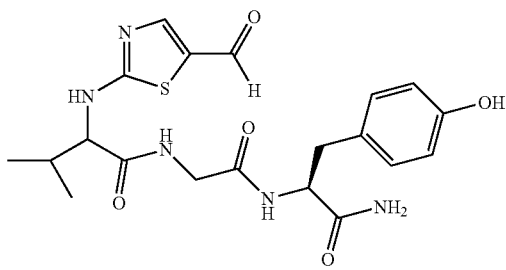 [SMILES: CC(C)C(Nc1ncc(C=O)s1)C(=O)NCC(=O)N[C@@H](Cc1ccc(O)cc1)C(N)=O]

Following the procedure described in Example 4, except using the material from Example 20 (77 mg, 0.169 mmol), glycyl-L-tyrosinamide hydrochloride (159.5 mg, 0.583 mmol), EDC (190.3 mg, 0.993 mmol), 1-hydroxy-7-azabenzotriazole (29 mg, 0.213 mmol), anhydrous DMF (4 mL) and N-methylmorpholine (350 µL, 3.18 mmol), 86.7 mg (41%) of the title compound is obtained as an orange solid as a TFA salt. Purification is done by preparative HPLC (Condition A) using a PHENOMENEX® Luna Axia 30×100 mm S10 column from 15% Solvent B to 85% Solvent B over 11 min, ret, T=6.82-6.69 min. LC/MS (Condition A): ret. T=2.11-2.18 min, (M+H)$^+$ 448.18.

Example 32

N-(2-((S)-1-Amino-3-(4-hydroxyphenyl)-1-oxopropan-2-ylamino)-2-oxoethyl)-2-(5-(hydroxymethyl)thiazol-2-ylamino)-3-methylbutanamide

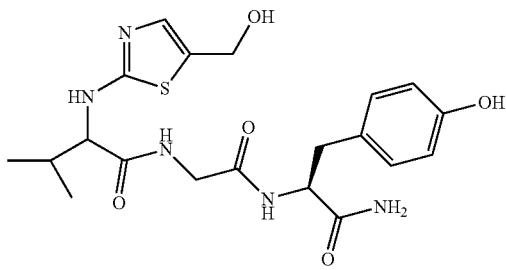 [SMILES: CC(C)C(Nc1ncc(CO)s1)C(=O)NCC(=O)N[C@@H](Cc1ccc(O)cc1)C(N)=O]

To a solution of material from Example 31 in EtOH/H$_2$O (4:1) (2.5 mL) is added sodium borohydride (25.5 mg, 0.674 mmol) in 2 equal portions over 5 min. The resulting light suspension is stirred at room temp for 2 h, quenched with MeOH (3 mL), stirred at room temp for 30 min, quenched with acetone (5 mL), and stirred at room temp for 45 min. All volatiles were evaporated off under a gentle stream of N$_2$ to give the title compound (quantitative yield) that is used in its entirety in the macrocyclization step. LC/MS (Condition A): ret. T=1.45 min, (M+H)$^+$ 450.20.

Example 33

2 Macrocycles—Thia-V(l)GY and Thia-V(d)GY

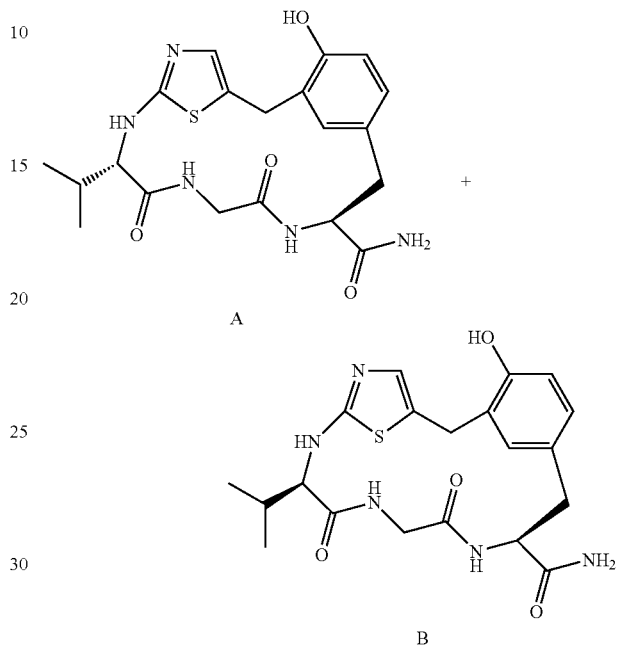

Following the procedure as described in Example 23, except using material from Example 32, nitromethane (10.0 mL), trifluoromethanesulfonic acid (340 µl, 3.83 mmol), and N-methylmorpholine (500 µlit, 4.55 mmol), 8.0 mg (19%) of Thia-V(l)GY macrocycle (Compound A) and 10.2 mg (22.%) of Thia-V(d)GY macrocycle (Compound B) were obtained as a white solid and a pale yellow solid, respectively. Purification is done by preparative HPLC (Condition A) using a PHENOMENEX® Luna Axia 30×100 mm S10 column from 10% Solvent B to 80% Solvent B over 12 min, ret. T=4.95 min. and 5.54 min, for macrocycles A and B, respectively.

For Macrocycle A:

LC/MS (Condition A): ret. T=1.59 min, (M+H)$^+$ 432.17. Analytical HPLC: (Condition A): >99%, ret. T=12.06 min, (Condition B): >96%, ret. T=12.44 min, (Condition C): >98%, ret. T=2.71 min, (Condition D): >99%, ret. T=2.70 min. $^1$H NMR (500 MHz, methanol-d$_4$) δ ppm 7.17 (1 H, s), 7.05 (1 H, dd, J=8.39, 1.98 Hz), 6.99 (1 H, d, J=1.83 Hz), 6.74 (1 H, d, J=8.24 Hz), 4.32 (1 H, d, J=15.56 Hz), 3.86-4.14 (2 H, m), 3.64 (1 H, d, J=8.24 Hz), 3.51 (1 H, d, J=15.56 Hz), 3.17-3.25 (1 H, m), 2.82 (1 H, dd, J=14.95, 10.99 Hz), 2.13 (1 H, dd, J=15.11, 6.87 Hz), 1.11 (3 H, d, J=6.71 Hz), 1.01 (3 H, d, J=6.71 Hz).

For Macrocycle B:

LC/MS (Condition A): ret. T=1.84 min, (M+H)$^+$ 432.17. Analytical HPLC: (Condition A): >93%, ret. T=12.68 min, (Condition B): >96%, ret. T=12.85 min, (Condition C): >89%, ret. T=2.86 min, (Condition D): >96%, ret. T=2.79 min. $^1$H NMR (500 MHz, methanol-d$_4$) δ ppm 7.21 (1 H, s), 6.94-7.08 (2 H, m), 6.75 (1 H, d, J=7.93 Hz), 3.92-4.18 (3 H, m), 3.73 (1 H, d, J=16.79 Hz), 3.56 (1 H, d, J=7.63 Hz), 3.14-3.25 (1 H, m), 2.89 (1 H, dd, J=14.80, 10.53 Hz), 2.12-2.30 (1 H, m), 0.98-1.15 (6 H, m).

Example 34

(S)-N-((S)-1-((S)-1-(2-((S)-1-Amino-3-(4-hydroxyphenyl)-1-oxopropan-2-ylamino)-2-oxoethylamino)-1-oxopropan-2-ylamino)-1-oxopropan-2-yl)-2-(5-formylthiazol-2-ylamino)-3-methylbutanamide and (R)-N-((S)-1-((S)-1-(2-((S)-1-Amino-3-(4-hydroxyphenyl)-1-oxopropan-2-ylamino)-2-oxoethylamino)-1-oxopropan-2-ylamino)-1-oxopropan-2-yl)-2-(5-formylthiazol-2-ylamino)-3-methylbutanamide

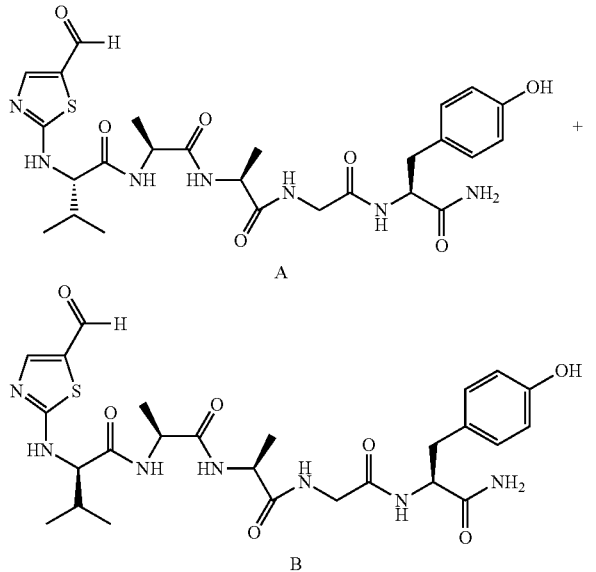

Following the procedure as described in Example 4, except using material from Example 27, glycyl-L-tyrosinamide hydrochloride (54.3 mg, 0.198 mmol), EDC (52.5 mg, 0.274 mmol), 1-hydroxy-7-azabenzotriazole (15.5 mg, 0.114 mmol), anhydrous DMF (2.0 mL), and N-methylmorpholine (140 µL, 1.273 mmol), 50.3 mg (36%) of title compound A and 28.7 mg (20.56%) of title compound B are obtained as white solids. Purification is done by preparative HPLC (Condition A) using a PHENOMENEX® Luna Axia 30×100 mm S10 column from 15% Solvent B to 90% Solvent B over 12 min, ret. T=6.95 min. and 7.33 min, for title compounds A and B, respectively.

For Title Compound A:
LC/MS (Condition A): ret. T=2.29 min, (M+H)$^+$ 590.33.
For Title Compound B:
LC/MS (Condition A): ret. T=2.39 min, (M+H)$^+$ 590.33.

Example 35

(S)-N-((S)-1-((S)-1-(2-((S)-1-Amino-3-(4-hydroxyphenyl)-1-oxopropan-2-ylamino)-2-oxoethylamino)-1-oxopropan-2-ylamino)-1-oxopropan-2-yl)-2-(5-(hydroxymethyl)thiazol-2-ylamino)-3-methylbutanamide

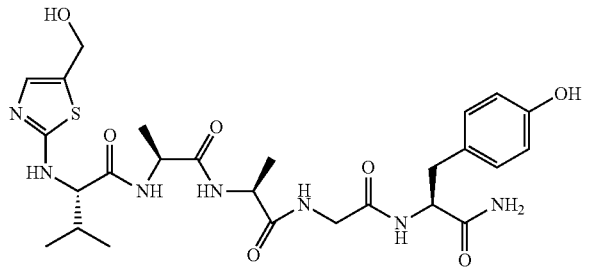 [SMILES: CC(C)[C@H](Nc1ncc(CO)s1)C(=O)N[C@@H](C)C(=O)N[C@@H](C)C(=O)NCC(=O)N[C@@H](Cc1ccc(O)cc1)C(N)=O]

Following the procedure as described in Example 32, except using the material from Example 34, Compound A, (50.3 mg, 0.071 mmol) and sodium borohydride (17.0 mg, 0.449 mmol), the title compound is isolated (quantitative yield) as a white solid that is used crude in the macrocyclization step. LC/MS (Condition A): ret. T=1.67 min, (M+H)$^+$ 592.31.

Example 36

Thia-V(l)AAGY (SEQ ID NO. 13) Macrocycle

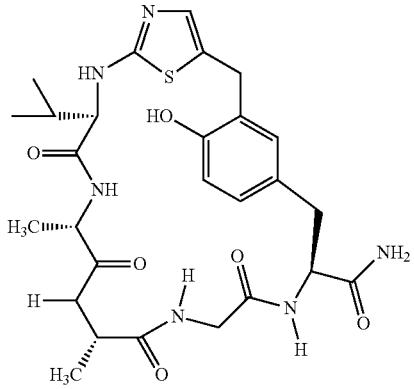 [SMILES: CC(C)[C@H]1Nc2ncc(s2)Cc2cc(ccc2O)C[C@@H](C(N)=O)NC(=O)CNC(=O)[C@H](C)CC(=O)[C@H](C)NC1=O]

Following the procedure as described in Example 23, except using material from Example 35, nitromethane (11.0 mL), trifluoromethanesulfonic acid (315 µlit, 3.55 mmol) and N-methylmorpholine (820 µlit, 7.46 mmol), and stirring at room temp, for 30 min, 26 mg (52.7%) of the title compound is isolated as a white solid as a TFA salt, Purification is done by preparative HPLC (Condition A) using a PHENOMENEX® Luna Axia 30×100 mm S10 column from 15% Solvent B to 85% Solvent B over 11 min, ret. T=5.57 min. LC/MS (Condition A): ret. T=2.00 min, (M+H)$^+$ 574.26. Analytical HPLC: (Condition A): >99%, ret. T=13.82 min, (Condition B): >99%, ret. T=14.01 min, (Condition C): >98%, ret. T=3.73 min, (Condition D): >99%, ret. T=3.60 min. $^1$H NMR (500 MHz, DMSO-d$_6$) δ ppm 9.40 (1 H, br. s.), 8.24 (1 H, br. s.), 8.13 (1 H, br. s.), 7.60 (1 H, br. s.), 7.46 (1 H, br. s.), 7.25 (1 H, br. s.), 7.15 (1 H, br. s.), 6.97 (1 H, s), 6.87 (2 H, d, J=7.93 Hz), 6.70 (1 H, d, J=8.24 Hz), 4.25-4.36 (1 H, m), 4.17 (1 H, t, J=7.17 Hz), 4.03 (1 H, t, J=6.87 Hz), 3.79-3.88 (2 H, m), 3.74 (2 H, d, J=15.56 Hz), 2.88-3.00 (1 H, m), 2.77-2.87 (1 H, m), 2.18 (1 H, d, J=5.80 Hz), 1.20 (3 H, d, J=7.02 Hz), 1.00 (3H, d, J=5.80 Hz), 0.94 (6 H, d, J=6.71 Hz).

Example 37

(R)-N-((S)-1-((S)-1-(2-((S)-1-Amino-3-(4-hydroxyphenyl)-1-oxopropan-2-ylamino)-2-oxoethylamino)-1-oxopropan-2-ylamino)-1-oxopropan-2-yl)-2-(5-(hydroxymethyl)thiazol-2-ylamino)-3-methylbutanamide

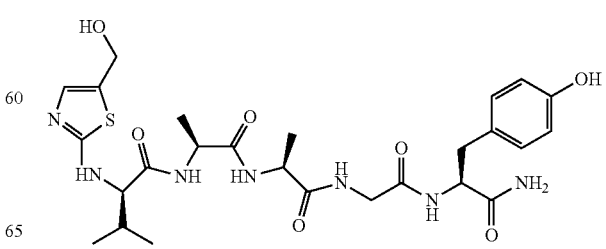

Following the procedure as described in Example 32, except using the material from Example 34, Compound B, (28.7 mg, 0.041 mmol) and sodium borohydride (10.7 mg, 0.283 mmol), the title compound is isolated (quantitative yield) as a white solid that is used crude in the macrocyclization step. LC/MS (Condition A): ret. T=1.90 min, (M+H)+ 592.30.

Example 38

Thia-V(d)AAGY Macrocycle

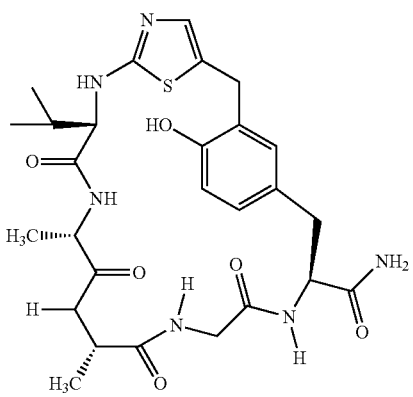 [SMILES: CC(C)[C@@H]1Nc2ncc(s2)Cc2cc(ccc2O)C[C@@H](C(N)=O)NC(=O)CNC(=O)[C@H](C)CC(=O)[C@H](C)NC1=O]

Following the procedure as described in Example 23, except using material from Example 37, nitromethane (6.0 mL), trifluoromethanesulfonic acid (182 μlit, 2.05 mmol) and N-methylmorpholine (474 μlit, 4.31 mmol), and stirring at room temp for 22 min, 10.8 mg (38.7%) of the title compound is isolated as a white solid as a TFA salt. Purification is done by preparative HPLC (Condition A) using a PHENOMENEX® Luna Axia 30×100 mm S10 column from 15% Solvent B to 85% Solvent B over 11 min, ret. T=5.93 min. LC/MS (Condition A): ret. T=2.02 min, (M+H)+ 574.28. Analytical HPLC: (Condition A): >93%, ret. T=14.92 min, (Condition B): >93%, ret. T=14.84 min, (Condition C): >95%, ret. T=6.13 min, (Condition D): >95%, ret. T=5.55 min.

Example 39

(2R,3S,4S)-2-(4-Methoxybenzyl)pyrrolidine-3,4-diol

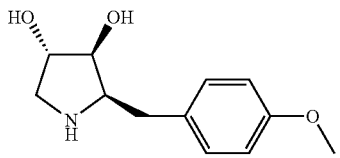 [SMILES: COc1ccc(C[C@H]2NC[C@H](O)[C@H]2O)cc1]

To a 500 mL round bottom flask containing solid (2R,3S, 4S)-4-hydroxy-2-(4-methoxybenzyl)pyrrolidin-3-yl acetate (513.3 mg, 1.935 mmol) and a magnetic stir bar is added 2M NH₃/MeOH (200 mL, 400 mmol). The resulting light tan solution is capped and stirred at room temp for 5 days. The solvent is removed in vacuo to give the title compound that is used directly "as is" in the next step. LC/MS (Condition A): ret. T=1.42 min, (M+H)+ 224.11.

Example 40 tert-Butyl 2-((2R,3S,4S)-3,4-dihydroxy-2-(4-methoxybenzyl)pyrrolidin-1-yl)-2-oxoethylcarbamate

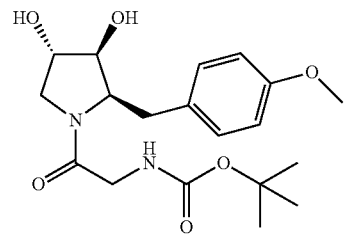 [SMILES: COc1ccc(C[C@@H]2[C@H](O)[C@@H](O)CN2C(=O)CNC(=O)OC(C)(C)C)cc1]

Following the procedure as described in Example 24, except using the material from Example 39 (432 mg, 1.935 mmol), 2-(tert-butoxycarbonylamino)acetic acid (486.1 mg, 2.77 mmol), 1-hydroxy-7-azabenzotriazole (134.0 mg, 0.984 mmol), CH₂Cl₂ (20 mL), N-methylmorpholine (1.1 mL, 10.01 mmol), and EDC (560.5 mg, 2.92 mmol), 709.1 mg (96%) of the title compound is obtained as a white solid. Purification is done by BIOTAGE® Silica gel chromatography on a 25 g Thompson Single Step silica cartridge using a linear gradient from 100% CH₂Cl₂ to 100% EtOAc/Hexanes over 12 column volumes. LC/MS (Condition A): ret. T=3.07 min, (M+Na) 403.20.

Example 41

2-Amino-1-((2R,3S,4S)-3,4-dihydroxy-2-(4-methoxybenzyl)pyrrolidin-1-yl)ethanone

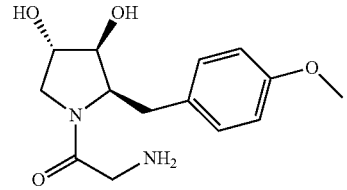 [SMILES: COc1ccc(C[C@@H]2[C@H](O)[C@@H](O)CN2C(=O)CN)cc1]

Following the procedure as described in Example 11, except using material from Example 40 (350 mg, 0.920 mmol), CH₂Cl₂ (35 mL, trifluoroacetic acid (500 μlit, 6.49 mmol) and stirring at room temp for 45 min, the title compound is isolated (quantitative yield) as a mono TFA salt and is used crude, "as is", in the next step. LC/MS (Condition A): ret. T=1.54 min, (M+H)+ 281.19.

Example 42 tert-Butyl (S)-1-(2-(2-((2R,3S,4S)-3,4-dihydroxy-2-(4-methoxybenzyl)pyrrolidin-1-yl)-2-oxoethylamino)-2-oxoethylamino)-1-oxopropan-2-ylcarbamate

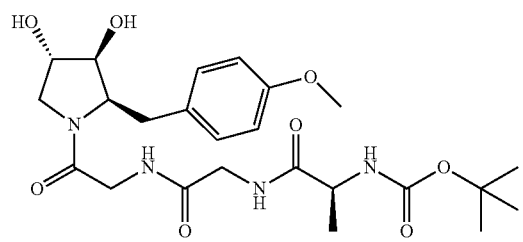 [SMILES: COc1ccc(C[C@@H]2[C@H](O)[C@@H](O)CN2C(=O)CNC(=O)CNC(=O)[C@H](C)NC(=O)OC(C)(C)C)cc1]

Following the procedure as described in Example 24, except using material from Example 41, (S)-2-(2-(tert-butoxycarbonylamino)propanamido)acetic acid, 1.00 H₂O (355.5 mg, 1.345 mmol), 1-hydroxy-7-azabenzotriazole (69.4 mg, 0.510 mmol), CH₂Cl₂ (10 mL), N-methylmorpholine (700 μL, 6.37 mmol), EDC (274.5 mg, 1.432 mmol) and stirring for 2 h, 630 mg (quantitative yield) of the title compound is isolated as a white sticky solid that contains an undetermined amount of 1-hydroxy-7-azabenzotriazole. Purification is done by BIOTAGE® Silica gel chromatography on a 12 g Thompson Single Step silica cartridge using a linear gradient from 100% CH₂Cl₂ to 100% (10% MeOH/CH₂C2) over 14 column volumes. LC/MS (Condition A): ret. T=2.88 min, (M+H)⁺ 509.31.

Example 43

(S)-2-Amino-N-(2-(2-((2R,3S,4S)-3,4-dihydroxy-2-(4-methoxybenzyl)pyrrolidin-1-yl)-2-oxoethylamino)-2-oxoethyl)propanamide

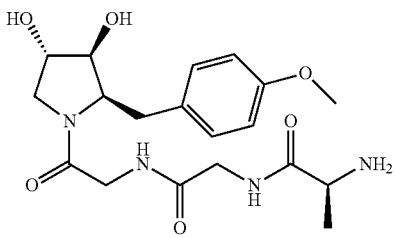 [SMILES: COc1ccc(C[C@@H]2[C@H](O)[C@@H](O)CN2C(=O)CNC(=O)CNC(=O)[C@H](C)N)cc1]

Following the procedure as described in Example 111, except using material from Example 42 (330 mg, 0.649 mmol), CH₂Cl₂ (30 mL), TFA (350 μlit, 4.54 mmol) and stirring at room temp for 5.5 h, the title compound is isolated (quantitative yield) as a TFA salt. LC/MS (Condition A): ret. T=1.84 min, (M+H)⁺ 409.13.

Example 44

(S)-N-(2-(2-((2R,3S,4S)-3,4-Dihydroxy-2-(4-methoxybenzyl)pyrrolidin-1-yl)-2-oxoethylamino)-2-oxoethyl)-2-(2-(5-formylthiazol-2-ylamino)acetamido)propanamide

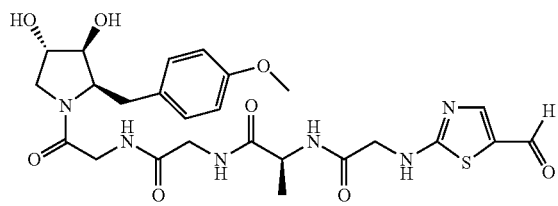 [SMILES: COc1ccc(C[C@@H]2[C@H](O)[C@@H](O)CN2C(=O)CNC(=O)CNC(=O)[C@H](C)NC(=O)CNc2ncc(C=O)s2)cc1]

Following the procedure as described in Example 7, except using material from Example 43 (52.2 mg, 0.128 mmol), material from Example 3 (38.4 mg, 0.128 mmol, 1-hydroxy-7-azabenzotriazole (13.3 mg, 0.098 mmol), anhydrous DMF (2 mL), N-methylmorpholine (91 μlit, 0.828 mmol), EDC (41.5 mg, 0.216 mmol) and stirring at room temp for 2.5 h, 35.7 mg (40.4%) of the title compound is isolated as a yellow film, as a mono TFA salt. Purification is done by preparative HPLC (Condition A) using a PHENOMENEX® Luna Axia 30×100 mm S10 column from 15% Solvent B to 85% Solvent B over 12 min, ret. T=7.02 min. LC/MS (Condition A): ret. T=2.13 min, (M+H)⁺ 577.26. Analytical HPLC: (Condition A): >92%, ret. T=14.30 min, (Condition B): >91%, ret. T=15.52 min.

Example 45

(S)-N-(2-(2-((2R,3S,4S)-3,4-Dihydroxy-2-(4-methoxybenzyl)pyrrolidin-1-yl)-2-oxoethylamino)-2-oxoethyl)-2-(2-(5-(hydroxymethyl)thiazol-2-ylamino)acetamido)propanamide

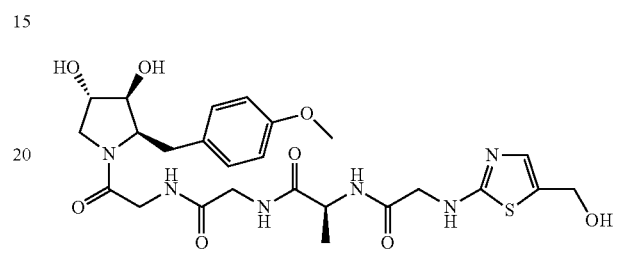

Following the procedure as described ion Example 32, except using material from Example 44 (21.4 mg, 0.031 mmol), EtOH/H₂O (4:1) (2.0 mL) and sodium borohydride (7.2 mg, 0.190 mmol), the title compound is isolated (quantitative yield) and is used crude, "as is", in the macrocyclization step. LC/MS (Condition A): ret. T=1.90 min, (M+Na) 601.29.

Example 46

Macrocycle Anisomycin-GGAG-Thia (SEQ ID NO. 13)

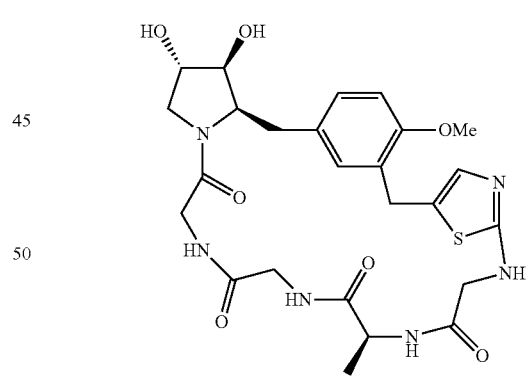

Following the procedure as described in Example 23, except using material from Example 45 (18 mg, 0.031 mmol), nitromethane (5 mL), trifluoromethanesulfonic acid (135 μlit, 1.520 mmol), N-methylmorpholine (350 μlit, 3.18 mmol), and stirring at room temp. for 25 min, 12 mg (53.2%) of the title compound is isolated as a colorless film as a TFA salt. Purification is done by preparative HPLC (Condition A) using a PHENOMENEX® Luna Axia 30×100 mm S10 column from 10% Solvent B to 85% Solvent B over 12 min, ret. T=6.63 min. LC/MS (Condition A): ret. T=2.02 min, (M+H)⁺ 561.27. Analytical HPLC: (Condition A): >99%, ret. T=14.53 min, (Condition B): >99%, ret. T=15.48 min, (Condition C): >99%, ret. T=3.63 min, (Condition D): >99%, ret. T=3.88 min.

Example 47

(S)-2-Amino-3-(3-((2-aminothiazol-5-yl)methyl)-4-hydroxyphenyl)propanoic acid

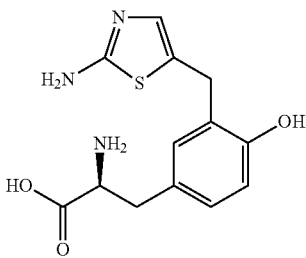 [SMILES: Nc1ncc(Cc2cc(C[C@H](N)C(=O)O)ccc2O)s1]

To a suspension of (2-aminothiazol-5-yl)methanol (35 mg, 0.269 mmol) and L-Tyrosine (199.6 mg, 1.102 mmol) in nitromethane (3.00 mL) is added trifluoromethanesulfonic acid (170 μL, 1.914 mmol). The resulting solution is sonicated for 15 sec, then heated at 80° C. for 18 h. The reaction is evaporated to dryness and the residue is purified by preparative HPLC (Condition A) using a PHENOMENEX® Luna Axia 30×100 mm S10 column from 0% Solvent B to 60% Solvent B over 12 min, ret. T=5.14 min. The product fractions are poured thru a washed WATERS OASIS® MCX 20 cc (1 g) LP extraction cartridge and washed with additional MeOH (50 mL). Elution with Aldrich 2.0M NH$_3$/MeOH (20 mL) followed by evaporation gives 48.7 mg (55.6%) of the title compound as a light tan solid. LC/MS (Condition A): ret. T=0.63 min, (M+H)$^+$ 294.05. Analytical HPLC: (Condition C): >95%, ret. T=3.26 min, (Condition D): >90%, ret. T=3.00 min. $^1$H NMR (500 MHz, DMSO-d$_6$+D$_2$O) δ ppm 6.86-7.04 (2 H, m), 6.67-6.76 (1 H, m), 6.58-6.67 (1 H, m), 3.74 (2 H, br. s.), 3.33 (1 H, br. s.), 3.02 (1 H, d, f=10.07 Hz), 2.68 (1 H, br. s.).

Example 48

(S)-tert-Butyl 2-(tert-butoxycarbonylamino)-4-thioureidobutanoate

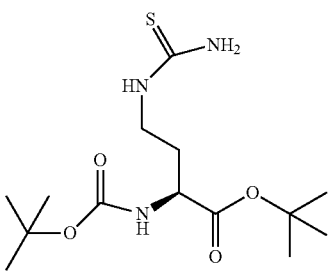 [SMILES: CC(C)(C)OC(=O)N[C@@H](CCNC(N)=S)C(=O)OC(C)(C)C]

A suspension of calcium carbonate (6.18 g, 61.8 mmol) in water (80 mL) is treated sequentially with thiophosgene (1.81 mL, 23.06 mmol) and a solution of (S)-tert-butyl 4-amino-2-(tert-butoxycarbonylamino)butanoate, HCl (5.012 g, 16.13 mmol) in chloroform (80 ml). The resulting 2 phase reaction is allowed to stir at room temp for 36 h. The reaction is filtered thru a ground glass frit and the organic and water layers are separated. The water layer is extracted twice with CH$_2$Cl$_2$, the organic layers are combined, dried over MgSO$_4$, filtered and the solvent removed in vacuo. The resulting residue is dissolved in 7M NH$_3$ in MeOH (115.1 mL, 806 mmol), and is stirred at room temp for 10 min. The solvent is removed in vacuo to give 5.38 g (quantitative yield) of the title compound as a buff solid, that is used directly, without further purification, in the next step. LC/MS (Condition A): ret. T=3.28 min, (M+Na) 356.19.

Example 49

(S)-tert-Butyl 2-(tert-butoxycarbonylamino)-4-(5-formylthiazol-2-ylamino)butanoate

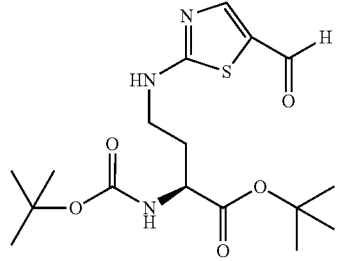 [SMILES: CC(C)(C)OC(=O)N[C@@H](CCNc1ncc(C=O)s1)C(=O)OC(C)(C)C]

To a solution of material from Example 48 (5.25 g, 15.75 mmol) in a mixture of THF (178 mL) and acetic acid (29.6 mL), is added sequentially sodium acetate (1.55 g, 18.91 mmol) and 2-bromomalonaldehyde (2.75 g, 17.33 mmol) and the reaction is stirred at room temp. for 2 h. The solvent is removed in vacuo and the residue is partitioned between water (25 mL) and CH$_2$Cl$_2$ (40 mL). The aqueous phase is extracted with CH$_2$Cl$_2$ (2×20 mL), neutralized to pH 8 with solid sodium bicarbonate and extracted again with CH$_2$Cl$_2$ (3×25 mL). The organic layers are combined, washed with brine, dried over Na$_2$SO$_4$, filtered and evaporated to dryness. The residue is purified by BIOTAGE® Silica gel chromatography on a 160 g Thompson Single Step silica cartridge using a linear gradient from 60% Hexanes/Ethyl Acetate to 50% Hexanes/Ethyl Acetate over 5 column volumes to give 3.8 g (62.6%) of the title compound as a yellow foam. LC/MS (Condition A): ret. T=3.52 min, (M+Na) 408.15. $^1$H NMR (400 MHz, DMSO-d$_6$) δ ppm 9.64 (1 H, s), 8.94 (1 H, br. s.), 8.06 (1 H, s), 7.28 (1 H, d, J=7.78 Hz), 3.79-3.96 (1 H, m), 1.92-2.05 (1 H, m), 1.75-1.92 (1 H, m), 1.43 (3 H, br. s.), 1.40 (18 H, d, J=1.76 Hz).

Example 50

(S)-2-Amino-4-(5-formylthiazol-2-ylamino)butanoic acid

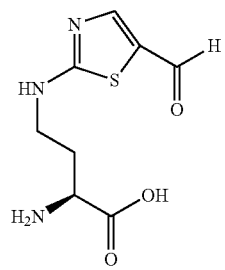

Following the procedure as described in Example 11, except using material from Example 49 (3.8 g, 9.86 mmol), CH₂Cl₂ (41 mL), trifluoroacetic acid (8.21 mL, 107 mmol) and stirring at room temp for 16 h, 6.76 g (quantitative yield) of the title compound is isolated as a thick syrup as a TFA salt that is used directly "as is" in the next reaction. LC/MS (Condition A): ret. T=0.62 min, (M+H)⁺ 230.15.

Example 51

(S)-2-(((9H-Fluoren-9-yl)methoxy)carbonylamino)-4-(5-formylthiazol-2-ylamino)butanoic acid

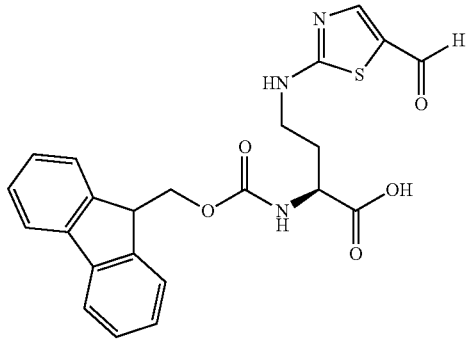 [SMILES: O=Cc1cnc(NCC[C@H](NC(=O)OCC2c3ccccc3-c3ccccc32)C(=O)O)s1]

To a solution of the crude material from Example 50 (6.76 g, 9.86 mmol) in a mixture of THF (74.0 ml) and water (24.7 ml) is added sequentially sodium bicarbonate (4.97 g, 59.2 mmol), and (9H-fluoren-9-yl)methyl 2,5-dioxopyrrolidin-1-yl carbonate (3.33 g, 9.86 mmol) and the reaction is stirred at room temp. for 1.5 h. The solvent is removed in vacuo and the residue is partitioned between water (25 mL) and EtOAc (25 mL). The organic layer is discarded, and the aqueous layer treated with 1N HCl until pH 3 is achieved. The aqueous layer is extracted with CH₂Cl₂ (3×25 mL), the organic layers are combined, washed with brine, dried over MgSO₄, filtered and evaporated to dryness to give 1.03 g (20.8%) of the title compound as a pale orange solid. LC/MS (Condition A): ret. T=3.59 min, (M+H)⁺ 452.14. ¹H NMR (400 MHz, DMSO-d₆) δ ppm 12.75 (1 H, br. s.), 9.65 (1 H, s), 8.98 (1 H, br. s.), 8.06 (1 H, s), 7.91 (2 H, d, J=7.53 Hz), 7.68-7.83 (3 H, m), 7.39-7.47 (3 H, m), 7.30-7.39 (3 H, m), 4.19-4.39 (3 H, m), 3.97-4.10 (1 H, m), 3.41 (2 H, d, J=4.52 Hz), 2.10 (1 H, dd, J=13.55, 4.77 Hz), 1.90 (1 H, dd, J=13.55, 9.79 Hz).

Example 52

N,N'-(Ethane-1,2-diylbis(azanediyl))bis(thioxomethylene)dibenzamide

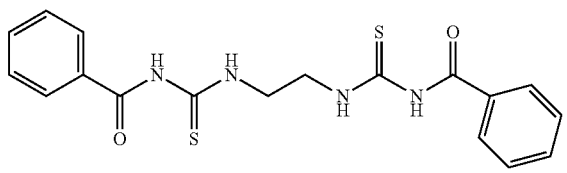 [SMILES: O=C(NC(=S)NCCNC(=S)NC(=O)c1ccccc1)c1ccccc1]

To an ice cold solution of ethane-1,2-diamine (2.23 g, 37.1 mmol) in CH₂Cl₂ (100 mL) is added benzoyl isothiocyanate (12.41 g, 76 mmol) dropwise and the resulting suspension is stirred at room temp for 18 h. The reaction is filtered thru a ground glass frit and the resulting solid is washed with CH₂Cl₂ to give 10.2 g (71%) of the title compound as a white solid. LC/MS (Condition A): ret. T=3.67 min, (M+H)⁺ 387.13. ¹H NMR (400 MHz, DMSO-d₆) δ ppm 10.98 (2 H, br. s.), 7.86-8.01 (4 H, m), 7.60-7.72 (2 H, m), 7.47-7.58 (4 H, m), 3.88-4.09 (4 H, m).

Example 53

1,1'-(Ethane-1,2-diyl)dithioureae

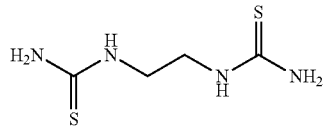

To a suspension of material from Example 52 (6.07 g, 15.71 mmol) in MeOH (80 mL) is added dropwise aqueous 5M sodium hydroxide (12.56 mL, 62.8 mmol) and the reaction is stirred at room temp for 18 h. The reaction is filtered thru a ground glass frit and the resulting solid is washed with MeOH to give 2.7 g (96%) of the title compound. LC/MS (Condition A): ret. T=0.58 min, (M+Na)⁺ 201.16.

Example 54

2,2'-(Ethane-1,2-diylbis(azanediyl))dithiazole-5-carbaldehyde

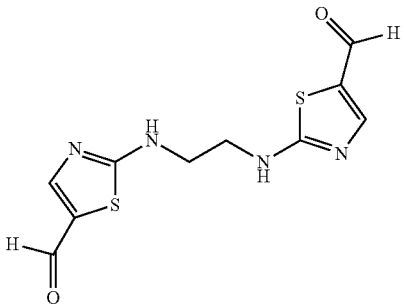 [SMILES: O=Cc1cnc(NCCNc2ncc(C=O)s2)s1]

To a suspension of material from Example 53 (2.7 g, 15.14 mmol) in THF (70 mL) is added N,N-DIEA (7.94 mL, 45.4 mmol), followed by 2-bromomalonaldehyde (6.86 g, 45.4 mmol) and the reaction is heated to 65° C. for 5 h. The solvent is removed in vacuo and the resulting residue is partitioned between water and CH₂Cl₂. The aqueous layer is back extracted with CH₂Cl₂, the organic layers are combined, washed with water, brine, dried over Na₂SO₄, filtered and evaporated to dryness. The resulting residue is triturated with CH₂Cl₂ and filtered to give 354 mg (8%) of the title compound as a tan solid. LC/MS (Condition A): ret. T=1.87 min, (M+H)⁺ 283.05. ¹H NMR (400 MHz, DMSO-d₆) δ ppm 9.66 (2 H, s), 9.04 (2 H, br. s.), 8.08 (2 H, s), 3.59 (4 H, br. s.).

Example 55

N,N'-(Propane-1,3-diylbis(azanediyl))bis(thioxomethylene)dibenzamide

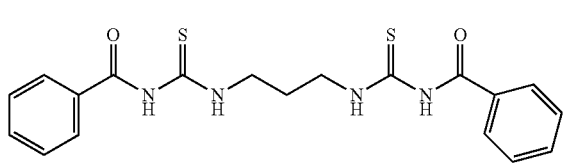 [SMILES: O=C(NC(=S)NCCCNC(=S)NC(=O)c1ccccc1)c1ccccc1]

To an ice cold solution of propane-1,3-diamine (2.77 g, 37.4 mmol) in CH$_2$Cl$_2$ (60 mL) is added dropwise benzoyl isothiocyanate (12.50 g, 77 mmol). The reaction mixture is stirred at room temp for 3 h and the solvent is removed in vacuo. The residue is suspended in MeOH (80 ml) and filtered to give 13.2 g (88%) of the title compound as a white solid. LC/MS (Condition A): ret. T=3.81 min, (M+H)$^+$ 401.14.

Example 56

1,1'-(Propane-1,3-diyl)dithiourea

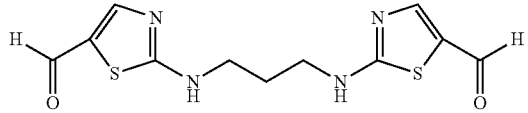 [SMILES: O=Cc1cnc(NCCCNc2ncc(C=O)s2)s1]

Following the procedure from Example 53, except using material from Example 55 (6.82 g, 17.03 mmol), aqueous 5M sodium hydroxide (13.62 mL, 68.1 mmol) and stirring at room temp for 3 h, followed by concentration, 2.52 g (77%) of the title compound is isolated as a white solid. LC/MS (Condition A): ret. T=0.43 min, (M+H)$^+$ 193.17.

Example 57

2,2'-(Propane-1,3-diylbis(azanediyl))dithiazole-5-carbaldehyde

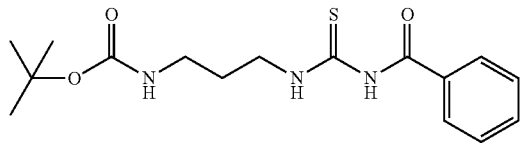 [SMILES: CC(C)(C)OC(=O)NCCCNC(=S)NC(=O)c1ccccc1]

To a suspension of material from Example 56 (2.5 g, 13.00 mmol) in THF (80 mL) is added N,N-diisopropylethylamine (5.90 mL, 33.8 mmol), followed by 2-bromomalonaldehyde (4.91 g, 32.5 mmol). The reaction mixture is heated to 65° C. for 3 h. The reaction is filtered thru a ground glass frit and the resulting solid is washed with EtOAc, suspended in MeOH and filtered again to give 673 mg (17%) of the title compound as a tan solid. LC/MS (Condition A): ret. T=2.02 min, (M+H)$^+$ 297.17. $^1$H NMR (400 MHz, DMSO-d$_6$) δ ppm 9.64 (2 H, s), 8.97 (2 H, br. s.), 8.06 (2 H, s), 1.90 (2 H, t, J=6.90 Hz).

Example 58 tert-Butyl 3-(3-benzoylthioureido)propylcarbamate

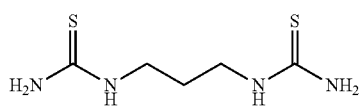

To an ice cold solution of tert-butyl 3-aminopropylcarbamate (3.56 g, 20.43 mmol) in CH$_2$Cl$_2$ (80 mL) is added dropwise benzoyl isothiocyanate (3.50 g, 21.45 mmol). The reaction mixture is stirred at room temp for 2 h after which the solvent is removed in vacuo. The resulting residue is partitioned with CH$_2$Cl$_2$ and water, the water layer is extracted with CH$_2$Cl$_2$, the organic layers are combined, washed with brine, dried over Na$_2$SO$_4$, filtered and evaporated to dryness to give 6.89 g (quantitative yield) of the title compound. LC/MS (Condition A): ret. T=3.56 min, (M+H)$^+$ 338.26.

Example 59 tert-Butyl 3-thioureidopropylcarbamate

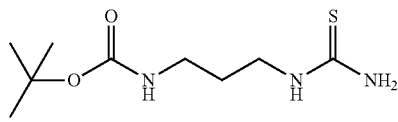

To a solution of material from Example 58 (6.89 g, 20.43 mmol) in MeOH (40 mL) is slowly added aqueous 5M NaOH (4.49 mL, 22.47 mmol) and the reaction is allowed to stir for 1 h at room temp. The solvent is removed in vacuo, the residue is neutralized with acetic acid and partitioned between water and EtOAc. The water layer is extracted with EtOAC, the organic layers are combined, washed with brine, dried over Na$_2$SO$_4$, filtered and evaporated to dryness to give 3.43 g (50.2%) of the title compound. LC/MS (Condition A): ret. T=2.54 min, (M+Na) 256.13.

Example 60 tert-Butyl 3-(5-formylthiazol-2-ylamino)propylcarbamate

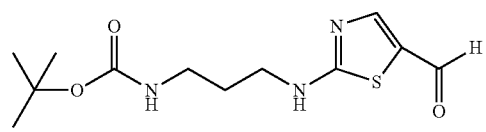 [SMILES: CC(C)(C)OC(=O)NCCCNc1ncc(C=O)s1]

To a solution of material from Example 59 (3.4 g, 10.20 mmol) in a mixture of THF (30 mL) and acetic acid (5.00 mL) is added sodium acetate (1.004 g, 12.24 mmol) followed by 2-bromomalonaldehyde (1.540 g, 10.20 mmol). The resulting mixture is stirred at room temp for 18 h, then filtered thru a ground glass frit and the filtrate is concentrated in vacuo. The resulting residue treated with EtOAc, filtered thru a ground glass frit and the filtrate is extracted with sodium bicarbonate, water, brine, dried over Na$_2$SO$_4$, filtered and evaporated to dryness. The residue is purified by BIOTAGE® Silica gel chromatography on an 80 g Thompson Single Step silica cartridge using a linear gradient from 30% EtOAc/hexanes to 100% EtOAc over 11.25 column volumes to give 960 mg (29.7%) of the title compound as a yellow solid. LC/MS (Condition A): ret. T=2.92 min, (M+Na)$^+$ 308.13. $^1$H NMR (400 MHz, DMSO-d$_6$) δ ppm 9.64 (1 H, s), 8.83-8.98 (1 H, m), 8.06 (1 H, s), 6.89 (1 H, t, J=5.40 Hz), 3.31 (2 H, d, J=5.27 Hz), 2.99 (2 H, q, J=6.69 Hz), 1.69 (2 H, t, J=7.03 Hz), 1.39 (9 H, s).

Example 61

(2,2'-(Propane-1,3-diylbis(azanediyl))bis(thiazole-5,2-diyl))dimethanol

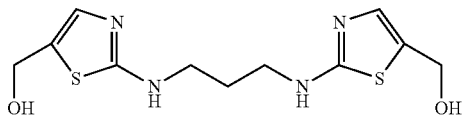 [SMILES: OCc1cnc(NCCCNc2ncc(CO)s2)s1]

Following the procedure described in Example 32, except using material from Example 57 (20.4 mg, 0.069 mmol), EtOH/H₂O (4:1) (4 mL), and sodium borohydride (24 mg, 0.634 mmol), the title compound is isolated (quantitative yield) that is used crude in the next step. LC/MS (Condition A): ret. T=0.33 min, (M+H)⁺ 301.08.

Example 62

(2S,2'S)-3,3'-(3,3'-(2,2'-(Propane-1,3-diylbis (azanediyl))bis(thiazole-5,2-diyl))bis(methylene)bis (4-hydroxy-3,1-phenylene))bis(2-(2-aminoaceta-mido)propanamide)

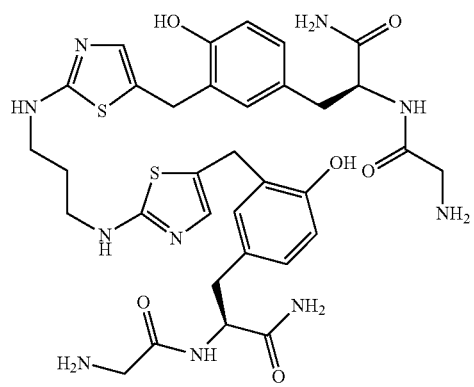 [SMILES: NCC(=O)N[C@@H](Cc1ccc(O)c(Cc2cnc(NCCCNc3ncc(Cc4cc(C[C@H](NC(=O)CN)C(N)=O)ccc4O)s3)s2)c1)C(N)=O]

Following the procedure described in Example 23, except using material from Example 61, (20.73 mg, 0.069 mmol), (S)-2-(2-aminoacetamido)-3-(4-hydroxyphenyl)propana-mide, HCl (84 mg, 0.307 mmol), nitromethane (2 mL), trif-luoromethanesulfonic acid (250 µl, 2.82 mmol) and stirring at room temp for 110 min, 44.3 mg (66.4%) of the title compound is isolated as a solid as a TFA salt. Purification is done by preparative HPLC (Condition A) using a PHENOM-ENEX® Luna Axia 30×100 mm S10 column from 15% Solvent B to 100% Solvent B over 11 min, ret. T=4.54 min. LC/MS (Condition A): ret. T=1.58 min, (M+H)⁺ 739.38. ¹H NMR (500 MHz, methanol-d₄) δ ppm 6.91-7.16 (6 H, m), 6.76 (2 H, d, J=8.24 Hz), 4.60 (2 H, dd, J=8.24, 6.10 Hz), 3.92 (4 H, s), 3.68-3.78 (2 H, m), 3.54-3.66 (2 H, m), 3.46 (4 H, t, J=6.87 Hz), 3.06 (2 H, dd, J=14.04, 6.10 Hz), 2.82 (2 H, dd, J=13.73, 8.55 Hz), 2.07 (2 H, t, J=6.87 Hz).

Example 63

Bis((9H-fluoren-9-yl)methyl)(2S,2'S)-1,1'-(2,2'-(2S, 2'S)-3,3'-(3,3'-(2,2'-(propane-1,3-diylbis(azanediyl)) bis(thiazole-5,2-diyl))bis(methylene)bis(4-hydroxy-3,1-phenylene))bis(1-amino-1-oxopropane-3,2-diyl) bis(azanediyl)bis(2-oxoethane-2,1-diyl))bis (azanediyl)bis(3-(4-hydroxyphenyl)-1-oxopropane-2, 1-diyl)dicarbamate

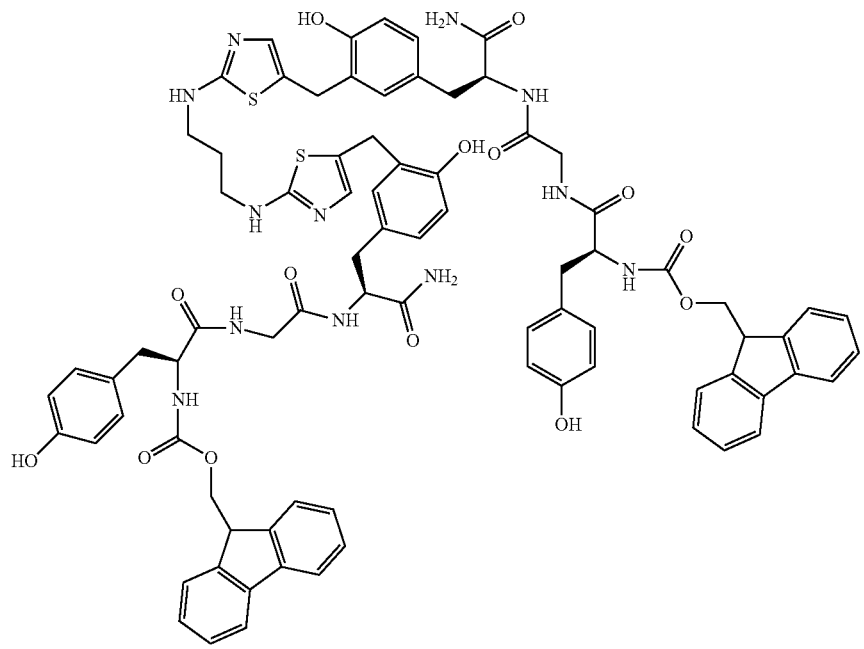 [SMILES: NC(=O)[C@H](Cc1ccc(O)c(Cc2cnc(NCCCNc3ncc(Cc4cc(C[C@H](NC(=O)CNC(=O)[C@H](Cc5ccc(O)cc5)NC(=O)OCC5c6ccccc6-c6ccccc65)C(N)=O)ccc4O)s3)s2)c1)NC(=O)CNC(=O)[C@H](Cc1ccc(O)cc1)NC(=O)OCC1c2ccccc2-c2ccccc21]

Following the procedure as described in Example 7, except using material from Example 35 (44 mg, 0.060 mmol), (R)-2-(((9H-fluoren-9-yl)methoxy)carbonylamino)-3-(4-hydroxyphenyl)propanoic acid (54.3 mg, 0.135 mmol), 1-hydroxy-7-azabenzotriazole (6.3 mg, 0.046 mmol), anhydrous DMF (2 mL), N-methylmorpholine (27 μl, 0.246 mmol), EDC (27.5 mg, 0.143 mmol) and stirring at room temp for 2 h, 9.3 mg (8%) of the title compound is isolated as a white solid. Purification is done by preparative HPLC (Condition A) using a PHENOMENEX® Luna Axia 30×100 mm S10 column from 30% Solvent B to 100% Solvent B over 11 min, ret. T=9.01 min. LC/MS (Condition A): ret. T=3.57 min, (M+2H)/2 755.93 (MW=1508).

This compound may be prepared using a method similar to that described in Example 23.

Example 65

(9H-Fluoren-9-yl)methyl(S)-1-((S)-1-((S)-1-((S)-1-amino-3-(4-hydroxyphenyl)-1-oxopropan-2-ylamino)-1-oxopropan-2-ylamino)-1-oxopropan-2-ylamino)-3-(4-hydroxyphenyl)-1-oxopropan-2-ylcarbamate

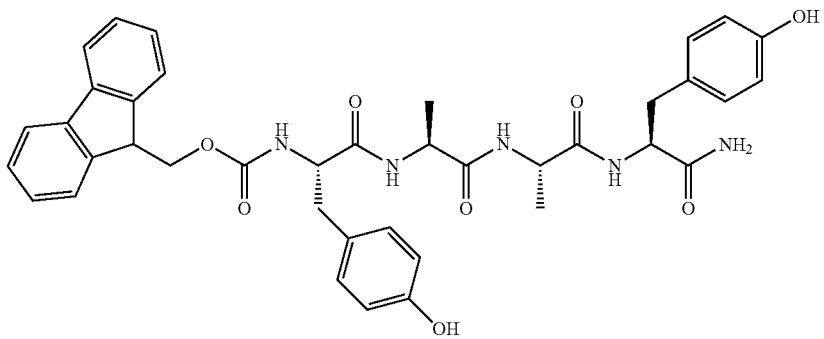

Example 64

T3T-Y(Fmoc)-G-Y-T3T-Y-G-Y(Fmoc) (SEQ ID NO. 15) Macrocycle

Following the procedure described in Example 7, except using (S)-2-amino-N-((S)-1-((S)-1-amino-3-(4-hydroxyphenyl)-1-oxopropan-2-ylamino)-1-oxopropan-2-yl)propanamide (40 mg, 0.124 mmol), Fmoc-L Tyrosine (52.6 mg, 0.130 mmol), 1-hydroxy-7-azabenzotriazole (9.5 mg, 0.070 mmol), anhydrous DMF (1.2 mL), N-methylmorpholine (16 μL, 0.146 mmol), EDC (28.5 mg, 0.149 mmol) and stirring at room temp for 4 h 15 min, 48.4 mg (47.5%) of the title compound is isolated as an off white solid. Purification is done by preparative HPLC (Condition A) using a PHENOMENEX® Luna Axia 30×100 mm S10 column from 35% Solvent B to 100% Solvent B over 11 min, ret. T=8.79 min. LC/MS (Condition A): ret. T=3.46 min, (M+H)⁺ 708.32. Analytical HPLC: (Condition A): >99%, ret. T=21.87 min, (Condition B): >99%, ret. T=22.15 min, (Condition C): >98%, ret. T=13.82 min, (Condition D): >99%, ret. T=12.79 min.

Example 66

α-helical Conformation of the MSP Peptide

To examine the α-helicity of the macrocycle stabilized peptides prepared according to the methods of the present invention, the far-UV circular dichrosim (CD) spectra of linear and macrocyclic peptides were measured and compared. Linear peptide of Example 93 and MSP of Example 93 as dry powder were prepared. A sample of each was weighed into a fresh 20 mL glass vial, and dissolved in anhydrous methanol (B&J), with vortexing for ~1 min, to yield solutions with concentrations of 200 μM. The concentrations were based on the observed mass of peptide and the respective formula weights. The solutions were transferred to 1.8 mL polypropylene tubes, and centrifuged in a table top microcentrifuge for 5 min at rt and 14,000 rpm to pellet any insoluble material. The supernatants were transferred to clean 1.8 mL tubes for

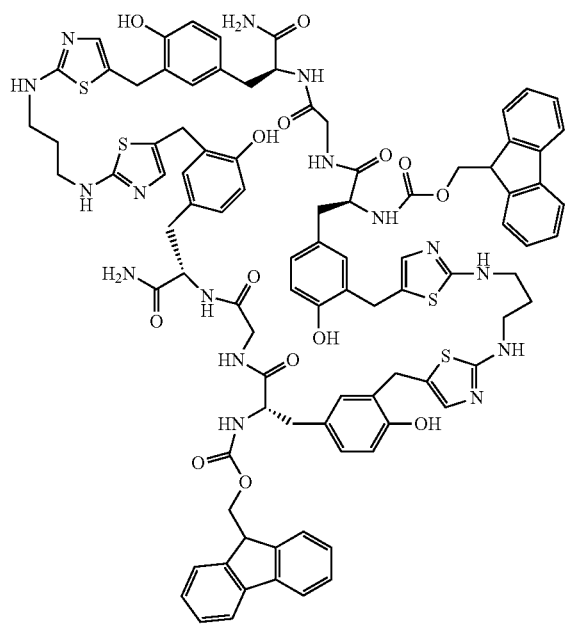 [SMILES: NC(=O)[C@@H]1Cc2ccc(O)c(c2)CC2=CN=C(NCCCNC3=NC=C(Cc4cc(ccc4O)C[C@@H](C(N)=O)NC(=O)CNC(=O)[C@@H](NC(=O)OCC4c5ccccc5-c5ccccc54)Cc4ccc(O)c(c4)CC4=CN=C(NCCCNC5=NC=C(Cc6cc(ccc6O)C[C@H](NC(=O)OCC6c7ccccc7-c7ccccc76)C(=O)NCC(=O)N1)S5)S4)S3)S2]

preparing final samples for analysis by circular dichroism (CD). Two sets of samples were prepared, one in 100% methanol at 200 µM peptide, the other in 50% aqueous methanol at 100 µM peptide prepared by adding an equal volume of ddH$_2$O to stock methanol solutions.

Samples were transferred to clean 1 mm quartz cuvettes and CD analysis performed in a JASCO J=815 instrument, and temperature maintained at 25° C. Each peptide sample was scanned from 200-450 nm, using a bandwidth of 1.00 nm, standard sensitivity, data pitch of 0.1 nm, digital integration time of 4.0 sec, a scan speed of 20 nm/min, and 6 acquisitions averaged per sample. Blank solvent samples (100% methanol and 50% aqueous methanol) were recorded simultaneously and subtracted from the peptide spectra prior to final analysis. For calculation of mean residue molar ellipticity ($\Theta^{MRW}$), the peptide concentration was multiplied by 12 to reflect the number of peptide residues in each molecule. Following blank corrections, the CD data for each peptide in each solvent was corrected for total mean residue ellipticity, and the secondary structure composition estimated by deconvolution using CDPRO module within the JASCO software. Three different algorithms were used for convolution (SELCON, CDSSTR and CONTIN), using the data obtained from 200-240 nm and a 56 protein reference data set. Each algorithm yielded similar distribution of secondary structure elements, and the final results reported as the mean and standard deviation from the three deconvolutions.

Figure 5:
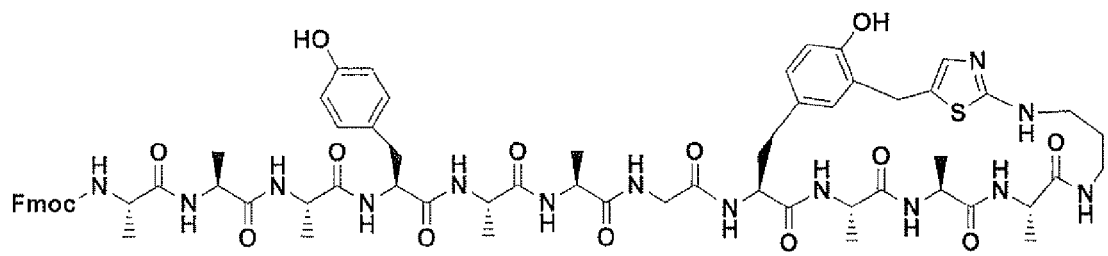
FIG. 5 shows circular dichroism (CD) data, presented as mean residue molar ellipticity (deg cm²/dmol) versus wavelength (nm) for Examples 91 and 93, both in methanol. Example 91 is shown in solid line and Example 93 in dashed line.
Figure 5:
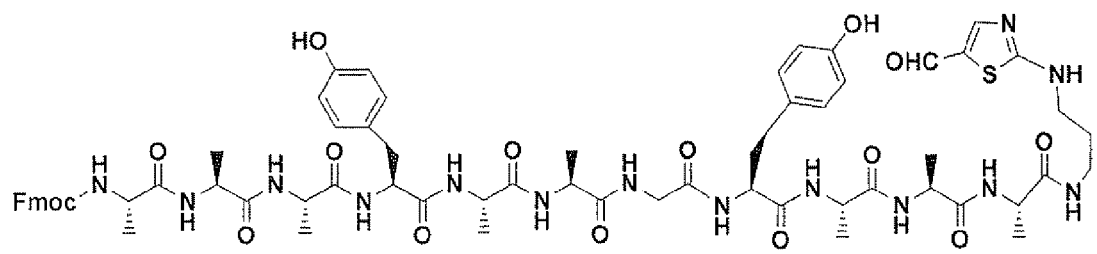
Figure 5:
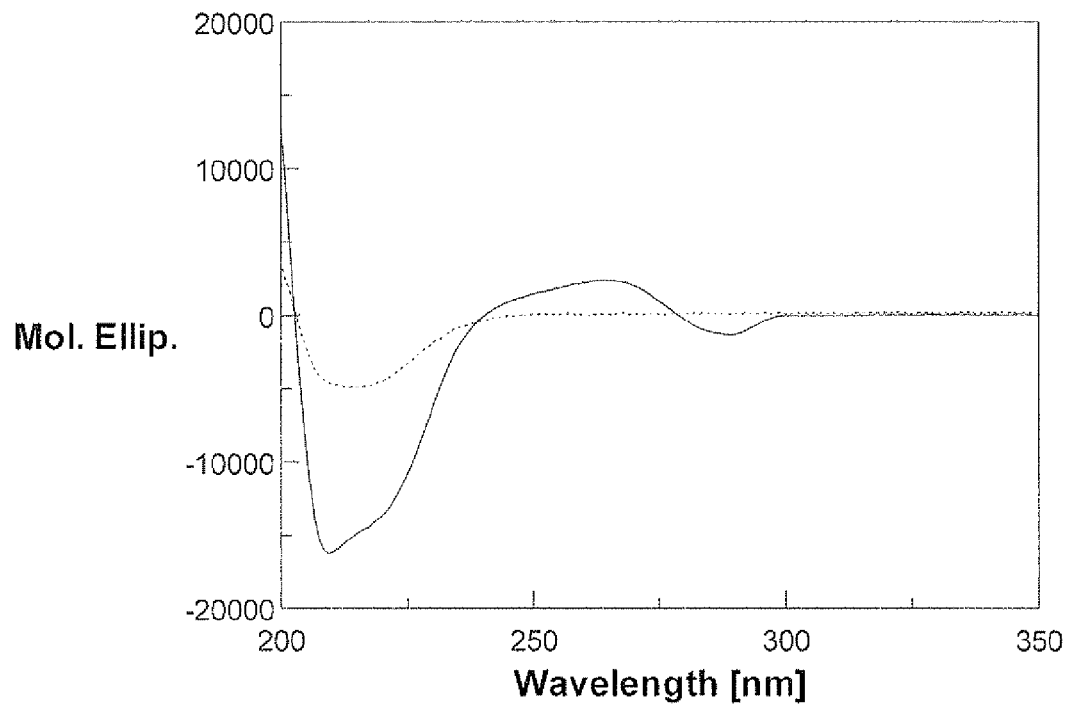

The deconvolution algorithms yield secondary structural elements of two types of α-helical structure, two types of α-strand structure, β-turn structure, and unstructured or random structure. The results reflect the average of summed α-helical forms, summed β-strand forms, the β-turn and unstructured forms from the three algorithms for the peptides in 100% methanol. The overlaid spectra illustrate the difference in signal in the far uv-region (200-240 nm) for the two related peptides in 100% methanol. The cyclized analog appears in a highly α-helical conformation (53%) with relatively little β-structure (22%), whereas the acyclic analog shows the opposite-relatively little α-helix structure (9%) but occupying conformations with high β-strand and β-turn conformation (54%). Both contain similar percentages of unstructured conformation (27% vs. 33%) as shown in FIG. 5.

In addition to the observed differences in the CD spectra in the far uv-region, the two peptides exhibited significant differences in the near uv region (>260 nm). The covalent linkage present in the cyclized peptide strongly affects the observed CD signal in this range. Strong CD signals are observed, likely from the thiazole group (positive ellipticity at 260 nm), and tyrosines (negative ellipticity at 280 nm) not observed for the less constrained acyclic peptide.

In 50% aqueous methanol, similar trends in secondary structure were seen between the two peptides, although the percentages of secondary structure elements were different. That is, the cyclized analog contained less α-helical structure (23%) than in 100% methanol (53%), but still showed more α-helical structure (23% vs. 6%), less 03-structure (45% vs. 59%), and similar amounts of unstructured conformation (32% vs. 34%) versus the acyclic peptide. Thus, in both solvents the cyclized peptide contained more α-helical conformation than the acyclic peptide.

Example 67

Macrocycle

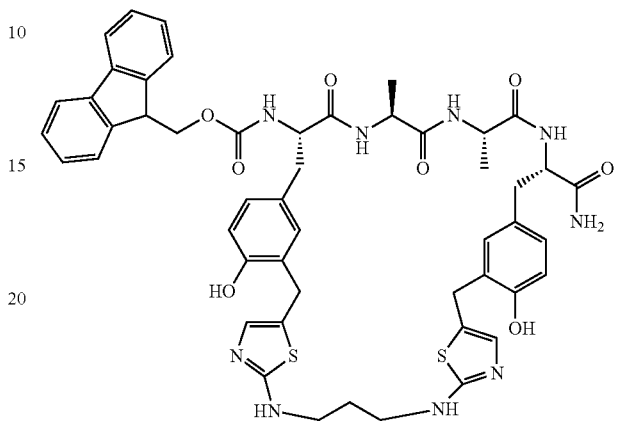

This compound may be prepared using a method similar to that described in Example 23.

Example 68

2-(3-Aminopropylamino)thiazole-5-carbaldehyde

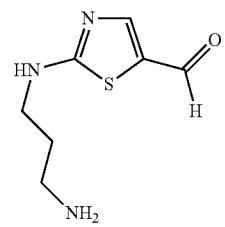 [SMILES: NCCCNc1ncc(C=O)s1]

To a solution of material from Example 60 (400 mg, 1.402 mmol) in CH$_2$Cl$_2$ (75 mL) is added HCl, 1.0M in diethyl ether (25 mL, 25.00 mmol) and the resulting pale yellow solution is stirred at room temp for 18 h. The solvent is removed in vacuo to give 356 mg (98%) of the title compound as a bis HCl salt by weight. LC/MS (Condition A): ret. T=0.522 min, (M+H)$^+$ 186.11.

Example 69

(S)-tert-Butyl 1-(3-(5-formylthiazol-2-ylamino)propylamino)-1-oxopropan-2-ylcarbamate

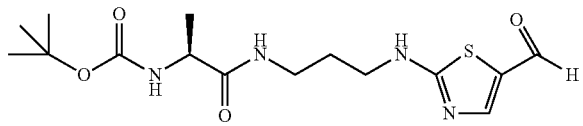 [SMILES: C[C@H](NC(=O)OC(C)(C)C)C(=O)NCCCNc1ncc(C=O)s1]

Following the procedure as described in Example 24, except using the material from Example 68 (254 mg, 0.984 mmol), N-alpha-t-BOC-L-Alanine (201 mg, 1.06 mmol), 1-hydroxy-7-azabenzotriazole (70.0 mg, 0.514 mmol), CH$_2$Cl$_2$ (15 mL), N-methylmorpholine (224 µlit, 2.04 mmol), and EDC (229 mg, 1.21 mmol), and stirring at room temp for 45 min., 267.3 mg (76%) of the title compound is obtained as a yellow solid. Purification is done by BIOTAGE® Silica gel chromatography on a 25 g Thompson Single Step silica cartridge using a linear gradient from 100% CH$_2$Cl$_2$ to 100% EtOAc, over 8.5 column volumes, with a hold at 100% EtOAc for 15 column volumes. LC/MS (Condition A): ret. T=2.54 min, (M+H)$^+$ 357.20.

Example 70

(S)-2-Amino-N-(3-(5-formylthiazol-2-ylamino)propyl)propanamide

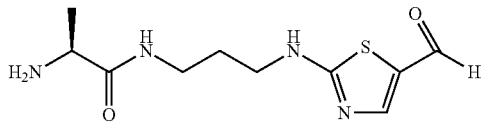 [SMILES: C[C@H](N)C(=O)NCCCNc1ncc(C=O)s1]

Following the procedure as described in Example 68, except using material from Example 69 (265 mg, 0.743 mmol), CH$_2$Cl$_2$ (50 mL), HCl, 11.0M in diethyl ether (5 mL, 5.00 mmol) and stirring at room temp for 2.5 days, 262 mg (quantitative yield) of the title compound is obtained as a pale yellow solid, as a bis HCl salt by weight. LC/MS (Condition A): ret. T=0.93 min, (M+H)$^+$ 257.14.

Example 71 tert-Butyl(S)-((S)-1-(3-(5-formylthiazol-2-ylamino)propylamino)-1-oxopropan-2-ylamino)-1-oxopropan-2-ylcarbamate

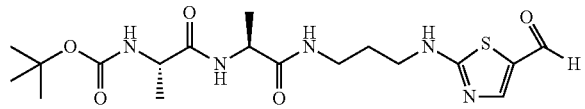 [SMILES: C[C@H](NC(=O)OC(C)(C)C)C(=O)N[C@@H](C)C(=O)NCCCNc1ncc(C=O)s1]

Following the procedure as described in Example 24, except using the material from Example 70 (260 mg, 0.790 mmol), N-alpha-t-BOC-L-Alanine (161 mg, 0.853 mmol), 1-hydroxy-7-azabenzotriazole (53.7 mg, 0.395 mmol), CH$_2$Cl$_2$ (15 mL), N-methylmorpholine (178 µlit, 1.62 mmol), and EDC (182 mg, 0.948 mmol), 223.5 mg (66.2%) of the title compound is obtained as an off white solid. Purification is done by BIOTAGE® Silica gel chromatography on a 25 g Thompson Single Step silica cartridge using a linear gradient from 100% CH$_2$Cl$_2$ to 100% ACN over 10 column volumes, with a hold at 100% ACN for 15 column volumes. LC/MS (Condition A): ret. T=2.59 min, (M+H)$^+$ 428.23.

Example 72

(S)-2-Amino-N-((S)-1-(3-(5-formylthiazol-2-ylamino)propylamino)-1-oxopropan-2-yl)propanamide

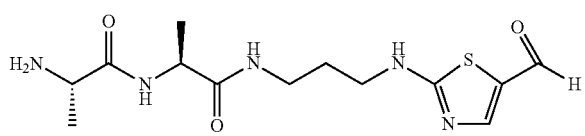 [SMILES: C[C@H](N)C(=O)N[C@@H](C)C(=O)NCCCNc1ncc(C=O)s1]

Following the procedure as described in Example 68, except using material from Example 71 (220 mg, 0.515 mmol), CH$_2$Cl$_2$ (85 mL), HCl, 1.0M in diethyl ether (14 mL, 14.00 mmol) and stirring at room temp for 3.5 h, 255.5 mg (quantitative yield) of the title compound is obtained as a yellow solid, as a 4 HCl salt by weight. LC/MS (Condition A): ret. T=1.18 min, (M+H)$^+$ 328.18.

Example 73 tert-Butyl(S)-1-((S)-1-((S)-1-(3-(5-formylthiazol-2-ylamino)propylamino)-1-oxopropan-2-ylamino)-1-oxopropan-2-ylamino)-1-oxopropan-2-ylcarbamate

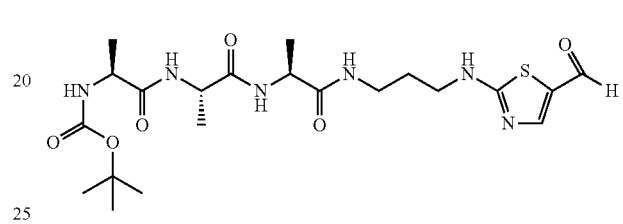

Following the procedure as described in Example 24, except using the material from Example 72 (255 mg, 0.539 mmol), N-alpha-t-BOC-L-Alanine (117 mg, 0.620 mmol), 1-hydroxy-7-azabenzotriazole (36.7 mg, 0.269 mmol), CH$_2$Cl$_2$ (10 mL), N-methylmorpholine (250 µlit, 2.27 mmol), EDC (124 mg, 0.647 mmol), and stirring at room temp for 18 h, 215.3 mg (80%) of the title compound is obtained as a white solid. The desired product crystallized out of the reaction, is collected by vacuum filtration and dried under high vacuum for several hours. LC/MS (Condition A): ret. T=2.70 min, (M+H)$^+$ 499.26. $^1$H NMR (500 MHz, methanol-d$_4$) δ ppm 9.61 (1 H, d, J=2.14 Hz), 7.96 (1 H, d, J=2.14 Hz), 4.16-4.38 (2 H, m), 3.92-4.07 (1 H, m), 3.43 (2 H, t, J=6.26 Hz), 1.88 (2 H, t, J=5.95 Hz), 1.26-1.51 (18 H, m).

Example 74

(S)-2-Amino-N-((S)-1-((S)-1-(3-(5-formylthiazol-2-ylamino)propylamino)-1-oxopropan-2-ylamino)-1-oxopropan-2-yl)propanamide

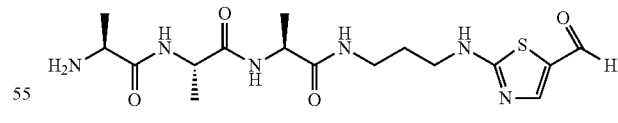

To a suspension of material from Example 73 (213 mg, 0.427 mmol) in Dioxane (10 mL), is added HCl, 4.0M in dioxane (92 mL, 368 mmol) and HCl, 1.0M in Et$_2$O (10.4 mL, 10.4 mmol). The resulting suspension is stirred at room temp 4 h and then the solvent is evaporated off under a gentle stream of N$_2$. The resulting residue is suspended in CH$_2$Cl$_2$ (60 mL) and the solvent is removed in vacuo (repeat 4 times) to give the title compound (quantitative yield) as an off white solid, as an HCl salt. LC/MS (Condition A): ret. T=1.35 min, (M+H)$^+$ 399.20.

Example 75
tert-Butyl (2S,5S,8S,11S)-16-(5-formylthiazol-2-ylamino)-1-(4-hydroxyphenyl)-5,8,11-trimethyl-3,6,9,12-tetraoxo-4,7,10,13-tetraazahexadecan-2-ylcarbamate

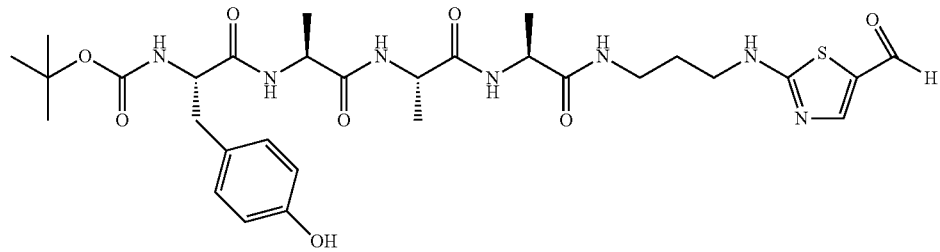 [SMILES: C[C@H](NC(=O)[C@H](C)NC(=O)[C@H](C)NC(=O)[C@H](Cc1ccc(O)cc1)NC(=O)OC(C)(C)C)C(=O)NCCCNc1ncc(C=O)s1]

Following the procedure as described in Example 7, except using the material from Example 74 (57 mg, 0.143 mmol), (S)-2-(tert-butoxycarbonylamino)-3-(4-hydroxyphenyl)propanoic acid (47.5 mg, 0.169 mmol), 1-hydroxy-7-azabenzotriazole (9.1 mg, 0.067 mmol), DMF (3 mL), N-methylmorpholine (64 µlit, 0.582 mmol), EDC (30.2 mg, 0.158 mmol), and stirring at room temp for 1 h, 118.1 mg (93%) of the title compound is obtained as a yellow film, as a TFA salt. Purification is done by preparative HPLC (Condition A) using a PHENOMENEX® Luna Axia 30×100 mm S10 column from 30% Solvent B to 100% Solvent B over 11 min, ret. T=6.91 min. LC/MS (Condition A): ret. T=2.89 min, (M+H)$^+$ 662.45.

Example 76
tert-Butyl (2S,5S,8S,11S)-16-(5-(hydroxymethyl)thiazol-2-ylamino)-1-(4-hydroxyphenyl)-5,8,11-trimethyl-3,6,9,12-tetraoxo-4,7,10,13-tetraazahexadecan-2-ylcarbamate

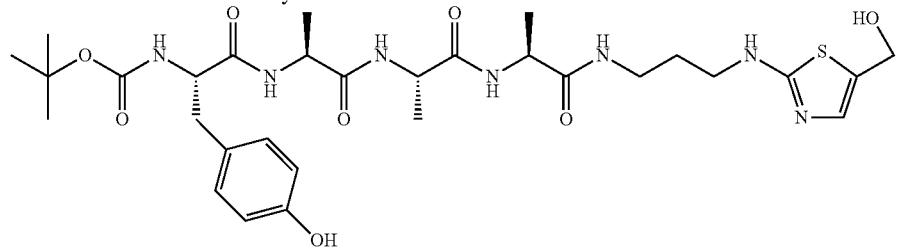

Following the procedure as described in Example 32, except using the material from Example 75 (106 mg, 0.119 mmol), EtOH/H$_2$O (4:1) (4 mL), sodium borohydride (32.7 mg, 0.864 mmol) and stirring at room temp for 1 h, the title compound is isolated (quantitative yield) that is used crude in the next step. LC/MS (Condition A): ret. T=2.51 min, (M+H)$^+$ 664.46.

Example 77
Macrocycle

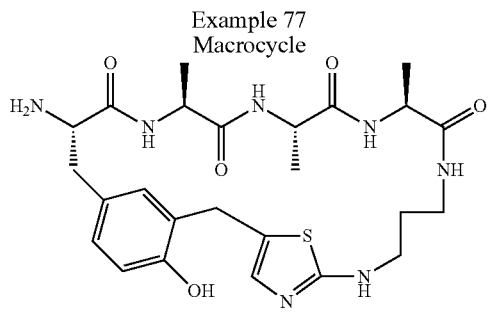

Following the procedure as described in Example 23, except using the material from Example 76, nitromethane (12 mL), trifluoromethanesulfonic acid (528 µlit, 5.95 mmol) and N-methylmorpholine (1.4 mL, 12.73 mmol), 10 mg (15.4%) of the title compound is isolated as a yellow film as a TFA salt. Purification is done by preparative HPLC (Condition A) using a PHENOMENEX® Luna Axia 30×100 mm S10 column from 10% Solvent B to 85% Solvent B over 12 min, ret. T=4.96 min. LC/MS (Condition A): ret. T=1.58 min, (M+H)$^+$ 546.36.

Example 78
(S)-tert-Butyl 1-carbamothioylpyrrolidine-2-carboxylate

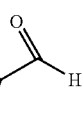

To a suspension of calcium carbonate (7.38 g, 73.8 mmol) in water (95 mL) is added thiophosgene (2.17 mL, 27.5 mmol), followed by a solution of (S)-tert-butyl pyrrolidine-2-carboxylate, HCl (4 g, 19.26 mmol) in chloroform (95 ml) and the resulting two phase reaction is stirred at room temp for 18 h. The layers are separated, the aqueous layer is washed with CH$_2$Cl$_2$ (2×20 mL), the organic layers are combines, washed with brine (1×20 mL), dried over MgSO$_4$, filtered and evaporated to dryness. The resulting pale yellow oil is treated with 2M NH$_3$/MeOH (145 mL, 290 mmol) for 45 min, and the solvent removed in vacuo. The resulting crude product is purified by BIOTAGE® Silica gel chromatography on a 160 g Thompson Single Step silica cartridge using an isocratic mixture of 30% ethyl acetate/60% CH$_2$Cl$_2$ over 4 column volumes to give 1.08 g (23%) of the title compound as a grey solid. LC/MS (Condition A): ret. T=1.58 min, (M+Na) 253.14.

Example 79

(S)-tert-Butyl 1-(5-formylthiazol-2-yl)pyrrolidine-2-carboxylate

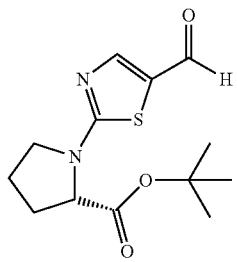

To a solution of material from Example 78 (1.075 g, 4.67 mmol) in a mixture of THF (51.3 mL) and acetic acid (8.55 mL) is added sodium acetate (0.46 g, 5.60 mmol), followed by 2-bromomalonaldehyde (0.82 g, 5.13 mmol) and the reaction is stirred at room temp for 2 h. The solvent is removed in vacuo, the residue is partitioned between water and $CH_2Cl_2$ and the water layer is extracted with $CH_2Cl_2$ (1×20 mL). The organic layers are combined, partitioned with water and treated with solid sodium bicarbonate until the water layer has pH=8. The water layer is extracted with $CH_2Cl_2$ (2×25 mL), the organic layers are combined, washed with brine, dried over $MgSO_4$, filtered and the solvent is removed in vacuo, The resulting residue is purified by BIOTAGE® Silica gel chromatography on a Thompson Single Step silica cartridge using an isocratic mixture of 40% ethyl acetate/60% $CH_2Cl_2$ to give 945 mg (68.1%) of the title compound as a yellow solid. LC/MS (Condition A): ret. T=3.23 min, (M+Na) 305.14. $^1$H NMR (400 MHz, chloroform-d) δ ppm 9.69 (1 H, s), 7.89 (1 H, s), 4.49 (1 H, br. s.), 3.36-3.87 (2 H, m), 2.32-2.51 (1 H, m), 2.03-2.29 (3 H, m), 1.46 (9 H, s).

Example 80

(S)-1-(5-Formylthiazol-2-yl)pyrrolidine-2-carboxylic acid

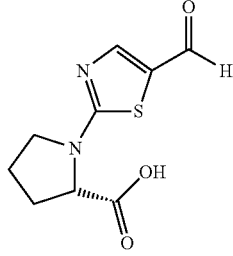

Following the procedure as described in Example 68, except using material from Example 79 (33.4 mg, 0.118 mmol), anhydrous $CH_2Cl_2$ (3 mL), HCl, 1.0M in Et2O (6 mL, 6.0 mmol) stirring at room temp for 48 h, the title compound (quantitative yield) is isolated as an HCl salt that is used directly "as is" in the next step. LC/MS (Condition A): ret. T=1.88 min, (M+H)$^+$ 227.05.

Example 81

(S)-N-((S)-1-((S)-1-((S)-1-Amino-3-(4-hydroxyphenyl)-1-oxopropan-2-ylamino)-1-oxopropan-2-ylamino)-1-oxopropan-2-yl)-1-(5-formylthiazol-2-yl)pyrrolidine-2-carboxamide

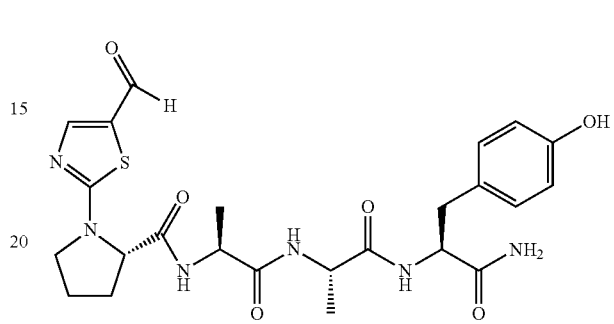

To a solution of material from Example 80 (25 mg, 0.110 mmol), (S)-2-amino-N-((S)-1-((S)-1-amino-3-(4-hydroxyphenyl)-1-oxopropan-2-ylamino)-1-oxopropan-2-yl)propanamide, TFA (25 mg, 0.057 mmol), and 1-hydroxy-7-azabenzotriazole (4 mg, 0.029 mmol) in anhydrous DMF (2 mL) is added sequentially EDC (12 mg, 0.063 mmol), followed by N-methylmorpholine (40 µl, 0.364 mmol). The resulting solution is stirred at room temp for 45 min, diluted with MeOH (5 mL) and purified by preparative HPLC (Condition A) using a PHENOMENEX® Luna Axia 30×100 mm S10 column from 15% Solvent B to 85% Solvent B over 11 min, ret. T=5.9 min. The fractions containing the desired product were evaporated to dryness to give 23 mg (63%) of the title compound as a white solid as a TFA salt. LC/MS (Condition A): ret. T=2.04 min, (M+H)$^+$ 531.27.

Example 82

(S)-N-((S)-1-((S)-1-((S)-1-Amino-3-(4-hydroxyphenyl)-1-oxopropan-2-ylamino)-1-oxopropan-2-ylamino)-1-oxopropan-2-yl)-1-(5-(hydroxymethyl)thiazol-2-yl)pyrrolidine-2-carboxamide

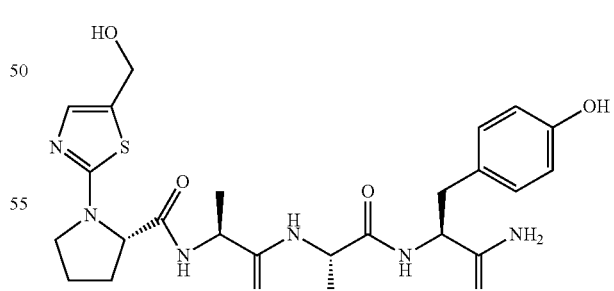

Following the procedure as described in Example 32, except using material from Example 81 (6.4 mg, 0.012 mmol), EtOH/$H_2O$ (4:1) (3 mL), sodium borohydride (4.2 mg, 0.111 mmol) and stirring at room temp for 2 h, the title compound is isolated (quantitative yield) that is used crude in the next step. LC/MS (Condition A): ret, T=1.54 min, (2M+Na) 1087.51.

Example 83

Macrocycle

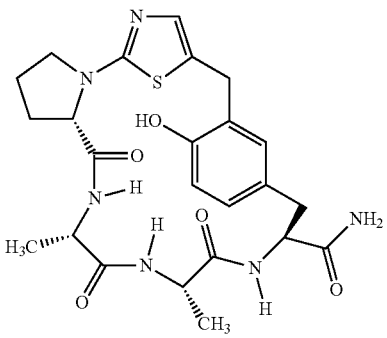 [SMILES: C[C@@H]1NC(=O)[C@H](C)NC(=O)[C@@H]2CCCN2C2=NC=C(Cc3cc(ccc3O)C[C@@H](C(N)=O)NC1=O)S2]

This compound may be prepared using a method similar to that described in Example 23.

Example 84

Boc-Fmoc DAP Phe dipeptide

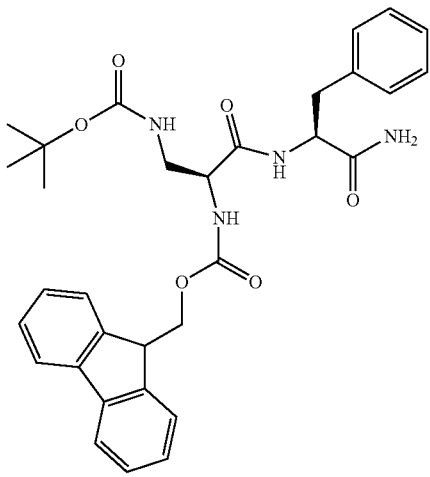 [SMILES: CC(C)(C)OC(=O)NC[C@H](NC(=O)OCC1c2ccccc2-c2ccccc21)C(=O)N[C@@H](Cc1ccccc1)C(N)=O]

To a suspension of (R)-2-(((9H-fluoren-9-yl)methoxy)carbonylamino)-3-(tert-butoxycarbonylamino)propanoic acid (1.06 g, 2.486 mmol), (S)-2-amino-3-phenylpropanamide (417 mg, 2.54 mmol), and 1-hydroxy-7-azabenzotriazole (171 mg, 1.256 mmol), in $CH_2Cl_2$ (80 mL), is added EDC (520 mg, 2.71 mmol), followed immediately by N-methylmorpholine (270 µL, 2.456 mmol) and the resulting suspension is stirred at room temp for 2.5 days. The resulting precipitate is filtered off and dried under high vacuum for several hours to give 1.42 g (92%) of the title compound as a white solid. LC/MS (Condition A): ret. T=4.20 min, $(M+H)^+$ 573.42.

Example 85 tert-Butyl(S)-2-amino-3-((S)-1-amino-1-oxo-3-phenylpropan-2-ylamino)-3-oxopropylcarbamate

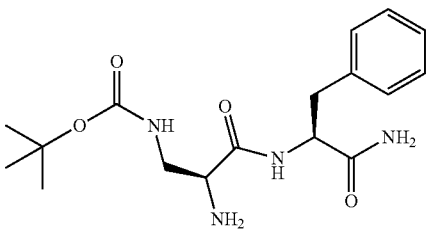 [SMILES: CC(C)(C)OC(=O)NC[C@H](N)C(=O)N[C@@H](Cc1ccccc1)C(N)=O]

To a suspension of material from Example 84 (411 mg, 0.718 mmol) in anhydrous THF (5 mL) is added piperidine (415 µlit, 4.19 mmol) and the resulting pale yellow suspension is stirred at room temp for 18 h. The solvent is removed in vacuo and the resulting residue is purified by preparative HPLC (Condition A) using a PHENOMENEX® Luna Axia 30×100 mm S10 column from 25% Solvent B to 90% Solvent B over 11 min, ret. T=4.88 min. The product fractions are poured thru a washed WATERS OASIS® MCX 20 cc (1 g) LP extraction cartridge and washed with additional MeOH (50 mL). Elution with Aldrich 2.0M $NH_3$/MeOH (20 mL) followed by evaporation gives 124.2 mg (49.4%) of the title compound as a white solid. LC/MS (Condition A): ret. T=2.34 min, $(M+H)^+$ 351.25. $^1H$ NMR (500 MHz, methanol-$d_4$) δ ppm 7.11-7.43 (5 H, m), 4.65 (1 H, dd, J=8.39, 5.65 Hz), 3.35-3.40 (1 H, m), 3.07-3.29 (3 H, m), 2.96 (1 H, dd, J=13.89, 8.70 Hz), 1.45 (9 H, s).

Example 86

(9H-Fluoren-9-yl)methyl (2S,5S,11S,14S,17S)-1-amino-5-(aminomethyl)-2-benzyl-18-(4-hydroxyphenyl)-1,14-dimethyl-1,4,7,10,13,16-hexaoxo-3,6,9,12,15-pentaazaoctadecan-7-ylcarbamate

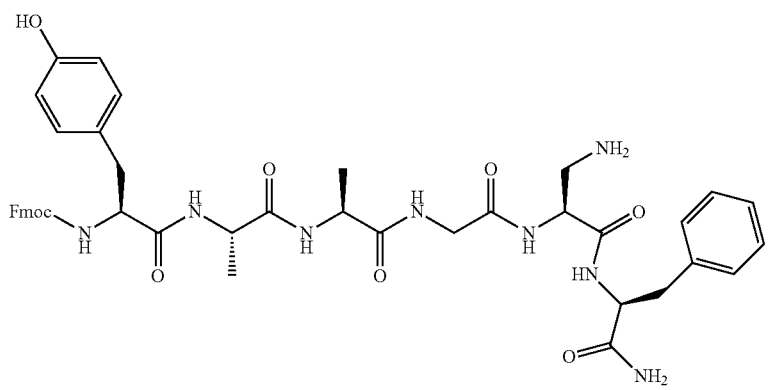

Following the procedure as described in Example 7, except using material from Example 85 (62.9 mg, 0.180 mmol), Fmoc-YAAG-OH peptide (96 mg, 0.159 nm mol), 1-hydroxy-7-azabenzotriazole (12.22 mg, 0.090 m mol), anhydrous DMF (4.0 mL), N-methylmorpholine (20 μl, 0.182 mmol), EDC (37.9 mg, 0.197 mmol) and stirring at room temp for 1.75 h, the Boc protected product is isolated. Purification is done by preparative HPLC (Condition A) using a PHENOMENEX® Luna Axia 30×100 mm S10 column from 35% Solvent B to 100% Solvent B over 10 min, ret. T=10.2 min. The fractions containing the BOC protected desired product are evaporated to dryness, redissolved in CH$_2$Cl$_2$ (10 mL) and treated with TFA (20 mL) for 2 h. Evaporation of the solvent in vacuo and drying under high vacuum gives 177.9 mg (77%, 2 steps) of the title compound as a clear film, as a TFA salt. LC/MS (Condition A): ret. T=3.39 min, (M+H)$^+$ 835.49.

Example 87

(9H-Fluoren-9-yl)methyl (2S,5S,11S,14S,17S)-1-amino-2-benzyl-5-((2-(5-formylthiazol-2-ylamino)acetamido)methyl)-18-(4-hydroxyphenyl)-11,14-dimethyl-1,4,7,10,13,16-hexaoxo-3,6,9,12,15-pentaazaoctadecan-17-ylcarbamate

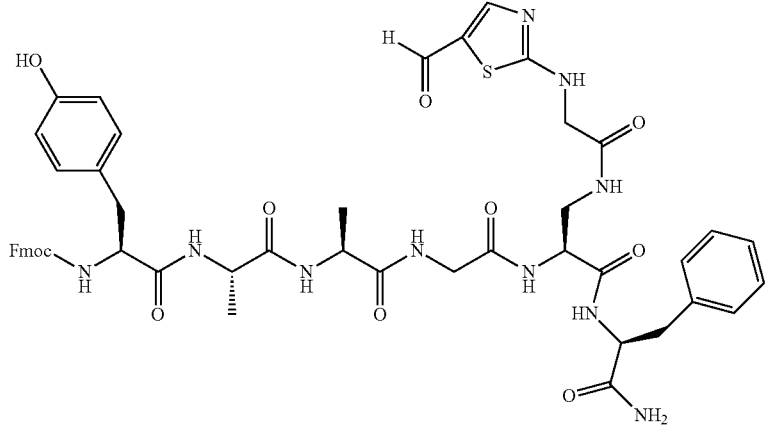

Following the procedure as described in Example 7, except using material from Example 86 (177.9 mg, 0.138 mmol), 2-(5-formylthiazol-2-ylamino)acetic acid, 1.00 HCl (33.7 mg, 0.152 mmol), 1-hydroxy-7-azabenzotriazole (9.7 mg, 0.071 mmol) anhydrous DMF (4 mL), N-methylmorpholine (106 μL, 0.964 mmol) and EDC (29.1 mg, 0.152 mmol), 90.8 mg (59%) of the title compound is isolated as a pale yellow solid as a TFA salt. Purification is done by preparative HPLC (Condition A) using a PHENOMENEX® Luna Axia 30×100 mm S10 column from 35% Solvent B to 100% Solvent B over 10 min, ret. T=9.07 min. LC/MS (Condition A): ret. T=3.66 min, (M+H)$^+$ 1003.68.

Example 88

(9H-Fluoren-9-yl)methyl (2S,5S,11S,14S,17S)-1-amino-2-benzyl-5-((2-(5-(hydroxymethyl)thiazol-2-ylamino)acetamido)methyl)-18-(4-hydroxyphenyl)-11,14-dimethyl-1,4,7,10,13,16-hexaoxo-3,6,9,12,15-pentaazaoctadecan-17-ylcarbamate

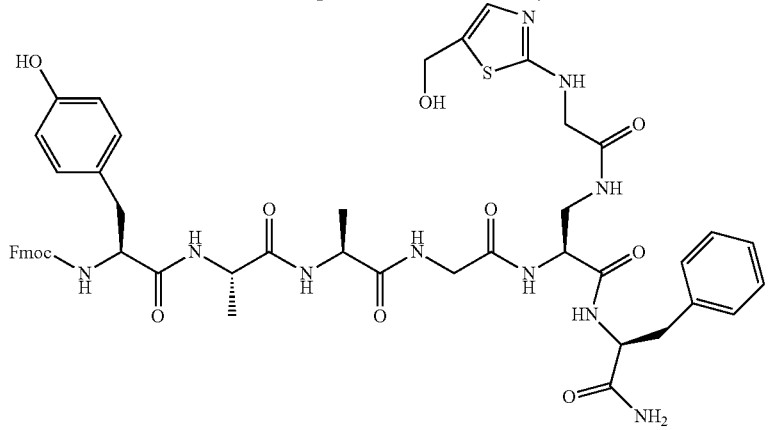

Following the procedure as described in Example 32, except using material from Example 87 (16 mg, 0.014 mmol), EtOH/H$_2$O (4:1) (5 mL), sodium borohydride (6.3 mg, 0.167 mmol) and stirring at room temp for 2.5 h, the title compound is isolated (quantitative yield) that is used crude in the next step. LC/MS (Condition A): ret. T=3.37 min, (2M+Na) 1005.75.

Example 89

Macrocycle

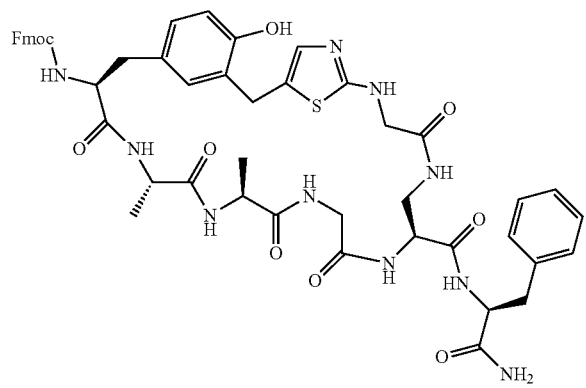

This compound may be prepared using a method similar to that described in Example 23.

Example 90

(S)-Allyl 2-((S)-2-(((9H-fluoren-9-yl)methoxy)carbonylamino)-3-(tert-butoxycarbonylamino)propanamido)-4-methylpentanoate

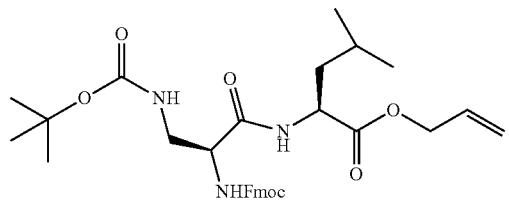

Following the procedure as described in Example 24, except using suspension of (R)-2-(((9H-fluoren-9-yl)methoxy)carbonylamino)-3-(tert-butoxycarbonylamino)propanoic acid (500 mg, 1.172 mmol), L-leucine allyl ester p-toluenesulfonate salt (411 mg, 1.196 mmol), 1-hydroxy-7-azabenzotriazole (80 mg, 0.586 mmol), CH$_2$Cl$_2$ (40 mL), N-methylmorpholine (0.258 mL, 2.345 mmol), and EDC (247 ing, 1.290 mmol), 137 mg (20.16%) of the title compound is isolated as a white solid. Purification is done by BIOTAGE® Silica gel chromatography on a 90 g Thompson Single Step silica cartridge using a linear gradient from 100% Hexanes to 100% (1:1 EtOAc/Hexanes) over 12 column volumes. LC/MS (Condition A): ret. T=4.50 min, (2M+Na) 1181.97.

Example 91

C-terminal Macrocycle Peptide

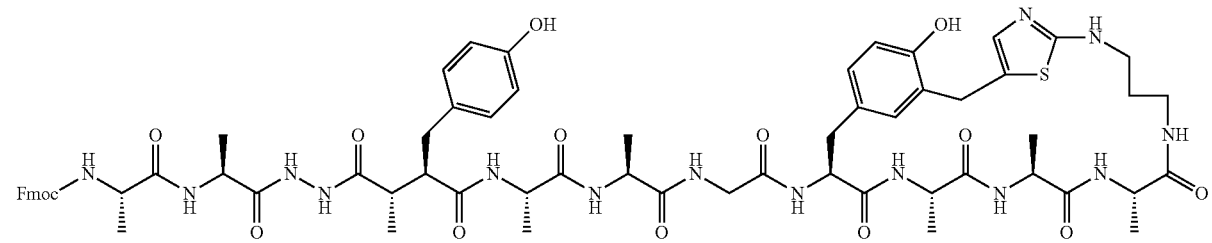

Following the procedure as described in Example 7, except using material from Example 77 (10 mg, 0.015 mmol), (5S,8S,11S,14S,17S,20S)-1-(9H-fluoren-9-yl)-14-(4-hydroxybenzyl)-5,8,11,17,20-pentamethyl-3,6,9,12,15,18,21-heptaoxo-2-oxa-4,7,10,13,16,19,22-heptaazatetracosan-24-oic acid (12.37 mg, 0.015 mmol), 1-hydroxy-7-azabenzotriazole (1.5 mg, 0.011 mmol), DMF (1.0 mL), N-methylmorpholine (7.0 µl, 0.064 mmol), EDC (3.6 mg, 0.019 mmol) and stirring at room temp for 3 h, 2.2 mg (9%) of the title compound is isolated as an off white solid. Purification is done by preparative HPLC (Condition A) using a PHENOMENEX® Luna Axia 30×100 mm S10 column from 30% Solvent B to 100% Solvent B over 11 min, ret. T=10.13 min. A second purification is done by preparative HPLC (Condition B) using a PHENOMENEX® Luna Axia 30×100 mm S10 column from 10% Solvent B to 100% Solvent B over 12 min, ret. T=6.62 min. LC/MS (Condition A): ret. T=3.61 min, (M+Na) 1365.97. Analytical HPLC: (Condition A): >92%, ret. T=24.81 min, (Condition B): >94%, ret. T=26.01 min, (Condition C): >92%, ret. T=11.68 min, (Condition D): >96%, ret. T=12.64 min.

Example 92

(S)-2-Amino-N-((S)-1-((S)-1-((S)-1-(3-(5-formylthiazol-2-ylamino)propylamino)-1-oxopropan-2-ylamino)-1-oxopropan-2-ylamino)-1-oxopropan-2-yl)-3-(4-hydroxyphenyl)propanamide

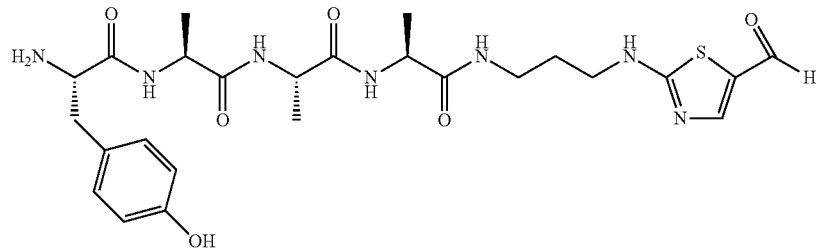 [SMILES: C[C@H](NC(=O)[C@H](C)NC(=O)[C@H](C)NC(=O)[C@@H](N)Cc1ccc(O)cc1)C(=O)NCCCNc1ncc(C=O)s1]

Following the procedure as described in Example 3, except using material from Example 75 (100.2 mg, 0.129 mmol), CH$_2$Cl$_2$ (2 mL), TFA (2 mL, 26 mmol) and stirring at room temp for 2 h, the title compound (quantitative yield) is isolated as an off white solid, as a TFA salt, that is used directly "as is" in the next coupling step. LC/MS (Condition A): ret. T=1.88 min, (M+H)$^+$ 562.37.

Example 93

(9H-Fluoren-9-yl)methyl (2S,5S,8S,11S,14S,17S,23S,26S,29S,32S)-37-(5-formylthiazol-2-ylamino)-11,23-bis(4-hydroxybenzyl)-5,8,14,17,26,29,32-heptamethyl-3,6,9,12,15,18,21,24,27,30,33-undecaoxo-4,7,10,13,16,19,22,25,28,31,34-undecaazaheptatriacontan-2-ylcarbamate

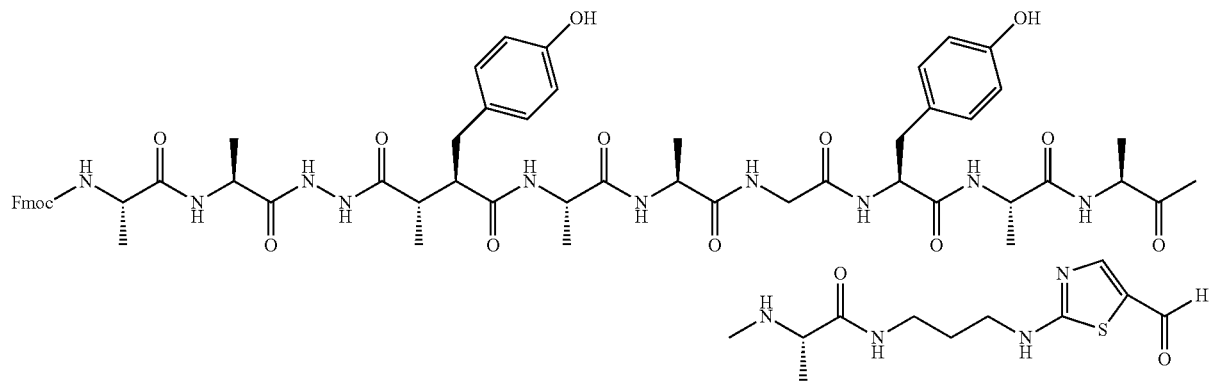

To a solution of material from Example 92 (87 mg, 0.129 mmol), (5S,8S,11S,14S,17S,20S)-1-(9H-fluoren-9-yl)-14-(4-hydroxybenzyl)-5,8,11,17,20-pentamethyl-3,6,9,12,15,18,21-heptaoxo-2-oxa-4,7,10,13,16,19,22-heptaazatetracosan-24-oic acid (59 mg, 0.063 mmol), and 1-hydroxy-7-azabenzotriazole (10.5 mg, 0.08 mmol) in anhydrous DMF (5.0 mL) is added sequentially N-methylmorpholine (100.0 μl, 0.910 mmol), followed by EDC (28.8 mg, 0.150 mmol). The resulting pale yellow solution is stirred at room temp for 18 h, during which time it slowly turns cloudy. The crude reaction is diluted with a solution of TFA (100 μlit) in methanol (1.5 mL) and much solid precipitates out of the reaction. The reaction is centrifuged for 20 min and the supernatant is pipetted off. The resulting plug of solid is washed sequentially with Et$_2$O (2×8 mL), MeOH (8 mL), and is purified by preparative HPLC (Condition A) using a PHENOMENEX® Luna Axia 30×100 mm S10 column from 40% Solvent B to 100% Solvent B over 10 min, ret. T=8.88 min, to give 2.4 mg (2.78%) of the title compound as an off-white solid. LC/MS (Condition A): ret. T=3.73 min, (M+H)$^+$ 1359.92.

Example 94 tert-Butyl (S)-1-((S)-1-((S)-1-(3-(5-(hydroxymethyl)thiazol-2-ylamino)propylamino)-1-oxopropan-2-ylamino)-1-oxopropan-2-ylamino)-1-oxopropan-2-ylcarbamate

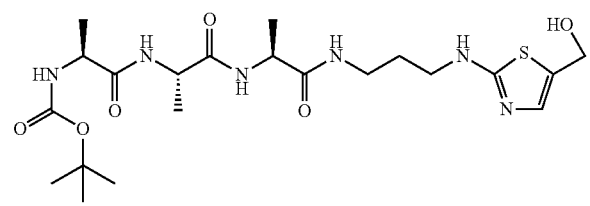 [SMILES: C[C@H](NC(=O)OC(C)(C)C)C(=O)N[C@@H](C)C(=O)N[C@@H](C)C(=O)NCCCNc1ncc(CO)s1]

Following the procedure as described in Example 32, except using material from Example 73 (2.5 mg, 5.01 µmol), EtOH/H₂O (4:1) (500 µlit), sodium borohydride (1.1 mg, 29.0 µmol) and stirring at room temp for 40 min, the title compound is isolated (quantitative yield) and is used crude in the next step. LC/MS (Condition A): ret. T=2.22 min, (M+H)⁺ 501.29.

Example 95

(5S,8S,11S)-5-(3-((2-(3-((S)-2-((S)-2-((S)-2-Amino-propanamido)propanamido)propanamido)propy-lamino)thiazol-5-yl)methyl)-4-hydroxybenzyl)-1-(9H-fluoren-9-yl)-8,11-dimethyl-3,6,9,12-tetraoxo-2-oxa-4,7,10,13-tetraazapentadecan-15-oic acid

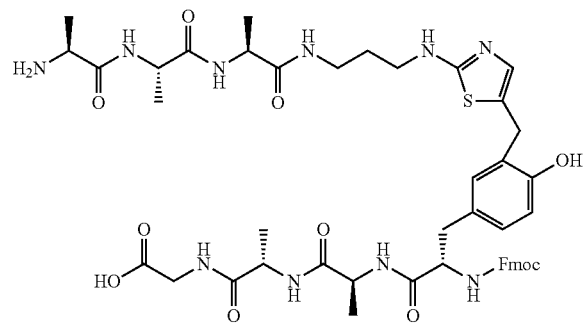

To a suspension of material from Example 95 (2.5 mg, 5.01 µmol) and (5S,8S,11S)-1-(9H-fluoren-9-yl)-5-(4-hydroxybenzyl)-8,11-dimethyl-3,6,9,12-tetraoxo-2-oxa-4,7,10,13-tetraazapentadecan-15-oic acid (3.0 mg, 5.01 µmol) in nitromethane (500 µlit) is added trifluoromethanesulfonic acid (13.3 µlit, 150 µmol) and the resulting dark blue solution is stirred at room temp for 2.5 min. The reaction is cooled to −20° C., quenched with N-methylmorpholine (35 µlit, 318 µmol) and evaporated to dryness to give the title compound (not isolated). LC/MS (Condition A): ret. T=2.85 min, (M+H)⁺ 985.63.

Example 96

Solid Phase Synthesis of Peptide Intermediates

The H-Ala-Tyr-NH₂ and H-Ala-Ala-Tyr-NH₂ peptides were prepared by solid phase synthesis using a Liberty microwave peptide synthesizer (CEM Corp., Matthews, N.C.). The Fmoc deprotection and the coupling steps were performed at 75° C. using microwave heating provided by power pulsing sequences of 20 W. The reaction temperatures were monitored with a fiberoptic probe inserted into the reaction vessel. The synthesis was started from 1.0 mmol of Fmoc-protected Sieber amide resin (0.72 mmol/g) placed into a 50 mL polypropylene vessel. The amino acids were coupled using the 1.0 mmol scale method provided by the manufacturer. At the beginning of each coupling step, the Fmoc group was removed by two 5 minute treatment with 5% piperazine in DMF containing 0.1 M HOBt. After 5 20 mL DMF washes, Fmoc-Ala-OH and Fmoc-Tyr(tBu)-OH were successively coupled by activation with 0.5 M HCTU (4 eq.) in DMF and 2 M DIEA (8 eq.) in NMP for 5 minutes. At the end of each coupling, the resin was washed with 5 20 mL DMF washes. Upon completion of the sequence assembly, the resin was washed with DCM and dried in vacuo. The peptides were then released from their respective resins by treatment with (95:5) TFA/water (10 mL) for 90 minutes at room temperature. The spent resin was filtered off and rinsed with additional cleavage solution (2×3 mL). The combined filtrates were evaporated to −4 mL and the product was precipitated by addition of ether (45 mL). The precipitated product was cooled to 0° C. for 30 minutes, collected by centrifugation, washed with additional ether and dried to yield an off-white solid in 85-90% yield.

The peptides were purified by preparative RP-HPLC on a Shimadzu Model LC-8A liquid chromatograph as follows. Each peptide was dissolved into water (7 mL), filtered through a 0.45 micron filter, and injected into a PHENOMENEX® C18 column (21.2×100 mm; 5). A gradient of 1-25% B in A over 30 min. or 1-30% B in A over 40 min was used to elute the product at 15 mL/min with UV detection at 220 nm. Solvent A: 0.1% TFA in water; Solvent B: 0.1% TFA in AcCN. The fractions containing a clean product as determined by analytical HPLC were combined and lyophilized to yield an at least 99% pure product as a white lyophilate. The identity and purity of each peptide were determined by LC-MS analysis in electrospray mode. In each case, the experimentally measured molecular weight was within 1.0 Daltons of the calculated mono-isotopic molecular weight.

Similarly, the Fmoc-Tyr-Ala-Ala-Gly-OH (SEQ ID NO. 16) and Fmoc-Ala-Ala-Ala-Tyr-Ala-Ala-Gly-OH (SEQ ID NO. 17) peptides were prepared by solid phase synthesis using a Liberty microwave synthesizer and the methods described earlier in this Example. In both cases, the synthesis was started from 0.25 mmol of Fmoc-Gly-Wang resin (0.71 mmol/g) and the desired amino acid sequence was assembled using the 0.25 mmol scale method provided by the manufacturer. Upon completion of the sequence assembly, the resin was washed with DCM and dried in vacuo. The peptides were then released from their respective resins by treatment with TFA/Triisopropylsilane/water/Dithiothreitol (94:2:2:2; v:v:v:w) (10 mL) for 30 minutes at 38° C. on an Accent microwave cleavage system (CEM, Matthews, N.C.). The spent resin was filtered off and rinsed with additional cleavage solution. The combined filtrates were concentrated and the peptide products were precipitated by addition of diethyl ether (25 mL), collected by centrifugation, washed with diethyl ether (3×15 mL) and dried to yield the desired peptides as white solids in 89-94% purity, as determined by analytical HPLC. The identity of each peptide was confirmed by LC-MS analysis in electrospray mode.

Example 97

(S)-tert-Butyl 2-(2-(((9H-fluoren-9-yl)methoxy)carbonylamino)-3-(4-hydroxyphenyl)propanamido)acetate

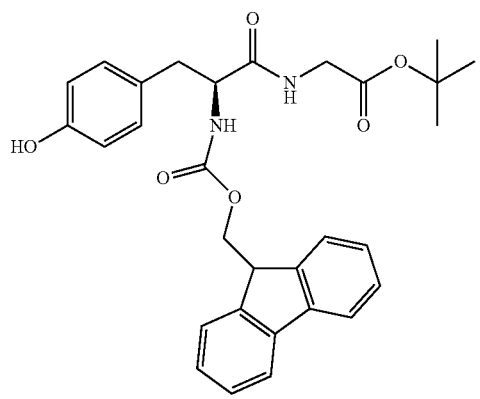 [SMILES: CC(C)(C)OC(=O)CNC(=O)[C@H](Cc1ccc(O)cc1)NC(=O)OCC1c2ccccc2-c2ccccc21]

Following the procedure as described in Example 24, except using Fmoc-Tyrosine (4.97 g, 12.32 mmol), tert-butyl 2-aminoacetate, 1.00HCl (2.168 g, 12.94 mmol), 1-hydroxy-7-azabenzotriazole (0.503 g, 3.70 mmol), $CH_2Cl_2$ (125 mL), N-methylmorpholine (1.490 mL, 13.55 mmol), EDC (2.61 g, 13.61 mmol) and stirring at room temp for 18 h, 6.76 g (quantitative yield) of the title compound is isolated as a white, sticky solid. Purification is done by BIOTAGE® Silica gel chromatography on a 90 g Thompson Single Step silica cartridge using a linear gradient from 100% $CH_2Cl_2$ to 50% EtOAc/$CH_2Cl_2$ over 10 column volumes. LC/MS (Condition A): ret. T=3.98 min, (M+H)$^+$ 517.27. $^1$H NMR (500 MHz, methanol-d$_4$) δ ppm 7.80 (2 H, d, J=7.63 Hz), 7.58 (2 H, d, J=7.32 Hz), 7.25-7.45 (4 H, m), 7.09 (2 H, d, J=7.93 Hz), 6.71 (2 H, d, J=8.24 Hz), 4.36 (2 H, dd, J=9.92, 6.26 Hz), 4.15-4.25 (2 H, m), 3.84 (2 H, d, J=1.53 Hz), 3.11 (2 H, dd, J=13.89, 4.73 Hz), 2.79 (2 H, dd, J=13.89, 9.92 Hz), 1.48 (9 H, s).

Example 98

(S)-tert-Butyl 2-(2-amino-3-(4-hydroxyphenyl)propanamido)acetate

To a solution material from Example 97 (4.7 g, 9.10 mmol) in anhydrous DMF (30 mL) is added piperidine (15 mL, 152 mmol). The resulting solution is stirred at room temp for 45 rain and the solvent is removed in vacuo. The resulting residue was redissolved in 1,4-dioxane (50 mL), the solvent was removed in vacuo again and the resulting solid was dried under high vacuum for 18 h to give the title compound as a white solid in quantitative yield that contains 1 equivalent of 1-((9H-fluoren-9-yl)methyl)piperidine as a side product. LC/MS (Condition A): ret. T=2.30 rain, (M+H)$^+$ 295.

Example 99

(5S,8S)-tert-Butyl 1-(9H-fluoren-9-yl)-8-(4-hydroxybenzyl)-5-methyl-3,6,9-trioxo-2-oxa-4,7,10-triazadodecan-12-oate

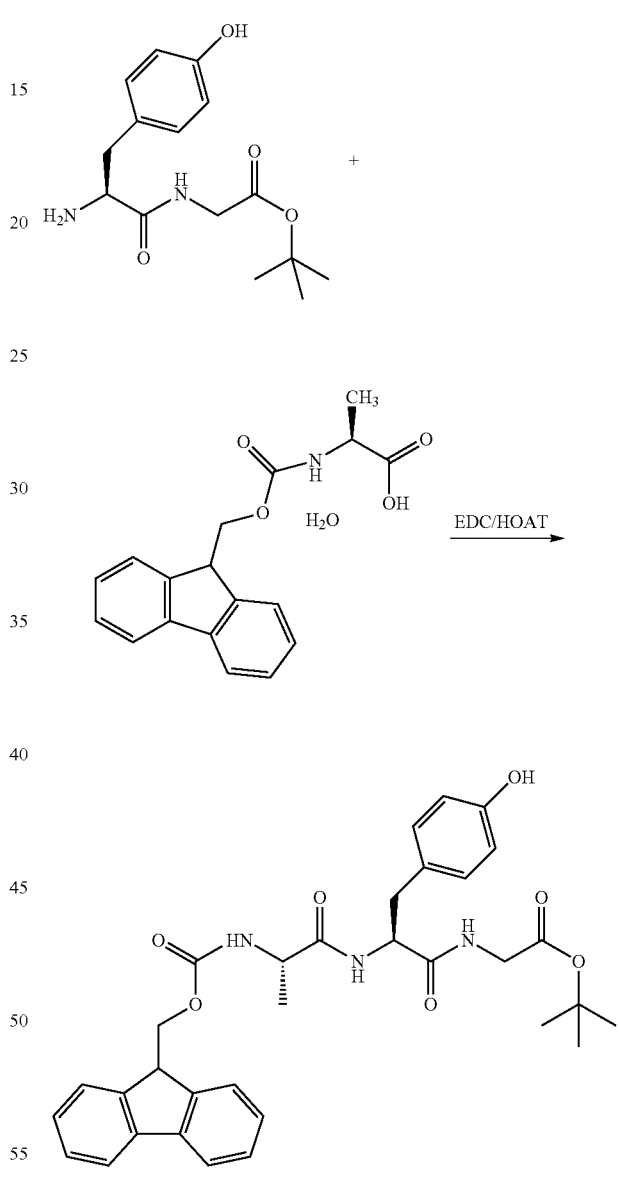

Following the general procedure as described in Example 24, except using a material from Example 98 (2.68 g, 9.10 mmol), (S)-2-(((9H-fluoren-9-yl)methoxy)carbonylamino)propanoic acid, 1.00H$_2$O (3.15 g, 9.56 mmol), t-hydroxy-7-azabenzotriazole (0.619 g, 4.55 mmol), CH$_2$C2 (45 mL), EDC (1.92 g, 10.0 mmol) and stirring at room temp for 1.5 h, 3.73 g (69.7%) of the title compound is isolated as an off white solid. Purification is done by BIOTAGE® Silica gel chromatography on a 300 g Thompson Single Step silica cartridge using a linear gradient from 100% CH$_2$Cl$_2$ to 75%

EtOAc/CH$_2$Cl$_2$ over 10 column volumes. LC/MS (Condition A): ret. T=4.05 min, (M+Na) 610.

Example 100 tert-Butyl 2-((S)-2-((S)-2-aminopropanamido)-3-(4-hydroxyphenyl)propanamido)acetate

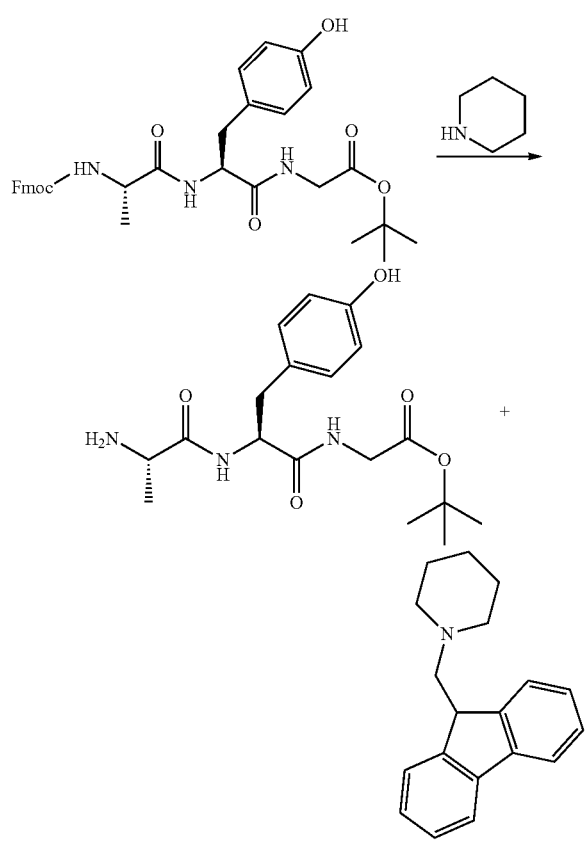

To a solution of material from Example 99 (577 mg, 0.579 mmol) in anhydrous DMF (4 mL) is added piperidine (1 mL, 10.1 mmol). The resulting solution is stirred at room temp for 20 min, then the solvent is removed in vacuo. The resulting solid is evaporated sequentially from ethyl acetate, 1,2-dichloroethane and dichloromethane and dried under high vacuum for several hours to give the title compound as a white solid in quantitative yield that contains 1 equivalent of 1-((9H-fluoren-9-yl)methyl)piperidine as a side product. LC/MS (Condition A): ret. T=4.05 min, (M+H)$^+$ 366.

Example 101

(S)-tert-Butyl 2-((S)-2-(2-(5-formylthiazol-2-ylamino)acetamido)propanamido)propanoate

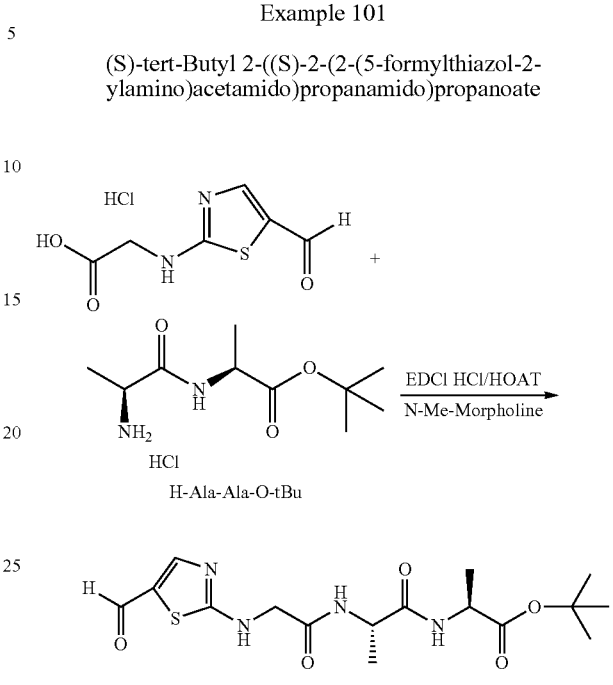

Following the general procedure as described in Example 24, except using 2-(5-formylthiazol-2-ylamino)acetic acid, 1.00 HCl (582 mg, 2.62 mmol), (S)-tert-butyl 2-((S)-2-aminopropanamido)propanoate hydrochloride (661 mg, 2.62 mmol), 1-hydroxy-7-azabenzotriazole (175 mg, 1.29 mmol), CH$_2$Cl$_2$ (30 mL), EDC (588 mg, 3.07 mmol) and stirring at room temp for 18 h, 781.5 mg (78%) of the title compound is isolated by filtration as a light pink solid. LC/MS (Condition A): ret. T=2.64 min, (M+H)$^+$ 385. $^1$H NMR (500 MHz, methanol-d$_4$) δ ppm 9.66 (1 H, s), 7.97 (1 H, s), 4.37-4.53 (1 H, m), 4.21-4.32 (1 H, m), 4.16 (2 H, d, J=0.92 Hz), 1.47 (9 H, s), 1.38 (6 H, dd, J=15.72, 7.17 Hz).

Example 102

(S)-2-((S)-2-(2-(5-Formylthiazol-2-ylamino)acetamido)propanamido)propanoic acid

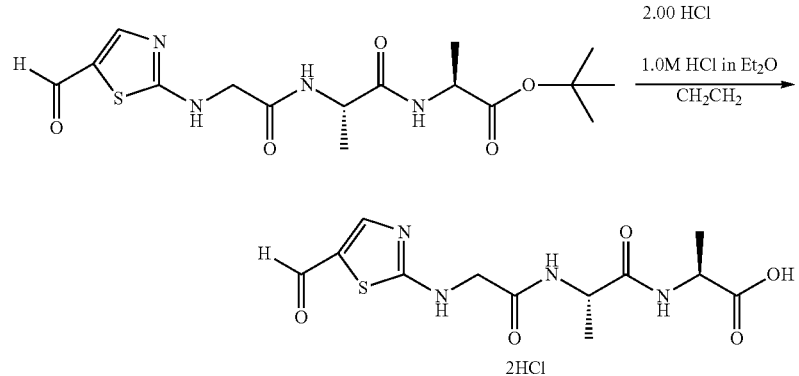

Following the general procedure as described in Example 68, except using material from Example 101 (780 mg, 2.03 mmol) and HCl, 1.0M in diethyl ether (125 mL, 125 mmol), the title compound is isolated in quantitative yield as a bis HCl salt by weight. LC/MS (Condition A): ret. T=1.3 min, (M+H)+ 329.

Example 103

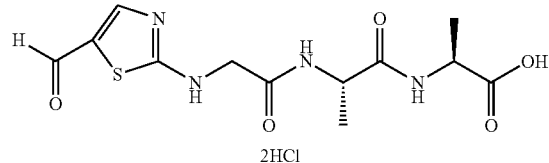

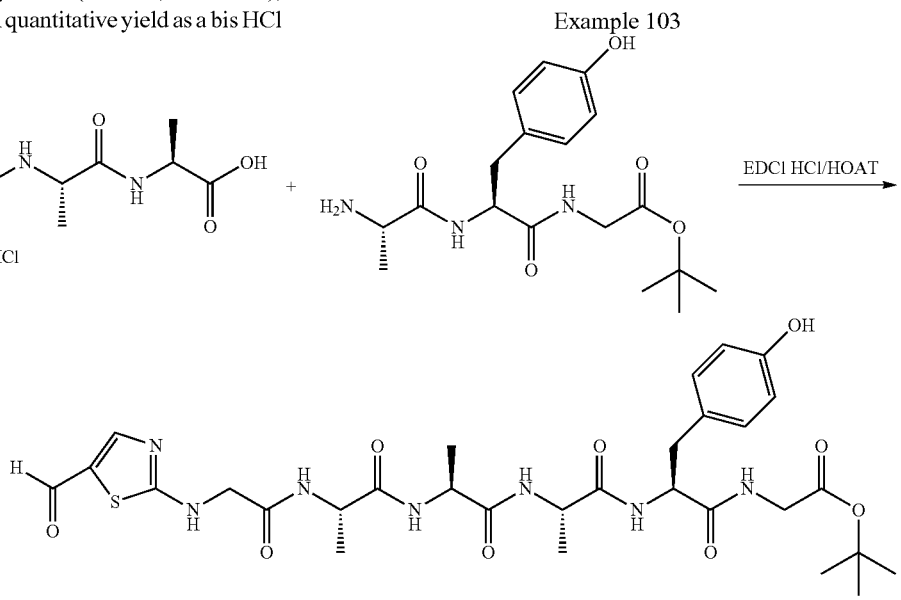

Following the general procedure as described in Example 7, except using material from Example 102 (283 mg, 0.705 mmol), material from Example 100 (212 mg, 0.580 mmol), 1-hydroxy-7-azabenzotriazole (45 mg, 0.331 mmol), DMF (5 mL), N-methylmorpholine (128 µL, 1.164 mmol), EDC (128 mg, 0.667 mmol) and stirring at room temp for 3 h. After the reaction is complete, the solvent is removed in vacuo and the residue is suspended in a mixture of ethyl acetate and dichloromethane, evaporated to dryness again and dried under high vacuum for 18 h. The residue is suspended in dichloromethane and filtered to afford the title compound (350 mg, 89%) of the title compound as a dark brown solid. LC/MS (Condition A): ret. T=2.85 min, (M+H)+ 676.

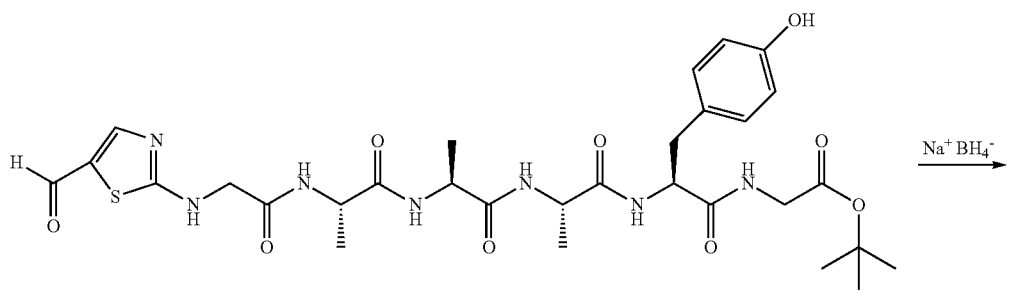

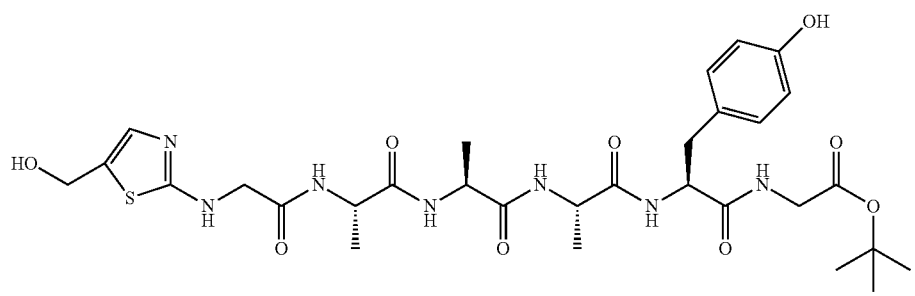

To a stirred solution of material from Example 103 (50.2 mg, 0.074 mmol) in absolute ethanol (5 mL) is added sodium borohydride (9.2 mg, 0.243 mmol) is two equal portions and the resulting faint suspension is stirred at room temp for 15 min. The reaction is quenched with methanol (5 mL), followed by acetone (70 μlit) and evaporated to dryness to give the title compound in quantitative yield. LC/MS (Condition A): ret. T=2.48 min, (M+H)$^+$ 678.

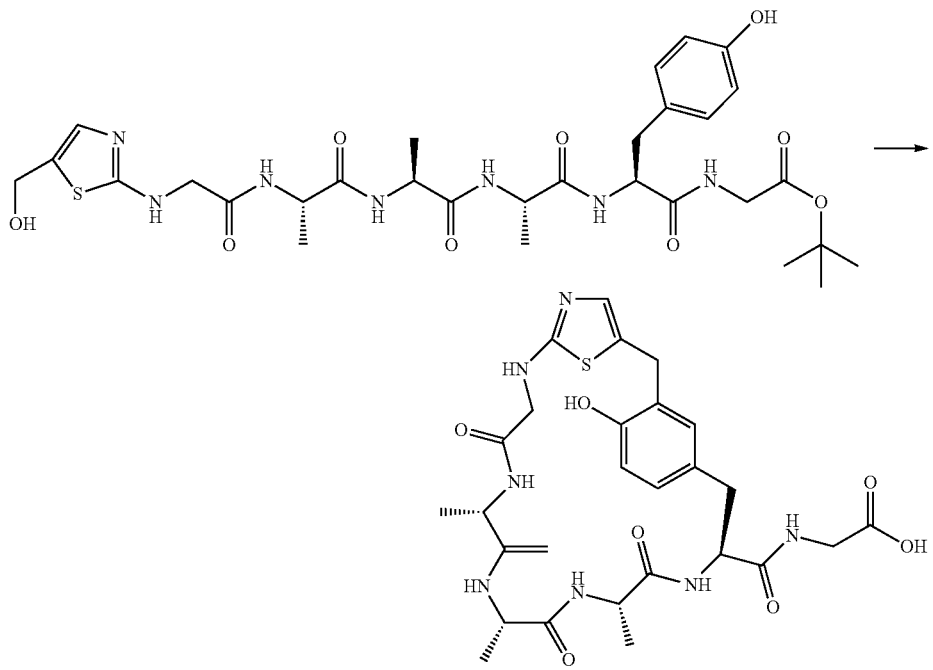

Example 105

Following the general procedure as described in Example 23, except using the material from Example 104 (40.0 mg, 0.059 mmol), nitromethane (5 mL), trifluoromethanesulfonic acid (528 μlit, 5.95 mmol), N-methylmorpholine (195 μL, 1.77 mmol), and stirring at room temp for 50 min, 17.8 mg (42%) of the title compound is isolated as a light tan film as a TFA salt. Purification is done by preparative HPLC (Condition A) using a PHENOMENEX® Luna Axia 30×100 mm S10 column from 10% Solvent B to 85% Solvent B over 11 min, ret. T=4.40 min. LC/MS (Condition A): ret. T=1.85 min, (M+H)$^+$ 604.

Example 106

(S)-Methyl 2-((tert-butoxycarbonyl)amino)-3-(2-((5-formylthiazol-2-yl)amino)acetamido)propanoate

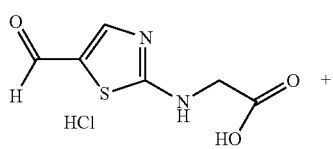

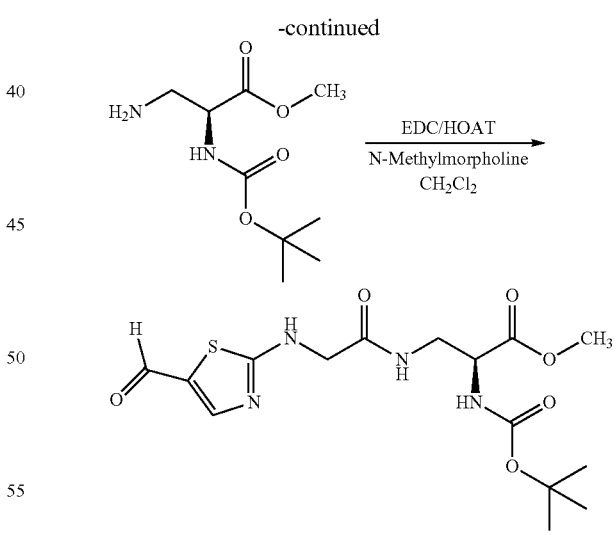

Following the general procedure as described in Example 24, except using 2-((5-formylthiazol-2-yl)amino)acetic acid, 1.00 HCl (150 mg, 0.674 mmol), (S)-methyl 3-amino-2-((tert-butoxycarbonyl)amino)propanoate (see U.S. Publication No. 2007/93414 A1, 164 mg, 0.751 mmol), -1-hydroxy-7-azabenzotriazole (45 mg, 0.331 mmol), CH$_2$C2 (5 mL), N-methylmorpholine (128 μL, 1.164 mmol), EDC (128 mg, 0.667 mmol) and stirring at room temp for 1 h, 108 mg (41.5%) of the title compound is isolated as an orange/red

Example 107

(S)-Methyl 2-((tert-butoxycarbonyl)amino)-3-(2-((5-(hydroxymethyl)thiazol-2-yl)amino)acetamido)propanoate

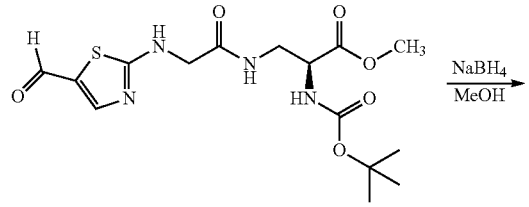

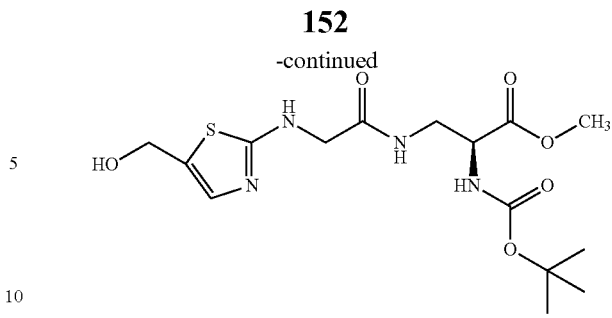

To a solution of material from Example 106 (10 mg, 0.026 mmol) in methanol (1.5 mL) is added sodium borohydride (3.5 mg, 0.093 mmol). The reaction is allowed to stir at room temp for 1 min, cooled to 0° C., quenched with trifluoroacetic acid (26.5 µL, 0.344 mmol) and the solvent removed in vacuo. The resulting residue is used immediately in the next reaction. LC/MS (Condition A): ret, T=2.54 min, (M+Na) 411.

Example 108

Macrocycle

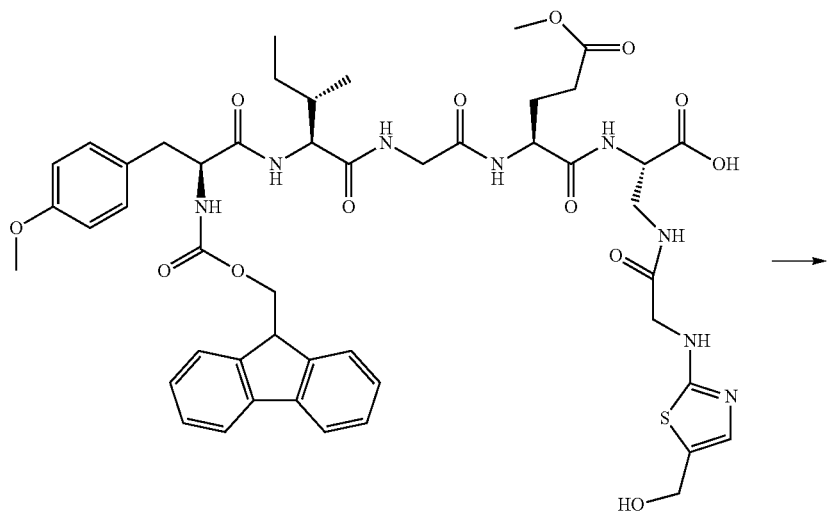

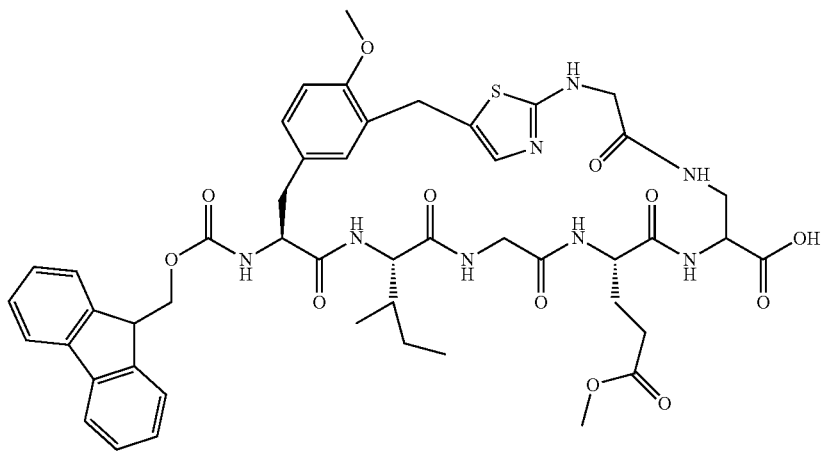

Following the general procedure as described in Example 23, except using (5S,8S,14S,17S)-8-((S)-sec-butyl)-1-(9H-fluoren-9-yl)-17-((2-((5-(hydroxymethyl)thiazol-2-yl)amino)acetamido)methyl)-14-(3-methoxy-3-oxopropyl)-5-(4-methoxybenzyl)-3,6,9,12,15-pentaoxo-2-oxa-4,7,10,13,16-pentaazaoctadecan-18-oic acid (5.5 mg, 5.57 μmol), nitromethane (1 mL), trifluoromethanesulfonic acid (20 μlit, 0.225 mmol), N-methylmorpholine (40 μL, 0.364 mmol) and stirring at room temp for 4 h, 2.7 mg (40.3%) of the title compound is isolated as a white solid as a TFA salt. Purification is done by preparative HPLC (Condition B) using a Waters Sunfire 19×150 mm S10 column from 5% Solvent B to 100% Solvent B over 20 min, flow rate=25 mL/min, ret. T=10.34 min. LC/MS (Condition A): ret. T=3.67 min, (M+H)+ 970.

Example 109

(2,2'-(Ethane-1,2-diylbis(azanediyl))bis(thiazole-5,2-diyl))dimethanol

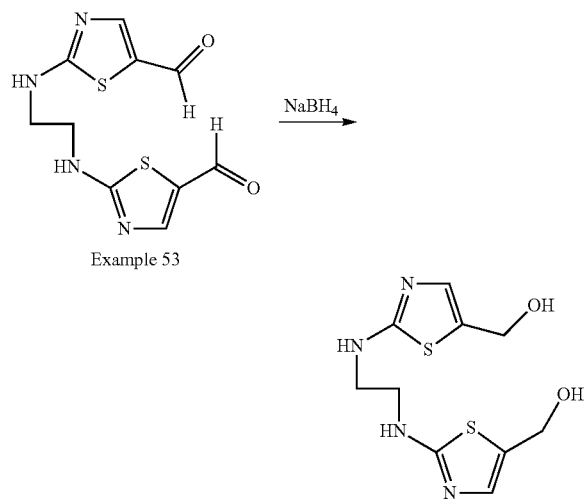

Example 53

To a suspension of material from Example 54 (3.7 mg, 0.013 mmol) in methanol (700 μL) is added sodium borohydride (1.9 mg, 0.050 mmol). The reaction is stirred at room temp for 30 min and evaporated to dryness under a gentle stream of N₂ to give the title compound that is used directly in the next step. LC/MS (Condition A): ret. T=0.36 min, (M+H)+ 287.

Example 110

T2T Peptide

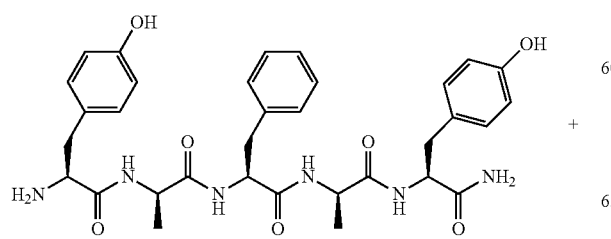

-continued

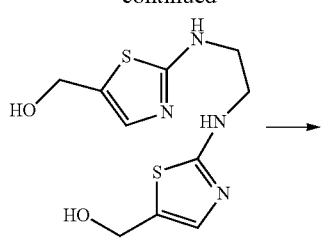

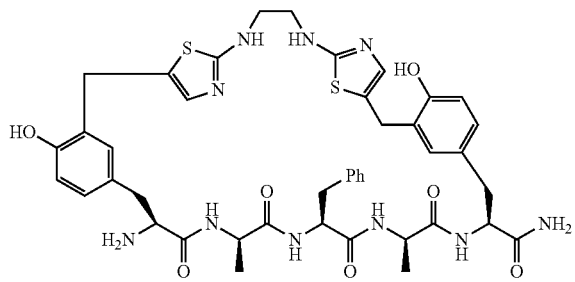

To a suspension of material from Example 109 (3.7 mg, 0.013 mmol), (S)-2-amino-N-(R-1-(((S)-1-((R-1-(((S)-1-amino-3-(4-hydroxyphenyl)-1-oxopropan-2-yl)amino)-1-oxopropan-2-yl)amino)-1-oxo-3-phenylpropan-2-yl)amino)-1-oxopropan-2-yl)-3-(4-hydroxyphenyl)propanamide (8.1 mg, 0.013 mmol), in nitroethane (750 μL) is added trifluororomethanesulfonic acid (88 μL, 0.991 mmol). The resulting solution is stirred at room temp for 40 min, cooled to −20° C., quenched with N-methylmorpholine (160 μL, 1.455 mmol) and the solvent is evaporated off under a gentle stream of N₂. The resulting residue is purified by preparative HPLC (Condition A) using a PHENOMENEX® Luna Axia 30×100 mm S10 column from 20% Solvent B to 95% Solvent B over 11 min, ret. T=5.8 min. to give 2.0 mg (13.4%) of the title compound as a white solid as a TFA salt. LC/MS (Condition A): ret. T=1.85 min, (M+Na) 905.

Example 111

(S)-Methyl 3-(3-benzoylthioureido)-2-(tert-butoxycarbonylamino)propanoate

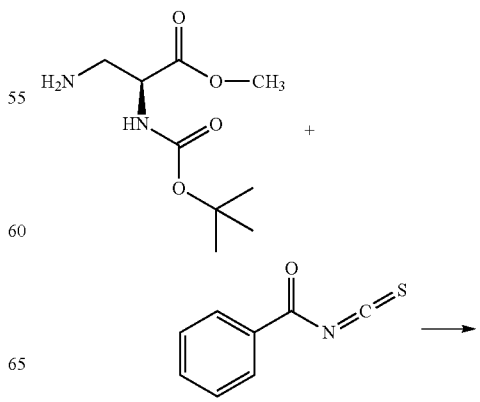

-continued

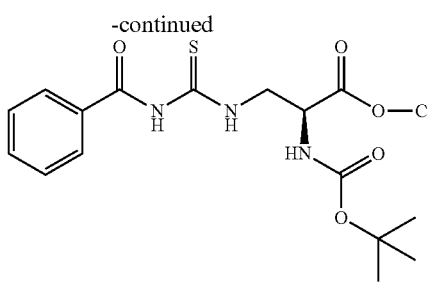

To an ice cold solution of (S)-methyl 3-amino-2-((tert-butoxycarbonyl)amino)propanoate (see US2007/93414A1, 10.3 g, 47.2 mmol) in anhydrous dichloromethane (170 mL) is slowly added benzoyl isothiocyanate (6.35 mL, 47.2 mmol). The reaction is stirred for 2.5 h while slowly warming to room temp. The solvent is removed in vacuo and the residue is purified by BIOTAGE® Silica gel chromatography on a 300 g Thompson Single Step silica cartridge using a linear gradient from 100% hexanes to 100% EtOAc over 10 column volumes to give 4.7 g (26.1%) of the title compound as a pale yellow solid. LC/MS (Condition A): ret. T=3.48 min, (M+Na) 404.

Example 112

(S)-2-(tert-Butoxycarbonylamino)-3-thioureidopropanoic acid

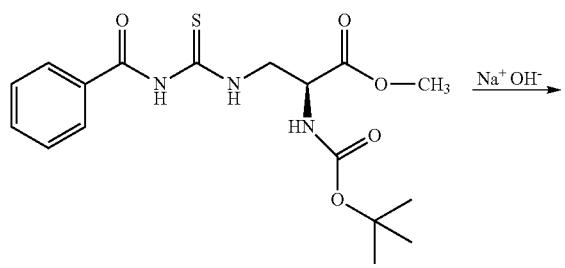

To a solution of material from Example 11 (4.65 g, 12.19 mmol) in a mixture of THF (29 mL) and water (36 mL) is slowly added sodium hydroxide (1.0M, 37.3 mL, 37.3 mmol). The resulting solution is stirred at room temp for 18 h, the solvent removed in vacuo, and the residue (that contains 1 equivalent of benzoic acid) is used without further purification in the next step. LC/MS (Condition A): ret. T=2.06 min, (M+Na) 286.

Example 113

(S)-2-(tert-Butoxycarbonylamino)-3-(5-formylthiazol-2-ylamino)propanoic acid

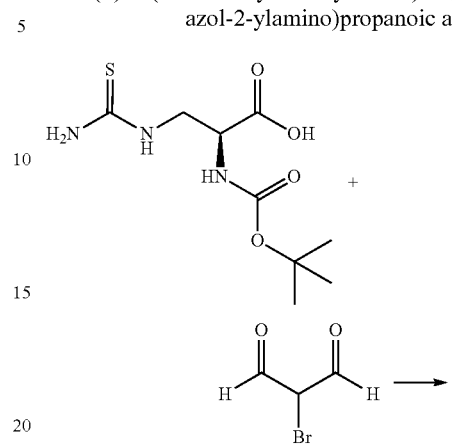

To a solution of material from Example 112 (3.21 g, 12.19 mmol) in a mixture of THF (107 mL) and acetic acid (29 mL) is added 2-bromomalonaldehyde (3.29 g, 21.79 mmol). The resulting solution is stirred at room temp for 60 h. The reaction is diluted with water (71 mL) and the resulting slurry is stirred at room temp for 1.5 h. The slurry is extracted with EtOAc (3×300 mL), the organic layers combined, washed with brine (1×50 mL), dried over $Na_2SO_4$, filtered and evaporated to dryness. The resulting residue is purified by BIOTAGE® Silica gel chromatography on a 80 g Thompson Single Step silica cartridge using a linear gradient from 100% $CHCl_3$ to 25% MeOH/$CHCl_3$ over 9 column volumes to give 1.5 g (39%) of the title compound as an orange/yellow film, $^1$H NMR (500 MHz, methanol-$d_4$) δ 9.65 (s, 1H), 7.97 (s, 1H), 4.49-4.37 (m, 1H), 3.93 (dd, J=13.9, 4.4 Hz, 1H), 3.72 (dd, J=14.0, 7.7 Hz, 1H), 1.45 (s, 914). LC/MS (Condition A): ret. T=2.46 min, (M+Na) 338.

Example 114

(S)-Methyl 2-(tert-butoxycarbonylamino)-3-(5-formylthiazol-2-ylamino)propanoate

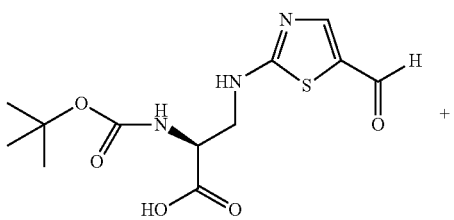

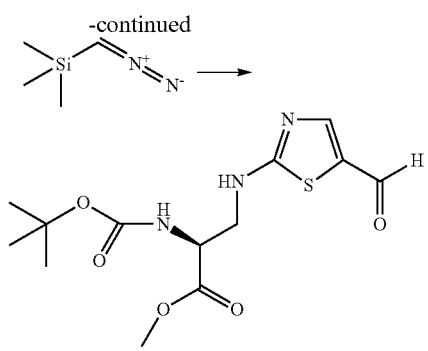

To a solution of material from Example 113 (prior to purification, contains 2.5 equivalents of benzoic acid, 314 mg, 0.506 mmol) in a mixture of dichloromethane (10 mL) and methanol (1 mL) is slowly added (diazomethyl)trimethylsilane (2.0M in hexanes, 2.0 mL, 4.0 mmol) and the resulting solution is stirred at room temp for 45 min. The solvent is removed in vacuo, the residue is redissolved in dichloromethane and purified by BIOTAGE® Silica gel chromatography on a 90 g Thompson Single Step silica cartridge using a linear gradient from 100% CH₂Cl₂ to 100% EtOAc over 10 column volumes to give 51.6 mg (31%) of the title compound as tan solid. LC/MS (Condition A): ret. T=2.72 min, (M+Na) 352.

Example 115

(S)-Methyl 2-(tert-butoxycarbonylamino)-4-iodobutanoate

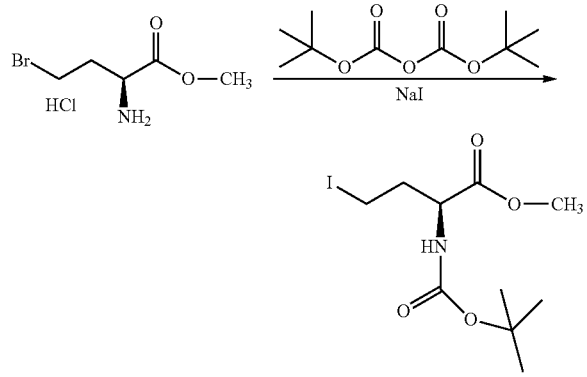

To an ice cold suspension of (S)-methyl 2-amino-4-bromobutanoate, 1.00 HCl (see WO2003/101948 A2, 4.42 g, 19.02 mmol) and N,N-diisopropylethylamine (9.97 mL, 57.1 mmol) in anhydrous THF (50 mL) is slowly added a solution of di-tert-butyldicarbonate (4.36 g, 19.97 mmol) in anhydrous THF (8 mL). The reaction is stirred for 18 h while warming to room temp. The solvent is removed in vacuo, and the residue is partitioned between EtOAc (450 mL) and aqueous saturated ammonium chloride (30 ml). The organic layer is washed with aqueous saturated sodium bicarbonate (1×30 mL), water (1×30 mL), brine (1×30 mL), dried over Na₂SO₄, filtered and evaporated to dryness. The residue is dissolved in acetone (450 mL). treated with sodium iodide (14.25 g, 95.1 mmol) and the reaction is refluxed for 18 h. The reaction is cooled to room temp, filtered thru a ground glass frit and the solvent removed in vacuo. The residue is dissolved in EtOAc (450 mL), washed with water (3×40 mL), brine (1×40 mL), dried over Na₂SO₄, filtered, evaporated to dryness and purified by BIOTAGE® Silica gel chromatography on a 80 g Thompson Single Step silica cartridge using 100% CH₂Cl₂ over 10 column volumes to give 3.9 g (60%) of the title compound as a thick oil. LC/MS (Condition A): ret. T=3.40 min, (M+Na) 366.

Example 116

(S)-Methyl 4-((tert-butoxycarbonyl)(5-formylthiazol-2-yl)amino)-2-((tert-butoxycarbonyl)amino) butanoate

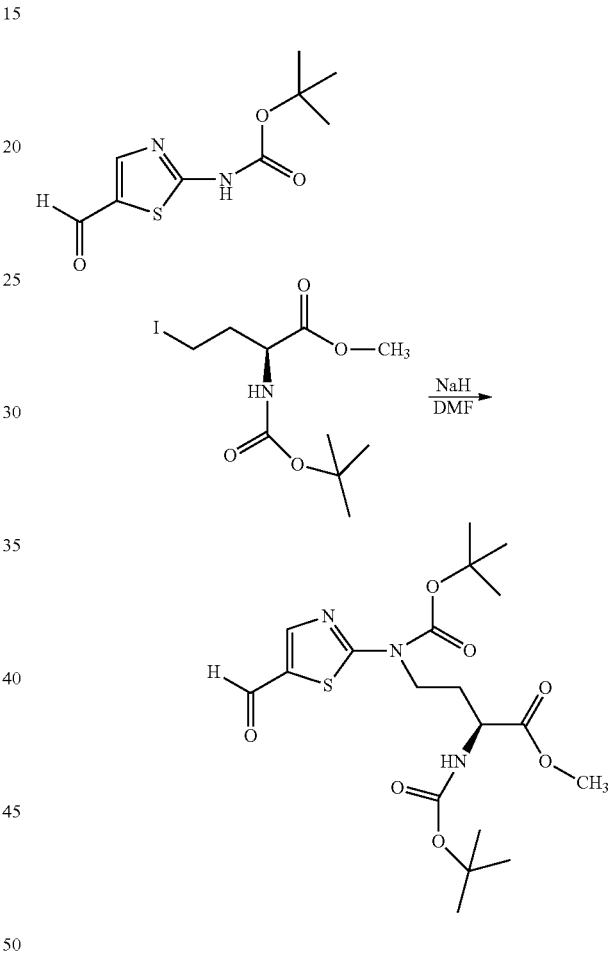

To a dry 2-5 mL microwave vial under N₂ is added tert-butyl (5-formylthiazol-2-yl)carbamate (100 mg, 0.438 mmol) and anhydrous DMF (2.5 mL). The resulting dark solution stirred at room temp for 5 min, treated with sodium hydride (22.13 mg, 0.876 mmol), flushed with N₂ for 15 min, then treated with material from Example 115 (301 mg, 0.876 mmol) and securely capped. The resulting dark solution is stirred at room temp for 30 min, then heated in a microwave heating unit for 15 min at 80° C. under high power. The reaction is diluted with ethyl acetate (200 mL), washed with water (6×25 mL), brine (1×25 mL), dried over Na₂SO₄, filtered, the solvent removed in vacuo and the resulting residue purified by BIOTAGE® Silica gel chromatography on a 25 g Thompson Single Step silica cartridge using 100% CH₂Cl₂ to 75% EtOAc/CH₂Cl₂ over 11 column volumes to give 176.7 mg (91%) of the title compound as a thick oil, LC/MS (Condition A): ret. T=3.83 min, (M+Na) 466.

Example 117

(S)-4-((tert-Butoxycarbonyl)(5-formylthiazol-2-yl)amino)-2-((tert-butoxycarbonyl)amino)butanoic acid

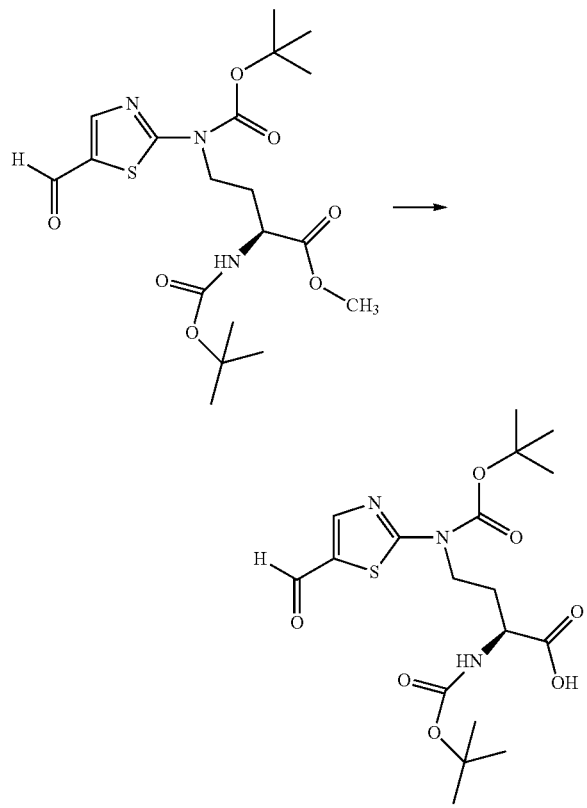

To a dry 2-5 mL microwave vial under N₂ is added material from Example 116 (120 mg, 0.271 mmol) and anhydrous 1,2-dichloroethane (3 mL). The resulting solution is flushed with N₂, treated with trimethylstannanol (60 mg, 0.332 mmol), securely capped and heated in a microwave heating unit at 60-78° C. for 6.5 h. The reaction is diluted with ethyl acetate (75 mL), and the organic layer is washed with 0.5N aqueous HCl (3×15 mL), brine (15 mL), dried over Na₂SO₄, filtered and evaporated to dryness to give 11 mg (95%) of the title compound as a pale yellow glass that contains 0.5 equivalents of the tin reagent. LC/MS (Condition A): ret. T=3.69 min, (M+Na) 452.

Example 118

(S)-2-((tert-Butoxycarbonyl)amino)-3-(2-((5-formylthiazol-2-yl)amino)acetamido)propanoic acid

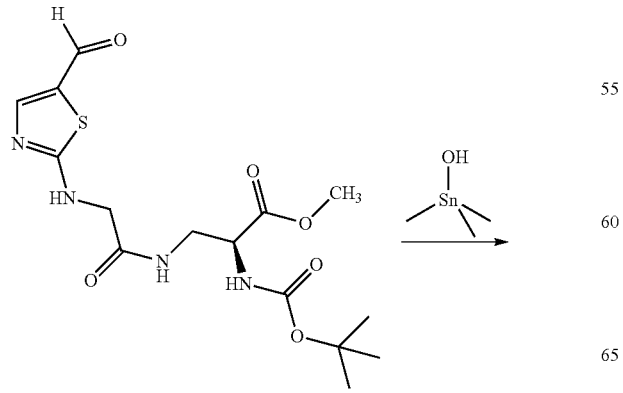

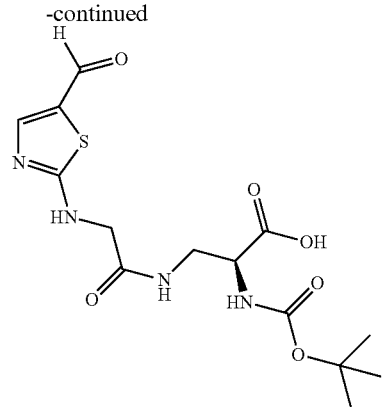

Following the general procedure as described in Example 117, except using material from Example 106 (100 mg, 0.259 mmol), 1,2-dichloroethane (2.5 mL), trimethylstannanol (140 mg, 0.0.776 mmol), and heating in a microwave for 2.5 h at 80° C. under normal power, 41.4 mg (43%) of the title compound is isolated as a thick oil that contains 0.25 equivalents of the tin reagent. LC/MS (Condition A): ret. T=2.28 min, (M+H)⁺ 373.

Example 119

(S)-Methyl 2-amino-3-(2-((5-formylthiazol-2-yl)amino)acetamido)propanoate, 2.0 HCl, 0.3 Diethyl Ether

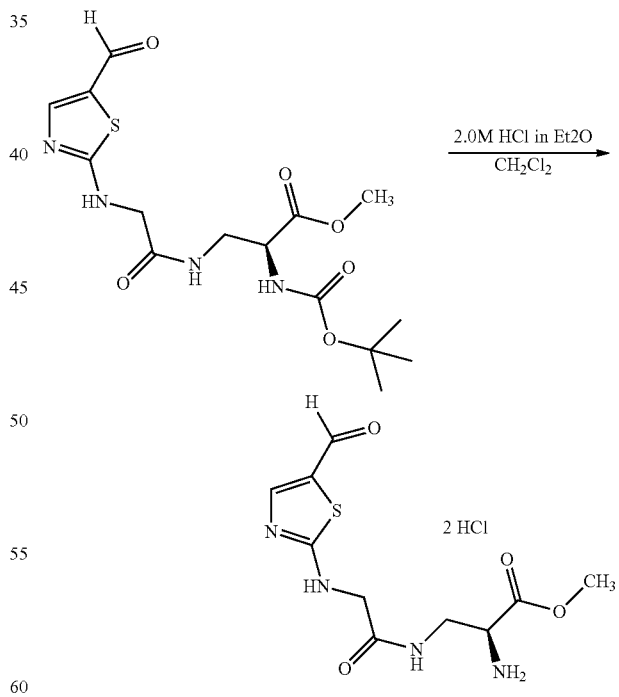

To a suspension of material from Example 106 (307 mg, 0,794 mmol) in anhydrous dichloromethane (20 mL) is added 2.0 M HCl in diethylether (30 mL, 30 mmol). The resulting solution is stirred at room temp for 3.3 h, during which time a yellow precipitate forms. The reaction is cooled to 0° C. and filtered through a ground glass frit to give 295 mg (97%) of the title compound as a yellow solid. LC/MS (Condition A): ret. T=3.69 min, (M+Na) 309.

Example 120 tert-Butyl((S)-4-(((S)-1-amino-3-(4-hydroxyphenyl)-1-oxopropan-2-yl)amino)-3-((tert-butoxycarbonyl)amino)-4-oxobutyl)(5-formylthiazol-2-yl)carbamate

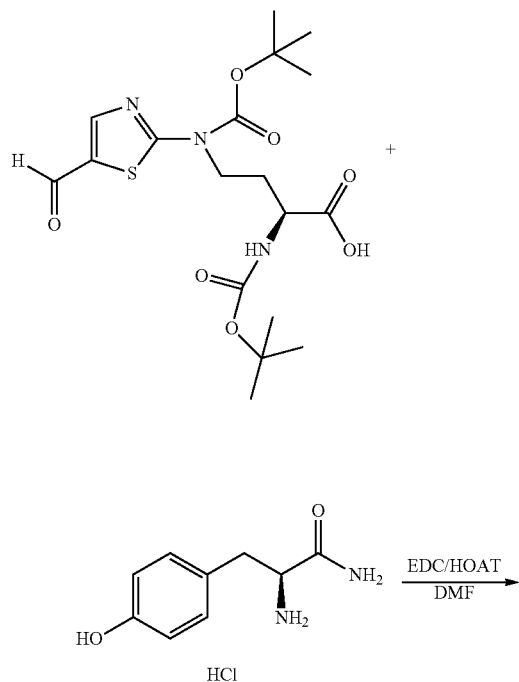

Following the general procedure as described in Example 7, except using material from Example 117 (24 mg, 0.056 mmol), (S)-2-amino-3-(4-hydroxyphenyl)propanamide, 1.00HCl (12.71 mg, 0.059 mmol), 1-hydroxy-7-azabenzotriazole (3.8 mg, 0.028 mmol), DMF (2 mL), N-methylmorpholine (7.4 µL, 0.067 mmol), EDC (12.9 mg, 0.067 mmol) and stirring at room temp for 1 h, 10.8 mg (27.4%) of the title compound is isolated as a pale yellow film as a TFA salt. Purification is done by preparative HPLC (Condition A) using a PHENOMENEX® Luna Axia 30×100 mm S10 column from 22% Solvent B to 100% Solvent B over 11 min, ret. T=10.02 min. LC/MS (Condition A): ret. T=3.54 min, (M+Na) 614.

Example 121

(S)-2-Amino-N-((S)-1-amino-3-(4-hydroxyphenyl)-1-oxopropan-2-yl)-4-((5-formylthiazol-2-yl)amino)butanamide, 1.00 TFA

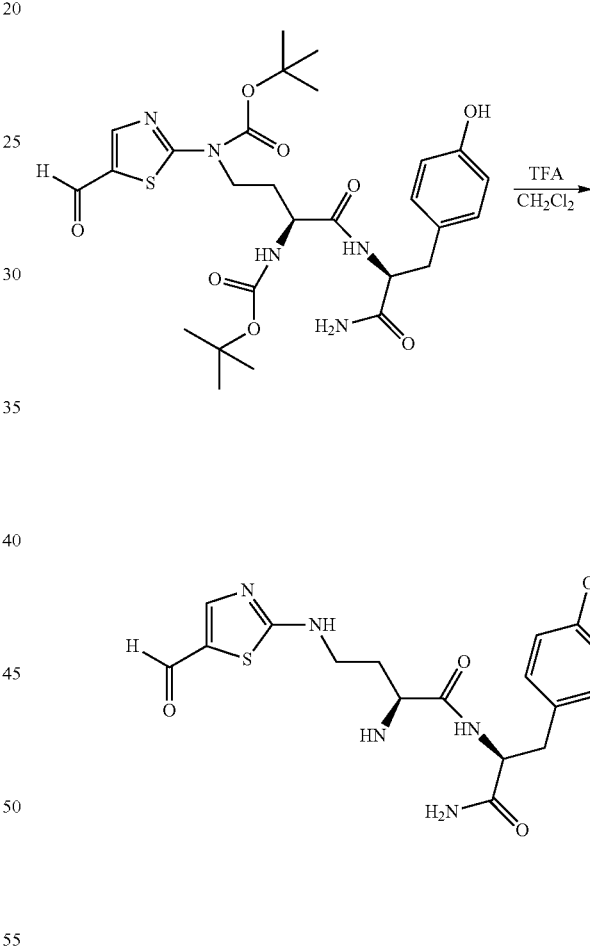

Following the general procedure as described in Example 11, except using material from Example 120 (10.8 mg, 0.015 mmol), methylene chloride (250 µL) and TFA (1.0 mL), 12 mg of the title compound is obtained in quantitative yield as a TFA salt. Purification is done by preparative HPLC (Condition A) using a PHENOMENEX® Luna Axia 30×100 mm S10 column from 5% Solvent B to 85% Solvent B over 11 min, ret. T=1.46 min. LC/MS (Condition A): ret. T=1.42 min, (M+Na) 414.

Example 122

(9H-Fluoren-9-yl)methyl((2S,8S,11S,14S,17S,20S,23S)-1-amino-2,14-bis(4-hydroxybenzyl)-8,11,17,20-tetramethyl-1,4,7,10,13,16,19,22-octaoxo-3,6,9,12,15,18,21-heptaazatetracosan-23-yl)carbamate, 1.00 TFA

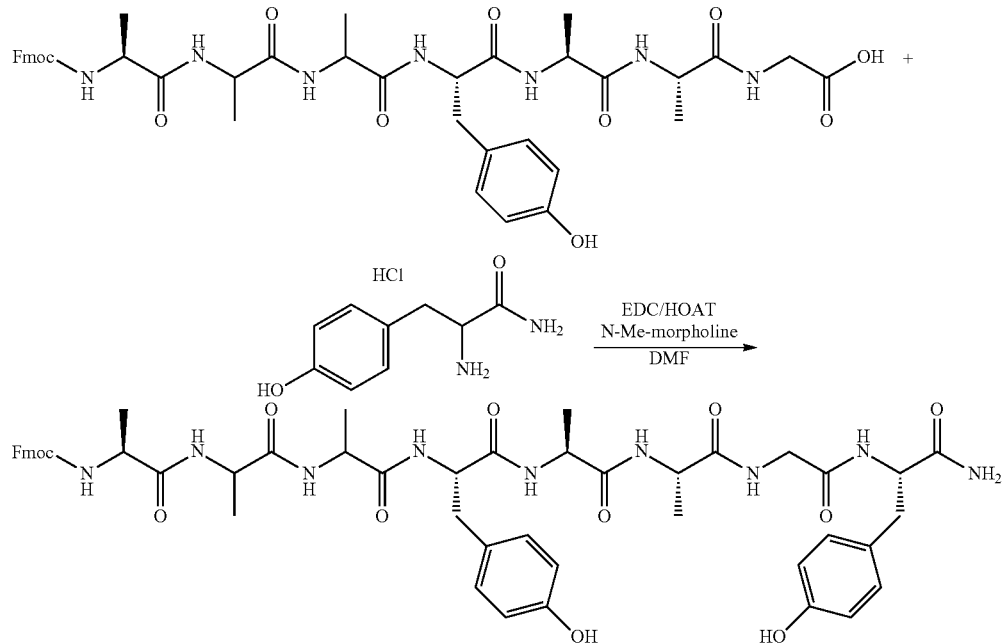

Following the general procedure as described in Example 7, except using (5S,8S,11S,14S,17S,20S)-1-(9H-fluoren-9-yl)-14-(4-hydroxybenzyl)-5,8,11,17,20-pentamethyl-3,6,9,12,15,18,21-heptaoxo-2-oxa-4,7,10,13,16,19,22-heptaaza-tetracosan-24-oic acid (12.5 from Example 120 (10.8 mg, 0.015 mmol), L-Tyrosinamide hydrochloride (4.325 g, 0.020 mmol), 1-hydroxy-7-azabenzotriazole (1.0 mg, 7.7 μmol), DMF (5 mL), N-methylmorpholine (10 μL, 0.091 mmol), EDC (3.5 mg, 0.018 mmol) and stirring at room temp for 1 h, 3.2 mg (17.2%) of the title compound is isolated as a white solid as a TFA salt. Purification is done by preparative HPLC (Condition A) using a PHENOMENEX® Luna Axia 30×100 mm S10 column from 25% Solvent B to 100% Solvent B over 10 in, ret. T=9.03 min. LC/MS (Condition A): ret. T=3.54 min, (M+Na) 1000.

Example 123

T2T Peptide

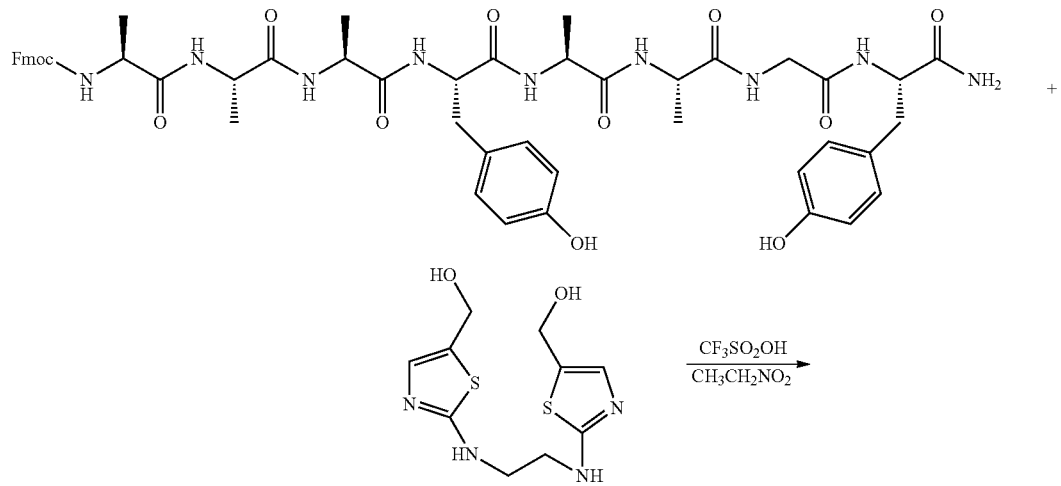

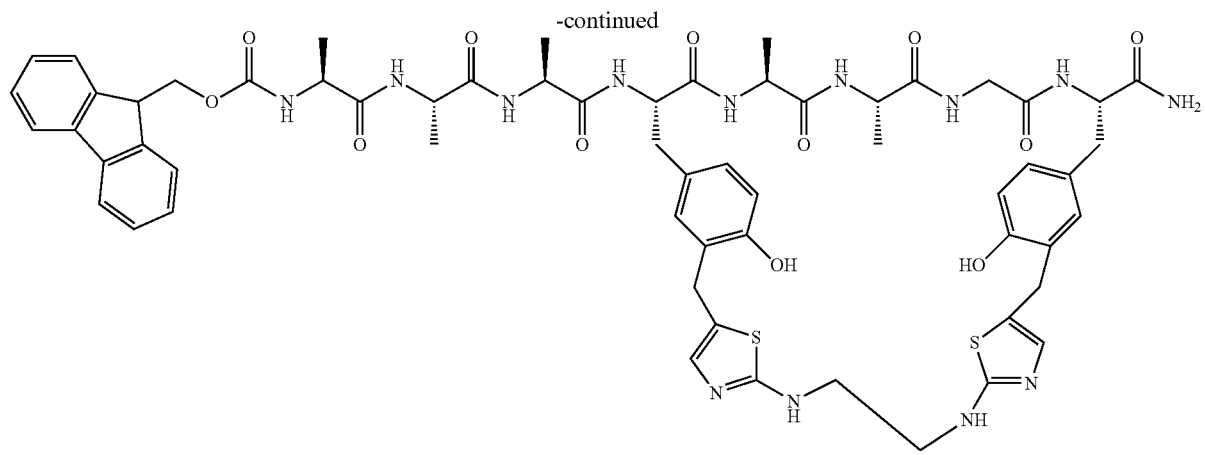

Following the general procedure as described in Example 110, except using material from Example 122 (2.1 mg, 1.74 mol), material from Example 109 (0.5 mg, 1.74 μmol), nitroethane (400 μL), trifluororomethanesulfonic acid (20 μL, 0.225 mmol), N-methylmorpholine (37.4 μL, 0.34 mmol) and stirring at room temp for 35 min, 0.5 mg (14%) of the title compound is obtained as a white film as a TFA salt. Purification is done by preparative HPLC (Condition A) using a PHENOMENEX® Luna Axia 30×100 mm S10 column from 20% Solvent B to 100% Solvent B over 12 min, ret. T=9.1 min. LC/MS (Condition A): ret. T=3.2 min, (M+Na) 1250.

Example 124

Reduced Peptide

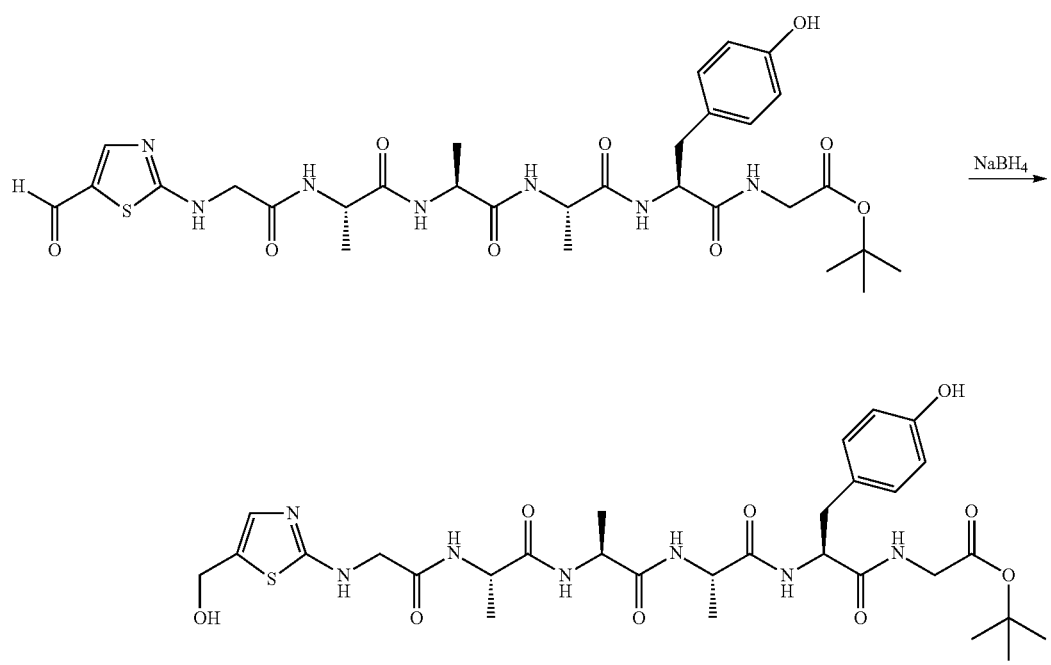

Following the general procedure as described in Example 8, except using material from Example 103 (149 mg, 0.220 mmol), EtOH/H$_2$O (4:1) (10 mL), sodium borohydride (50.1 mg, 1.32 mmol) and stirring at room temp for 18 h, 191 mg (quantitative yield) of the title compound is obtained as a light tan solid. LC/MS (Condition A): ret. T=3.54 min, (M+H)$^+$ 678.

Example 125

Macrocycle

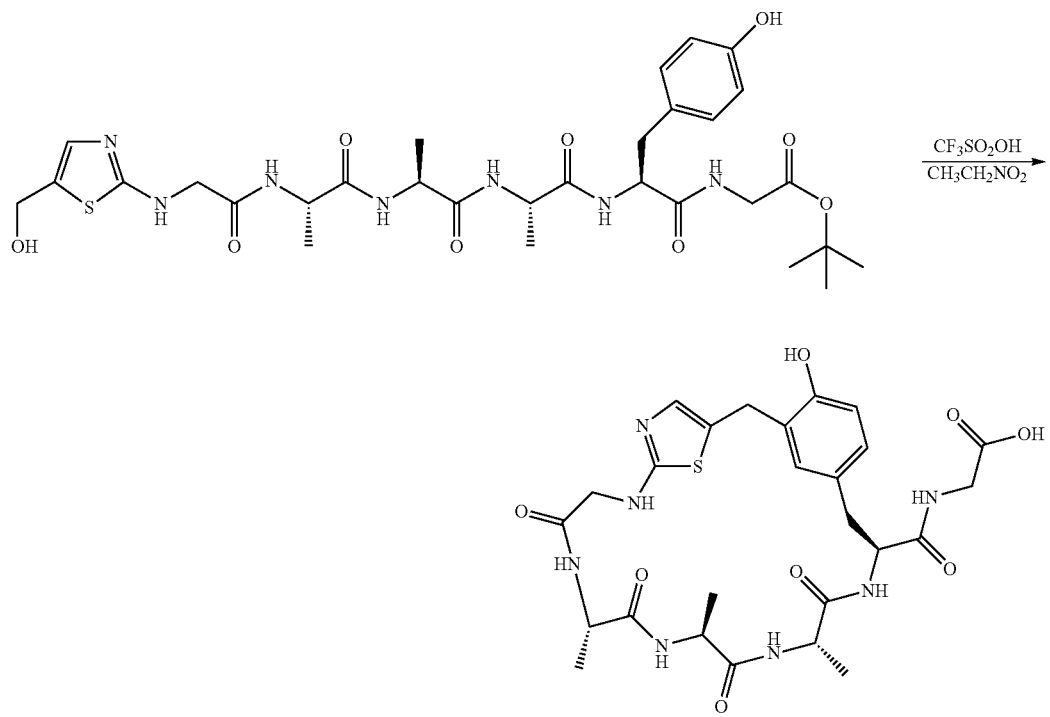 [SMILES: C[C@H](NC(=O)CNc1ncc(CO)s1)C(=O)N[C@@H](C)C(=O)N[C@@H](C)C(=O)N[C@@H](Cc1ccc(O)cc1)C(=O)NCC(=O)OC(C)(C)C ; "CF3SO2OH" ; "CH3CH2NO2" ; C[C@@H]1NC(=O)CNc2ncc(s2)Cc2cc(ccc2O)C[C@@H](C(=O)NCC(=O)O)NC(=O)[C@H](C)NC(=O)[C@H](C)NC1=O]

Following the general procedure as described in Example 110, except using material from Example 124 (100 mg, 0.148 mmol), nitroethane (26 mL)) trifluororomethanesulfonic acid (550 μL, 6.19 mmol), N-methylmorpholine (1.6 mL, 14.55 mmol) and stirring at room temp for 20 min, 37 mg (35%) of the title compound is obtained as a yellow solid as a TFA salt. Purification is done by preparative HPLC (Condition A) using a PHENOMENEX® Luna Axia 30×100 mm S10 column from 5% Solvent B to 85% Solvent B over 10 min, ret. T=5.25 min. LC/MS (Condition A): ret. T=1.77 min, (M+H)+ 604.

Example 126

Peptide, 1.00 TFA

Following the general procedure as described in Example 7 except using material from Example 92 (15 mg, 0.022 mmol), material from Example 125 (15.9 mg, 0.022 mmol), 1-hydroxy-7-azabenzotriazole (1.5 mg, 0.011 mmol), DMF (2 mL), N-methylmorpholine (15 μL, 0.133 mmol), EDC (5.5 mg, 0.029 mmol) and stirring at room temp for 18 h, 19.1 mg (70%) of the title compound is isolated as a white film as a TFA salt. Purification is done by preparative HPLC (Condition A) using a PHENOMENEX® Luna Axia 30×100 mm S10 column from 10% Solvent B to 90% Solvent B over 11 min, ret. T=7.39 min. LC/MS (Condition A): ret. T=2.38 min, (M+Na) 1170.

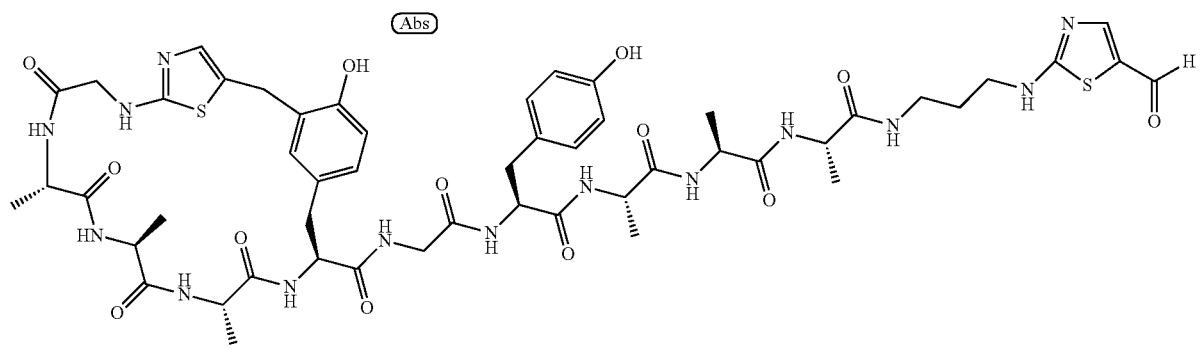 [SMILES: C[C@@H]1NC(=O)CNC2=NC=C(Cc3cc(ccc3O)C[C@@H](C(=O)NCC(=O)N[C@@H](Cc3ccc(O)cc3)C(=O)N[C@@H](C)C(=O)N[C@@H](C)C(=O)N[C@@H](C)C(=O)NCCCNc3ncc(C=O)s3)NC(=O)[C@H](C)NC(=O)[C@H](C)NC1=O)S2]

Example 127

Reduction

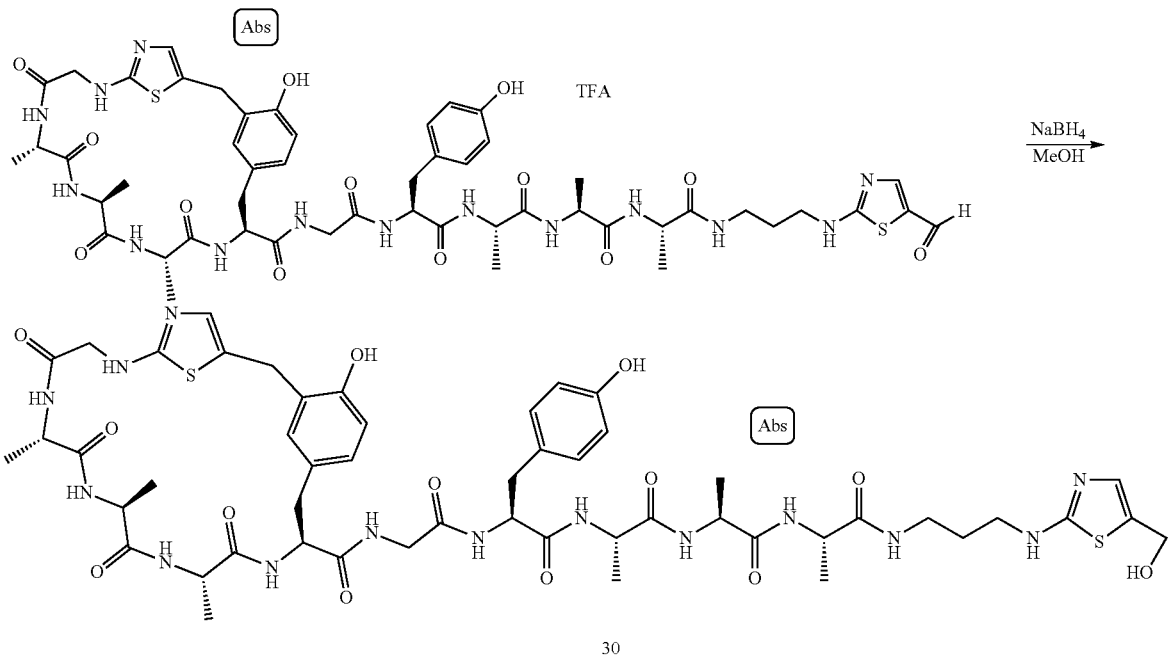

Following the general procedure as described in Example 109, except using material from Example 126 (1.8 mg, 1.43 mol), methanol (3 mL), sodium borohydride (0.5 mg, 0.013 mmol) and stirring for 2 h, the title compound (1.43 μmol) is obtained as a white solid in quantitative yield. LC/MS (Condition A): ret. T=2.38 min, (M+H)+ 1149.

Example 128 tert-Butyl ((2S,5S,8S,11S)-16-((5-(hydroxymethyl)thiazol-2-yl)amino)-1-(4-hydroxyphenyl)-5,8,11-trimethyl-3,6,9,12-tetraoxo-4,7,10,13-tetraazahexadecan-2-yl)carbamate

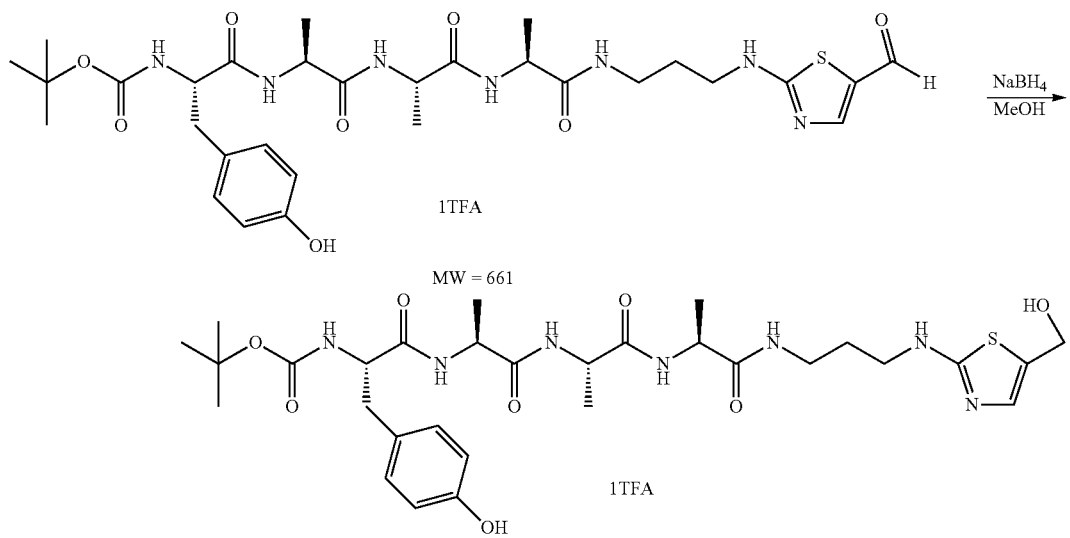

Following the general procedure as described in Example 109, except using material from Example 75 (20 mg, 0.026 mol), methanol (3 mL), sodium borohydride (5 mg, 0.13 mmol) and stirring for 70 min, the title compound (0.026 mol) is obtained as a white solid in quantitative yield. LC/MS (Condition A): ret. T=1.32 min, (M−Boc−17) 563.

Example 129

Macrocycle

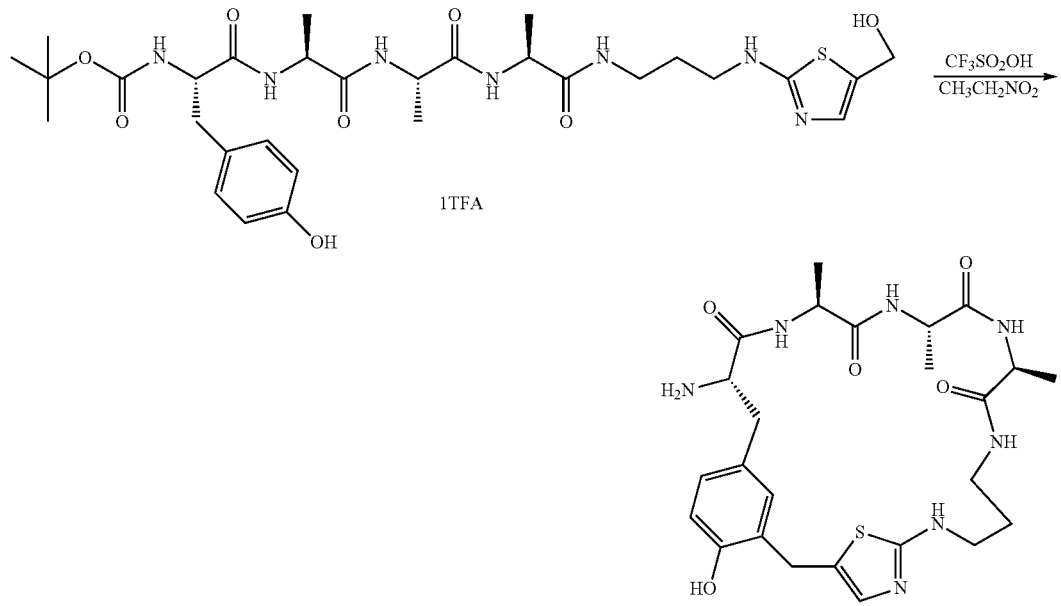

Following the general procedure as described in Example 110, except using material from Example 128 (17.3 mg, 0.026 mmol), nitroethane (10 mL), trifluororomethanesulfonic acid (165 µL, 1.86 mmol), N-methylmorpholine (400 µL, 3.64 mmol) and stirring at room temp for 35 min, 10.7 mg (62%) of the title compound is obtained as a white film as a TFA salt. Purification is done by preparative HPLC (Condition A) using a PHENOMENEX® Luna Axia 30×100 mm S10 column from 5% Solvent B to 85% Solvent B over 10 min, ret. T=5.09 min. LC/MS (Condition A): ret. T=1.65 min, (M+H)⁺ 546.

Example 130

Double Macrocycle

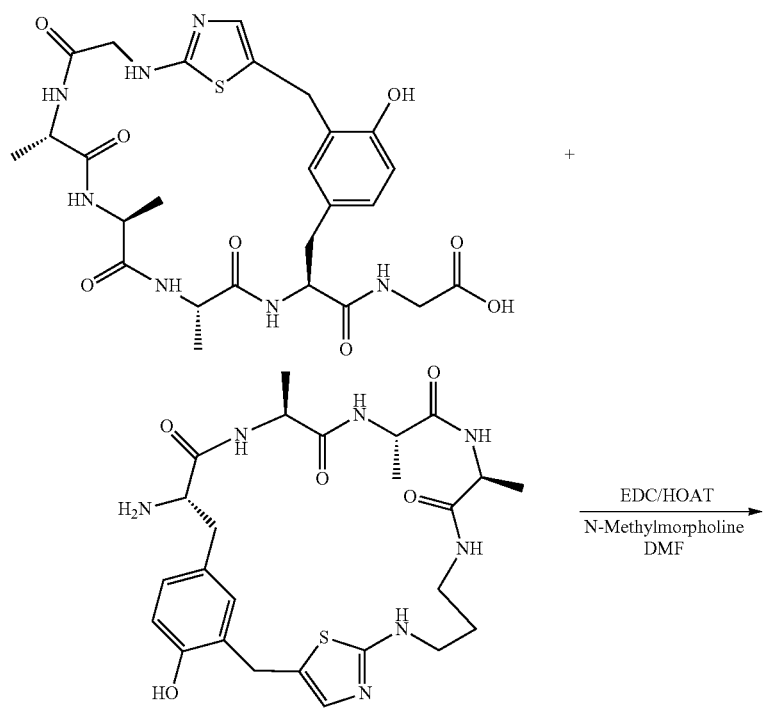

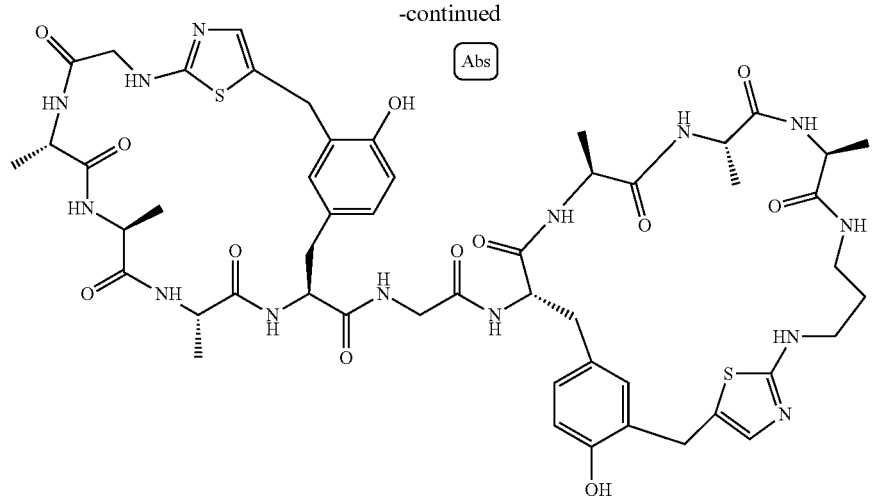

Following the general procedure as described in Example 7, except using material from Example 125 (4.9 mg, 6.82 μmol), material from Example 129 (4.5 mg, 6.82 μmol), 1-hydroxy-7-azabenzotriazole (0.5 mg, 3.41 mol), DMF (500 μL), N-methylmorpholine (5 μL, 0.045 mmol), EDC (1.9 mg, 9.91 μmol) and stirring at room temp for 3 h, 4.3 mg (48%) of the title compound is isolated as a white film as a TFA salt. Purification is done by preparative HPLC (Condition A) using a PHENOMENEX® Luna Axia 30×100 mm S10 column from 15% Solvent B to 95% Solvent B over 11 min, ret. T=6.14 min. LC/MS (Condition A): ret. T=2.28 min, (M/2+H)$^+$ 567. Analytical HPLC: (Condition A): >96%, ret. T=17.25 min, (Condition B): >93%, ret. T 18.49 min.

Example 131

Double Macrocycle

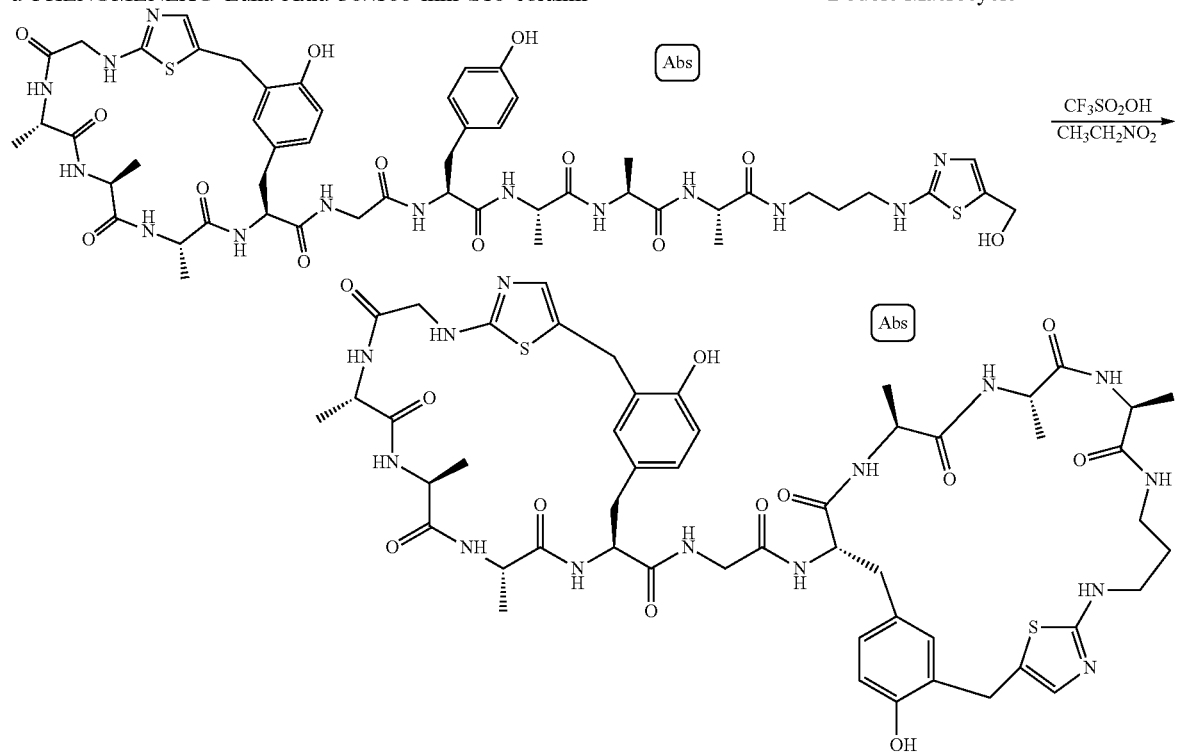

To a suspension of material from Example 127 (1.43 mol) in nitroethane (2.0 mL) is added trifluoromethanesulfonic acid (27 μlit, 304 μmol). The resulting solution is stirred at room temp for 20 min, cooled to −20° C., quenched with N-methylmorpholine (66.8 μL, 608 μmol) and the solvent removed under a gentle stream of $N_2$. By long column HPLC using Analytical HPLC: (Condition A) and Analytical HPLC: (Condition B), the product from this experiment is identical to that from Experiment 130.

Example 132
Peptide
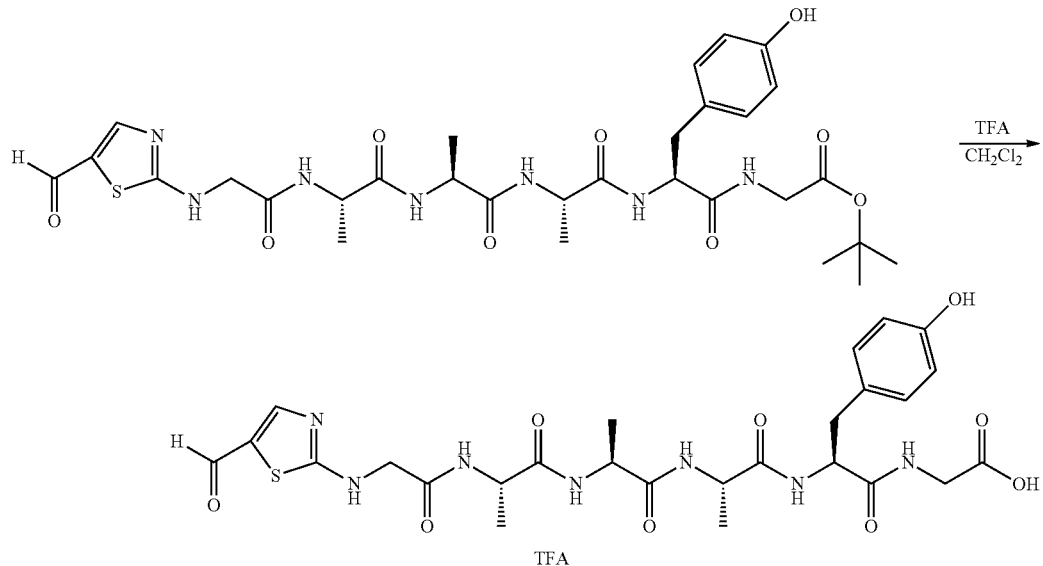
To a solution of material from Example 103 (325 mg, 0.481 mmol) in CH$_2$Cl$_2$ (10 mL) is added trifluoroacetic acid (1.7 mL, 22.07 mmol). The resulting pale yellow solution is allowed to stir at room temp for 18 h, and the solvent is removed in vacuo to give the title compound (0.481 mmol, quantitative yield) as a TFA salt. LC/MS (Condition A): ret. T=1.81 min, (M+H)$^+$ 620.
Example 133
Peptide
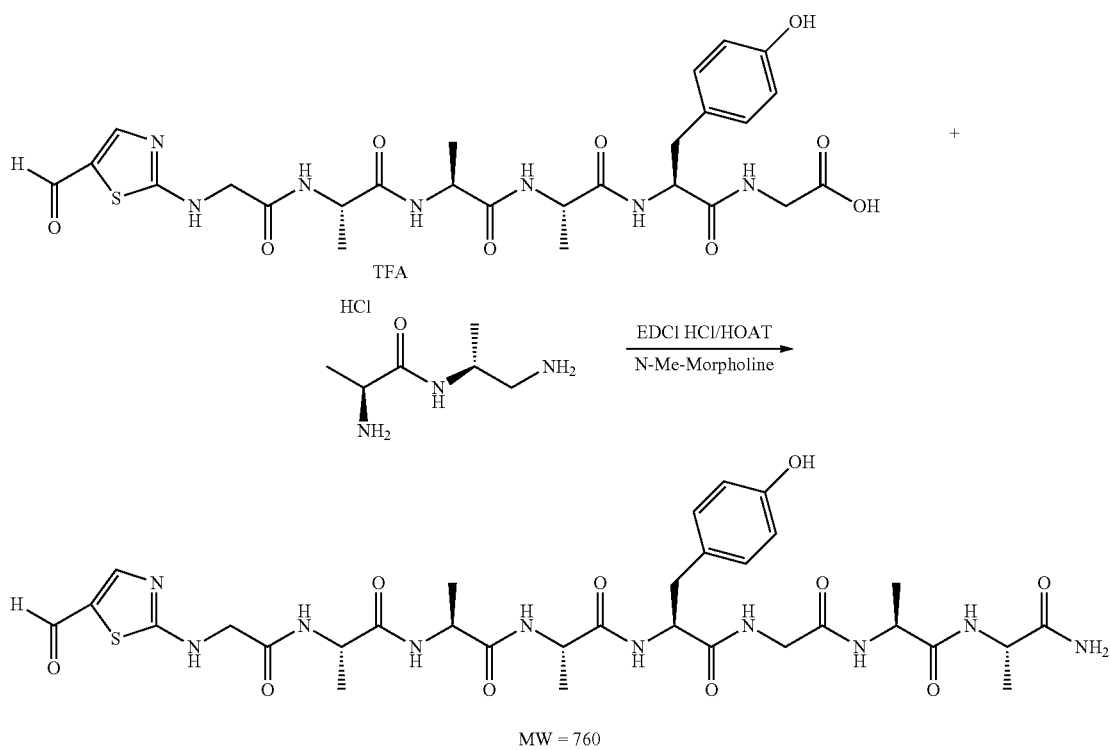

Following the general procedure as described in Example 7, except using material from Example 132 (298 mg, 0.481 mmol), H-Ala-Ala-NH$_2$. HCl (94 mg, 0.481 mmol), 1-hydroxy-7-azabenzotriazole (32.7 mg, 0.241 mmol), DMF (4 mL), N-methylmorpholine (400 μL, 0.045 mmol), EDC (138 mg, 0.722 mmol) and stirring at room temp for 3 h. The solvent is removed under a gentle stream of N$_2$, the residue suspended in MeOH (15 mL), and the title compound (170 mg, 46.5%) is collected by filtration as a brown solid. LC/MS (Condition A): ret, T=2.28 min, (M+H)$^+$ 761.

Example 134

Reduced Peptide

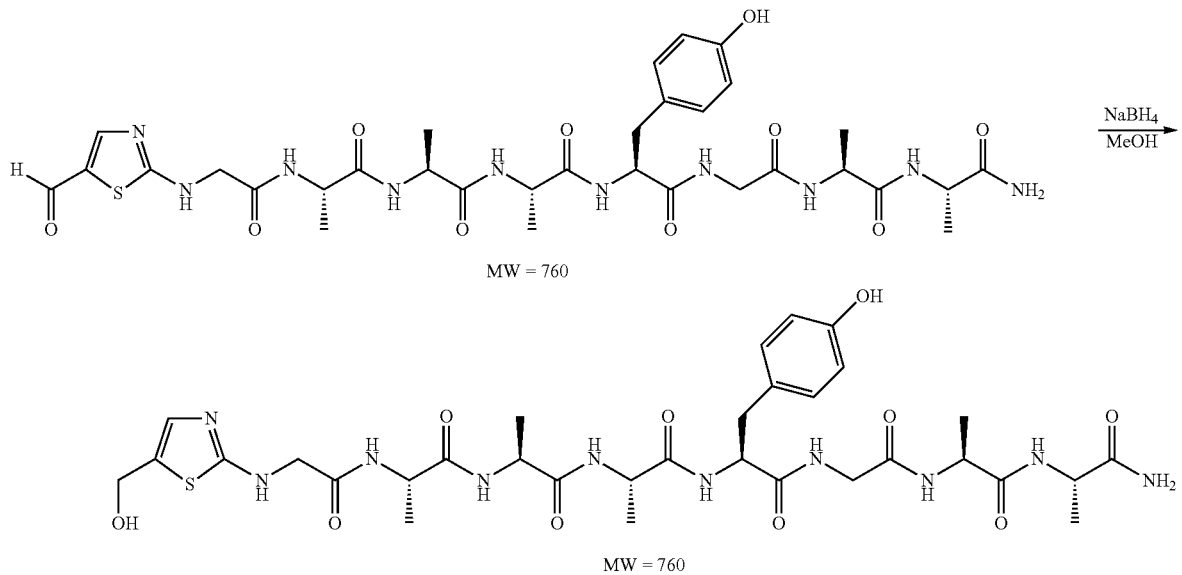

Following the general procedure as described in Example 128, except using material from Example 133 (43 mg, 0.057 mmol), MeOH (9 mL), sodium borohydride (16.3 mg, 0.431 mmol) and stirring for 18 h, the title compound (0.057 mmol, quantitative yield) is isolated as a solid, that is used without further purification. LC/MS (Condition A): ret. T=1.71 min, (M+Na) 785.

Example 135

Macrocycle

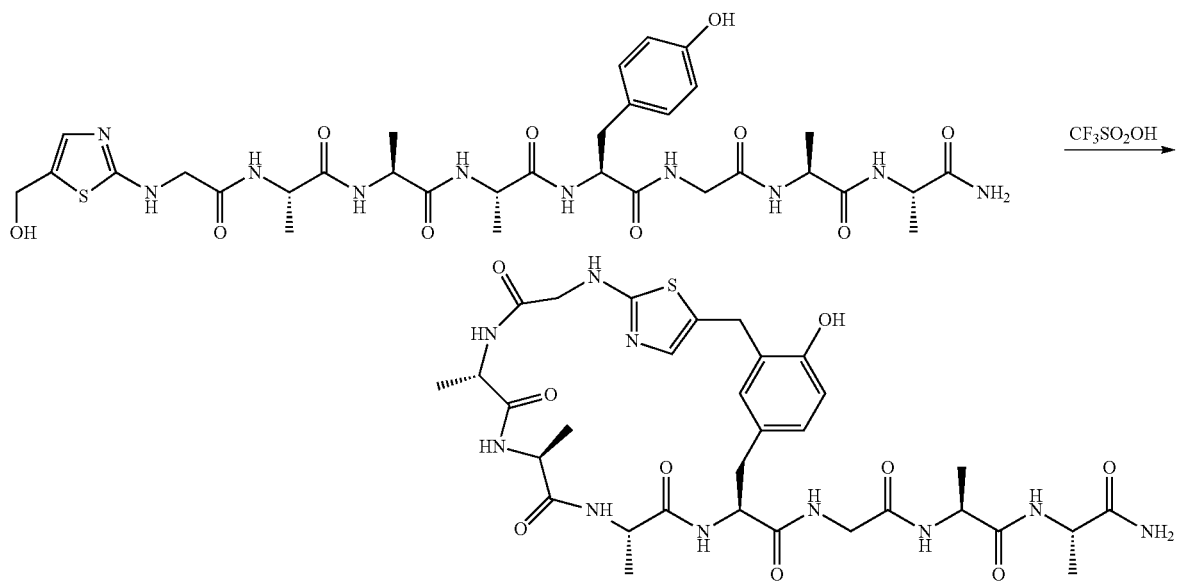

To a solution of material from Example 134 (5.8 mg, 7.6 µmol) in nitroethane (700 µL) is added trifluoromethanesulfonic acid (700 µL). The resulting pale yellow reaction is stirred at room temp for 45 min, cooled to −20° C., quenched with N-methylmorpholine (150 µL, 1.36 mmol) and the solvent evaporated under a gentle stream of $N_2$. Purification of the resulting residue is done by preparative HPLC (Condition A) using a PHENOMENEX® Luna Axia 30×100 mm S10 column from 10% Solvent B to 95% Solvent B over 11 min, ret. T=6.14 min to give 2.5 mg (62%) of the title compound as a pale yellow film. LC/MS (Condition A): ret. T=−1.82 min, $(M+H)^+$ 745.

Example 136 tert-Butyl ((S)-1-(((S)-1-(((S)-1-(((S)-1-amino-3-(4-hydroxyphenyl)-1-oxopropan-2-yl)amino)-1-oxopropan-2-yl)amino)-1-oxopropan-2-yl)amino)-3-(4-hydroxyphenyl)-1-oxopropan-2-yl)carbamate, 1.00 TFA

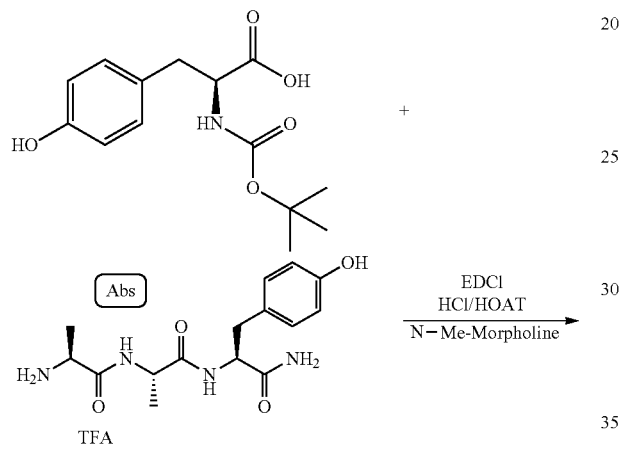

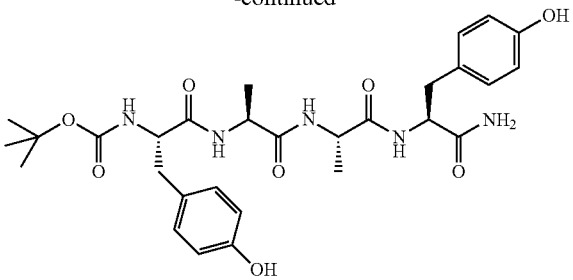

Following the general procedure as described in Example 7, except using N-[(tert-butoxy)carbonyl]-L-tyrosine (15.7 mg, 0.056 mmol), (S)-2-amino-N-((S)-1-(((S)-1-amino-3-(4-hydroxyphenyl)-1-oxopropan-2-yl)amino)-1-oxopropan-2-yl)propanamide, 1.00 TFA (23.2 mg, 0.053 mmol), 1-hydroxy-7-azabenzotriazole (3.6 mg, 0.27 mmol), DMF (1.5 mL), N-methylmorpholine (12.1 µL, 0.112 mmol), EDC (12.2 mg, 0.064 mol) and stirring at room temp for 18 h, 24 mg (65%) of the title compound is isolated as a white solid as a TFA salt. Purification is done by preparative HPLC (Condition A) using a PHENOMENEX® Luna Axia 30×100 mm S10 column from 20% Solvent B to 100% Solvent B over 10 min, ret. T=6.86 min. LC/MS (Condition A): ret. T=2.72 min, (2M+Na) 1194.

Example 137

Macrocycle

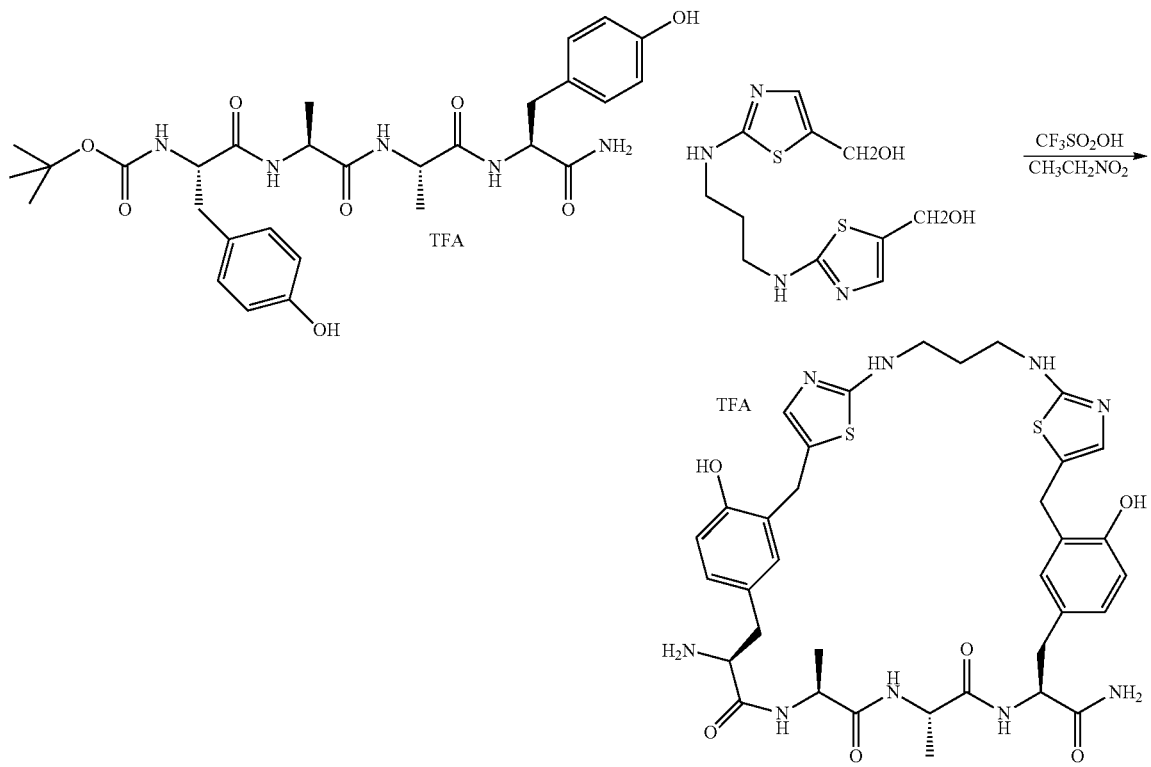

Following the general procedure as described in Example 110, except using material from Example 136 (5 mg, 7.15 μmol), material from Example 61 (2.0 mg, 6.75 μmol), nitroethane (760 μL), trifluoromethanesulfonic acid (45 μL, 507 μmol), N-methylmorpholine (84 μL, 760 μmol) and stirring at room temp for 15 min, 2 mg (29%) of the title compound is obtained as a colorless film as a TFA salt. Purification is done by preparative HPLC (Condition A) using a PHENOMENEX® Luna Axia 30×100 mm S10 column from 5% Solvent B to 95% Solvent B over 11 min, ret. T=5.01 min. LC/MS (Condition A): ret. T=1.68 min, $(M+H)^+$ 750.

The foregoing detailed description has been given for clearness of understanding only and no unnecessary limitations should be understood therefrom as modifications will be obvious to those skilled in the art.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth and as follows in the scope of the appended claims.

---

We claim:

1. A method for preparing a macrocycle stabilized peptide (MSP), comprising the steps of:
   a) providing a linear peptide having Formula (I)

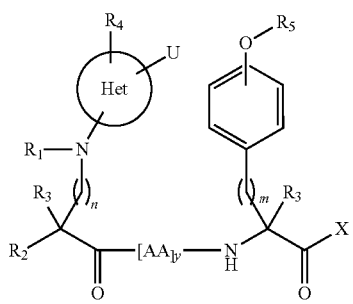

(I)

wherein
Het is a 5-membered heteroaromatic ring;
$R_1$ is selected from H, $C_{1-6}$alkyl, and an amino protecting group;
$R_2$ is the side chain of a natural or unnatural amino acid; or $R_1$ and $R_2$, $R_2$ and $R_3$, $R_1$ and $R_3$ are taken together with the atom(s) to which they are attached to form a ring;
$R_3$, at each occurrence, is independently selected from H and $C_{1-6}$alkyl;
U is selected from aldehyde, protected aldehyde, and —$CH_2OP$;
P is selected form H, $C_{1-6}$alkyl, or an alcohol protecting group;
$R_4$ is selected from H, $C_{1-6}$alkyl, heteroalkyl, and halogen;
$R_5$ is selected from H, $C_{1-6}$alkyl, and heteroalkyl;
X is selected from OB, $NR_aR_a$ and $[AA]_z$;
B is selected from H, $C_{1-6}$alkyl, and a carboxylic acid protecting group;
$R_a$ is H or $C_{1-6}$alkyl;

AA is any natural or unnatural amino acid;
n and m are each an integer from 0-6, provided when n is not zero, $R_2$ is OP, $NR_aR_a$;
y is an integer from 1 to 10; and
z is an integer from 1 to 10;
   b) reacting the peptide in the presence of an activating reagent alkylsulfonic acid to form a MSP comprising at least one covalent linkage.

2. The method of claim 1, wherein the linear peptide has Formula I(a)

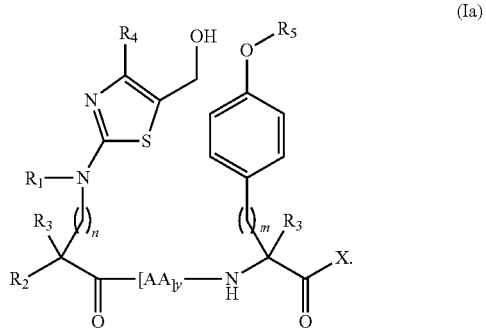

(Ia)

3. The method of claim 2, wherein
n is 0;
$R_2$ is H, methyl, isopropyl, isobutyl, sec-butyl, hydroxymethyl, 1-hydroxyethyl, sulfhydrylmethyl, 2(methylthio)ethyl, benzyl, 4-hydroxybenzyl, 3-indolylmethyl, carboxymethyl, 2-carboxyethyl, carbamidomethyl, 2-carbamidomethyl, 4-aminobutyl, 3-guanadinylpropyl and 4-imidzaolylmethyl; or $R_1$ and $R_2$ are taken together to form a pyrrolidine ring.

4. The method of claim 1, wherein the alkylsulfonic acid is methanesulfonic acid or trifluoromethanesulfonic acid.

5. The method of claim 1, wherein the MSP comprises an α-helix.

* * * * *